(12) United States Patent
Ebert et al.

(10) Patent No.: US 11,788,144 B2
(45) Date of Patent: Oct. 17, 2023

(54) METHODS OF IDENTIFYING AND TREATING A PERSON HAVING A PREDISPOSITION TO OR AFFLICTED WITH A CARDIOMETABOLIC DISEASE

(71) Applicants: The Brigham and Women's Hospital, Inc., Boston, MA (US); The General Hospital Corporation, Boston, MA (US)

(72) Inventors: Benjamin Levine Ebert, Brookline, MA (US); Siddhartha Jaiswal, Cambridge, MA (US); Sekar Kathiresan, Newton, MA (US)

(73) Assignees: The Brigham and Women's Hospital, Inc., Boston, MA (US); The General Hospital Corporation, Boston, MA (US)

(*) Notice: Subject to any disclaimer, the term of this patent is extended or adjusted under 35 U.S.C. 154(b) by 0 days.

(21) Appl. No.: 17/403,024

(22) Filed: Aug. 16, 2021

(65) Prior Publication Data
US 2022/0170100 A1 Jun. 2, 2022

Related U.S. Application Data

(63) Continuation of application No. 15/529,010, filed as application No. PCT/US2015/062787 on Nov. 25, 2015, now Pat. No. 11,168,369.

(60) Provisional application No. 62/084,127, filed on Nov. 25, 2014.

(51) Int. Cl.
| | | |
|---|---|---|
| *C12Q 1/6883* | (2018.01) | |
| *C12Q 1/6886* | (2018.01) | |
| *G01N 33/68* | (2006.01) | |

(52) U.S. Cl.
CPC ......... *C12Q 1/6883* (2013.01); *C12Q 1/6886* (2013.01); *C12Q 2600/156* (2013.01); *C12Q 2600/158* (2013.01); *G01N 33/68* (2013.01); *G01N 2800/32* (2013.01)

(58) Field of Classification Search
None
See application file for complete search history.

(56) References Cited

U.S. PATENT DOCUMENTS

| | | |
|---|---|---|
| 9,574,241 B2 | 2/2017 | Ferrando et al. |
| 10,683,552 B2 | 6/2020 | McCarroll et al. |
| 11,168,369 B2 | 11/2021 | Ebert et al. |
| 11,613,786 B2 | 3/2023 | McCarroll et al. |
| 2003/0092019 A1 | 5/2003 | Meyer et al. |
| 2009/0093543 A1* | 4/2009 | Xue ............ A61P 9/00 426/601 |
| 2010/0197518 A1 | 8/2010 | Xu et al. |
| 2011/0263523 A1* | 10/2011 | Viguie ........ A61K 31/7068 435/6.12 |
| 2014/0127690 A1 | 5/2014 | Bejar et al. |
| 2015/0031641 A1 | 1/2015 | Levine et al. |
| 2018/0010185 A1 | 1/2018 | Ebert et al. |
| 2021/0123105 A1 | 4/2021 | McCarroll et al. |

FOREIGN PATENT DOCUMENTS

| | | |
|---|---|---|
| JP | 2005151854 A | 6/2005 |
| WO | WO-2006/026074 A2 | 3/2006 |

OTHER PUBLICATIONS

Do (Curr Cardiol Rep 2013 15:345).*
Al-Zahrani et al., "Fludarabine-Based Conditioning Chemotherapy for Allogeneic Hematopoietic Stem Cell Transplantation in Acquired Severe Aplastic Anemia," Biol Blood Marrow Transplant, 17:717-722 (2011).
Anonymous: "ASXL1 Gene—GeneCards," GeneCards: https://www.genecards/org/cgi-bin/carddisp.pl?gene=ASXL1&keywords=asxl1 (2020).
Bonnefond et al., "Association between large detectable clonal mosaicism and type 2 diabetes with vascular complications," Nat Genetics, 45:1040-1043 (2013).
Chan et al., "Role of DNMT3A, TET2, and IDH1/2 Mutations in Pre-Leukemic Stem Cells in Acute Myeloid Leukemia," Int J Hematol, 98(6): 648-657 (2013).
Extended European Search Report for EP Application No. 19195023.7 dated Apr. 14, 2020.
Genovese et al., "Clonal Hematopiesis and Blood-Cancer Risk Inferred from Blood DNA sequence," New Engl J Med, 371(26):2477-2487 (2014).
Hansson., "Inflammation, Atherosclerosis, and Coronary Artery Disease," The New England Journal Of Medicine, 352(16): 1685-1695 (2005).
Hou et al., "DNMT3A mutations in acute myeloid leukemia: stability during disease evolution and clinical implications," Blood, 119(2): 559-568 (2012).
International Preliminary Report on Patentability for International Application No. PCT/US2015/062787 dated May 30, 2017.
International Search Report and Written Opinion for International Application No. PCT/US2015/062187 dated May 15, 2016.
International Search Report and Written Opinion for International Application No. PCT/US2015/62787 dated May 4, 2016.
Jaiswal et al., Age-Related Clonal Hematopiesis Associated with Adverse Outcomes, New Engl J Med, 371(26):2488-2498 (2014).
Jaiswal et al., "Age-Related Clonal Hematopoiesis Associated with Adverse Outcomes—Online Supplementary Appendix," New England Journal of Medicine, 371(26): 2488-2498 (2014).

(Continued)

Primary Examiner — Amanda Haney
(74) Attorney, Agent, or Firm — Foley Hoag LLP; Brendan T. Jones

(57) ABSTRACT

The invention relates to method for identifying and selecting a subject with increased risk of developing a cardiometabolic disease and optionally, providing a personalized medicine method, which may involve sequencing at least part of a genome of one or more cells in a blood sample of the subject and identifying from the sequencing one or more mutations in one or more somatic mutations.

12 Claims, 19 Drawing Sheets

Specification includes a Sequence Listing.

(56) References Cited

OTHER PUBLICATIONS

Jan et al., "Clonal Evolution of Preleukemic Hematopoietic Stem Cells Precedes Human Acute Myeloid Leukemia," Sci Transl Med, 4(149) (44 pages) (2012).
Kulasekararaj et al., "Somatic mutations identify a subgroup of aplastic anemia patients who progress to myelodysplastic syndrome," Blood, 124(17):2698-2704 (2014).
Leifert, Anaemia and cigarette smoking, Int J Lab Hem, 30(3):177-184 (2008).
Louw et al., "Guideline for the treatment of myelodysplastic syndromes (MDS) in South Africa," S Afr Med J, 101:900-906 (2011).
Muenlein et al., "Occurrence of the JAK2 V617F mutation in patients with peripheral aterial disease, " Am J Hemtaol, 90(1):E17-E21 (2014).
Mummidi et al., "Evolution of Human and Non-human Primate CC Chemokine Receptor 5 Gene and mRNA," Journal of Biological Chemistry, 275(25):18946-18961 (2000).
Park et al., "Reciprocal regulation of LXRox activity by ASXL1 and ASXL2 in lipogenesis," Biochemical And Biophysical Research Communications, 443(2): 489-494 (2013).
Partial European Search Report for EP application No. EP19195023 dated Dec. 10, 2019.
Shlush et al., "Identification of pre-leukemic hematopoietic stem cells in acute leukemia," Nature, 506(7488): 328-333 (2014).
Thol et al., "Incidence and Prognostic Influence of DNMT3A Mutations in Acute Myeloid Leukemia," Journal of Clinical Oncology, 29(21):2889-2896 (2011).
Thol et al., "Rare Occurene of DNMT3A Mutations in Myelodysplastic Syndromes," Haematologica, 96(2):1870-1873 (2011).
Tong et al., "A Meta-Analysis of the Relationship between Cigarette Smoking and Incidence of Myelodysplastic Syndromes," Plos ONE, 8(6):e67537 (2013).
Xie et al., "Age-related mutations associated with clonal hematopoietic expansion and malignancies," Nat Med, 20:1472-1478 (2014).
Yaghootkar et al., "Genetic Evidence for a Normal-Weight 'Metabolically Obese' Phenotype Linking Insulin Resistance, Hypertension, Coronary Arterty Disease, and Type 2 Diabetes," Diabetes 63(12):4369-4377 (2014).

* cited by examiner

| Carrier Status | Relative CAC [95% CI] | P-value | CAC Median [IQR] |
|---|---|---|---|
| Non-Carrier | 1 | | 154 [14, 535] |
| Carrier | 2.60 [1.23, 5.47] | 0.01 | 310 [91, 864] |

```
                        SEQUENCE LISTING

<160> NUMBER OF SEQ ID NOS: 46

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 1
nnnnnnnnnn nnnnnnnnnn ngg                                             23

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other

<400> SEQUENCE: 2
nnnnnnnnnn nnngg                                                      15

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 3
nnnnnnnnnn nnnnnnnnnn ngg                                              23

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other

<400> SEQUENCE: 4
nnnnnnnnnn nngg                                                        14

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 5
nnnnnnnnnn nnnnnnnnnn nnagaaw                                          27

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 6
nnnnnnnnnn nnnnagaaw                                                   19

<210> SEQ ID NO 7
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 7
nnnnnnnnnn nnnnnnnnnn nnagaaw                                        27

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other

<400> SEQUENCE: 8
nnnnnnnnnn nnnagaaw                                                  18

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 9
nnnnnnnnnn nnnnnnnnnn nggng                                          25

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other
```

```
<220> FEATURE:
<221> NAME/KEY: modified_base
<222> LOCATION: (16)..(16)
<223> OTHER INFORMATION: a, c, t, g, unknown or other

<400> SEQUENCE: 10
nnnnnnnnnn nnggng                                                              17

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 11
nnnnnnnnnn nnnnnnnnnn nggng                                                    25

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 12
nnnnnnnnnn nnggng                                                              16

<210> SEQ ID NO 13
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 13
nnnnnnnnnn nnnnnnnnnn gtttttgtac tctcaagatt tagaaataaa tcttgcagaa      60
gctacaaaga taaggcttca tgccgaaatc aacaccctgt cattttatgg cagggtgttt     120
tcgttattta attttt                                                    137
```

<210> SEQ ID NO 14
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 14
nnnnnnnnnn nnnnnnnnnn gttttttgtac tctcagaaat gcagaagcta caaagataag    60
gcttcatgcc gaaatcaaca ccctgtcatt ttatggcagg gtgttttcgt tatttaattt   120
ttt                                                                 123

<210> SEQ ID NO 15
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 15
nnnnnnnnnn nnnnnnnnnn gttttttgtac tctcagaaat gcagaagcta caaagataag    60
gcttcatgcc gaaatcaaca ccctgtcatt ttatggcagg gtgtttttt                110

<210> SEQ ID NO 16
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 16
nnnnnnnnnn nnnnnnnnnn gtttagagc tagaaatagc aagttaaaat aaggctagtc    60
cgttatcaac ttgaaaaagt ggcaccgagt cggtgctttt tt                       102

<210> SEQ ID NO 17
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 17
nnnnnnnnnn nnnnnnnnnn gtttagagc tagaaatagc aagttaaaat aaggctagtc    60
cgttatcaac ttgaaaaagt gttttttt                                        88

```
<210> SEQ ID NO 18
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 18
nnnnnnnnnn nnnnnnnnnn gttttagagc tagaaatagc aagttaaaat aaggctagtc    60
cgttatcatt tttttt                                                    76

<210> SEQ ID NO 19
<211> LENGTH: 20
<212> TYPE: DNA
<213> ORGANISM: Homo sapiens

<400> SEQUENCE: 19
gagtccgagc agaagaagaa                                                20

<210> SEQ ID NO 20
<211> LENGTH: 20
<212> TYPE: DNA
<213> ORGANISM: Homo sapiens

<400> SEQUENCE: 20
gagtcctagc aggagaagaa                                                20

<210> SEQ ID NO 21
<211> LENGTH: 20
<212> TYPE: DNA
<213> ORGANISM: Homo sapiens

<400> SEQUENCE: 21
gagtctaagc agaagaagaa                                                20

<210> SEQ ID NO 22
<211> LENGTH: 7
<212> TYPE: PRT
<213> ORGANISM: Simian virus 40

<400> SEQUENCE: 22

Pro Lys Lys Lys Arg Lys Val
1               5

<210> SEQ ID NO 23
<211> LENGTH: 16
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 23

Lys Arg Pro Ala Ala Thr Lys Lys Ala Gly Gln Ala Lys Lys Lys Lys
1               5                   10                  15

<210> SEQ ID NO 24
<211> LENGTH: 9
<212> TYPE: PRT
<213> ORGANISM: Unknown
```

```
<220> FEATURE:
<223> OTHER INFORMATION: Description of Unknown:
      C-myc NLS sequence

<400> SEQUENCE: 24

Pro Ala Ala Lys Arg Val Lys Leu Asp
1               5

<210> SEQ ID NO 25
<211> LENGTH: 11
<212> TYPE: PRT
<213> ORGANISM: Unknown
<220> FEATURE:
<223> OTHER INFORMATION: Description of Unknown:
      C-myc NLS sequence

<400> SEQUENCE: 25

Arg Gln Arg Arg Asn Glu Leu Lys Arg Ser Pro
1               5                   10

<210> SEQ ID NO 26
<211> LENGTH: 38
<212> TYPE: PRT
<213> ORGANISM: Homo sapiens

<400> SEQUENCE: 26

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
            35

<210> SEQ ID NO 27
<211> LENGTH: 42
<212> TYPE: PRT
<213> ORGANISM: Unknown
<220> FEATURE:
<223> OTHER INFORMATION: Description of Unknown:
      IBB domain from importin-alpha sequence

<400> SEQUENCE: 27

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
            35                  40

<210> SEQ ID NO 28
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 28

Val Ser Arg Lys Arg Pro Arg Pro
1               5

<210> SEQ ID NO 29
<211> LENGTH: 8
<212> TYPE: PRT
<213> ORGANISM: Unknown
```

```
<220> FEATURE:
<223> OTHER INFORMATION: Description of Unknown:
      Myoma T protein sequence

<400> SEQUENCE: 29

Pro Pro Lys Lys Ala Arg Glu Asp
1               5

<210> SEQ ID NO 30
<211> LENGTH: 8
<212> TYPE: PRT
<213> ORGANISM: Homo sapiens

<400> SEQUENCE: 30

Pro Gln Pro Lys Lys Lys Pro Leu
1               5

<210> SEQ ID NO 31
<211> LENGTH: 12
<212> TYPE: PRT
<213> ORGANISM: Mus musculus

<400> SEQUENCE: 31

Ser Ala Leu Ile Lys Lys Lys Lys Lys Met Ala Pro
1               5                   10

<210> SEQ ID NO 32
<211> LENGTH: 5
<212> TYPE: PRT
<213> ORGANISM: Influenza virus

<400> SEQUENCE: 32

Asp Arg Leu Arg Arg
1               5

<210> SEQ ID NO 33
<211> LENGTH: 7
<212> TYPE: PRT
<213> ORGANISM: Influenza virus

<400> SEQUENCE: 33

Pro Lys Gln Lys Lys Arg Lys
1               5

<210> SEQ ID NO 34
<211> LENGTH: 10
<212> TYPE: PRT
<213> ORGANISM: Hepatitis delta virus

<400> SEQUENCE: 34

Arg Lys Leu Lys Lys Lys Ile Lys Lys Leu
1               5                   10

<210> SEQ ID NO 35
<211> LENGTH: 10
<212> TYPE: PRT
<213> ORGANISM: Mus musculus

<400> SEQUENCE: 35

Arg Glu Lys Lys Lys Phe Leu Lys Arg Arg
1               5                   10

<210> SEQ ID NO 36
<211> LENGTH: 20
<212> TYPE: PRT
```

<213> ORGANISM: Homo sapiens

<400> SEQUENCE: 36

Lys Arg Lys Gly Asp Glu Val Asp Gly Val Asp Glu Val Ala Lys Lys
1               5                   10                  15

Lys Ser Lys Lys
            20

<210> SEQ ID NO 37
<211> LENGTH: 17
<212> TYPE: PRT
<213> ORGANISM: Homo sapiens

<400> SEQUENCE: 37

Arg Lys Cys Leu Gln Ala Gly Met Asn Leu Glu Ala Arg Lys Thr Lys
1               5                   10                  15

Lys

<210> SEQ ID NO 38
<211> LENGTH: 23
<212> TYPE: DNA
<213> ORGANISM: Homo sapiens

<400> SEQUENCE: 38
caccactgcc atagagaggc ggc                                         23

<210> SEQ ID NO 39
<211> LENGTH: 23
<212> TYPE: DNA
<213> ORGANISM: Homo sapiens

<400> SEQUENCE: 39
gagaggcggc caccactgcc atc                                         23

<210> SEQ ID NO 40
<211> LENGTH: 13
<212> TYPE: DNA
<213> ORGANISM: Homo sapiens

<400> SEQUENCE: 40
cagcagtatg tat                                                    13

<210> SEQ ID NO 41
<211> LENGTH: 13
<212> TYPE: DNA
<213> ORGANISM: Homo sapiens

<400> SEQUENCE: 41
gggattcttc tct                                                    13

<210> SEQ ID NO 42
<211> LENGTH: 13
<212> TYPE: DNA
<213> ORGANISM: Homo sapiens

<400> SEQUENCE: 42
agagaagaat ccc                                                    13

<210> SEQ ID NO 43
<211> LENGTH: 10
<212> TYPE: DNA
<213> ORGANISM: Homo sapiens

```
<400> SEQUENCE: 43
ggtcttctgg                                                              10

<210> SEQ ID NO 44
<211> LENGTH: 10
<212> TYPE: DNA
<213> ORGANISM: Homo sapiens

<400> SEQUENCE: 44
ccagaagacc                                                              10

<210> SEQ ID NO 45
<211> LENGTH: 11
<212> TYPE: DNA
<213> ORGANISM: Homo sapiens

<400> SEQUENCE: 45
taggaggtta g                                                            11

<210> SEQ ID NO 46
<211> LENGTH: 11
<212> TYPE: DNA
<213> ORGANISM: Homo sapiens

<400> SEQUENCE: 46
ctaacctcct a                                                            11
```

METHODS OF IDENTIFYING AND TREATING A PERSON HAVING A PREDISPOSITION TO OR AFFLICTED WITH A CARDIOMETABOLIC DISEASE

RELATED APPLICATIONS AND INCORPORATION BY REFERENCE

This application is a continuation of U.S. patent application Ser. No. 15/529,010, filed on May 23, 2017, which claims the benefit of international application serial number PCT/US15/62787, filed Nov. 25, 2015, which claims benefit of and priority to U.S. provisional patent application Ser. No. 62/084,127 filed Nov. 25, 2014.

SEQUENCE LISTING

The instant application contains a Sequence Listing which has been submitted electronically in ASCII format and is hereby incorporated by reference in its entirety. Said ASCII copy, created on Jan. 14, 2021, is named BRB-00801_SL.txt and is 13,143 bytes in size.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to identifying individuals with a predisposition to cardiovascular disease. In particular, the invention relates to method for identifying and selecting a subject with increased risk of developing a cardiometabolic disease and optionally a hematological cancer, and in some instances, providing a personalized medicine method.

BACKGROUND OF THE INVENTION

Cancer is thought to arise via stepwise acquisition of genetic or epigenetic changes that transform a normal cell (Nowell P C. Science 1976; 194:23-8). Hence, the existence of a pre-malignant state bearing only the initiating lesions may be detectable in some individuals with no other signs of disease. For example, multiple myeloma (MM) is frequently preceded by monoclonal gammopathy of unknown significance (MGUS) (Kyle R A et al. The New England journal of medicine 2002; 346:564-9), and chronic lymphocytic leukemia (CLL) is commonly preceded by monoclonal B-lymphocytosis (MBL) (Rawstron A C et al. The New England journal of medicine 2008; 359:575-83).

Several lines of evidence have suggested that clonal hematopoiesis due to an expansion of cells harboring an initiating driver mutation might be an aspect of the aging hematopoietic system. Clonal hematopoiesis in the elderly was first demonstrated in studies that found that approximately 25% of healthy women over the age of 65 have a skewed pattern of X-chromosome inactivation in peripheral blood cells (Busque L et al. Blood 1996; 88:59 65, Champion K M et al. British journal of haematology 1997; 97:920 6) which in some cases is associated with mutations in TET2 (Busque L et al. Nature genetics 2012; 44: 1179-81). Large-scale somatic events such as chromosomal insertions and deletions and loss of heterozygosity (LOH) also occur in the blood of ~2% of individuals over the age of 75 (Jacobs K B et al. Nature genetics 2012; 44:651-8, Laurie C C et al. Nature genetics 2012; 44:642-50). Pre-leukemic hematopoietic stem cells (HSCs) harboring only the initiating driver mutation have been found in the bone marrow of patients with AML in remission (Jan M et al. Science translational medicine 2012; 4: 149ral8, Shlush L I et al. Nature 2014; 506:328-33). Furthermore, a substantial proportion of the population carries cells with t(14; 18) translocations, although the lesion is generally present in fewer than 1 in 1000 cells (Roulland S et al. t(14; 18) Journal of clinical oncology: official journal of the American Society of Clinical Oncology 2014; 32: 1347-55).

Recent sequencing studies have identified a set of recurrent mutations in several types of hematological malignancies (Mardis E R et al. The New England journal of medicine 2009; 361 1058-66, Bejar R et al. The New England journal of medicine 2011; 364:2496-506, Papaemmanuil E et al. The New England journal of medicine 2011; 365: 1384-95, Walter et al. Leukemia 2011; 25: 1153-8, Welch J S et al. Cell 2012; 150:264-78, Cancer Genome Atlas Research N. Genomic and epigenomic landscapes of adult de novo acute myeloid leukemia. The New England journal of medicine 2013; 368:2059-74, Papaemmanuil E et al. Blood 2013; 122:3616-27; quiz 99, Walter M J et al. Leukemia 2013; 27: 1275-82, Zhang J et al. Proceedings of the National Academy of Sciences of the United States of America 2013; 110: 1398-403, Morin R D et al. Nature 2011; 476:298-303, Lenz G et al. Science 2008; 319: 1676-9, Lohr J G et al. Proceedings of the National Academy of Sciences of the United States of America 2012; 109:3879-84, Neumann M et al. Blood 2013; 121:4749-52). However, the frequency of these somatic mutations in the general population is unknown. Citation or identification of any document in this application is not an admission that such document is available as prior art to the present invention.

SUMMARY OF THE INVENTION

The present invention relates to Applicants' hypothesis that somatically acquired single nucleotide variants (SNVs) and small insertions/deletions (indels) might be increasingly detectable in the blood of otherwise healthy individuals as a function of age.

The invention relates to method for identifying and selecting a subject with increased risk of developing a cardiometabolic disease and optionally a hematological cancer, which may comprise the steps of: (a) sequencing at least part of a genome which may comprise one or more genes selected from the group consisting of DNMT3A, TET2, ASXLI, TP53, JAK2 and SF3B1 of one or more cells in a blood sample of the subject, (b) identifying from said sequencing one or more mutations in one or more genes selected from the group consisting of DNMT3A, TET2, ASXL1, TP 53, JAK2 and SF3B1, wherein presence of said mutation(s) indicates an increased risk of developing a cardiometabolic disease and optionally a hematological cancer.

The invention also relates to a method for identifying and selecting a subject with an increased risk of developing a cardiometabolic disease and optionally a hematological cancer and providing a personalized medicine method, said method which may comprise the steps of (a) sequencing at least part of a genome which may comprise one or more genes selected from the group consisting of DNMT3A, TET2, ASXLI, TP53, JAK2 and SF3B1 of one or more cells in a blood sample of the subject, (b) identifying from said sequencing one or more mutations in one or more genes selected from the group consisting of DNMT3A, TET2, ASXLI, TP 53, JAK2 and SF3B1, wherein presence of said mutation(s) indicates an increased risk of developing a cardiometabolic disease and optionally a hematological cancer, and (c) initiating a treatment or monitoring regimen to suppress said mutation(s) in the subject, thereby decreasing risk of developing a cardiometabolic disease and optionally a hematological cancer.

The presence of said mutation(s) in the above embodiments may indicate an increase in red blood cell distribution width (RDW).

The cardiometabolic disease may be atherosclerosis, coronary heart disease (CHD) or ischemic stroke (IS) or type 2 diabetes (T2D).

In embodiments wherein an increased risk for hematological cancer is also screened in addition to a cardiometabolic disease, the hematological cancer may be a leukemia, a lymphoma, a myeloma or a blood syndrome. The leukemia may be an acute myeloid leukemia (AML), chronic myelogenous leukemia (CML) or chronic lymphocytic leukemia (CLL). The blood syndrome may be myelodysplastic syndrome (MDS) or myeloproliferative neoplasm (MPN).

The one more cells in the blood sample may be derived from hematopoietic stem cells (HSCs), committed myeloid progenitor cells having long term self-renewal capacity or mature lymphoid cells having long term self-renewal capacity.

In some embodiments the part of the genome that is sequenced may be an exome. In other embodiments, the sequencing may be whole exome sequencing (WES) or targeted gene sequencing.

In an advantageous embodiment, the subject is a human. In other embodiments, the human may exhibit one or more risk factors of being a smoker, having a high level of total cholesterol or having high level of high-density lipoprotein (HDL).

The mutations of at least DNMT3A, TET2, ASXL1, TP53, JAK2 and SF3B1 may be frameshift mutations, nonsense mutations, missense mutations or splice-site variant mutations.

If the mutation is in DNMT3A, the mutation may advantageously be a mutation in exons 7 to 23. In a particularly advantageous embodiment, the mutation in DNMT3A is a mutation selected from the group consisting of P307S, P307R, R326H, R326L, R326C, R326S, R366P, R366H, R366G, A368T, F414L, F414S, F414C, C497Y, Q527H, Q527P, Y533C, G543A, G543S, G543C, L547H, L547P, L547F, M548I, M548K, G550R, W581R, W581G, W581C, G646V, G646E, L653W, L653F, V657A, V657M, R659H, Y660C, R676W, R676Q, G685R, G685E, G685A, D686Y, D686G, G699R, G699S, G699D, P700S, P700R, P700Q, D702N, D702Y, V704M, V704G, I705F, I705T, I705S, C710S, S714C, N717S, N7171, P718L, R720H, R720G, Y724C, R729Q, R729W, R729G, F731L, F732del, F732S, F732L, F734L, F734C, Y735C, Y735N, Y735S, R736H, R736C, R736G, L737H, L737V, L737F, L737R, A741V, R749C, R749L, F751L, F752del, F752C, F752L, F752I, F752V, L754R, L754H, F755S, F755I, F755L, M7611, M761V, G762C, S770W, S770P, R771Q, F772I, F772V, L773R, E774K, E774D, D781G, R792H, G796D, G796V, N797Y, N797H, P799R, P799H, R803S, P804S, P804L, S828N, K829R, Q842E, P849L, D857N, W860R, F868S, G869S, G869V, M880V, S881R, S881I, R882H, R882P, R882C, R882G, Q886R, G890D, L901R, L901H, P904L, F909C and A910P.

If the mutation is in TET2, the mutation is advantageously selected from the group consisting of S282F, N312S, L346P, S460F, D666G, P941S, and C1135Y.

If this mutation is in ASXL1, the mutation is advantageously a mutation in exon 11-12.

If the mutation is in TP53, the mutation is advantageously a mutation selected from the group consisting of S46F, G105C, G105R, G105D, G108S, G108C, R101L, R110C, T118A, T118R, T1181, L130V, L130F, K132Q, K132E, K132W, K132R, K132M, K132N, C135W, C135S, C135F, C135G, Q136K, Q136E, Q136P, Q136R, Q136L, Q136H, A138P, A138V, A138A, A138T, T140I, C141R, C141G, C141A, C141Y, C141S, C141F, C141W, V143M, V143A, V143E, L145Q, L145R, P151T, P151A, P151S, P151H, P152S, P152R, P152L, T155P, R158H, R158L, A159V, A159P, A159S, A159D, A161T, A161D, Y163N, Y163H, Y163D, Y163S, Y163C, K164E, K164M, K164N, K164P, H168Y, H168P, H168R, H168L, H168Q, M169I, M169T, M169V, T170M, E171K, E171Q, E171G, E171A, E171V and E171D, V172D, V173M, V173L, V173G, R174W, R175G, R175C, R175H, C176R, C176G, C176Y, C176F, C176S, P177R, P177R, P177L, H178D, H178P, H178Q. H179Y, H179R, H179Q, R181C, R181Y, D186G, G187S, P190L, P190T, H193N, H193P, H193L, H193R, L194F, L194R, I195F, I195N, I195T, V197L, G199V, Y205N, Y205C, Y205H, D208V, R213Q, R213P, R213L, R213Q, H214D, H214R, S215G, S215I, S215R, V216M, V217G, Y220N, Y220H, Y220S, Y220C, E224D, I232F, I232N, I232T, I232S, Y234N, Y234H, Y234S, Y234C, Y236N, Y236H, Y236C, M237V, M237K, M2371, C238R, C238G, C238Y, C238W, N239T, N239S, S241Y, S241C, S241F, C242G, C242Y, C242S, C242F, G244S, G244C, G244D, G245S, G245R, G245C, G245D, G245A, G245V, G245S, M246V, M246K, M246R, M246I, N247I, R248W, R248G, R248Q, R249G, R249W, R249T, R249M, P250L, 125 IN, L252P, 1254S, 1255F, 1255N, I255S, L257Q, L257P, E258K, E258Q, D259Y, S261T, G262D, G262V, L265P, G266R, G266E, G266V, R267W, R267Q, R267P, E271K, V272M, V272L, R273S, R273G, R273C, R273H, R273P, R273L, V274F, V274D, V274A, V274G, V274L, C275Y, C275S, C275F, A276P, C277F, P278T, P278A, P278S, P278H, P278R, P278L, G279E, R280G, R280K, R280T, R2801, R280S, D281N, D281H, D281Y, D281G, D281E, R282G, R282W, R282Q, R282P, E285K, E285V, E286G, E286V, E286K, K320N, L330R, G334V, R337QR337L, A347T, L348F, T377P.

If the mutation is in JAK2, the mutation is advantageously selected from the group consisting of N533D, N533Y, N533S, H538R, K539E, K539L, 1540T, 1540V, V617F, R683S, R683G, del/ins537-539L, del/ins538-539L, del/ins540-543MK, del/ins540-544MK, del/ins541-543K, del542-543, del543-544 and ins 11546-547.

If the mutation is in SF3B1, the mutation is advantageously selected from the group consisting of G347V, R387W, R387Q, E592K, E622D, Y623C, R625L, R625C, H662Q, H662D, K666N, K666T, K666E., K666R, K700E, V701F, A708T, G740R, G740E, A744P, D781G and E783K.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of and "consists essentially of have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 16. (A) Forest plot for odds ratio (OR) of having a somatic mutation in those presenting with myocardial infarction (MI) compared to those without MI (referent). Results are shown for 2 cohorts (ATVB and PROMIS) and stratified by age groups. (B) Counts for number of mutations seen in cases versus controls for the most frequently mutated genes.

DETAILED DESCRIPTION OF THE INVENTION

The incidence of hematological malignancies increases with age and is associated with recurrent somatic mutations in specific genes. Applicants hypothesized that such mutations would be detectable in the blood of some individuals not known to have hematological disorders.

Applicants analyzed whole exome sequencing data from peripheral blood cell DNA of 17, 182 individuals who were unselected for hematologic phenotypes. Applicants looked for somatic mutations by identifying previously characterized single nucleotide variants (SNVs) and small insertions/deletions (indels) in 160 genes recurrently mutated in hematological malignancies. The presence of mutations was analyzed for association to hematological phenotypes, survival, and cardiovascular events.

Detectable somatic mutations were rare in individuals younger than 40, but rose appreciably with age. At ages 70-79, 80-89, and 90-108 these clonal mutations were observed in 9.6% (220 out of 2299), 11.7% (37 out of 317), and 18.4% (19 out of 103) of individuals, respectively. The majority of the variants occurred in 3 genes: DNMT3A, TET2, and ASXL1.

The presence of a somatic mutation was associated with increased risk of developing hematologic malignancy (HR 11, 95% confidence interval [95%>CI] 3.9-33), increased all-cause mortality (HR 1.4, 95% CI 1.1-1.8), and increased risk of incident coronary heart disease (HR 2.0, 95% CI 1.2-3.4) and ischemic stroke (HR 2.6, 95% CI 1.4-4.8).

Clonal hematopoiesis of indeterminate potential (CHIP) is a common pre-malignant condition in the elderly, and is associated with increased risk of transformation to hematologic malignancy and increased all-cause mortality, possibly due to increased cardiometabolic disease.

Figure 8:
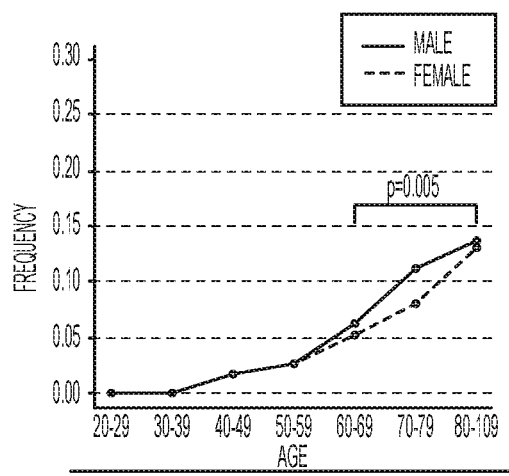
FIG. 8. Factors associated with clonality A) Frequency of mutation for males and females by age group. For those 60 or older, being male is associated with having a detectable clone (OR 1.3, 95% CI 1.1-1.5, p=0.005 by multivariable logistic regression using age, sex, T2D and BMI as covariates). B) Frequency of mutation for those with and without type 2 diabetes by age group. C) Frequency of mutation for non-Hispanics, Hispanics, and South Asians by age group.
Figure 8:
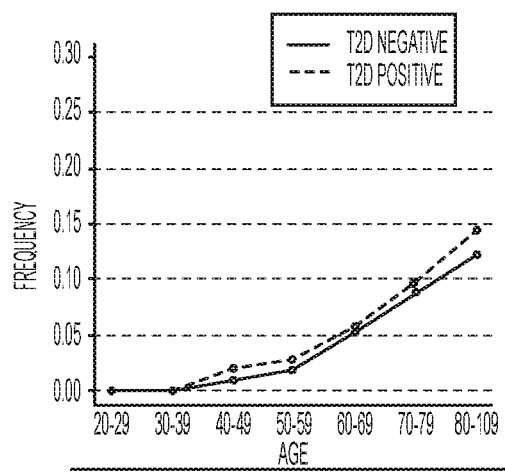
Figure 8:
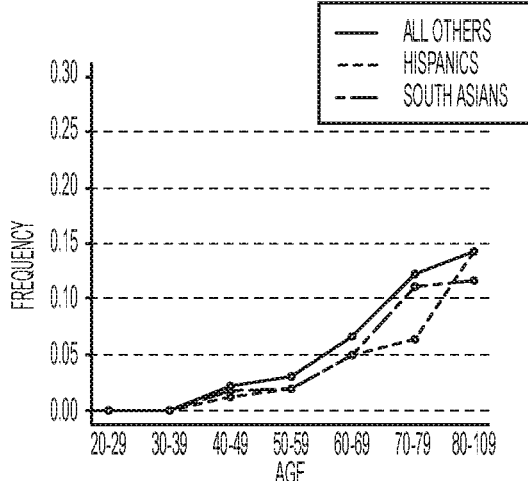

Cardiovascular disease is the leading cause of death worldwide. Given the association of somatic mutations with all-cause mortality beyond that explicable by hematologic malignancy and T2D, Applicants performed association analyses from two cohorts comprising 3,353 subjects with available data on coronary heart disease (CHD) and ischemic stroke (IS). After excluding those with prevalent events, Applicants found that those carrying a mutation had increased cumulative incidence of both CHD and IS (FIGS. 5A and 5B). In multivariable analyses that included age, sex, T2D, systolic blood pressure, and body mass index as covariates, the hazard ratio of incident CHD and IS was 2.0 (95% CI 1.2-3.5, P=0.015) and 2.6 (95% CI 1.3-4.8, P=0.003) in the individuals carrying a somatic mutation as compared to those without (FIG. 5C and 5D, FIG. 8).

For a subset of individuals, the traditional risk factors of smoking, total cholesterol, and high-density lipoprotein were also available; the presence of a somatic mutation remained significantly associated with incident CHD and IS even in the presence of these risk factors, and the risk was even greater in those with VAF>0.10 (Supplementary Table S12). Elevated RDW and high-sensitivity C-reactive protein (hsCRP) have also been associated with adverse cardiac outcomes (ToneUi M et al. Circulation 2008; 117: 163-8, Ridker P M et al. The New England journal of medicine 2002; 347: 1557-65), possibly reflecting an underlying inflammatory cause. In a multivariable analysis of 1,795 subjects from JHS, those with a mutation and RDW>14.5% had a markedly increased risk of incident CHD, and this effect was independent of hsCRP (Supplementary Table SI 3).

Applicants find that somatic mutations leading to clonal outgrowth of hematopoietic cells are frequent in the general population. This entity, which Applicants term clonal hematopoiesis with indeterminate potential (CHIP), is present in over 10% of individuals over 70, making it one of the most common known pre-malignant lesions. The exact prevalence of CHIP is dependent on how cancer-causing mutations are defined and on the sensitivity of the technique used to detect mutations, and thus may substantially exceed this estimate. Unlike other pre-malignant lesions, CHIP appears to involve a substantial proportion of the affected tissue in most individuals; based on the proportion of alleles with the somatic mutation, Applicants find that a median of 18% of peripheral blood leukocytes are part of the abnormal clone. CHIP also persists over time; in all tested cases, the mutations were still present after 4 to 8 years.

The genes most commonly mutated in CHIP are DNMT3A, TET2, and ASXL1. This is consistent with previous studies that have found DNMT3A and TET2 mutations to be frequent and early events in AML and MDS (Jan M et al. Science translational medicine 2012; 4: 149ra18, Shlush L1 et al. Nature 2014; 506-328-33, Papaemmanuil E et al. The New England journal of medicine 2011; 365: 1384-95, Welch J S et al. Cell 2012; 150:264-78). Murine models of DNMT3A or TET2 loss-of-function demonstrate that mutant HSCs have altered methylation patterns at pluripotency genes and a competitive advantage compared to wild-type HSCs, but mice rarely develop frank malignancy, and then only after long latency (Jeong M et al. Nature genetics 2014; 46:17-23, Koh K P et al. Cell stem cell 2011; 8:200-13, Challen G A et al. Nature genetics 2012; 44:23-31, Moran-Crusio K et al. Cancer cell 201; 20: 11-24). Similarly, Applicants' data show that humans with CHIP can live for many years without developing hematological malignancies, though they do have increased risk relative to those without mutations.

TET2 and DNMT3A are frequently mutated in some lymphoid malignancies, and the initiating event for such tumors may occur in a HSC (Neumann M et al. Blood 2013; 121:4749-52, Quivoron C et al. Cancer cell 2011; 20:25-38, Odejide O et al. Blood 2014; 123: 1293-6, Asmar F et al. Haematologica 2013; 98: 1912-20, Couronne L et al. The New England journal of medicine 2012; 366:95-6). While it is most likely that these mutations occur in a HSC, it also possible that they occur in committed myeloid progenitors or mature lymphoid cells that have acquired long-term self-renewal capacity.

The use of somatic mutations to aid in the diagnosis of patients with clinical MDS is becoming widespread. Applicants' data demonstrate that the majority of individuals with clonal mutations in peripheral blood do not have MDS or another hematological malignancy, nor do the majority develop a clinically diagnosed malignancy in the near term. At this time, it would be premature to genetically screen healthy individuals for the presence of a somatic clone, as the positive predictive value for current or future malignancy is low.

The invention relates to method for identifying and selecting a subject with increased risk of developing a cardiometabolic disease and optionally a hematological cancer, which may comprise the steps of: (a) sequencing at least part of a genome which may comprise one or more genes selected from the group consisting of DNMT3A, TET2, ASXLI, TP53, JAK2 and SF3B1 of one or more cells in a blood sample of the subject, (b) identifying from said sequencing one or more mutations in one or more genes selected from the group consisting of DNMT3A, TET2, ASXLI, TP 53, JAK2 and SF3B1, wherein presence of said mutation(s) indicates an increased risk of developing a cardiometabolic disease and optionally a hematological cancer.

The invention also relates to a method for identifying and selecting a subject with an increased risk of developing a cardiometabolic disease and optionally a hematological cancer and providing a personalized medicine method, said method which may comprise the steps of (a) sequencing at least part of a genome which may comprise one or more genes selected from the group consisting of DNMT3A, TET2, ASXLI, TP53, JAK2 and SF3B1 of one or more cells in a blood sample of the subject, (b) identifying from said sequencing one or more mutations in one or more genes selected from the group consisting of DNMT3A, TET2, ASXLI, TP 53, JAK2 and SF3B1, wherein presence of said mutation(s) indicates an increased risk of developing a cardiometabolic disease and optionally a hematological cancer, and (c) initiating a treatment or monitoring regimen to suppress said mutation(s) in the subject, thereby decreasing risk of developing a cardiometabolic disease and optionally a hematological cancer.

The presence of said mutation(s) in the above embodiments may indicate an increase in red blood cell distribution width (RDW).

The cardiometabolic disease may be atherosclerosis, coronary heart disease (CHD) or ischemic stroke (IS).

In embodiments wherein an increased risk for hematological cancer is also screened in addition to a cardiometabolic disease, the hematological cancer may be a leukemia, a lymphoma, a myeloma or a blood syndrome. The leukemia may be an acute myeloid leukemia (AML) or chronic myelogenous leukemia (CML). The blood syndrome may be myelodysplasia syndrome (MDS).

The one more cells in the blood sample may be hematopoietic stem cells (HSCs), committed myeloid progenitor cells having long term self-renewal capacity or mature lymphoid cells having long term self-renewal capacity.

In some embodiments the part of the genome that is sequenced may be an exome. In other embodiments, the sequencing may be whole exome sequencing (WES).

In an advantageous embodiment, the subject is a human. In other embodiments, the human may exhibit one or more risk factors of being a smoker, having a high level of total cholesterol or having high level of high-density lipoprotein (HDL).

The mutations of at least DNMT3A, TET2, ASXL1, TP53, JAK2 and SF3B1 may be frameshift mutations, nonsense mutations, missense mutations or splice-site variant mutations.

If the mutation is in DNMT3A, the mutation may advantageously be a mutation in exons 7 to 23. In a particularly advantageous embodiment, the mutation in DNMT3A is a mutation selected from the group consisting of P307S, P307R, R326H, R326L, R326C, R326S, R366P, R366H, R366G, A368T, F414L. F414S, F414C, C497Y, Q527H, Q527P, Y533C, G543A, G543S, G543C, L547H, L547P, 1547F, M548I, M548K, G550R, W581R, W581G, W581C, G646V, G646E, L653W, L653F, V657A, V657M, R659H, Y660C, R676W, R676Q, G685R, G685E, G685A, D686Y, D686G, G699R, G699S, G699D, P700S, P700R, P700Q, D702N, D702Y, V704M, V704G, 1705F, 1705T, 1705S, C710S, S714C, N717S, N7171, P718L, R720H, R720G, Y724C, R729Q, R729W. R729G, F731L, F732del, F732S, F732L, F734L, F734C, Y735C, Y735N, Y735S, R736I1, R736C, R736P, L737H, L737V, L737F, L737R, A741V, R749C, R749L, F751L, F752del, F752C, F752L, F752I, F752V, L754R, L754H, F755S, F755I, F755L, M761I, M761V, G762C, S770W, S770P, R771Q, F772I, F772V, L773R, E774K, E774D, D781G, R792H, G796D. G796V, N797Y, N797H, P799H, P799H, R803S, P804S, P804L, S828N, K829R, Q842E, P849L, D857N, W860R, F868S, G869S, G869V, M880S, S881H, S881I, R882H, R882P, R882C, R882G, Q886R, G890D, L901R, L901H, P904L, F909C and A910P.

If the mutation is in TET2, the mutation is advantageously selected from the group consisting of S282F, N312S, L346P, S460F, D666G, P941S, and C1135Y.

If this mutation is in ASXL1, the mutation is advantageously a mutation in exon 11-12.

If the mutation is in TP53, the mutation is advantageously a mutation selected from the group consisting of S46F, G105C, G105R, G105D, G108S, G108C, R110L, R110C, T118A, T118R, T118I, L130V, L130F, K132Q, K132E, K132W, K132R, K132M, K132N, C135W, C135S, C135F, C135G, Q136K, Q136E, Q136P, Q136R, Q136L, Q136H, A138P, A138V, A138A, A138T, T140L, C141R, C141G, C141A, C141Y, C141S, C141F, C141W, V143M, V143A, V143E, L145Q, L145R, P151T, P151A, P151S, P151H, P152S, P152R, P152L, T155P, R158H, R158L, A159V, A159P, A159S, A159D, A161T, A161D, Y163N, Y163H, Y163D, Y163S, Y163C, K164E, K164M, K164N, K164P, H168Y, H168P, H168R, H168L, H168Q, M169I, M169T, M169V, T170M, E171K, E171Q, E171G, E171A, E171V and E171D, V172D, V173M, V173L, V173G, R174W, R175G, R175C, R175H, C176R, C176G, C176Y, C176F, C176S, P177R, P177R, P177L, H178D, H178P, H178Q, H179Y, H179R, H179Q, R181C, R181Y, D186G, G187S, P190L, P190T, H193N, H193P, H193L, H193R, L194F, L194R, I195F, I195N, I195T, V197L, G199V, Y205N, Y205C, Y205H, D208V, R213Q, R213P, R213L, R213Q, H214D, H214R, S215G, S215I, S215R, V216M, V217G, Y220N, Y220H, Y220S, Y220C, E224D, I232F, I232N, I232T, I232S, Y234N, Y234H, Y234S, Y234C, Y236N, Y236H, Y236C, M237V, M237K, M237I, C238R, C238G, C238Y, C238W, N239T, N239S, S241Y, S241C, S241F, C242G, C242Y, C242S, C242F, G244S, G244C, G244D, G245S, G245R, G245C, G245D, G245A, G245V, G245S, M246V, M246K, M246R, M246I, N247I, R248W, R248G, R248Q, R249G, R249W, R249T, R249M, P250L, 125 IN, L252P, I254P, I255F, I255N, I255S, L257Q, L257P, E258K, E258Q, D259Y, S261T, G262D, G262V, L265P, G266R, G266E, G266V, R267W, R267Q, R267P, E271K, V272M, V272L, R273S, R273G, R273C, R273H, R273P, R273L, V274F, V274D, V274A, V274G, V274L, C275Y, C275S, C275F, A276P, C277F, P278T, P278A, P278S, P278H, P278R, P278L, G279E, R280G, R280K, R280T, R280I, R280S, D281N, D28I H, D281 Y, D281G, D281E, R282G, R282W, R282Q, R282P, E285K, E285V, E286G, E286V, E286K, K320N, L330R, G334V, R337QR337L, A347T, L348F, T377P.

If the mutation is in JAK2, the mutation is advantageously selected from the group consisting of N533D, N533Y, N533S, H538R, K539E, K539L, I540T, I540V, V617F, R683S, R683G, del/ins537-539L, del/ins538-539L, del/ins540-543MK, del/ins540-544MK, del/ins541-543K, del542-543, del543-544 and ins 11546-547.

If the mutation is in SF3B1, the mutation is advantageously selected from the group consisting of G347V, R387W, R387Q, E592K, E622D, Y623C, R625L, R625C, H662Q, H662D, K666N, K666T, K666E, K666R, K700E, V701F, A708T, G740R, G740E, A744P, D781G and E783K.

Aging is associated with a large increase in the prevalence of atherosclerosis and cancer. Applicants recently analyzed whole exome sequencing data from over 17,000 individuals who were unselected for hematological phenotypes and found that at least 10% of humans age 70 or older harbor a mutation in a known cancer-causing gene in their blood cells (Jaiswal et al., NEJM 2014). Surprisingly, the presence of these mutations was associated with an increased risk of myocardial infarction (hazard ratio [HR]=2.0) and ischemic stroke (HR=2.6) in ~3,000 individuals for whom long-term follow-up information was available. It is unknown if somatic mutations that cause clonal expansion of hematopoietic stem cells also affect the function of differentiated blood cells such as macrophages, which are considered to be important mediators of atherosclerosis. Preliminary mouse data indicates that at least one of these mutations (TET2) does indeed directly alter blood cell function to lead to accelerated atherosclerosis. This application seeks to definitively establish whether these somatic mutations in blood cells are causally linked to atherosclerosis. Applicants expand the initial findings by assessing whether mice bearing mutations in DNMT3A, TET2, or JAK2 in their blood cells have accelerated atherosclerosis. Applicants probe the molecular mechanism of accelerated atherosclerosis in these mice. Applicants look for alterations in expression of liver X receptor (LXR), peroxisome proliferator activated receptor gamma (PPARG), and lipopolysaccharide (LPS) target genes in mutant macrophages using RNA-seq, DNase footprinting, and bisulfite sequencing. Applicants identify and validate therapeutic targets in macrophages with these somatic mutations using drug screens in newly created cell-line models.

Atherosclerosis is the leading cause of death in the United States; however, little is known about non-lipid risk factors in humans. This application relates to a mechanism behind the proposed causal association between these somatic mutations in blood cells and atherosclerosis.

Figure 1:
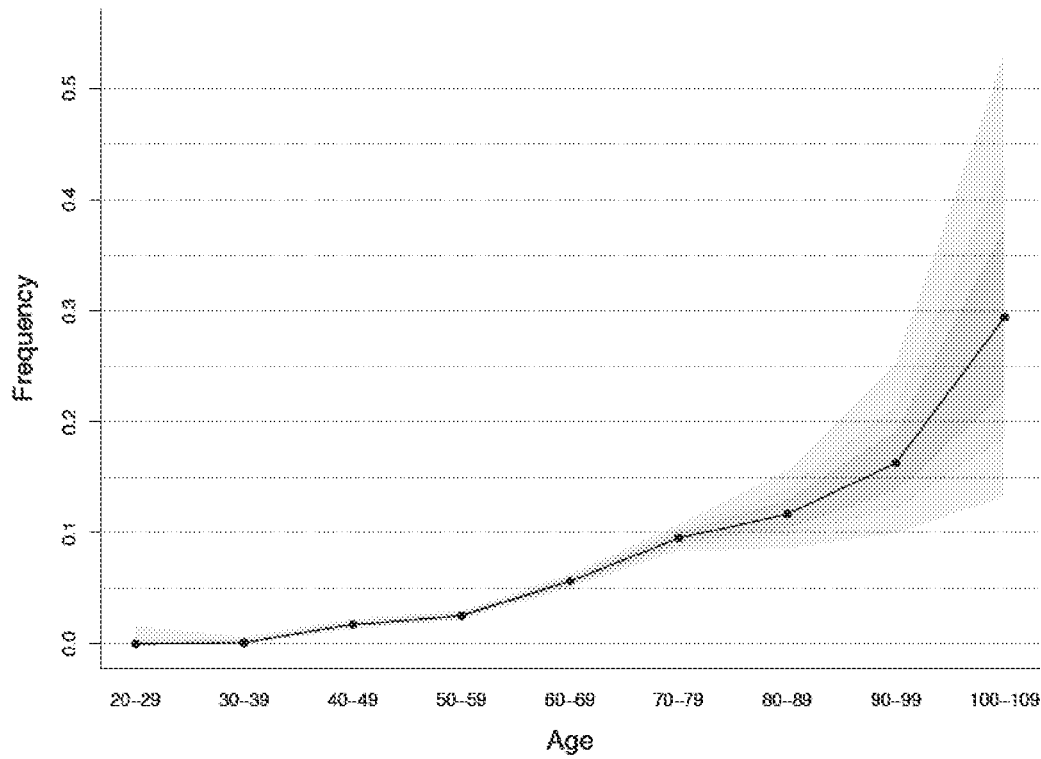
FIG. 1. Prevalence of somatic mutation by age. Colored bands represent 50th, 75th, and 95th percentiles.

Cancer is thought to arise via the stepwise acquisition of genetic or epigenetic mutations that transform a normal cell (P. C. Nowell, Science 194, 23-28 (1976), J. S. Welch et al., Cell 150, 264-278 (2012)). For most hematological cancers, the genes that are frequently mutated are now known (R. Bejar et al, N Engl J Med 364, 2496-2506 (2011, N. Cancer Genome Atlas Research, Genomic and epigenomic landscapes of adult de novo acute myeloid leukemia. N Engl J Med 368, 2059-2074 (2013), E. Papaemmanuil et al, Blood 122, 3616-3627; quiz 3699 (2013), T. Haferlach et al, Leukemia 28, 241-247 (2014)). Applicants hypothesized that these mutations would be detectable in the blood cells of some individuals not known to have hematological disorders, and that the presence of these mutations would represent a pre-malignant state. To test this hypothesis, Applicants examined whole exome sequencing data from large cohorts who were unselected for hematological phenotypes (S. Jaiswal et al, N Engl J Med 371, 2488-2498 (2014), G. Genovese et al, N Engl J Med 371, 2477-2487 (2014), M. Xie et al., Nat Med 20, 1472-1478 (2014)). The DNA source for these exomes was peripheral blood cells. Applicants found that ~10% of individuals over the age of 70 harbored a detectable mutation in their blood cells (FIG. 1). The majority of the mutations could be accounted for by loss-of-function mutations in 3 genes, DNMT3A, TET2, and ASXLI, while activating mutations in JAK2 were the fifth most common mutation. These mutations are common in myeloid malignancies. Compared to those without mutations, persons who harbored these mutations were over 10 times more likely to develop a hematologic malignancy over the next several years, confirming that this condition is a bona fide pre-malignant entity (D. P. Steensma et al., Blood 126, 9-16 (2015)).

Figure 5:
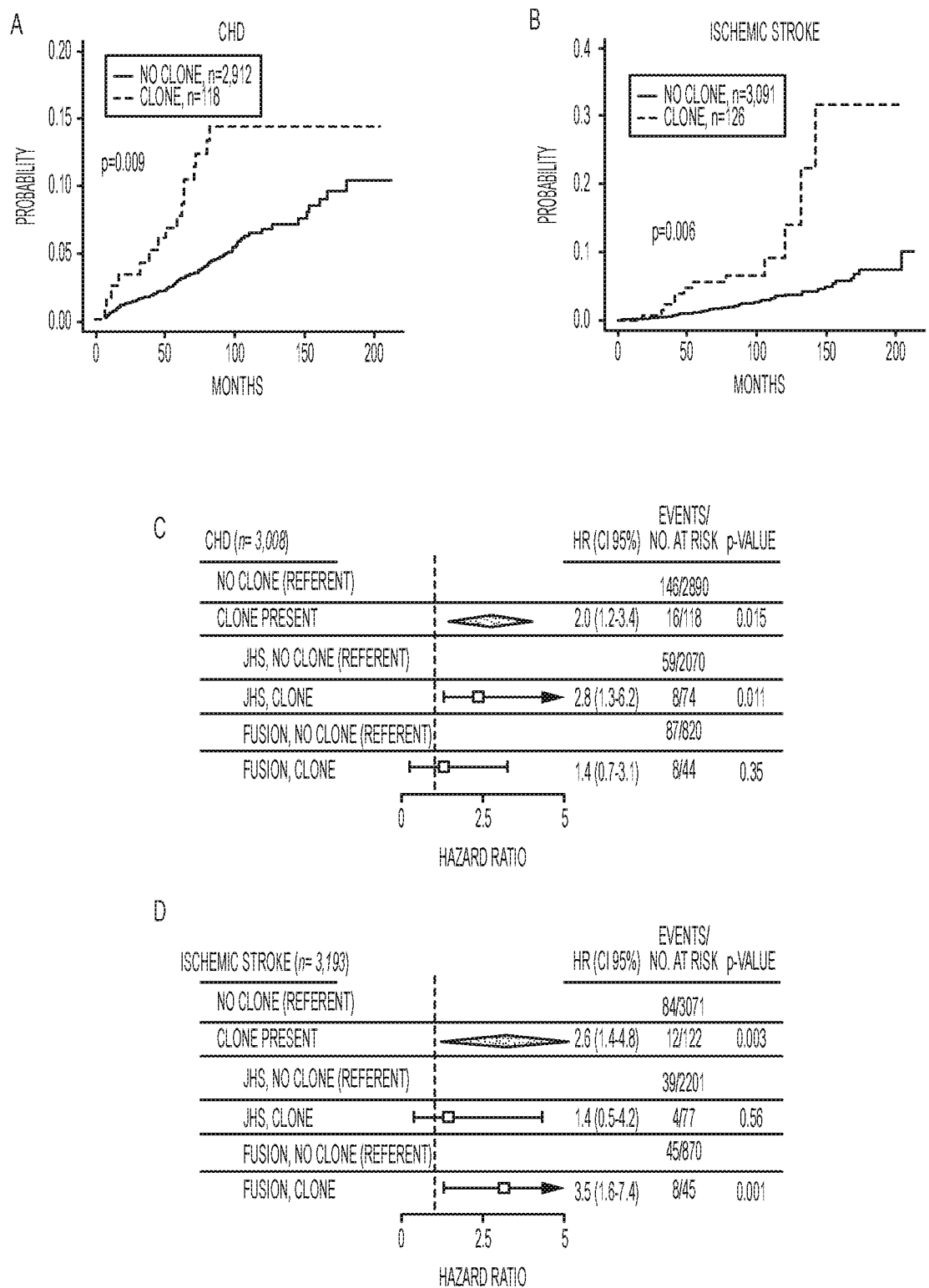
FIG. 5. Association of somatic mutations with incident cardiovascular disease. A-B) Cumulative incidence plots for incident coronary heart disease (CHD) (A) and ischemic stroke (B). Curves were generated from competing risks data with death as the competing risk. Those with prevalent events were excluded from the analyses. C-D) Forest plots for risk of developing incident CHD (C) and ischemic stroke (D) in those with somatic mutations. Diamond represents the results of fixed-effects meta-analysis using beta-coefficients from competing risks regressions for both cohorts, and horizontal lines are 95 percent confidence intervals. Age groups (less than 50, 50-59, 60-69, and 70 or greater), T2D status, sex, systolic blood pressure groups (less than 140 mm Hg, 140-160 mm Hg, and greater than 160 mm Hg), and body mass index groups (less than 25, 25-35, and greater than 35) were included as categorical covariates in the competing risks regression models, with death as the competing risk. Those with prevalent events were excluded from the analyses.

Surprisingly, the presence of these mutations was also associated with an increased risk of mortality that could not be explained by hematological malignancy alone. Applicants found that those with mutations had a higher rate of having a fatal myocardial infarction (MI) or ischemic stroke. When Applicants looked at risk of developing incident coronary heart disease or ischemic stroke, Applicants found that the presence of mutations was an even stronger risk factor than smoking, hypertension, or elevated cholesterol (FIG. 5).

Figure 16:
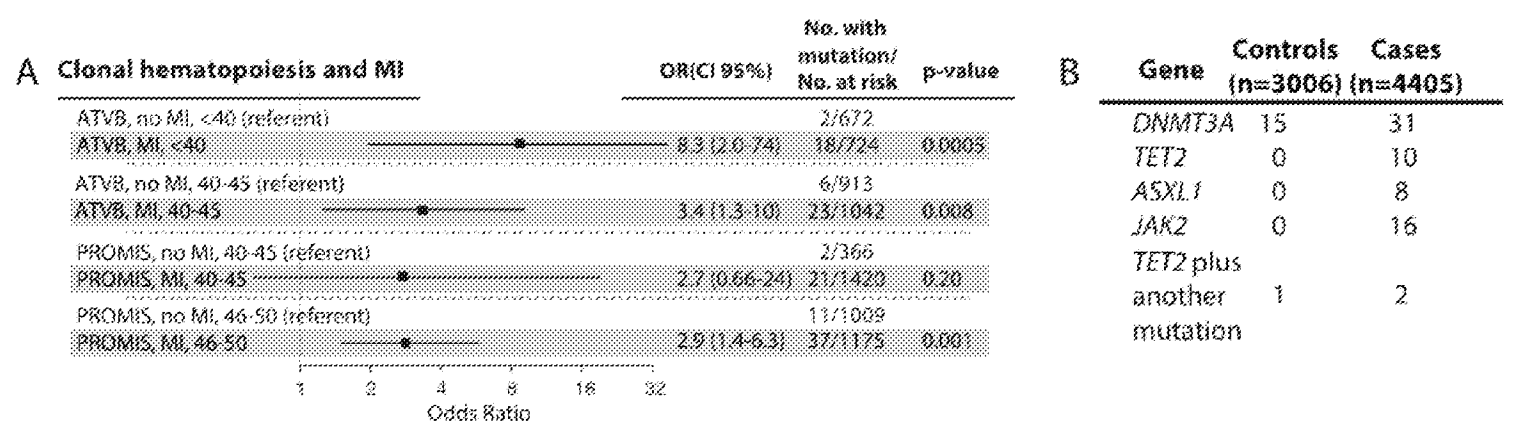

To replicate these findings, Applicants examined whole exome sequencing data from two large case-control cohorts designed to study early-onset MI. The cases (n=4,405) were individuals from Italy or Pakistan who had blood cells collected for DNA sequencing at the time of presentation of MI, and controls (n=3,006) were age-matched healthy individuals from the same populations. Applicants found an even greater risk associated with mutations in these cohorts; the presence of a mutation was over 8 times more likely in the MI cases as compared to age-matched controls for those 40 or younger, and 3 times more likely in those age 41-50 (FIG. 16A). DNMT3A, TET2, ASXL1, and JAK2 were the most frequently mutated genes, and were strongly enriched in the cases (FIG. 16B).

These genetic studies have firmly established a statistical link between the presence of these mutations and atherosclerotic disease, but alone cannot establish causality. It is possible that this association is merely a correlation, and that the presence of mutations is a molecular marker of aging. However, a few observations suggest a causal relationship. First, Applicants' human genetic data shows a dose-response relationship between the size of the mutant clone and risk of atherosclerotic disease. There is a greatly increased risk of incident coronary heart disease (HR=4.4) in those with a mutant allele fraction of >0.10 (meaning >20% of the blood cells harbor the mutation, including the macrophages in vessel walls), while those with clones smaller than this size had no increased risk. Second, there is a large body of evidence to suggest that macrophages are important in the development of atherosclerosis (K. J. Moore et al., Nat Rev Immunol 13, 709-721 (2013)). They are the most prevalent cell type within vessel wall lesions, and are critical for reverse cholesterol transport (RCT), the process by which excess lipid is exported from tissues for clearance by the liver (M. Cuchel et al, Circulation 113, 2548-2555 (2006)). Third, inflammation and alterations in blood cell parameters are linked to adverse cardiovascular outcomes in epidemiological studies (R. Ross, N Engl J Med 340, 115-126 (1999), P. Libby, Nature 420, 868-874 (2002), P. Libby et al, Am J Med 116 Suppl 6A, 9S-165 (2004), P. M. Ridker et al, N Engl J Med 347, 1557-1565 (2002), M. Tonelli et al, Circulation 117, 163-168 (2008), M. Madjid et al, J Am Coll Cardiol 44, 1945-1956 (2004)).

Wild-type mice have much lower baseline cholesterol and triglyceride levels than humans in modern societies. Therefore, a standard experimental model is to use mice lacking low-density lipoprotein receptor (Ldlr-I-) (E. Maganto-Garcia et al., Current protocols in immunology/edited by John E. Coligan . . . [et al.] Chapter 15, Unit 15 24 11-23 (2012)). These mice rapidly develop atherosclerosis when fed a high cholesterol diet. By transplanting bone marrow into Ldlr-I- mice from a genetically defined mouse strain, one can test the effect of a genetic perturbation in hematopoietic cells on the development of atherosclerosis.

In general, studies of experimental atherosclerosis have revealed two relevant processes that can be influenced by macrophages: 1) reverse cholesterol transport, and 2) the local inflammatory milieu. The importance of macrophage reverse cholesterol transport is exemplified by mice in which both liver X receptor genes have been knocked out in the hematopoietic compartment (LXRαβ-1-) (R. K. Tangirala et al., Proceedings of the National Academy of Sciences of the United States of America 99, 11896-11901 (2002)). Recipients transplanted with marrow from these mice develop accelerated atherosclerosis and have a lipid accumulation phenotype in several tissues. LXRs are a class of nuclear receptors expressed in macrophages, hepatocytes, and intestinal epithelium that activate transcription of genes involved in cholesterol transport and lipid metabolism when bound by ligand. In the absence of LXR mediated transcription, macrophages do not efficiently upregulate expression of the cholesterol transporters ABCA1 and ABCG1. This leads to a defect in exporting cholesterol to acceptor molecules such as high-density lipoprotein (HDL) and Apo-AI, ultimately resulting in foam cell formation in tissues such as the vessel wall, skin, and spleen.

The role of inflammation in atherosclerosis has also been well studied. Mice that are deficient in toll-like receptor (TLR)-2 (A. E. Mullick et al, J Clin Invest 115, 3149-3156 (2005)), TLR4 (K. S. Michelsen et al., Proceedings of the National Academy of Sciences of the United States of America 101, 10679-10684 (2004)), or inflammasome (P. Duewell et al, Nature 464, 1357-1361(2010)) signaling have reduced atherosclerosis, whereas mice that lack the inflammatory repressor BCL6 in macrophages have accelerated atherosclerosis (G. D. Barish et al., Cell Metab 15, 554-562 (2012)). Macrophage mediated inflammation results in recruitment of other immune cells and intimal hyperplasia, resulting in increased lesion size and instability. Additional evidence indicates that inflammatory signaling may also directly inhibit macrophage RCT (A. Castrillo et al, Mol Cell 12, 805-816 (2003)). Finally, activation of another class of nuclear receptors, PPARs, ameliorates atherosclerosis by increasing macrophage RCT via LXR activation (A. Chawla et al., Mol Cell 7, 161-171 (2001)), as well as by attenuating inflammation via induction of the transcriptional repressors BCL6, NCOR1, and NCOR2 (G. Pascual et al., Nature 437, 759-763 (2005), A. Chawla, Circ Res 106, 1559-1569 (2010)).

Figure 17:
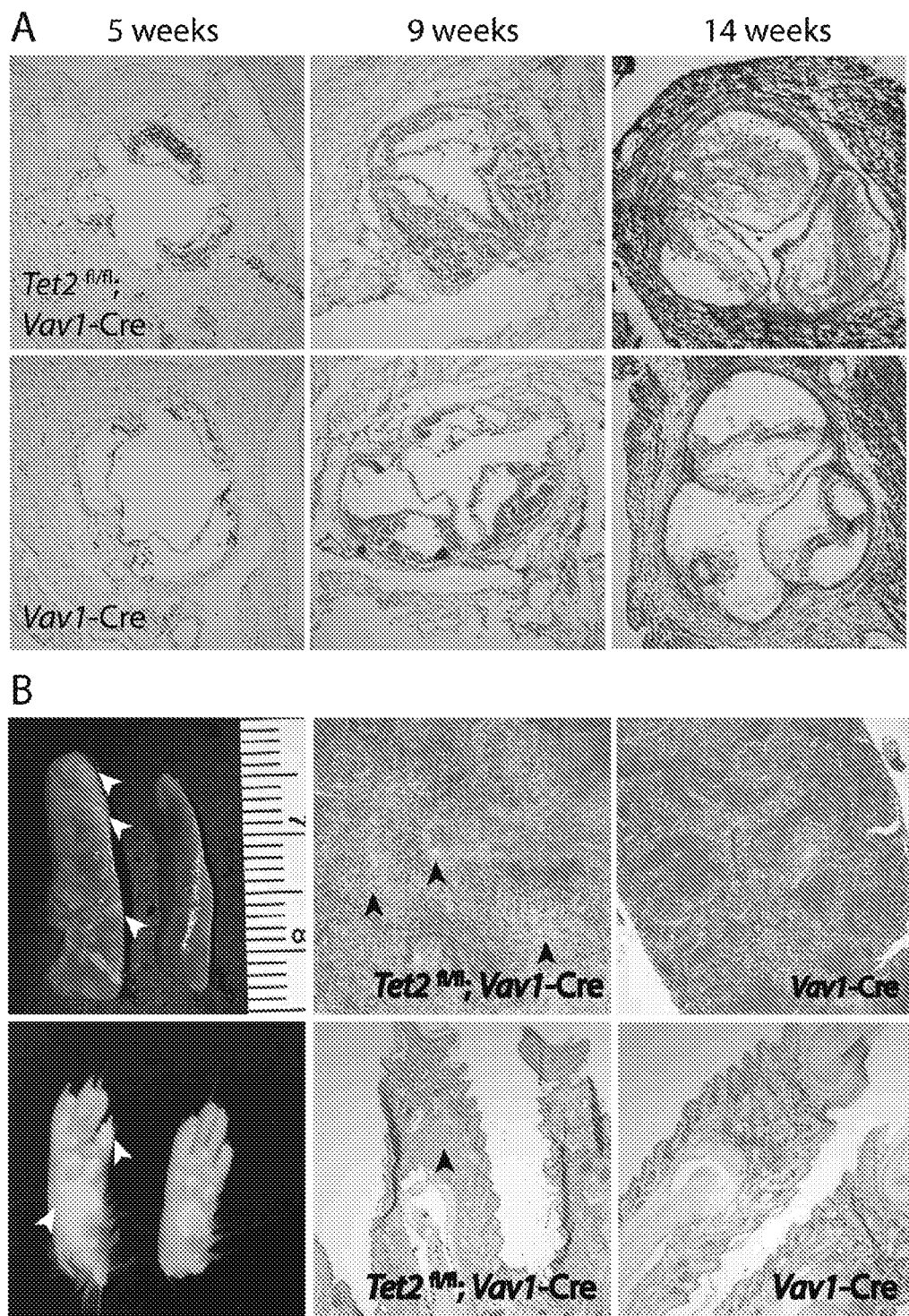
FIG. 17. (A) Low power sections of the aortic root from recipients of Tet2-/-marrow (top row) or control marrow (bottom row) are shown at three time-points after initiation of diet. The left and center columns are oil red O stained, and the right column is Masson's trichrome. (B) Spleen (top row, H&E) and digit (bottom row, oil red O) histology are shown in mice after 14 weeks on diet. Note the large fat deposits (white arrowheads) and sheets of lipid-laden macrophages in the tissues (black arrowheads) of Tet2-/- recipients.

To test the hypothesis that mutations in blood cells are causally linked to atherosclerosis, Applicants turned to defined mouse models. Applicants crossed Tet2$^{fl/fl}$ mice to Vav1-Cre mice; the resultant Tet2$^{fl/fl}$, Vav1-Cre mice have exon 3 of TETE2 deleted, leading to complete loss of Tet2 function in all of their hematopoietic cells. Previous studies have demonstrated that hematopoietic stem cells (HSCs) from these mice have a differentiation defect that results in a progressive increase in HSC frequency and consequent clonal expansion of the mutant cells in a competitive transplant setting (K. Moran-Crusio et al., Cancer cell 20, 11-24 (2011)). Thus, this model system recapitulates the clonal advantage of TET2 mutant hematopoietic cells seen in humans. Applicants then transplanted bone marrow from these mice, or control Vav1-Cxo, mice, into Ldlr−/− recipient mice and initiated high cholesterol diet. Tissues were then examined at several time points. The results from these preliminary experiments are clear; mice that received Tet2-I-bone marrow had not only increased lesion size in the aortic root (FIG. 17 A), but also striking numbers of lipid-laden macrophages in the spleen, skin, and peritoneal fluid (FIG. 17B). This phenotype is remarkably similar to the one described for mice transplanted with ΣXKαβ-I-marrow (R. K. Tangirala et al., Proceedings of the National Academy of Sciences of the United States of America 99, 11896-11901 (2002)). In summary, these results point to a marked deficit of reverse cholesterol transport in macrophages that lack TET2, of which one manifestation is accelerated atherosclerosis.

The present invention relates to determining the effect of mutations in TET2, DNMT3A, and JAK2 on atherosclerosis development in vivo. Applicants has already generated or obtained models for DNMT3A loss-of-function$^{(Dnmt.3d^{f/f})}$ mice) (S. Nguyen et al., Dev Dyn 236, 1663-1676 (2007)) and JAK2 gain-of-function (floxed Jak2 V617F knock-in heterozygous mice) (A. Mullally et al., Cancer cell 17, 584-596 (2010)). Unfortunately, there are no publicly available mouse models of ASXL1 that mimic the mutations seen in humans, which are truncating mutations in exon 12. Applicants hypothesize that introducing these mutations into hematopoietic cells lead to accelerated atherosclerosis using the Ldlr–/– transplant system described above. Applicants perform the transplants described above and analyze mice after 5, 9, and 14 weeks on high-cholesterol (1.25%) diet. Lesion size and cellular composition, as well serum lipid profiles are measured. Applicants also examine lipid content of macrophages in the spleen, lung, liver, skin, intestines, and peritoneal fluid to determine if there is a global defect in macrophage RCT. It is important to note that the mice are not expected to develop a leukemic phenotype within this time frame. Applicants also determine whether other cells within the hematopoietic compartment besides macrophages can contribute to the phenotype. Applicants cross the TET2, DNMT3A, and JAK2 mutant mice to mice that have CD2-Cre (lymphoid specific) or PF4-Cre (platelet specific), then perform transplants into Ldlr-I-mice and determine the extent of atherosclerosis in each model after 9 weeks on diet. Adgrel-Cre mice, which express Cre in mature macrophages only, are used to test the hypothesis that the mutations do not necessarily need to occur in stem cells to exert a phenotype.

It is possible that macrophages are the cells responsible for the phenotype, but that the mutations must occur in stem cells in order to have a functional effect due to altered differentiation. If the mutant strains crossed with Adgrel-Cre do not have a phenotype, Applicants isolate monocyte precursors (J. Hettinger et al., Nat Immunol 14, 821-830 (2013)) from mutant Vavl-Cre mice and transplant these into recipient Ldlr-I-mice to test the hypothesis that monocytes/macrophages alone can recapitulate the phenotype.

The present application also relates to determining the mechanism by which mutations in TET2, DNMT3A, and JAK2 lead to altered macrophage function and accelerated atherosclerosis. As detailed above, much experimental evidence indicates that macrophage function has a profound effect on the development of atherosclerosis. Applicants hypothesize that mutations in TET2, DNMT3A, and JAK2 lead to accelerated atherosclerosis by inhibiting macrophage reverse cholesterol transport, increasing macrophage-mediated inflammation, or both. Applicants characterize the transcriptional response of mutant macrophages to induction of RCT and inflammation by agonists of LXRs. PPARG, and TLR4.

To ensure robustness of results, Applicants utilize 2 types of primary macrophages: thioglycollate-induced peritoneal macrophages and bone-marrow derived macrophages grown in vitro in the presence of cytokines. The specific agonists to be used are GW3965 (LXR alpha/beta agonist), pioglitazone (PPARG agonist), and LPS (TLR4 agonist). Gene expression are assessed by RNA-sequencing. Gene set enrichment analysis are used to determine the extent of transcriptional changes for various classes of genes by comparing expression in mutant/wild-type cells that have been treated to mutant/wild-type cells that are not treated. For these experiments, gene expression are measured at two time-points after exposure to agonists to also assess the kinetics of the transcriptional response.

Applicants are uncovering the mechanistic link between the specific mutations and alterations in gene expression in response to the agonists listed above. Applicants perform DNase footprinting and bisulfite sequencing to molecularly determine the how mutant macrophages are altered in response to the specific agonists. Peritoneal macrophages are used in these experiments because they represent an in vivo baseline epigenetic state. DNase footprinting provides a powerful method to infer transcription factor binding in a genome-wide manner by identifying DNA sequence motifs that are protein bound. Bisulfite sequencing provides single base resolution of cytosine methylation. As TET2 and DNMT3A are enzymes that alter DNA methylation, it is likely that perturbing their function result in an abnormal epigenetic state. For example, TET2 converts 5-methylcytosine to 5-hydroxymethylcytosine, which ultimately leads to de-methylation. As methylation at promoters and enhancers anti-correlates with gene expression and transcription factor binding, Applicants hypothesize that loss of TET2 function results in abnormal methylation of cis-regulatory elements for LXR/PPARG targets, reduced binding of transcription factors at these elements, and ultimately attenuated expression of the target genes. DNMT3A, a de novo DNA methyltransferase, has a function that opposes that of TET2. Applicants hypothesize that de novo methylation at cis-regulatory elements of proinflammatory genes is necessary to attenuate an inflammatory response in macrophages, and that this regulatory check is lacking in DNMT3A null macrophages. Unlike TET2 and DNMT3A, JAK2 is unique in that it is an activator of STAT signaling, not an epigenetic regulator. STAT transcription factors are known to activate a variety of genes involved in the immune response. Applicants hypothesize that constitutive STAT signaling in the setting of JAK2 activating mutations results in a stronger/more protracted pro-inflammatory phenotype in mutant macrophages, which are determined by assessing the transcriptional response to LPS. Applicants are performing functional assays to assess the physiological effect of the mutations on macrophage activity. Applicants assess cholesterol efflux, cholesterol uptake, efferocytosis, LPS tolerance, and M1/M2 polarization in mutant and wild-type macrophages in response to the specific agonists. Applicants hypothesize that one or more of these processes are altered due to the mutations.

While DNase footprinting is a powerful technique, it relies upon knowing DNA motifs for specific transcription factors to accurately assign binding. Furthermore, enhancers are inferred from transcription factor binding, rather than by assessing chromatin marks. Therefore, Applicants also consider chromatin immunoprecipitation sequencing for LXR alpha and beta, PPARG, Re1A, Re1B, c-REL, STAT3, and STAT5, as well as the canonical histone marks for enhancers (H3K4me1, H3K4me3, H3K27ac, H3K27me3). Finally, Applicants also consider assessment of 5-hydroxymethylcytosine as technology to detect this mark continues to improve.

The present invention also relates to identifying molecules and pathways that can reverse the pro-atherogenic phenotype of mutant macrophages. Applicants are identifying therapeutic targets for macrophages that have mutations in TET2, DNMT3A, or JAK2. Applicants hypothesize that specific molecules or pathways can be targeted to reverse some aspects of the pro-atherogenic phenotype of mutant macrophages. Applicants are testing whether existing agonists for LXR and PPARG can reverse the phenotype in the bone marrow transplant models. Mice are placed on drug after 8 weeks on high cholesterol diet, and plaque size are compared between treated/untreated and mutant/wild-type mice after an additional 12 weeks on diet. While these approaches may prove efficacious in mice, current LXR and PPARG agonists are not considered front-line drugs in humans because of side-effects and the potential for serious adverse events. Thus, Applicants are identifying novel targets that can reverse the phenotype specifically in mutant macrophages. Applicants utilize THP-1 cells, a monocytic leukemia cell line that retains the ability differentiate into macrophages and is responsive to LXR and PPARG agonists. Frameshift mutations in TET2 and DNMT3A are created by CRISP-Cas9, while JAK2 V617F are introduced lentivirally. Applicants also introduce artificial reporters that activate fluorescence by LXR agonists, PPARG agonists, or LPS (via NF-κB activation). Applicants are screening the cells using a highly targeted drug library of 481 molecules that affect distinct cellular pathways and processes (A. Basu et al, Cell 154, 1151-1161 (2013)). The read-out is an image-based assessment of fluorescence intensity from the reporter. The aim is to identify molecules that preferentially activate or repress the reporter in mutant, but not wild-type macrophages. Applicants are also testing individual compounds that show desired activity in the mouse bone marrow transplant model, as well as in in vitro assays in primary macrophages.

The small molecule approach described above may not yield any viable candidates for a variety of reasons. In this case, a second screen is performed using a CRISPR-Cas9/small-guide RNA system to inactivate all protein-coding genes. Briefly, THP-1 cells with reporter are transduced with Cas9 and a pooled library of small guide RNA molecules. After inducing macrophage differentiation, Applicants identify cells that activate or repress the reporter in response to agonists. DNA sequencing is used to determine which guides are present, and the positive hits are further validated to ensure that they preferentially affect mutant cells.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), wo 2014/093709 (PCT/US2013/074812), wo 2014/093622 (PCT/US2013/074667), wo 2014/093635 (PCT/US2013/074691), wo 2014/093655 (PCT/US2013/074736), wo 2014/093712 (PCT/US2013/074819), wo 2014/093701 (PCT/US2013/074800), wo 2014/018423 (PCT/US2013/051418), wo 2014/204723 (PCT/US2014/041790), wo 2014/204724 (PCT/US2014/041800), wo 2014/204725 (PCT/US2014/041803), wo 2014/204726 (PCT/US2014/041804), wo 2014/204727 (PCT/US2014/041806), wo 2014/204728 (PCT/US2014/041808), wo 2014/204729 (PCT/US2014/041809), wo 2015/089351 (PCT/US2014/069897), wo 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089465 (PCT/US2014/070135), WO 2015/089486 (PCT/US2014/070175), PCT/US2015/051691, PCT/US2015/051830. Reference is made to PCT application designating, inter alia, the United States, application No. PCT/US 14/41806, filed Jun. 10, 2014. Reference is made to PCT application designating, inter alia, the United States, application No. PCT/US14/41806, filed Jun. 10, 2014.

Each of these patents, patent publications, and applications, and all documents cited therein or during their prosecution ("appin cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013); One-Step Generation of Mice Carrying Mutations in Multiple Genes by CRISPR/Cas-Mediated Genome Engineering. Wang F L, Yang F L, Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Piatt R J, Scott D A, Church G M, Zhang F. Nature. 2013 Aug. 22; 500(7463): 472-6. doi: 10.1038/Nature12466. Epub 2013 Aug. 23;

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A, Matoba, S., Zhang, Y., & Zhang, F. Cell August 28. pii: S0092-8674(13)01015-5. (2013;

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi: 10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308. (2013); Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science Dec. 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Ce//Feb. 27. (2014). 156(5):935-49;

Genome-wide binding of the CRISPR endonuclease Cas9 in mammalian cells. Wu X., Scott D A., Kriz A J., Chiu A C, Hsu P D., Dadon D B., Cheng A W., Trevino A E., Konermann S., Chen S., Jaenisch R., Zhang F., Sharp P A. Nat Biotechnol. (2014) Apr. 20. doi: 10.1038/nbt.2889, CRISPR-Cas9 Knockin Mice for Genome Editing and Cancer Modeling, Piatt et al., Cell 159(2): 440-455 (2014) DOI: 10.1016/j.cell.2014.09.014, Development and Applications of CRISPR-Cas9 for Genome Engineering, Hsu et al, Cell 157, 1262-1278 (Jun. 5, 2014) (Hsu 2014), Genetic screens in human cells using the CRISPR/Cas9 system, Wang et al., Science. 2014 Jan. 3; 343(6166): 80-84. doi: 10.1126/science.1246981, Rational design of highly active sgRNAs for CRISPR-Cas9-mediated gene inactivation, Doench et al, Nature Biotechnology published online 3 Sep. 2014; doi: 10.1038/nbt.3026, and In vivo interrogation of gene function in the mammalian brain using CRISPR-Cas9, Swiech et al, Nature Biotechnology; published online 19 Oct. 2014; doi: 10.1038/nbt.3055.

Genome-scale transcriptional activation by an engineered CRISPR-Cas9 complex, Konermann S, Brigham M D, Trevino A E, Joung J, Abudayyeh 00, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2): 139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using Staphylococcus aureus Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546): 186-91 (2015).

High-throughput functional genomics using CRISPR-Cas9, Shalem et al., Nature Reviews Genetics 16, 299-311 (May 2015).

Sequence determinants of improved CRISPR sgRNA design, Xu et al., Genome Research 25, 1147-1157 (August 2015).

A Genome-wide CRISPR Screen in Primary Immune Cells to Dissect Regulatory Networks, Parnas et al. Cell 162, 675-686 (Jul. 30, 2015).

CRISPR/Cas9 cleavage of viral DNA efficiently suppresses hepatitis B virus, Ramanan et al, Scientific Reports 5: 10833. doi: 10.1038/srep10833 (Jun. 2, 2015). Crystal Structure of Staphylococcus aureus Cas9, Nishimasu et al., Cell 162, 1113-1126 (Aug. 27, 2015).

BCL11 A enhancer dissection by Cas9-mediated in situ saturating mutagenesis, Canver et al, Nature 527(7577): 192-7 (Nov. 12, 2015) doi: 10.1038/nature15521. Epub 2015 Sep. 16.

Cpf1 Is a Single RNA-Guided Endonuclease of a Class 2 CRISPR-Cas System, Zetsche et al, Cell 163, 759-71 (Sep. 25, 2015).

Discovery and Functional Characterization of Diverse Class 2 CRISPR-Cas Systems, Shmakov et al, Molecular Cell, 60(3), 385-397 doi: 10.1016fj.molcel.2015.10.008 Epub Oct. 22, 2015.

each of which is incorporated herein by reference, and discussed briefly below:

Cong et al. engineered type II CRISPR/Cas systems for use in eukaryotic cells based on both *Streptococcus thermophilus* Cas9 and also *Streptoccocus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR/Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via nonhomologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED 12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the FiNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage. Piatt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays. Shalem et al. (2015) described ways in which catalytically inactive Cas9 (dCas9) fusions are used to synthetically repress (CRISPRi) or activate (CRISPRa) expression, showing, advances using Cas9 for genome-scale screens, including arrayed and pooled screens, knockout approaches that inactivate genomic loci and strategies that modulate transcriptional activity.

Shalem et al. (2015) described ways in which catalytically inactive Cas9 (dCas9) fusions are used to synthetically repress (CRISPRi) or activate (CRISPRa) expression, showing, advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Mention is also made of Tsai et al, "Dimeric CRISPR RNA-guided FokI nucleases for highly specific genome editing," Nature Biotechnology 32(6): 569-77 (2014) which is not believed to be prior art to the instant invention or application, but which may be considered in the practice of the instant invention. Mention is also made of Konermann et al., "Genome-scale transcription activation by an engineered CRISPR-Cas9 complex," doi: 10.1038/nature14136, incorporated herein by reference.

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2Kb window of genomic sequence flanking the type H CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used. In some embodiments it may be preferred in a CRISPR complex that the tracr sequence has one or more hairpins and is 30 or more nucleotides in length, 40 or more nucleotides in length, or 50 or more nucleotides in length; the guide sequence is between 10 to 30 nucleotides in length, the CRISPR/Cas enzyme is a Type II Cas9 enzyme. In embodiments of the invention the terms guide sequence and guide RNA are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (available online from Novocraft Technologies), ELAND (Illumina, San Diego, CA), SOAP (see Li, et al., Bioinformatics, 2008 Mar. 1; 24(5):713-4), and Maq (*Mapping and Assembly with Quality project hosted online by SourceForge*). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10-30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence may be selected to target any target sequence. In some embodiments, the target sequence is a sequence within a genome of a cell. Exemplary target sequences include those that are unique in the target genome. For example, for the *S. pyogenes* Cas9, a unique target sequence in a genome may include a Cas9 target site of the form MMMMMMMMMNNNNNNNNNNNNXGG (SEQ ID NO: 1) where NNNNNNNNNNNNXGG (SEQ ID NO: 2) (N is A, G, T, or C; and X can be anything) has a single occurrence in the genome. A unique target sequence in a genome may include an *S. pyogenes* Cas9 target site of the form MMMMMMMMMNNNNNNNNNNNXGG (SEQ ID NO: 3) where NNNNNNNNNNNXGG (SEQ ID NO: 4) (N is A, G, T, or C; and X can be anything) has a single occurrence in the genome. For the *S. thermophilus* CRISPR1 Cas9, a unique target sequence in a genome may include a Cas9 target site of the form MMMMMMIMMNNNNNNNNNNNNXXAGAAW (SEQ ID NO: 5) where NNNNNNNNNNNNXXAGAAW (SEQ ID NO: 6) (N is A, G, T, or C; X can be anything; and W is A or T) has a single occurrence in the genome. A unique target sequence in a genome may include an *S. thermophilus* CRISPR1 Cas9 target site of the form MMMMMMMMMNNNNNNNNNNNXXAGAAW (SEQ ID NO: 7) where NNNNNNNNNNNXXAGAAW (SEQ ID NO: 8) (N is A, G, T, or C; X can be anything; and W is A or T) has a single occurrence in the genome. For the *S. pyogenes* Cas9, a unique target sequence in a genome may include a Cas9 target site of the form MMMMMMMMMNNNNNNNNNNNNXGGXG (SEQ ID NO: 9) where NNNNNNNNNNNNXGGXG (SEQ ID NO: 10) (N is A, G, T, or C; and X can be anything) has a single occurrence in the genome. A unique target sequence in a genome may include an *S. pyogenes* Cas9 target site of the form MMMMMMMMMNNNNNNNNNNNXGGXG (SEQ ID NO: 11) where NNNNNNNNNNNXGGXG (SEQ ID NO: 12) (N is A, G, T, or C; and X can be anything) has a single occurrence in the genome. In each of these sequences "M" may be A, G, T, or C, and need not be considered in identifying a sequence as unique. In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at the Institute for Theoretical Chemistry at the University of Vienna, using the centroid structure prediction algorithm (see e.g. A. R. Gruber et al., 2008, Cell 106(1): 23-24; and P A Carr and G M Church, 2009, Nature Biotechnology 27(12): 1151-62).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgttttgtactctcaagatt-taGAAAtaaatcttgcagaagctacaaagataa (1)
(SEQ ID NO: 13)
NNNNNNNNNNNNNNNNNNNNgttttgtactctcaagattta GAAAtaaatcttgcagaagctacaaagataaggcttcatgcc gaaatcaacaccctgtcattttatggcagggtgttttcgtta tttaaTTTTTT;

(2)
(SEQ ID NO: 14)
NNNNNNNNNNNNNNNNNNNNgttttgtactctcaGAAA tgcagaagctacaaagataaggcttcatgccgaaatcaa caccctgtcattttatggcagggtgttttcgttatttaa

TTTTTT;

(3)
(SEQ ID NO: 15)
NNNNNNNNNNNNNNNNNNNNgttttgtactctcaGAAA tgcagaagctacaaagataaggcttcatgccgaaatcaacac cctgtcattttatggcagggtgtTTTTTT;

(4)
(SEQ ID NO: 16)
NNNNNNNNNNNNNNNNNNNNgttttagagctaGAAA tagcaagttaaaataaggctagtccgttatcaacttgaaaaa gtggcaccgagtcggtgcTTTTTT;

(5)
(SEQ ID NO: 17)
NNNNNNNNNNNNNNNNNNNNgttttagagctaGAAATAG caagttaaaataaggctagtccgttatcaacttgaaaaagtg TTTTTT;
and (6)
(SEQ ID NO: 18)
NNNNNNNNNNNNNNNNNNNNgttttagagctagAAATAG caagttaaaataaggctagtccgttatcaTTTTTTTT.

TTTTT (SEQ ID NO: 18). In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, chimeric synthetic guide RNAs (sgRNAs) designs may incorporate at least 12 bp of duplex structure between the direct repeat and tracrRNA For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 19) in the EMX1 gene of the human genome, deep sequencing can be used to assess the level of modification at the following two off-target loci, 1: 5'-GAGTCCTAGCAGGAGAAGAA-3' (SEQ ID NO: 20) and 2: 5'-GAGTCTAAGCAGAAGAAGAA-3' (SEQ ID NO: 21). The concentration that gives the highest level of on-target modification while minimizing the level of off-target modification should be chosen for in vivo delivery. Alternatively, to minimize the level of toxicity and off-target effect, CRISPR enzyme nickase mRNA (for example *S. pyogenes* Cas9 with the D10A mutation) can be delivered with a pair of guide RNAs targeting a site of interest. The two guide RNAs need to be spaced as follows. Guide sequences and strategies to mimize toxicity and off-target effects can be as in WO 2014/093622 (PCT/US2013/074667).

The CRISPR system is derived advantageously from a type II CRISPR system. In some embodiments, one or more elements of a CRISPR system is derived from a particular organism comprising an endogenous CRISPR system, such as *Streptococcus pyogenes*. In preferred embodiments of the invention, the CRISPR system is a type II CRISPR system and the Cas enzyme is Cas9, which catalyzes DNA cleavage. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Cs3, Csf4, homologues thereof, or modified versions thereof.

In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Where the enzyme is not SpCas9, mutations may be made at any or all residues corresponding to positions 10, 762, 840, 854, 863 and/or 986 of SpCas9

(which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. Orthologs of SpCas9 can be used in the practice of the invention. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 (*S. pyogenes* Cas9) or saCas9 (*S. aureus* Cas9). StCas9" refers to wild type Cas9 from *S. thermophilus*, the protein sequence of which is given in the SwissProt database under accession number G3ECR1. Similarly, *S. pyogenes* Cas9 or spCas9 is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, StlCas9 and so forth. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif(PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defence in bacteria and archaea, Mole Cell 2010, January 15; 37(1): 7. The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. A pre-crRNA array consisting of a single spacer flanked by two direct repeats (DRs) is also encompassed by the term "tracr-mate sequences"). In certain embodiments, Cas9 may be constitutively present or inducibly present or conditionally present or administered or delivered. Cas9 optimization may be used to enhance function or to develop new functions, one can generate chimeric Cas9 proteins. And Cas9 may be used as a generic DNA binding protein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Vadous species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available through the server at Kazusa DNA Research Institute, and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 22); the NLS from nucleoplasmin (e.g. the nucleoplasmin bipartite NLS with the sequence KRPAATKKAGQAKKKK (SEQ ID NO: 23)); the c-myc NLS having the amino acid sequence PAAKRVKLD (SEQ ID NO: 24) or RQRRNELKRSP (SEQ ID NO: 25); the hRNPAI M9 NL.S having the sequence NQSSNFGPMKGGNFGGRSSGPYGGGGQYFAKPRNQGGY (SEQ ID NO: 26); the sequence RMRIZFKNKGKDTAELRRRRVEVSVELRKAKKDEQILKRRNV (SEQ ID NO: 27) of the IBB domain from importin-alpha; the sequences VSRKRPRP (SEQ ID NO: 28) and PPKKARED (SEQ ID NO: 29) of the myoma T protein; the sequence P[[O]]QPKKKPL (SEQ ID NO: 30) of human p53; the sequence SALIKKKKKMAP (SEQ ID NO: 31) of mouse c-abl IV; the sequences DRLRR (SEQ ID NO: 32) and PKQKKRK (SEQ ID NO: 33) of the influenza virus NS1; the sequence RKLKKKIKKL (SEQ ID NO: 34) of the Hepatitis virus delta antigen; the sequence REKKKFLKRR (SEQ ID NO: 35) of the mouse Mx1 protein; the sequence KRKGDEVDGVDEVAKKKSKK (SEQ ID NO: 36) of the human poly(ADP-ribose) polymerase; and the sequence RKCLQAGMNLEARKTKK (SEQ ID NO: 37) of the steroid hormone receptors (human) glucocorticoid. In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein. Only sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity. Since Cas9n and Cas9H840A nick opposite strands of DNA, substitution of Cas9n with Cas9H840A with a given sgRNA pair should have resulted in the inversion of the overhang type; but no indel formation is observed as with Cas9H840A indicating that Cas9H840A is a CRISPR enzyme substantially lacking all DNA cleavage activity (which is when the DNA cleavage activity of the mutated enzyme is about no more than 25%, 10%, 5%, 1%, 0.1%, 0.01%, or less of the DNA cleavage activity of the non-mutated form of the enzyme; whereby an example can be when the DNA cleavage activity of the mutated form is nil or negligible as compared with the non-mutated form, e.g., when no indel formation is observed as with Cas9H840A in the eukaryotic system in contrast to the biochemical or prokaryotic systems). Nonetheless, a pair of sgRNAs that will generate a 5' overhang with Cas9n should in principle generate the corresponding 3' overhang instead, and double nicking. Therefore, sgRNA pairs that lead to the generation of a 3' overhang with Cas9n can be used with another mutated Cas9 to generate a 5' overhang, and double nicking. Accordingly, in some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Or, RNA(s) of the CRISPR System can be delivered to a transgenic Cas9 animal or mammal, e.g., an animal or mammal that constitutively or inducibly or conditionally expresses Cas9; or an animal or mammal that is otherwise expressing Cas9 or has cells containing Cas9, such as by way of prior administration thereto of a vector or vectors that code for and express in vivo Cas9. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5 with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter. Delivery vehicles, vectors, particles, nanoparticles, formulations and components thereof for expression of one or more elements of a CRISPR system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence. two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a CRISPR enzyme, such as a Cas protein. CRISPR enzyme or CRISPR enzyme mRNA or CRISPR guide RNA or RNA(s) can be delivered separately; and advantageously at least one of these is delivered via a nanoparticle complex. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA. Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA. Additional administrations of CRISPR enzyme mRNA and/or guide RNA might be useful to achieve the most efficient levels of genome modification.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence. In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell. The break created by the CRISPR complex can be repaired by a repair processes such as the error prone non-homologous end joining (NHEJ) pathway or the high fidelity homology-directed repair (HDR). During these repair process, an exogenous polynucleotide template can be introduced into the genome sequence. In some methods, the HDR process is used modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome. Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function. The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%>, 85%, 90%>, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence. An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have
about 200 bp to about 2000 bp, about 600 bp to about 1000 bp, or more particularly about 700 bp to about 1000 bp. In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996). In a method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template. In other embodiments, this invention provides a method of modifying expression of a polynucleotide in a eukaryotic cell. The method comprises increasing or decreasing expression of a target polynucleotide by using a CRISPR complex that binds to the polynucleotide. In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target
polynucleotide. In fact, these sampling, culturing and re-introduction options apply across the aspects of the present invention. In one aspect, the invention provides for methods of modifying a target polynucleotide in a eukarvotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

Indeed, in any aspect of the invention, the CRISPR complex may comprise a CRISPR enzyme complexed with a guide sequence hybridized to a target sequence, wherein said guide sequence may be linked to a tracr mate sequence which in turn may hybridize to a tracr sequence.

As used herein "diagnosis" or "identifying a patient having" refers to a process of determining if an individual is afflicted with, or has a genetic predisposition to develop, a cardiometabolic disease.

As used herein, a "companion diagnostic" refers to a diagnostic method and or reagent that is used to identify subjects susceptible to treatment with a particular treatment or to monitor treatment and/or to identify an effective dosage for a subject or sub-group or other group of subjects. For purposes herein, a companion diagnostic refers to reagents, such as DNA isolation and sequencing reagents, that are used to detect somatic mutations in a sample. The companion diagnostic refers to the reagents and also to the test(s) that is/are performed with the reagent.

The present invention may be applied to other diseases in addition to cardiometabolic diseases and diseases affiliated with cardiometabolic diseases. In the present application, atherosclerosis is considered a cardiometabolic disease. The methods of the present invention may also be utilized for the diagnosis, prediction and treatment of other cancers in addition to hematological cancer. Other diseases which may be diagnosed, predicted or treated by methods of the present invention include, but are not limited to, autoimmune diseases (such as arthritis), other diseases involving decreased immunity (such as severe infection), dementia (such as Alzheimer's disease), diabetes, hypertension, Progeroid syndromes and other diseases involving in premature aging (such as Alzheimer's disease and Parkinson's disease).

The terms "treat," treating," "treatment," and the like refer to reducing or ameliorating a cardiovascular disease or symptoms associated therewith. It will be appreciated that, although not precluded, treating a cardiovascular disease or the risk of developing a cardiometabolic disease does not require that the disease or the risk be completely eliminated.

In the context of the present invention, a "treatment" is a procedure which alleviates or reduces the negative consequences of a cardiometabolic disease. Many cardiometabolic disease treatments are known in the art, and some are set forth herein. Any treatments or potential treatments can be used in the context of the present invention.

A treatment is not necessarily curative, and may reduce the effect of a cardiovascular disease by a certain percentage over an untreated a cardiovascular disease. The percentage reduction or diminution can be from 10% up to 20, 30, 40, 50, 60, 70, 80, 90, 95, 99 or 100%.

Methods of treatment may be personalized medicine procedures, in which the DNA of an individual is analyzed to provide guidance on the appropriate therapy for that specific individual. The methods of the invention may provide guidance as to whether treatment is necessary, as well as revealing progress of the treatment and guiding the requirement for further treatment of the individual.

As used herein, "inhibiting the development of," "reducing the risk of," "prevent," "preventing," and the like refer to reducing the probability of developing a cardiometabolic disease in a patient who may not have a cardiometabolic disease, but may have a genetic predisposition to developing a cardiometabolic disease. As used herein, "at risk," "susceptible to," or "having a genetic predisposition to," refers to having a propensity to develop a cardiometabolic disease. For example, a patient having a genetic mutation in a gene associated with a cardiometabolic disease has increased risk (e.g., "higher predisposition") of developing the disease relative to a control subject having a "lower predisposition" (e.g., a patient without a genetic mutation in a gene associated with a cardiometabolic disease).

As used herein, "reduces," "reducing," "inhibit," or "inhibiting," may mean a negative alteration of at least 10%, 15%, 25%, 50%, 75%, or 100%.

As used herein, "increases" or "increasing" may mean a positive alteration of at least 10%, 15%, 25%, 50%, 75%, or 100%.

A "therapeutically effective amount" refers to the amount of a compound required to improve, inhibit, or ameliorate a condition of a patient, or a symptom of a disease, in a clinically relevant manner. Any improvement in the patient is considered sufficient to achieve treatment. A sufficient amount of an active compound used to practice the present invention for the treatment of cardiovascular disease varies depending upon the manner of administration, the age, body weight, genotype, and general health of the patient. Ultimately, the prescribers or researchers will decide the appropriate amount and dosage regimen. Such determinations are routine to one of ordinary skill in the art.

From a therapeutic perspective, antihypertensives (such as diuretic medicines, beta-blocking agents, calcium-channel blockers, renin-angiotensin system agents), lipid-modifying medicines, anti-inflammatory agents, nitrates and antiarrhythmic medicines are considered strong candidates for a cardiometabolic disease treatment. Aspects of the invention relate to the administration of antihypertensives (such as diuretic medicines, beta-blocking agents, calcium-channel blockers, renin-angiotensin system agents), lipid-modifying medicines, nitrates and antiarrhythmic medicines separately to individuals in need thereof that may also possess different gene variants associated with a favorable response to each type of administration.

In other embodiments, treatment and/or prevention of cardiometabolic disease may involve aspirin, statins, steroidal or non-steroidal anti-inflammatory drugs, and/or epigenetic modifiers. The epigenetic modifiers may be non-specific DNA synthesis inhibitors, such as DNA methyltransferase inhibitors (such as, but not limited to 5-aza-2'-deoxycytidine or 5-azacytidine) or histone deacetylase inhibitors (such as varinostat, romidepsin, panobinostat, belinostat and entinostat).

Proprotein convertase subtilisin kexin 9 (PCSK9) is a member of the subtilisin serine protease family. PCSK9 is primarily expressed by the liver and is critical for the down regulation of hepatocyte LDL receptor expression. LDL-C levels in plasma are highly elevated in humans with gain of function mutations in PCSK9, classifying them as having severe hypercholesterolemia. When PCSK9 binds to the LDL receptor, the receptor is broken down and can no longer remove LDL cholesterol from the blood. If PCSK9 is blocked, more LDL receptors will be present on the surface of the liver and will remove more LDL cholesterol from the blood. Therefore, PCSK9 is an attractive target for CRISPR. PCS9K-targeted CRISPR may be formulated in a lipid particle and for example administered at about 15, 45, 90, 150, 250 and 400 µg kg intraveneously (see, e.g., Clinical Study Protocol Number ALN-PCSO2-001, *A Phase* 1, *Randomizet*4 *Single-blind Placebo-Controlled, Single Ascending Dose, Safety, Tolerability and Pharmacokinetics Study of ALN-PCS*02 *in Subjects with Elevated LDL-Cholesterol (LDL-C), Alnylam Pharmaceuticals,* 2013.

Bailey et al. (J Mol Med (Berl). 1999 January; 77(1):244-9) discloses insulin delivery by ex-vivo somatic cell gene therapy involves the removal of non-B-cell somatic cells (e.g. fibroblasts) from a diabetic patient, and genetically altering them in vitro to produce and secrete insulin. The cells can be grown in culture and returned to the donor as a source of insulin replacement. Cells modified in this way could be evaluated before implantation, and reserve stocks could be cryopreserved. By using the patient's own cells, the procedure should obviate the need for immunosuppression and overcome the problem of tissue supply, while avoiding a recurrence of cell destruction. Ex-vivo somatic cell gene therapy requires an accessible and robust cell type that is amenable to multiple transfections and subject to controlled proliferation. Special problems associated with the use of non-B-cell somatic cells include the processing of proinsulin to insulin, and the conferment of sensitivity to glucose-stimulated proinsulin biosynthesis and regulated insulin release. Preliminary studies using fibroblasts, pituitary cells, kidney (COS) cells and ovarian (CHO) cells suggest that these challenges could be met, and that ex-vivo somatic cell gene therapy offers a feasible approach to insulin replacement therapy. The system of Bailey et al. may be used/and or adapted to the CRISPR Cas system of the present invention for delivery to the liver.

The methods of Sato et al. (Nature Biotechnology Volume 26 Number 4 Apr. 2008, Pages 431-442) may be applied to the CRISPR Cas system of the present invention for delivery to the liver. Sato et al. found that treatments with the siRNA-bearing vitamin A-coupled liposomes almost completely resolved liver fibrosis and prolonged survival in rats with otherwise lethal dimethylnitrosamine-induced liver cirrhosis in a dose- and duration-dependent manner. Cationic liposomes (Lipotrust) containing 0,0'-ditetradecanoyl-N-(a-trimethylammonioacetyl) diethanolamine chloride (DC-6-14) as a cationic lipid, cholesterol and dioleoylphosphatidylethanolamine at a molar ratio of 4:3:3 (which has shown high transfection efficiency under serumcontaining conditions for in vitro and in vivo gene delivery) were purchased from Hokkaido System Science. The liposomes were manufactured using a freeze-dried empty liposomes method and prepared at a concentration of 1 mM (DC-16-4) by addition of double-distilled water (DDW) to the lyophilized lipid mixture under vortexing before use. To prepare VA-coupled liposomes, 200 nmol of vitamin A (retinol, Sigma) dissolved in DMSO was mixed with the liposome suspensions (100 nmol as DC-16-4) by vortexing in a 1.5 ml tube at 25 1 C. To prepare VA-coupled liposomes carrying siRNAgp46 (VA-lip-siRNAgp46), a solution of siRNAgp46 (580 pmol/ml in DDW) was added to the retinol-coupled liposome solution with stirring at 25 C. The ratio of siRNA to DC-16-4 was 1:11.5 (mol/mol) and the siRNA to liposome ratio (wt/wt) was 1:1. Any free vitamin A or siRNA that was not taken up by liposomes were separated from liposomal preparations using a micropartition system (VIVASPIN 2 concentrator 30,000 MWCO PES, VIVASCIENCE). The liposomal suspension was added to the filters and centrifuged at 1,500 g for 5 min 3 times at 25 1C. Fractions were collected and the material trapped in the filter was reconstituted with PBS to achieve the desired dose for in vitro or in vivo use. Three injections of 0.75 mg/kg siRNA were given every other day to rats. The system of Sato et al. may be used/and or adapted to the CRISPR Cas system of the present invention for delivery to the liver by delivering about 0.5 to 1 mg/kg of CRISPR Cas RNA in the liposomes as described by Sato et al. to humans.

The methods of Rozema et al. (PNAS, Aug. 7, 2007, vol. 104, no. 32) for a vehicle for the delivery of siRNA to hepatocytes both in vitro and in vivo, which Rozema et al. have named siRNA Dynamic PolyConjugates may also be applied to the present invention. Key features of the Dynamic Poly-Conjugate technology include a membrane-active polymer, the ability to reversibly mask the activity of this polymer until it reaches the acidic environment of endosomes, and the ability to target this modified polymer and its siRNA cargo specifically to hepatocytes in vivo after simple, low-pressure i.v. injection. SATA-modified siRNAs are synthesized by reaction of 5' aminemodified siRNA with 1 weight equivalents (wt eq) of Nsuccinimidyl-S-acetylthioacetate (SAT A) reagent (Pierce) and 0.36 wt eq of NaHCC>3 in water at 4° C. for 16 h. The modified siRNAs are then precipitated by the addition of 9 vol of ethanol and incubation at 80° C. for 2 h. The precipitate is resuspended in IX siRNA buffer (Dharmacon) and quantified by measuring absorbance at the 260-nm wavelength. PBAVE (30 mg/ml in 5mMTAPS, pH 9) is modified by addition of 1.5 wt % SMPT (Pierce). After a 1-h incubation, 0.8 mg of SMPT-PBAVE was added to 400 µl of isotonic glucose solution containing 5 mM TAPS (pH 9). To this solution was added 50 µg of SATA-modified siRNA. For the dose-response experiments where [PBAVE] was constant, different amounts of siRNA are added. The mixture is then incubated for 16 h. To the solution is then added 5.6 mg of Hepes free base followed by a mixture of 3.7 mg of CDM-NAG and 1.9 mg of CDM-PEG. The solution is then incubated for at least 1 h at room temperature before injection. CDM-PEG and CDM-NAG are synthesized from the acid chloride generated by using oxalyl chloride. To the acid chloride is added 1.1 molar equivalents polyethylene glycol monomethyl ether (molecular weight average of 450) to generate CDM-PEG or (aminoethoxy)ethoxy-2-(acetylamino)-2-deoxy-P-D-glucopyranoside to generate CDM-NAG. The final product is purified by using reverse-phase HPLC with a 0.1% TFA water/acetonitrile gradient. About 25 to 50 µg of siRNA was delivered to mice. The system of Rozema et al. may be applied to the CRISPR Cas system of the present invention for delivery to the liver, for example by envisioning a dosage of about 50 to about 200 mg of CRISPR Cas for delivery to a human.

In an aspect the invention provides methods, regents and companion diagnostics for identifying and treating subjects at risk for, or having a PCSK9 mediated disorder. The invention can be used to select therapeutic compositions and dosages, to predict and monitor responses and outcomes. Subjects may be treated to prevent, delay the onset of, or ameliorate the PCSK9 mediated disorder by promoting or inhibiting PCSK9 activity.

PCSK9 inhibitors can be used to treat patients with familial hypercholesterolemia (FH), clinical atherosclerotic cardiovascular disease (CVD), and other disorders requiring lowering of LDL cholesterol (LDL-C). PCSK9 inhibitors include evolocumab (Repatha™), Praulent, and Alnylam. Evolocumab is a human monoclonal IgG2 antibody which binds to PCSK9 and inhibits circulating PCSK9 from binding to the low density lipoprotein (LDL) receptor (LDLR), preventing PCSK9-mediated LDLR degradation and permitting LDLR to recycle back to the liver cell surface. By inhibiting the binding of PCSK9 to LDLR, evolocumab increases the number of LDLRs available to clear LDL from the blood, thereby lowering LDL-C levels.

Evolocumab can be administered alone or in combination with other agents. Evolocumab is used as an adjunct to diet and maximally tolerated statin therapy.

The liver X receptor (LXR) is a member of the nuclear receptor family of transcription factors and is related to nuclear receptors such as the PPARs, FXR and RXR. Liver X receptors (LXRs) are nuclear receptors involved in regulation of lipid metabolism, cholesterol homeostasis, and inflammatory responses in the central nervous system. Two isoforms of LXR have been identified and are referred to as LXRa and LXRp. LXRa expression is restricted to liver, kidney, intestine, fat tissue, macrophages, lung, and spleen and is highest in liver, whereas LXRP is expressed in almost all tissues and organs. Defects contribute to the pathogenesis of neurodegenerative diseases such as Alzheimer's disease, Parkinson's disease, multiple sclerosis, and Huntington's disease.

In an aspect the invention provides methods, regents and companion diagnostics for identifying and treating subjects at risk for, or having an LXR mediated disorder. Subjects are identified and can be treated to prevent, delay the onset of, or ameliorate the LXR mediated disorder by activating or inhibiting LXR activity. LXR agonists (e.g., hypocholamide, T0901317, GW3965, or N,N-dimethyl-3beta-hydroxy-cholenamide (DMHCA)) are useful to reduce the cholesterol level in serum and liver and inhibits the development of atherosclerosis in murine disease models. Certain LXR agonists (e.g. GW3965) improve glucose tolerance in a model of diet-induced obesity and insulin resistance by regulating genes involved in glucose metabolism in liver and adipose tissue.

Peroxisome proliferator-activated receptors (PPARs) are a group of nuclear receptor proteins that function as transcription factors regulating the expression of genes and play essential roles in the regulation of cellular differentiation, development, and metabolism. There are three main forms: PPARa; PPARβ/δ, and PPARy. The PPARy1 isoform is expressed in the spleen, intestine, and white adipose tissue, the PPARy2 is preferentially expressed in white and brown fat, and PPARy2 is most abundantly in fat cells, and plays a pivotal role in fat cell differentiation and lipid storage. Hereditary disorders of all PPARs have been described, leading to, for example, lipodystrophy, and insulin resistance.

In an aspect, the invention provides methods, reagents and diagnostics for identifying, monitoring, and treating inherited disorders. In certain embodiments, the disorders may have single genetic components. Advantageously, the invention is useful for complex multifactorial disorders that do not have a single genetic cause, such as, but not limited to, heart disease, diabetes, and obesity. Thus, multiple gene loci can be evaluated and treatments designed or adjusted accordingly. Accordingly, a subject's disease or disorder can be diagnosed as to relative contributions of variations in multiple genes. Accordingly, patient-specific treatments cam be selected involving multiple drugs in specific combinations and/or dosages. For example, depending on the presence of gene variants at genetic loci that determine propensity to develop a metabolic disease, patient-specific combinations and dosages of drugs to treat diabetes can be selected. According to the invention, in one embodiment, a patient suffering from a particular disease is diagnosed to determine the presence or absence of genetic variants associated with a disease or condition, and a treatment regime assigned accordingly. In particular, treatments that are likely to be effective or to which a subject is likely to be most sensitive are selected. In another embodiment, treatments which are predicted to result in unwanted patient-specific side effects are avoided.

Advantageously, the invention provides methods, reagents and diagnostics for identifying, monitoring, and treating diseases or disorders that arise spontaneously or develop over time. In certain embodiments, such disorders are clonal. By clonal it is meant that there is an aspect to the disease that results from appearance or enlargement (or disappearance) of a population of cells. One non-limiting example is a clonal population of cells that arises through a spontaneous mutation. Another non-limiting example is a clonal population of cells that arises from an external stimulation. For example, an autoimmune disorder may arise or be exacerbated by expansion or activation of a population of immune cells. Yet another example is loss of a highly diverse population of cells leaving a population arising from a small number of clones. For example, it has been observed that clonal diversity of immune cells capable of mounting an immune response diminishes with age. In certain embodiments, there is activation or inhibition of expression of one or more genes that develops over time. For example, expression levels can be monitored by measuring transcription or evaluating DNA methylation.

In an embodiment of the invention, a cholesterol level is monitored and a treatment to reduce cholesterol is initiated. One or more of DNMT3A, TET2, ASXLI, TP53, JAK2 and SF3B1 is tested for sequence and a cholesterol medication is selected accordingly, taking into account the alleles of DNMT3A, TET2, ASXLI, TP53, JAK2 and SF3B1 present in the subject and their correlation with effectiveness of treatment and minimization of undesired side effects such as liver function and muscle pain.

Provided herein are sensitive and specific methods to detect and closely monitor somatic mutations associated with disease, particularly a cardiometabolic disease and a hematological cancer. The companion diagnostic methods provided herein are based on the finding that clonal hematopoiesis due to somatic mutation is a common finding in the elderly, and most frequently involves DNMT3A, TET2, and ASXLI. This clinical entity, CHIP, is associated with increased risk of developing hematological malignancy, minimal changes in blood counts, increased overall mortality, and increased risk of cardiometabolic disease. In addition, the companion diagnostic method provided herein also is based on the finding that detecting mutations in DNMT3A, TET2, ASXLI, TP 53, JAK2 and SF3B1 specifically provides superior prognostic and treatment selection information as compared to other markers involved in cardiometabolic disease and a hematological cancer. In exemplary methods provided herein, the diagnostic and prognostic methods are companion methods to therapy with any treatment described herein.

In one embodiment, the companion diagnostic is used to monitor clonality of somatic mutations in a patient. In another embodiment, clonality is determined. Not being bound by a theory, the size of a clone harboring a somatic mutation, as described herein, can be used to monitor the effectiveness of a treatment.

In one embodiment, a patient is treated with a cholesterol lowering drug if a mutation in TET2, DNMT3A, and/or JAK2 is observed. Not being bound by a theory, TET2, DNMT3A, and/or JAK2 mutations result in a deficit of reverse cholesterol transport in macrophages and treatment with a cholesterol lowering drug described herein can ameliorate this deficit. In another embodiment, a patient is treated with an anti-inflammatory drug described herein, if a mutation in TET2, DNMT3A, and/or JAK2 is observed. Not being bound by a theory, TET2, DNMT3A, and/or JAK2 mutations result in a protracted inflammatory phenotype in macrophages and treatment with an anti-inflammatory drug described herein can ameliorate this phenotype.

The present invention also relates to identifying molecules, advantageously small molecules or biologies, that may be involved in inhibiting one or more of the mutations in one or more genes selected from the group consisting of DNMT3A, TET2, ASXLI, TP53, JAK2 and SF3B1. The invention contemplates screening libraries of small molecules or biologies to identify compounds involved in suppressing or inhibiting expression of somatic mutations or alter the cells phenotypically so that the cells with mutations behave more normally in one or more OfONMT3A, TET2, ASXLI, TP53, JAK2 and SF3B1.

High-throughput screening (HTS) is contemplated for identifying small molecules or biologies involved in suppressing or inhibiting expression of somatic mutations in one or more of DNMT3A, TET2, ASXLI, TP53, JAK2 and SF3B1. The flexibility of the process has allowed numerous and disparate areas of biology to engage with an equally diverse palate of chemistry (see, e.g., Inglese et al, Nature Chemical Biology 3, 438-441 (2007)). Diverse sets of chemical libraries, containing more than 200,000 unique small molecules, as well as natural product libraries, can be screened. This includes, for example, the Prestwick library (1,120 chemicals) of off-patent compounds selected for structural diversity, collective coverage of multiple therapeutic areas, and known safety and bioavailability in humans, as well as the NINDS Custom Collection 2 consisting of a 1,040 compound-library of mostly FDA-approved drugs (see, e.g., U.S. Pat. No. 8,557,746) are also contemplated.

The NIH's Molecular Libraries Probe Production Centers Network (MLPC) offers access to thousands of small molecules—chemical compounds that can be used as tools to probe basic biology and advance our understanding of disease. Small molecules can help researchers understand the intricacies of a biological pathway or be starting points for novel therapeutics. The Broad Institute's Probe Development Center (BIPDeC) is part of the MLPCN and offers access to a growing library of over 330,000 compounds for large scale screening and medicinal chemistry. Any of these compounds may be utilized for screening compounds involved in suppressing or inhibiting expression of somatic mutations in one or more of DNMT3A, TET2, ASXL1, TP53, JAK2 and SF3B1.

The phrase "therapeutically effective amount" as used herein refers to a nontoxic but sufficient amount of a drug, agent, or compound to provide a desired therapeutic effect.

As used herein "patient" refers to any human being receiving or who may receive medical treatment.

A "polymorphic site" refers to a polynucleotide that differs from another polynucleotide by one or more single nucleotide changes.

A "somatic mutation" refers to a change in the genetic structure that is not inherited from a parent, and also not passed to offspring.

Therapy or treatment according to the invention may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of the a cardiovascular disease, and how the patient responds to the treatment. Additionally, a person having a greater risk of developing a cardiovascular disease (e.g., a person who is genetically predisposed) may receive prophylactic treatment to inhibit or delay symptoms of the disease.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a cardiovascular disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for oral, rectal, intravenous, intramuscular, subcutaneous, inhalation, nasal, topical or transdermal, vaginal, or ophthalmic administration. Thus, the medicament may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, or aerosols.

In order to determine the genotype of a patient according to the methods of the present invention, it may be necessary to obtain a sample of genomic DNA from that patient. That sample of genomic DNA may be obtained from a sample of tissue or cells taken from that patient.

The tissue sample may comprise but is not limited to hair (including roots), skin, buccal swabs, blood, or saliva. The tissue sample may be marked with an identifying number or other indicia that relates the sample to the individual patient from which the sample was taken. The identity of the sample advantageously remains constant throughout the methods of the invention thereby guaranteeing the integrity and continuity of the sample during extraction and analysis. Alternatively, the indicia may be changed in a regular fashion that ensures that the data, and any other associated data, can be related back to the patient from whom the data was obtained. The amount/size of sample required is known to those skilled in the art.

Generally, the tissue sample may be placed in a container that is labeled using a numbering system bearing a code corresponding to the patient. Accordingly, the genotype of a particular patient is easily traceable.

In one embodiment of the invention, a sampling device and/or container may be supplied to the physician. The sampling device advantageously takes a consistent and reproducible sample from individual patients while simultaneously avoiding any cross-contamination of tissue. Accordingly, the size and volume of sample tissues derived from individual patients would be consistent.

According to the present invention, a sample of DNA is obtained from the tissue sample of the patient of interest. Whatever source of cells or tissue is used, a sufficient amount of cells must be obtained to provide a sufficient amount of DNA for analysis. This amount will be known or readily determinable by those skilled in the art.

DNA is isolated from the tissue/cells by techniques known to those skilled in the art (see, e.g., U.S. Pat. Nos. 6,548,256 and 5,989,431, Hirota et al, Jinrui Idengaku Zasshi. September 1989; 34(3):217-23 and John et al, Nucleic Acids Res. Jan. 25, 1991; 19(2):408; the disclosures of which are incorporated by reference in their entireties).

For example, high molecular weight DNA may be purified from cells or tissue using proteinase K extraction and ethanol precipitation. DNA may be extracted from a patient specimen using any other suitable methods known in the art.

It is an object of the present invention to determine the genotype of a given patient of interest by analyzing the DNA from the patent, in order to identify a patient carrying specific somatic mutations of the invention that are associated with developing a cardiovascular disease. In particular, the kit may have primers or other DNA markers for identifying particular mutations such as, but not limited to, one or more genes selected from the group consisting of DNMT3A, TET2, ASXL1, TP53, JAK2 and SF3B1.

There are many methods known in the art for determining the genotype of a patient and for identifying or analyzing whether a given DNA sample contains a particular somatic mutation. Any method for determining genotype can be used for determining genotypes in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, nucleic acid hybridization, polymerase chain reaction (PCR), RFLP analysis and size chromatography (e.g., capillary or gel chromatography), all of which are well known to one of skill in the art.

The methods of the present invention, such as whole exome sequencing and targeted amplicon sequencing, have commercial applications in diagnostic kits for the detection of the somatic mutations in patients. A test kit according to the invention may comprise any of the materials necessary for whole exome sequencing and targeted amplicon sequencing, for example, according to the invention. In a particular advantageous embodiment, a companion diagnostic for the present invention may comprise testing for any of the genes in disclosed herein. The kit further comprises additional means, such as reagents, for detecting or measuring the sequences of the present invention, and also ideally a positive and negative control.

The present invention further encompasses probes according to the present invention that are immobilized on a solid or flexible support, such as paper, nylon or other type of membrane, filter, chip, glass slide, microchips, microbeads, or any other such matrix, all of which are within the scope of this invention. The probe of this form is now called a "DNA chip". These DNA chips can be used for analyzing the somatic mutations of the present invention. The present invention further encompasses arrays or microarrays of nucleic acid molecules that are based on one or more of the sequences described herein. As used herein "arrays" or "microarrays" refers to an array of distinct polynucleotides or oligonucleotides synthesized on a solid or flexible support, such as paper, nylon or other type of membrane, filter, chip, glass slide, or any other suitable solid support. In one embodiment, the microarray is prepared and used according to the methods and devices described in U.S. Pat. Nos. 5,446,603; 5,545,531; 5,807,522; 5,837,832; 5,874,219, 6,114,122; 6,238,910; 6,365,418; 6,410,229; 6,420,114; 6,432,696; 6,475,808 and 6,489.159 and PCT Publication No. WO 01/45843 A2, the disclosures of which are incorporated by reference in their entireties.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988:85: 2444-2448.

Advantageous for use according to the present invention is the WU-BLAST (Washington University BLAST) version 2.0 software. WU-BLAST version 2.0 executable programs for several UNIX platforms can be downloaded from the FTP site for Blast at the Washington University in St. Louis website. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein)

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as $(N_{ref}\text{-}Ndi_f)*100/\text{-}N_{ref}$, wherein $Ndi_f$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC (N $N_{ref}$=8; N $Ndi_f$=2). "Homology" or "identity" can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, Proc Natl Acad Sci USA 1983; 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics.™. Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences. Without undue experimentation, the skilled artisan can consult with many other programs or references for determining percent homology.

The invention further encompasses kits useful for screening nucleic acids isolated from one or more patients for any of the somatic mutations described herein and instructions for using the oligonucleotide to detect variation in the nucleotide corresponding to one or more of the somatic mutations, such as but not limited to, one or more genes selected from the group consisting of DNMT3A, TET2, ASXL1, TP53, JAK2 and SF3B1, of the isolated nucleic acid.

Another aspect of the invention is a method of screening patients to determine those patients more likely to develop a cardiovascular disease comprising the steps of obtaining a sample of genetic material from a patient; and assaying for the presence of a genotype in the patient which is associated with developing cardiovascular diseases, any of the herein disclosed somatic mutations.

In other embodiments of this invention, the step of assaying is selected from the group consisting of: restriction fragment length polymorphism (RFLP) analysis, minisequencing, MALD-TOF, SINE, heteroduplex analysis, single strand conformational polymorphism (SSCP), denaturing gradient gel electrophoresis (DGGE) and temperature gradient gel electrophoresis (TGGE).

The present invention also encompasses a transgenic mouse which may express one or more of the herein disclosed somatic mutations. Methods for making a transgenic mouse are well known to one of skill in the art, see e.g., U.S. Pat. Nos. 7,709,695; 7,667,090; 7,655,700; 7,626,076; 7,566,812; 7,544,855; 7,538,258; 7,495,147; 7,479,579; 7,449,615; 7,432,414; 7,393,994; 7,371,920; 7,358,416; 7,276,644; 7,265,259; 7,220,892; 7,214,850; 7,186,882; 7,119,249; 7,1 12,715; 7,098,376; 7,045,678; 7,038,105; 6,750,375; 6,717,031; 6,710,226; 6,689,937; 6,657,104; 6,649,811; 6,613,958; 6,610,905; 6,593,512; 6,576,812; 6,531,645; 6,515,197; 6,452,065; 6,372,958; 6,372,957; 6,369,295; 6,323,391; 6,323,390; 6,316,693; 6,313,373; 6,300,540; 6,255,555; 6,245,963; 6,215,040; 6,211,428; 6,201,166; 6,187,992; 6,184,435; 6,175,057; 6,156,727; 6,137,029; 6,127,598; 6,037,521; 6,025,539; 6,002,067; 5,981,829; 5,936,138; 5,917,124; 5,907,078; 5,894,078; 5,850,004; 5,850,001; 5,847,257; 5,837,875; 5,824,840; 5,824,838; 5,814,716; 5,811,633; 5,723,719; 5,720,936; 5,688,692; 5,631,407; 5,620,881; 5,574,206 and 5,569,827. The transgenic mouse may be utilized to mimic cardiovascular disease conditions and may be useful to test novel treatments of cardiovascular disease in a mouse model.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Methods

Sample ascertainment. Subjects were ascertained from 22 population-based cohorts in 3 consortia (see Supplementary Table SI). These studies were performed using protocols approved by the ethics committees of all involved institutions, as well as with informed consent from all participants. Samples with missing age (116 subjects) or cell lines as the source of DNA (492 subjects) were excluded.

Whole Exome Sequencing and Targeted Amplicon Sequencing. DNA was obtained from individual cohorts and further processed at the Broad Institute of MIT and Harvard. Briefly, genomic DNA was subject to hybrid capture, sequencing, and alignment using the Broad Genomics Platform and Picard pipeline. BAM files were analyzed for SNVs using MuTect with OxoG filtering and indels using Indelocator (Cibulskis K et al. Nature biotechnology 2013; 31:213-9, Costello M et al. Nucleic acids research 2013; 41:e67). A clinically validated, targeted amplicon assay was used for sequencing of 95 genes in select samples.

Variant Calling

Applicants defined a list of pathogenic variants reported in the literature and/or the Catalog of Somatic Mutations In Cancer (COSMIC; hosted by the Wellcome Sanger Institute (WSI)) in human hematologic malignancies from 160 genes (see Lawrence, M S, et al. Nature 2014; 505:495-501, Supplementary Table S3). As a negative control, Applicants also searched for variants that were recurrently seen in non-hematologic malignancies (see Lawrence, M S, et al. Nature 2014; 505:495-501, Supplementary Table S5).

Statistics

All statistical analysis was performed using "R", a free software environment for statistical computing provided on the internet by the R Foundation.

Example 2: Results

Identification of candidate somatic mutations. To investigate the extent of clonal hematopoiesis with somatic mutation, Applicants analyzed whole exome sequencing data from peripheral blood cell DNA of 17,182 individuals who were selected without regard to hematological characteristics. Of these, 15,801 were cases and controls ascertained from 22 cohorts for type 2 diabetes (T2D) association studies, and the remaining 1,381 were additional, previously un-sequenced individuals from the Jackson Heart Study, a population-based cohort (Supplementary Table S1). The median age of individuals was 58 (range 19-108), 8,741 were women, and 7,860 had T2D.

The identification of somatic driver mutations in cancer has come largely from studies that have compared differences in DNA sequence between tumor and normal tissue from the same individual. Once mutations are identified, investigators may genotype samples for these somatic variants without relying on a matched normal tissue. Because Applicants had DNA from only one source (blood), Applicants limited Applicants' examination to variants previously described in the literature for 160 recurrently mutated candidate genes in myeloid and lymphoid malignancies (Supplementary Table S2). Potential false-positives were removed by utilizing variant-calling algorithms with filters for known artifacts such as strand-bias and clustered reads, as well as additional filtering for rare error modes using a panel of normal (Cibulskis K et al. Nature biotechnology 2013; 31:213-9). The lower limit of detection for variants depended on the depth of coverage. The median average sequencing depth over exons from the 160 genes was 84X, and ranged from 13 to 144. At a sequencing depth of 84X, the limit of detection for SNVs was at a variant allele fraction (VAF) of 0.035; for indels, the limit was 0.07.

Figure 14:
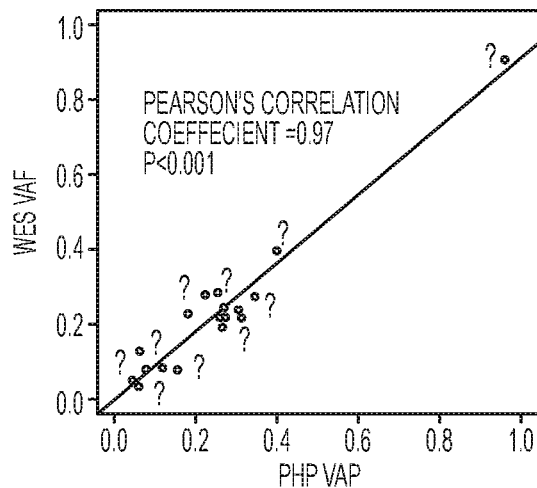
FIG. 14. Mutation validation and serial samples. A) Eighteen variants were validated using targeted, amplicon based re-sequencing ("Rapid Heme Panel", see Methods). Comparison of VAF between the two methods is shown for the 18 variants. WES, whole exome sequencing. RHP, Rapid Heme Panel. B) Peripheral blood DNA from 4 to 8 years after the initial DNA collection was available for 13 subjects in JHS who had detectable mutations on exome sequencing. As described in the Supplementary Methods, amplicon-based targeted re-sequencing was performed for a panel of 95 genes. Graphs represent individual subjects, with mutation variant allele frequency (VAF) from the initial and later time points shown. All of the initial mutations detected on exome sequencing were still present in the later sample, and 2 subjects had acquired new mutations.
Figure 14:
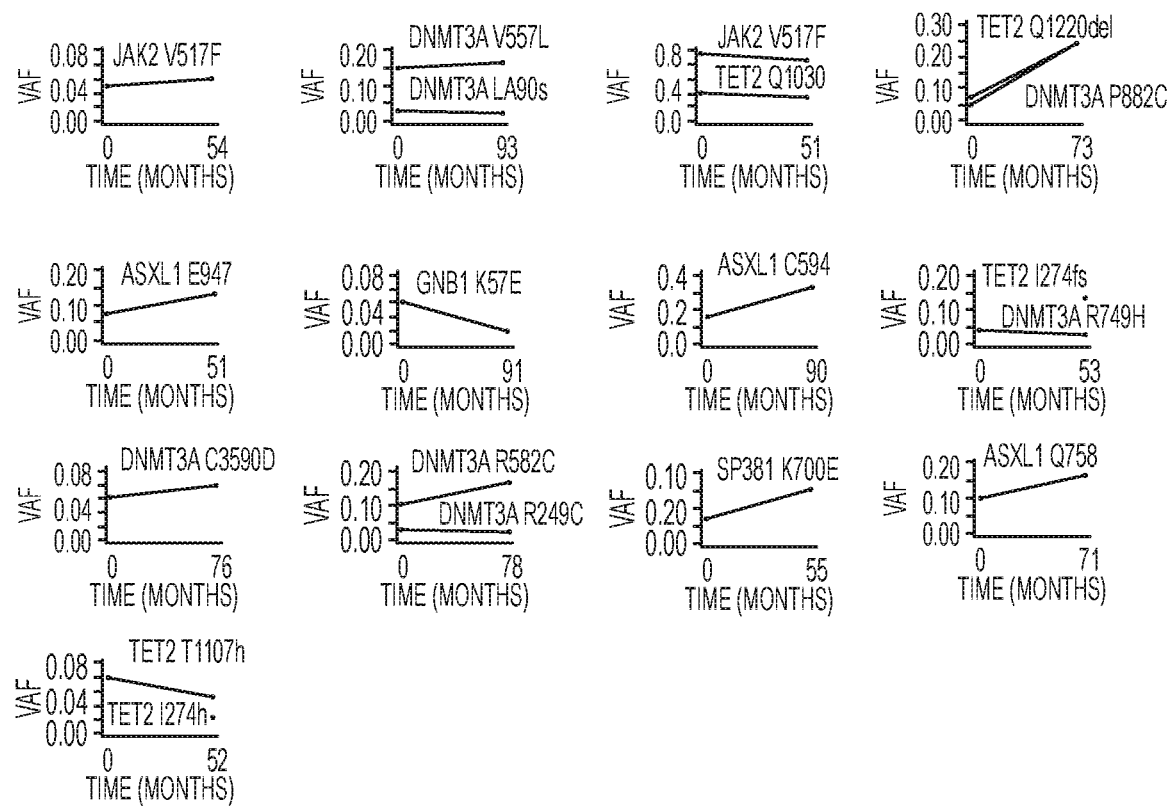

With this approach, Applicants identified a total of 805 candidate somatic variants (hereafter referred to as mutations) from 746 individuals in 73 genes (Supplementary Table S3 (Supplementary Table S3 discloses SEQ ID NOS 38, 33, 39, 39-46, respectively, in order of appearance)). As a negative control, Applicants searched for previously described, cancer-associated variants in 40 non-hematologic genes (Supplementary Table S4) (Lawrence M S et al. Nature 2014; 505:495-501) and found only 10 such variants in these genes. Below, Applicants show that the frequency of apparent mutations is exceedingly low in young people, and rises with age. These internal controls indicate that the rate of false discovery due to technical artifacts is low. Applicants also verified a subset of the variants using amplicon-based, targeted sequencing; 18/18 variants were confirmed with a correlation coefficient of 0.97 for the VAF between the two methods (FIG. 14A).

The frequency of clonal somatic mutation increases with age. Hematological malignancies, as well as other cancers and pre-malignant states, increase in frequency with age. Mutations were very rare in samples collected before the age of 40, but rose in frequency with each decade of life thereafter (FIG. 1). Mutations in genes implicated in hematological malignancies were found in 5.6% (95% CI 5.0-6.3%) of individuals age 60-69, 9.5% (95% Cl 8.4-10.8%) of individuals age 70-79, 11.7% (95% Cl 8.6-15.7%) of individuals age 80-89, and 18.4% (95% CI 12.1-27.0%) of individuals older than 90. These rates greatly exceed the incidence of clinically diagnosed hematologic malignancy in the general population (Surveillance, Epidemiology, and End Results (SEER) Program Populations (1969-2012), National Cancer Institute, DCCPS, Surveillance Research Program, Surveillance Systems Branch. 2014).

Figure 6:
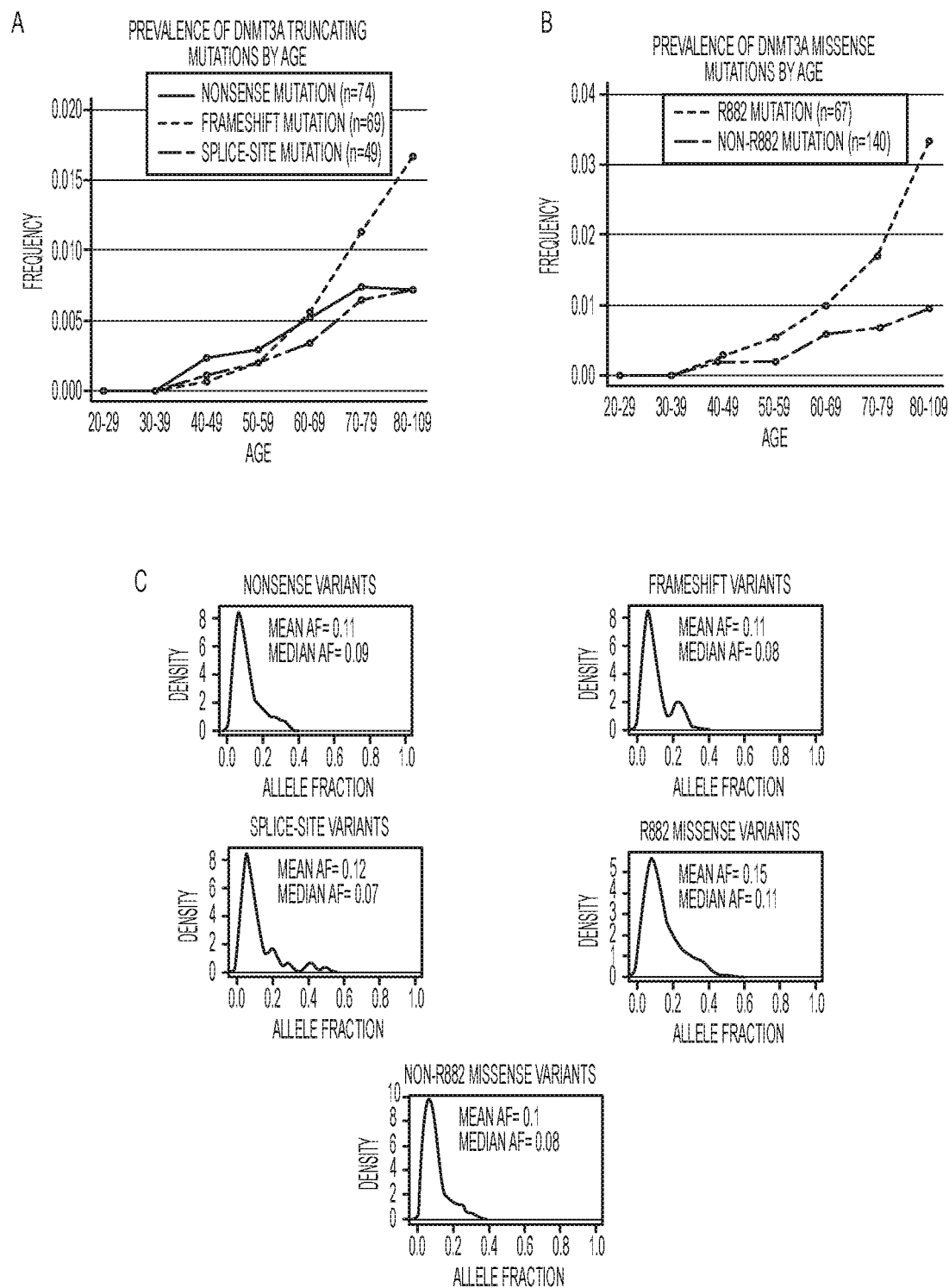
FIG. 6. Characteristics of DNMT3A variants. A) Frequency of DNMT3A nonsense, frameshift, and splice-site variants called as somatic by age group. B) Frequency of R882 and non-R882 missense variants called as somatic by age group. C) Allele fraction of called DNMT3A variants by mutation type.

Though Applicants searched for mutations in genes implicated in multiple hematologic malignancies, Applicants primarily identified genes that were most frequently mutated in acute myeloid leukemia (AML) and myelodysplasia syndrome (MDS). The most commonly mutated gene was DNMT3A (403 variants, FIG. 2A, FIG. 6), followed by TET2 (72 variants) and ASXL1 (62 variants). Of note, only exon 3 of TET2 was baited by exon capture (corresponding to ~50% of the coding region), and the portion of exon 12 of ASXL1 that accounts for ~50%> of the mutations in this gene had poor coverage depth. Thus, mutations in TET2 and ASXL1 are likely underrepresented in this study. Other frequently mutated genes included TP53 (33 variants), JAK2 (31 variants), and SF3B1 (27 variants).

Figure 2:
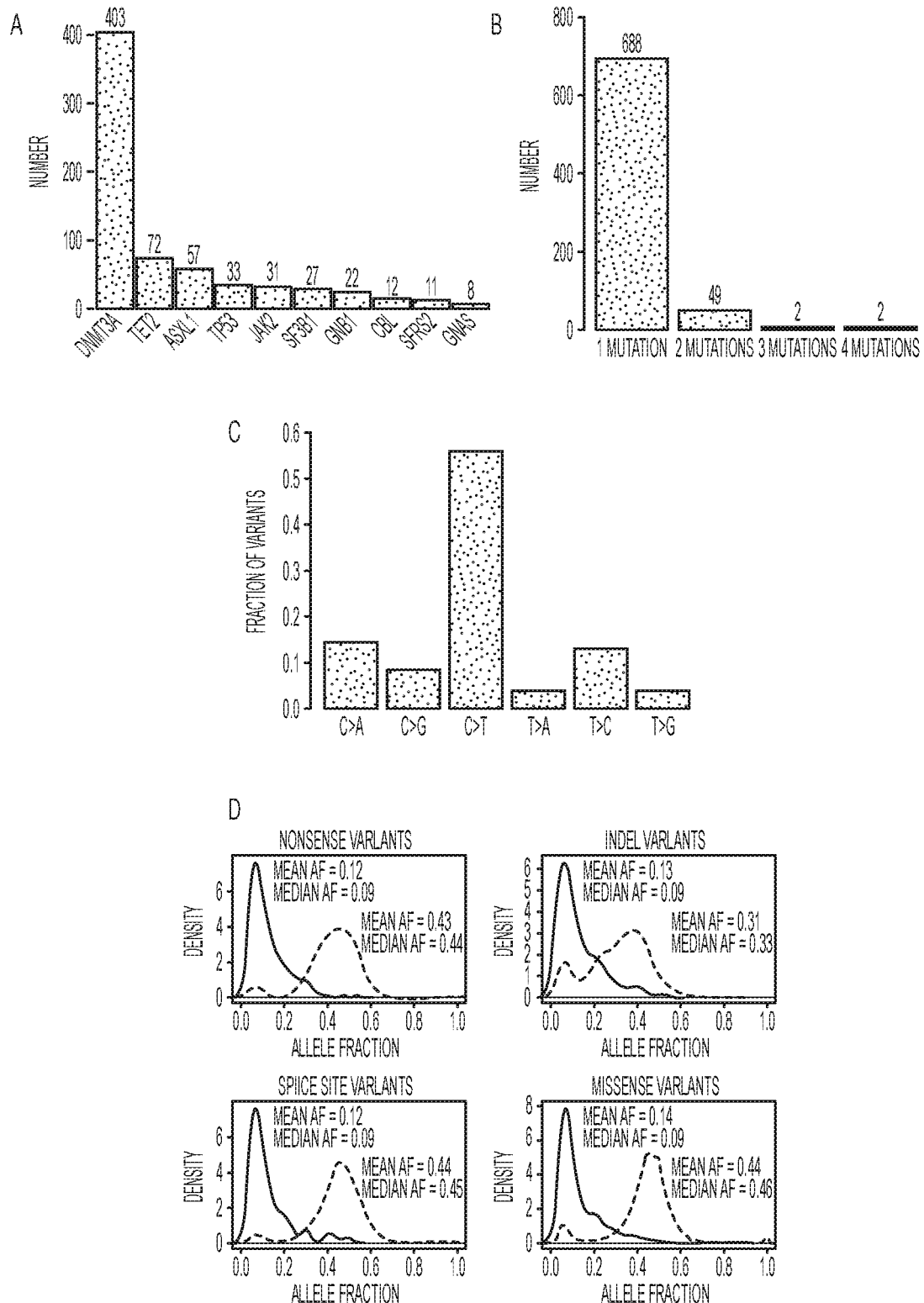
FIG. 2. Characteristics of called somatic variants. A) Ten most frequently mutated genes. B) Number of subjects with 1, 2, 3, or 4 called variants. C) Percentages of type of single nucleotide base pair changes seen in the called variants. D) Allele fractions of called somatic variants. Allele fraction defined as variant reads divided by variant plus reference reads. For variants on the X chromosome in men this number was divided by 2.
Figure 7:
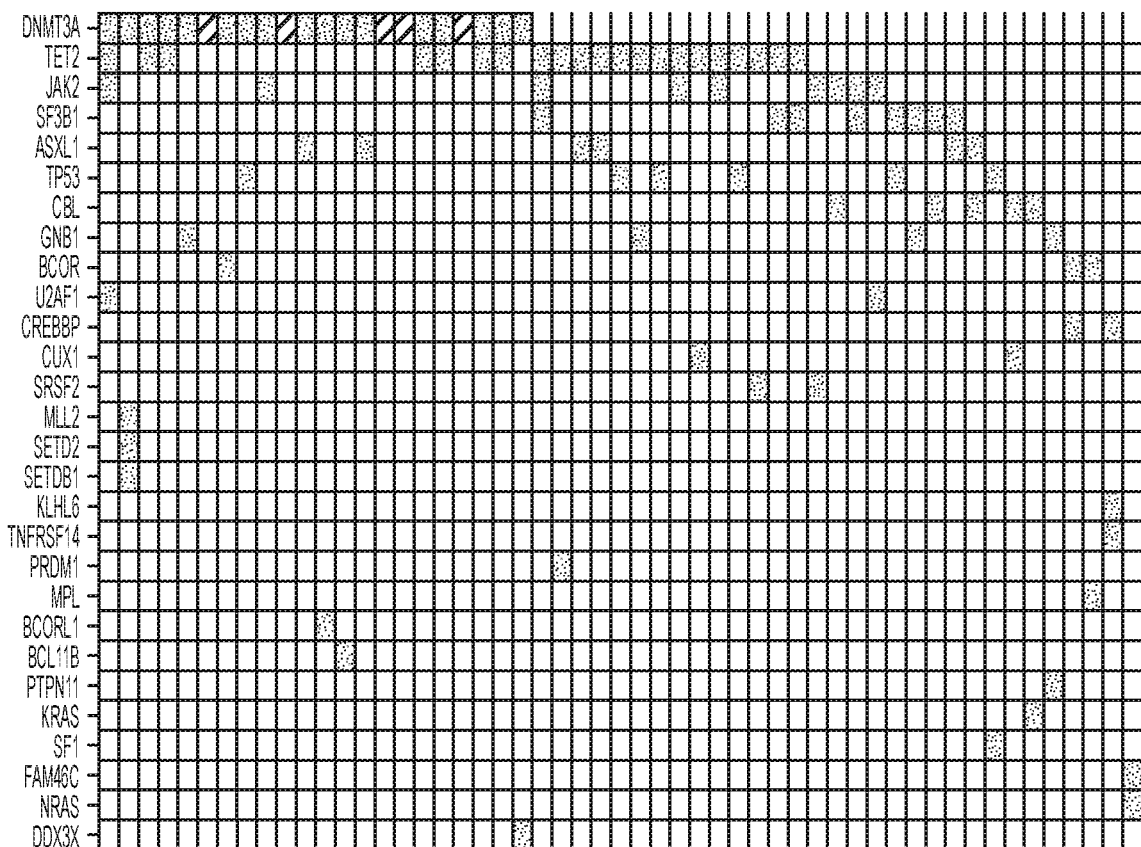
FIG. 7. Co-mutations A) Co-mutation plot, individuals are represented by columns. Black rectangles represent mutated genes, red rectangles represent 2 separate mutations in the same gene. B) Correlation plot for variant allele fraction (VAF) from the 49 subjects with 2 mutations.
Figure 7:
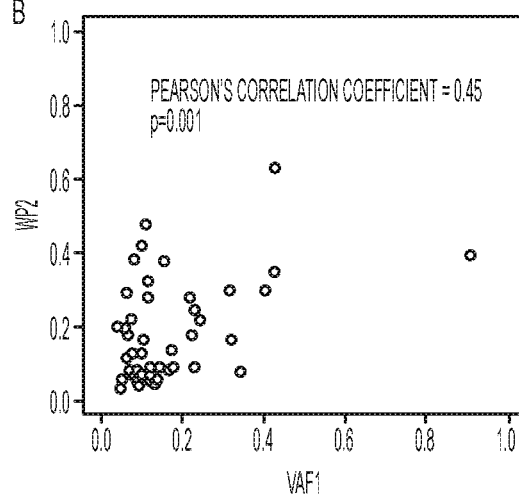

In sequencing studies of MDS and AML, most patients have mutations in 2 or more driver genes (the median number of recurrently mutated genes in de novo AML patients is five (Cancer Genome Atlas Research N. Genomic and epigenomic landscapes of adult de novo acute myeloid leukemia. The New England journal of medicine 2013; 368:2059-74)). In this study. Applicants found that 693 of 746 individuals with a detectable mutation had only 1 mutation in the set of genes Applicants examined, consistent with the hypothesis that these subjects had pre-malignant clones harboring only the initiating lesion (FIG. 2B, FIG. 7A-B).

The most common base pair change in the somatic variants was cytosine to thymine (C-T) transition (FIG. 2C), which is considered to be a somatic mutational signature of aging (Welch J S et al. Cell 2012; 150:264-78, Alexandrov L B et al. Nature 2013; 500:415-21). The median VAF for the identified mutations was 0.09, (FIG. 2D), suggesting that they are present in only a subset of blood cells, and supports their somatic, rather than germline, origin.

Somatic mutations persist over time. Blood cell DNA obtained 4 to 8 years after the initial DNA collection was available for targeted sequencing in 13 subjects with 17 somatic mutations (4 subjects had 2 mutations). In all cases, the mutations detected at the earlier time point were still present at the later time point. For 10 mutations, the VAF stayed the same or slightly decreased, and for 7 mutations, the VAF clearly increased. New mutations were detected in 2 subjects, but no subjects were diagnosed with hematological malignancies (FIG. 14B).

Figure 9:
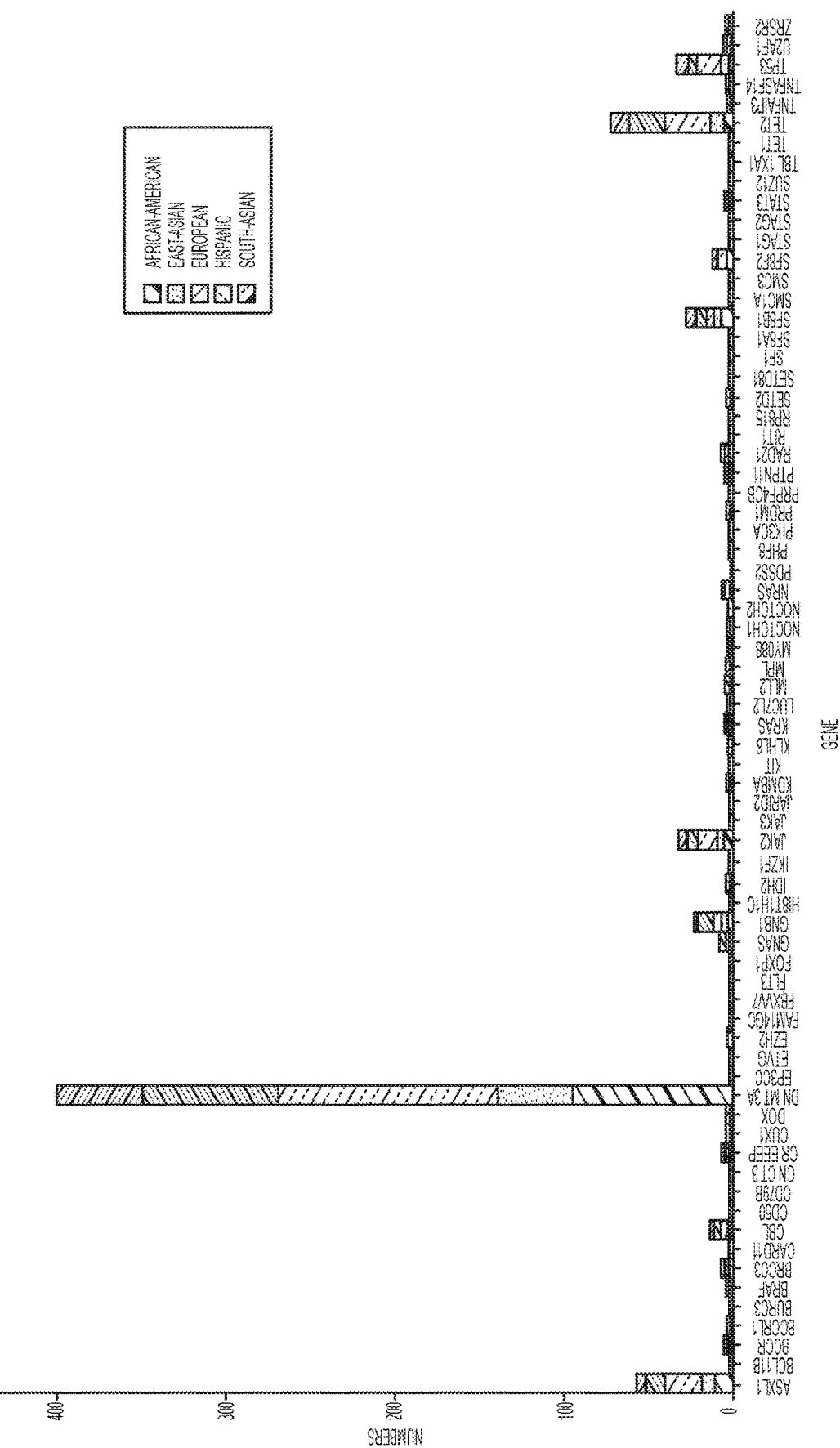
FIG. 9. Mutations by ethnic backgroundNumber of mutations for each gene stratified by ethnic background.

Risk factors associated with somatic mutation. To understand risk factors that contributed to having a detectable mutation, Applicants performed a multivariable logistic regression that included age, sex, T2D status, and ancestry as covariates (Supplementary Tables S6-7 and FIG. 8). As expected, age was the largest contributor to risk of having a mutation. MDS is characterized by a slight male preponderance. In those age 60 or older, men had an increased likelihood of having a detectable mutation compared to women (OR 1.3, 95% CI 1.1-1.5, p=0.005 by logistic regression). Hispanics and Native Americans are reported to have significantly lower incidence of MDS than other groups in the United States (Rollison D E et al. Blood 2008; 112:45-52). Applicants found that Hispanics had a lower risk of having a mutation relative to those of European ancestry, whereas other groups were not significantly different (Supplementary Table S6 and FIG. 8). Of the genes Applicants queried, the spectrum of mutations did not differ between ancestry groups (FIG. 9).

Association of somatic mutation with risk of hematologic malignancy. Pre-malignant states such as MGUS, MBL, and others are associated with an increased risk of subsequently developing a malignancy. Of the cohorts that contributed data to the study, two had longitudinal follow-up information on cancer that arose subsequent to DNA collection (JHS and MEC). Together, these comprised 3,342 subjects, including 134 (4%) in whom Applicants detected somatic mutations in the blood. In a median follow-up period of 95 months, 16 hematological malignancies were reported, of which 5 (31%) were in the group that had detectable mutations (Supplementary Table S11).

Figure 3:
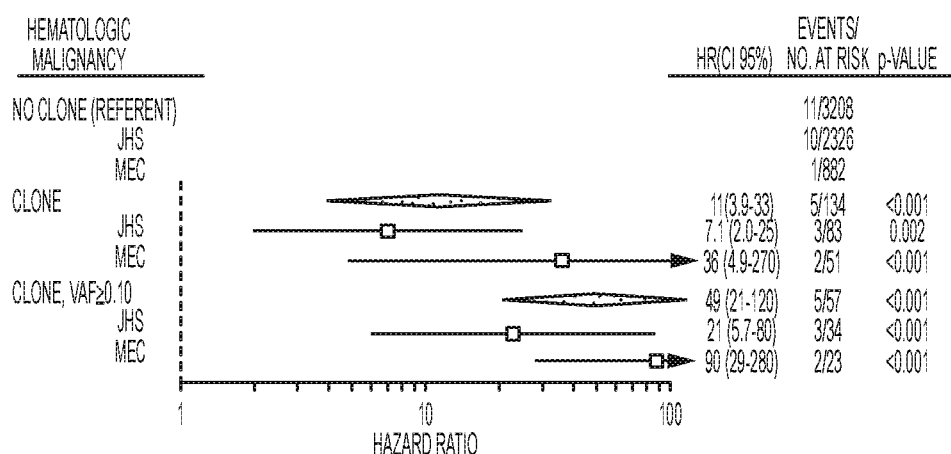
FIG. 3. Development of hematologic malignancies. A) Forest plot for risk of developing hematologic malignancy in those with somatic mutations overall and with VAF>0.10, relative to those without mutations. Diamond represents the results of fixed-effects meta-analysis for the 2 cohorts, and horizontal lines are 95 percent confidence intervals. Hazard ratios were estimated by competing risks regression with death as the competing risk. The analysis includes adjudicated cancer information from MEC and unadjudicated information by annual subject interview in JHS. For interview data, leukemia, lymphoma, multiple myeloma, blood cancer, and spleen cancer were considered hematologic malignancy. All models included age groups (less than 50, 50-59, 60-69, greater than 70), diabetes status, and sex as covariates. B) Cumulative incidence plot for developing hematologic malignancy. Curves were generated from competing risks data with death as the competing risk. C) VAF in subjects that did or did not develop hematologic malignancy, p-value from Wilcoxon test.
Figure 3:
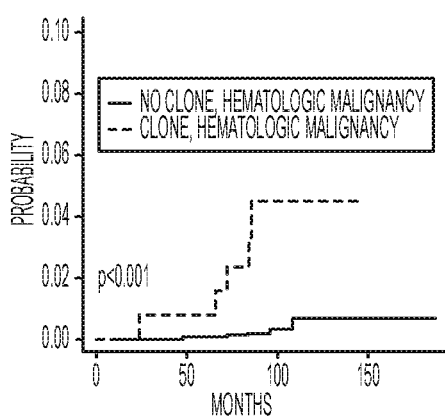
Figure 3:
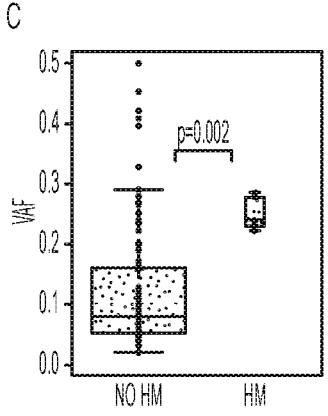

In a fixed-effects meta-analysis of the 2 cohorts adjusted for age, sex, and T2D, hematological malignancies were 11-fold more common in individuals with a detectable clone (95% o CI 3.9-33), a difference that was highly significant (p<0.001). In individuals with a VAF greater than 0.10 (indicating a higher proportion of cells in the blood carrying the mutation), the risk of developing a diagnosed hematological malignancy was nearly 50-fold (HR 49, 95% CI 21-120, p<0.001) (FIG. 3A). Consistent with this finding, individuals with a mutation who went on to be diagnosed with a hematological malignancy had a significantly higher mean VAF at the time of blood collection than those who did not (25.2% vs 12.0%, p=0.003 by Wilcoxon rank sum test, FIG. 3C).

While individuals with detectable mutations had a markedly increased risk of developing hematological malignancy, the absolute risk remained small; overall, approximately 4%) of individuals with a clone developed a hematological malignancy during the study period (FIG. 3B). This translates to a risk of developing hematological malignancy of ~0.5% per year overall, and ~1% per year in those with VAF>0.10.

Figure 10:
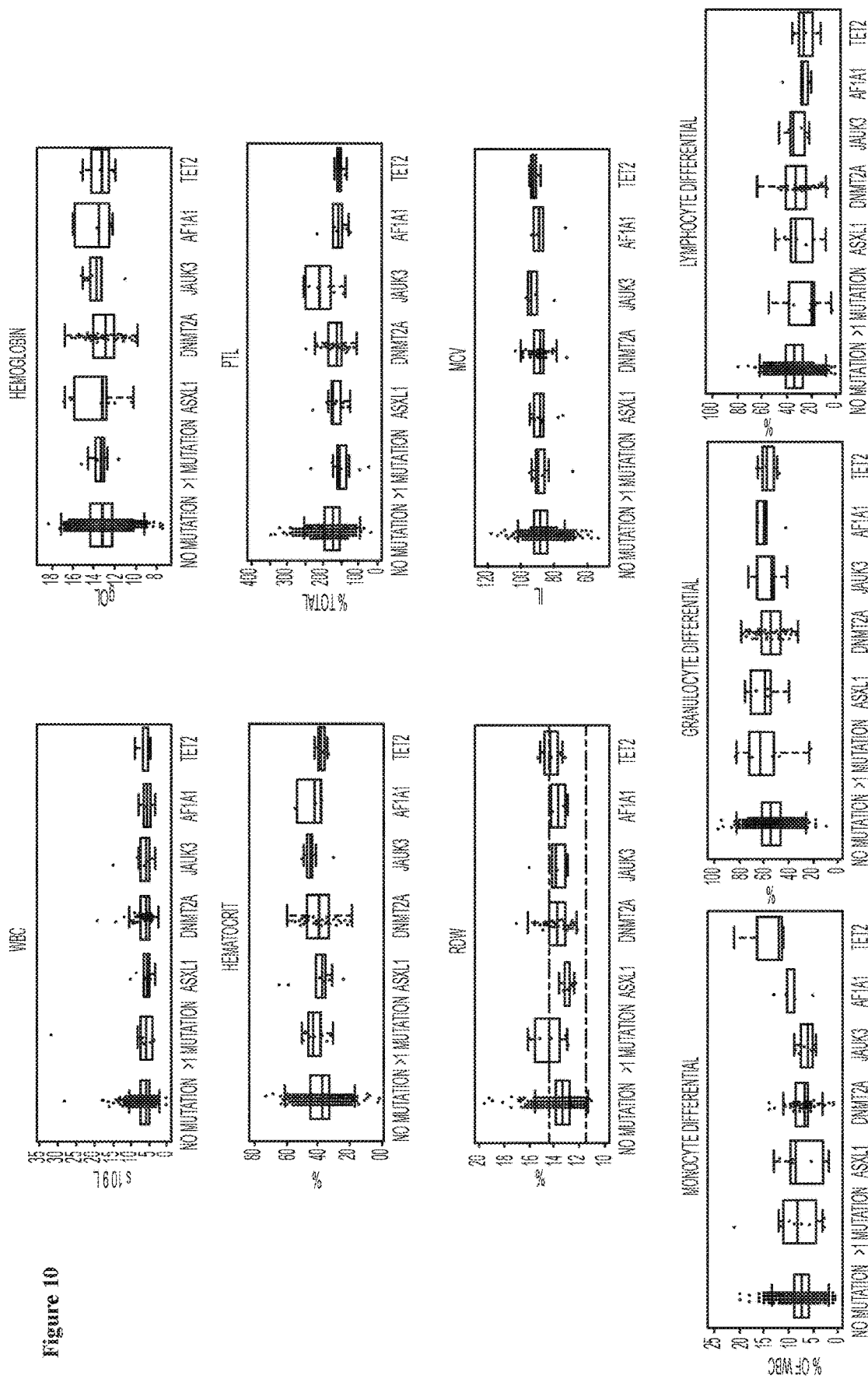
FIG. 10. Blood counts for individuals with and without detectable mutations. Dots represent individuals. Box represents 25th and 75th percentiles, line in box represents median. Whiskers represent 5th and 95th percentiles. For listed genes, individuals only had mutations in that gene, and not other genes. Dashed red lines represent 11.5% and 14.5%, the normal ranges for RDW. Abbreviations: WBC-white blood cell count, PLT-platelet count, RDW-red cell distribution width, MCV-mean corpuscular volume. Individuals were from Jackson Heart Study, Longevity Genes Project, Botnia. Helsinki-sib. or Malmo-sib.

Blood cell indices of individuals with somatic mutations. Somatic mutations found in MDS and AML lead to abnormal ditTerentiation, ineffective hematopoiesis, and cytopenias. Blood count data was available on 3,107 individuals from 5 cohorts (JHS, UA non-diabetic controls, Botnia, Malmo-sib, Helsinki-sib), including 139 subjects with a detectable mutation. When looking at individuals with single mutations (ASXL1, DNMT3A, JAK2, SF3B1, and TET2) or mutations in more than 1 gene versus those with no mutations, Applicants found no significant differences in mean white blood cell count, hemoglobin, platelet count, or white blood cell differential after accounting for age and sex (FIG. 10). The only statistically significant difference in blood cell indices was an increase in red blood cell distribution width (RDW), a parameter describing the variation in size of red blood cells (13.8% vs 13.4%, p=0.002 by Wilcoxon rank-sum test, Supplementary Table S8). This finding suggests that those carrying somatic mutations might have perturbations in hematopoiesis similar to those seen in MDS, even in the absence of cytopenias.

Applicants also asked whether the presence of a mutation was associated with increased likelihood of having abnormally low blood counts (Supplementary Table S9). Most of those with a mutation had no cytopenias, nor did they have a higher rate of any single cytopenia than those without mutations. A small fraction of subjects had multiple cytopenias, and these were enriched in the fraction with mutations (OR 3.0, p=0.037 by Fisher's exact test). Furthermore, among anemic subjects, those with mutations had a higher fraction of unexplained anemias than those without mutations (Supplementary Table S10).

Figure 4:
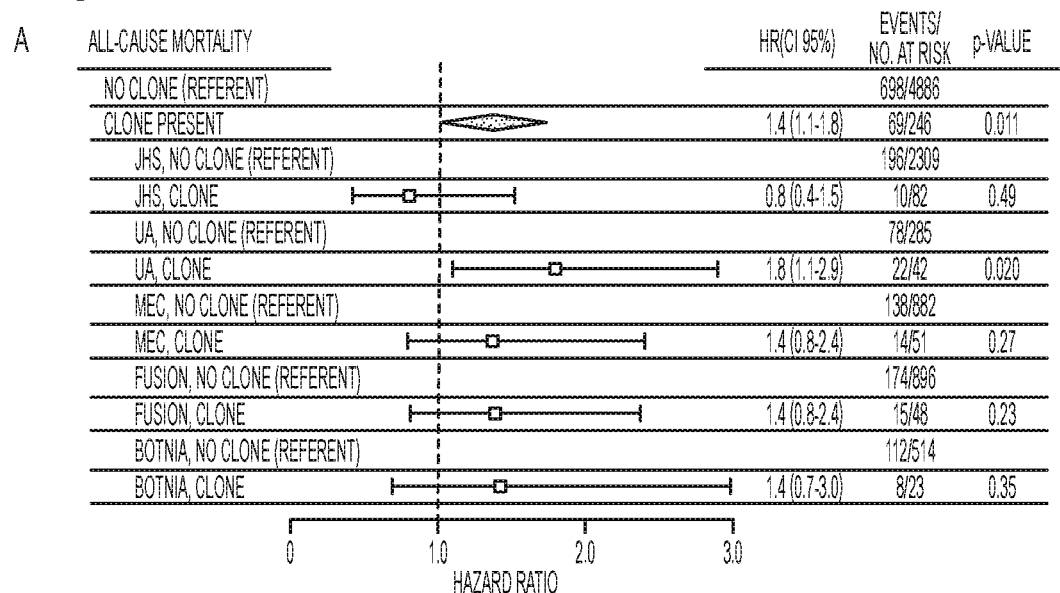
FIG. 4. Effect of somatic mutations on all-cause mortality. A) Forest plot for all-cause mortality risk associated with having a somatic clone. Diamond represents the results of fixed-effects meta-analysis of all cohorts, and horizontal lines are 95 percent confidence intervals. All models included age groups (less than 60, 60-69, 70-79, 80-89, and 90 or greater), diabetes status, and sex as covariates in a Cox proportional hazards model. Botnia includes Helsinki-sib and Diabetes-reg. B) Kaplan-Meier survival curves from the same cohorts as above, with p-values from log rank test. Left panel is those younger than 70 at time of DNA ascertainment, and right panel is those 70 or older. C) Cox proportional hazards model for all-cause mortality for those with or without mutations stratified by normal or high RDW. Diamond represents the results of fixed-effects meta-analysis of all cohorts, and horizontal lines are 95 percent confidence intervals. All models included age groups (less than 60, 60-69, 70-79, 80-89, and 90 or greater), diabetes status, and sex as covariates.
Figure 4:
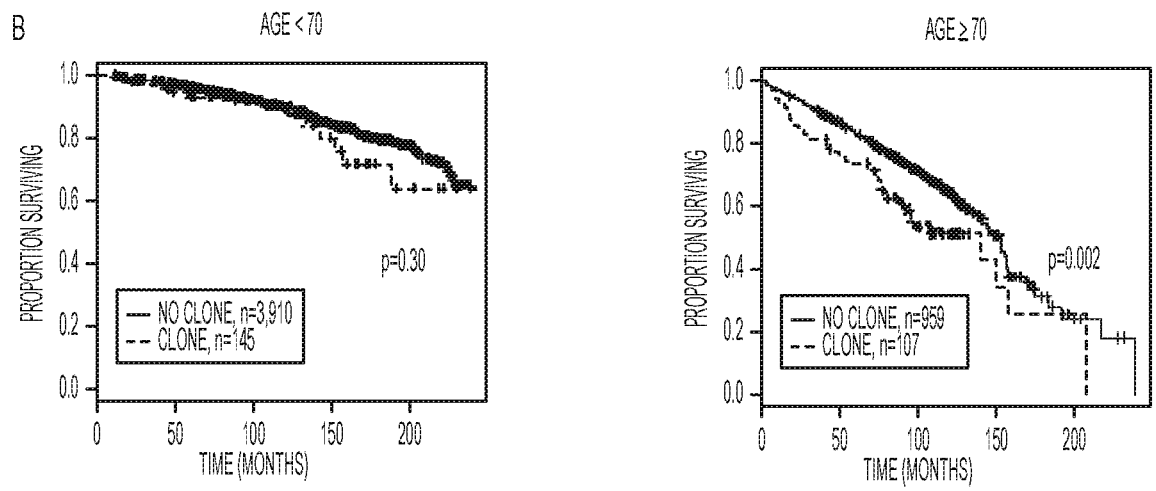
Figure 4:
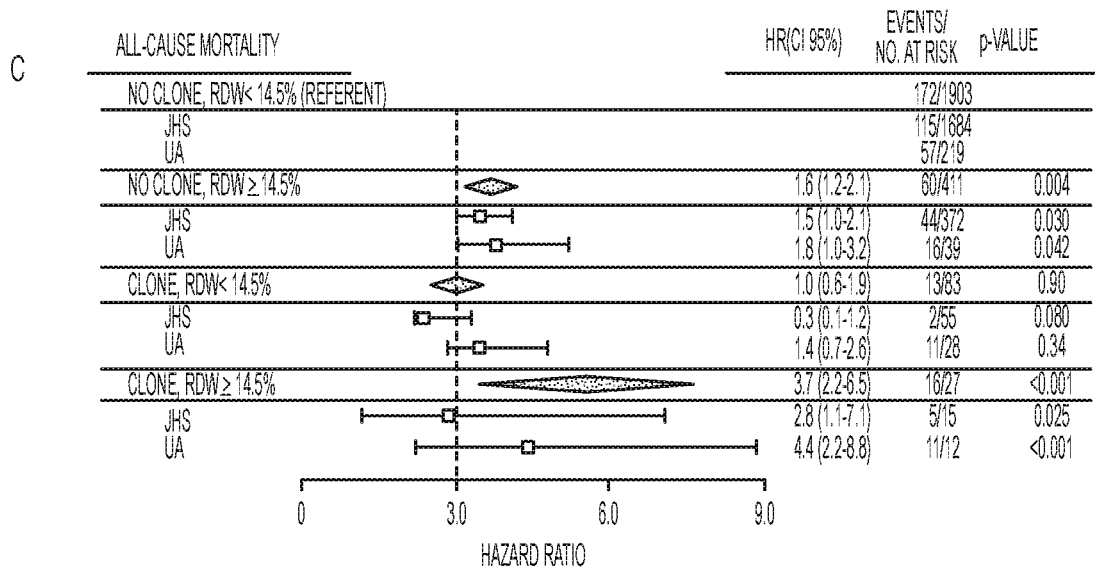
Figure 11:
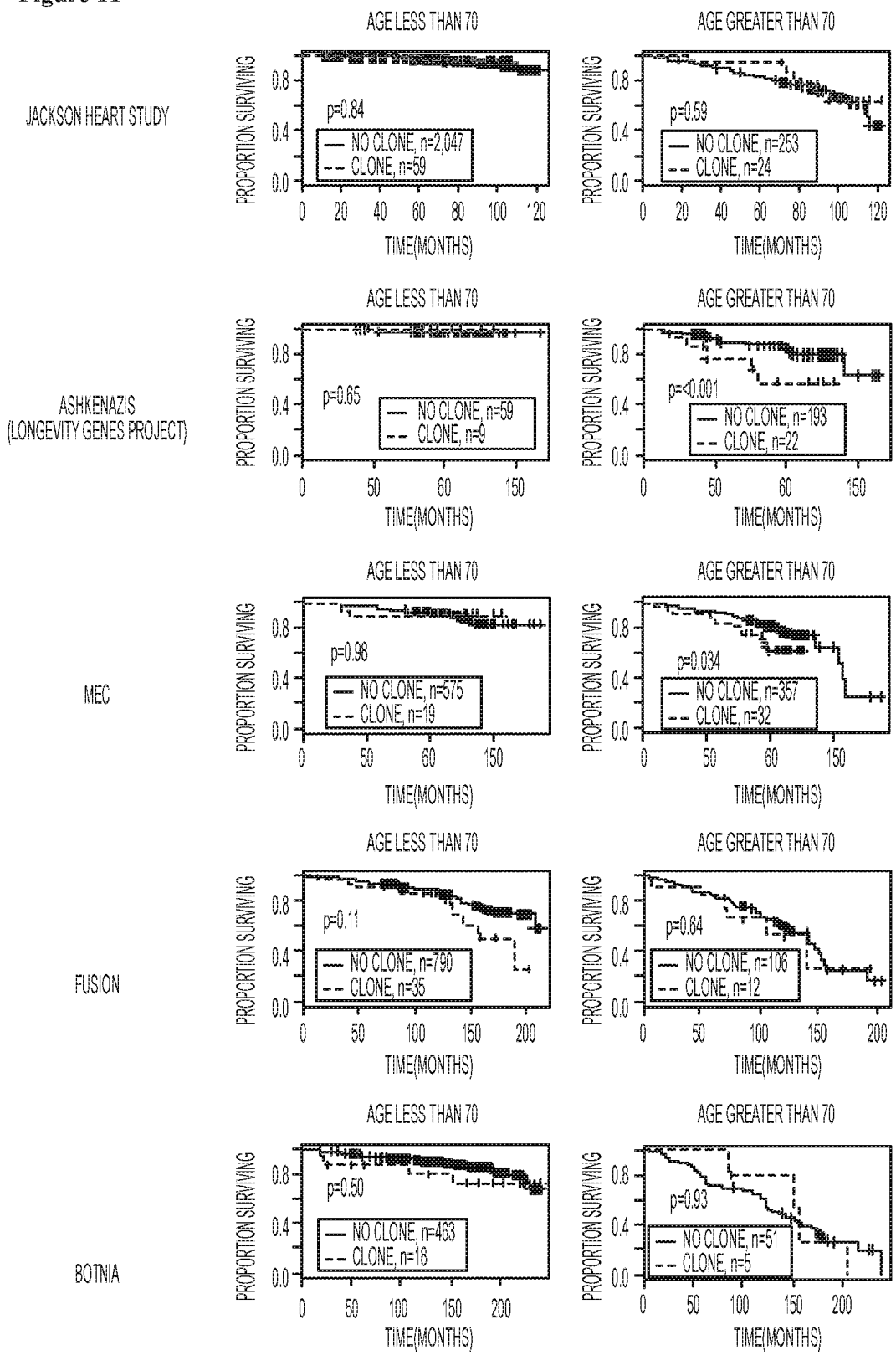
FIG. 11. Kaplan-Meier Curves for overall survival by cohorts.
Figure 15:
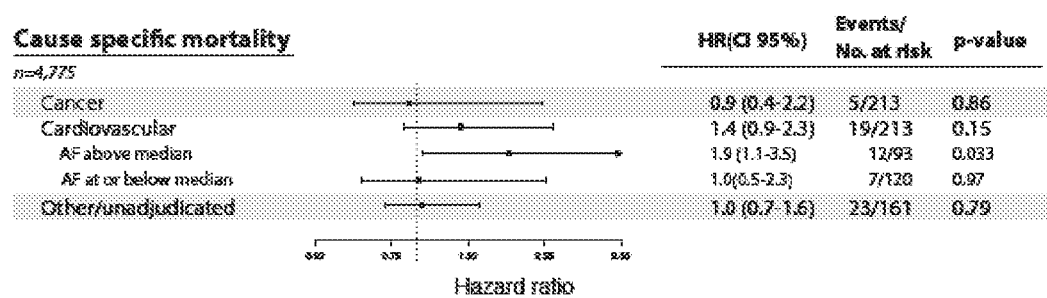
FIG. 15. Risk of cancer, cardiovascular, or other death associated with clonality. Hazard ratios obtained by competing risks regression, with death by other causes as the competing risk. Results shown are risk associated with clonality. For cancer deaths, only non-hematologic cancers were included. Cardiovascular deaths included strokes (hemorrhagic or ischemic) and fatal myocardial infarction. All regressions included age groups (less than 50, 50-59, 60-69, 70 or older), diabetes status, and gender as covariates. Individuals were from Botnia, FUSION, MEC, and Jackson Heart Study. For Jackson Heart Study, only cardiovascular outcomes were adjudicated (all other deaths were considered unadjudicated).

Association of somatic clones with overall survival. Applicants next assessed whether the presence of a somatic mutation had an effect on overall survival based on available data from 5,132 individuals in 7 cohorts (FIG. 4) with a median follow-up period of 96 months. In a model adjusted for age, sex, and T2D, carrying a mutation was associated with increased all-cause mortality (HR 1.4, p=0.018 by fixed-effects meta-analysis with beta-coefficients derived from Cox proportional hazards models for individual cohorts, FIG. 4A). Kaplan-Meier survival analysis within subjects 70 or older showed an increased risk of death in those with a mutation (p=0.002 by rank-sum test, FIG. 4B and FIG. 11). Death from hematologic neoplasms alone could not account for the observed increase in mortality, as only 1 individual with a mutation died from hematological malignancy. When Applicants performed a cause-specific mortality analysis, Applicants found that those with mutations had a higher risk of death due to cardiovascular causes, but not cancer (FIG. 15).

Figure 12:
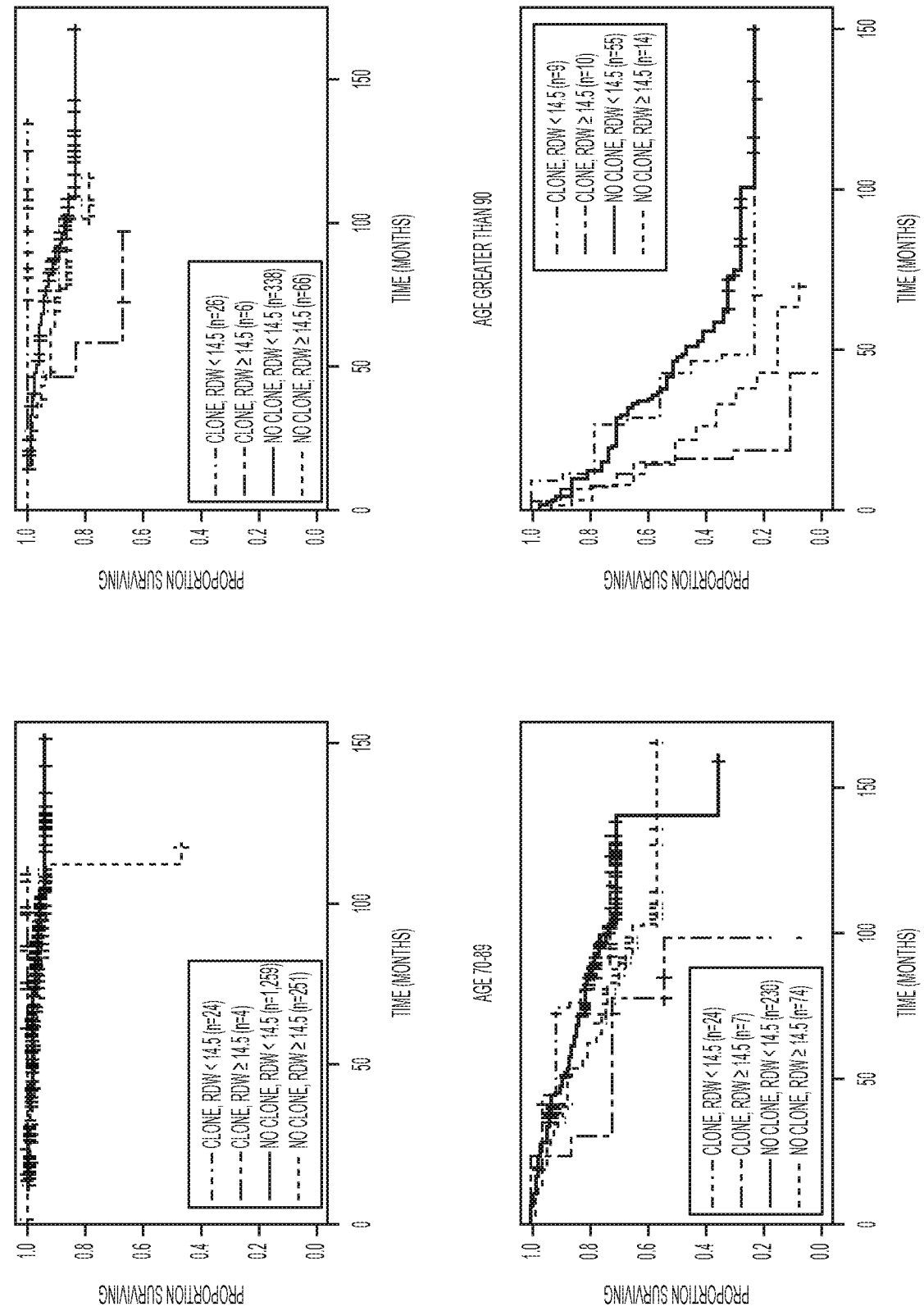
FIG. 12. Kaplan-Meier curves for individuals with or without clones, stratified by high (>14.5%) or normal (<14.5%) red cell distribution width. Hash marks represent censored individuals. Individuals were from Jackson Heart Study or Longevity Genes Project.
Figure 13:
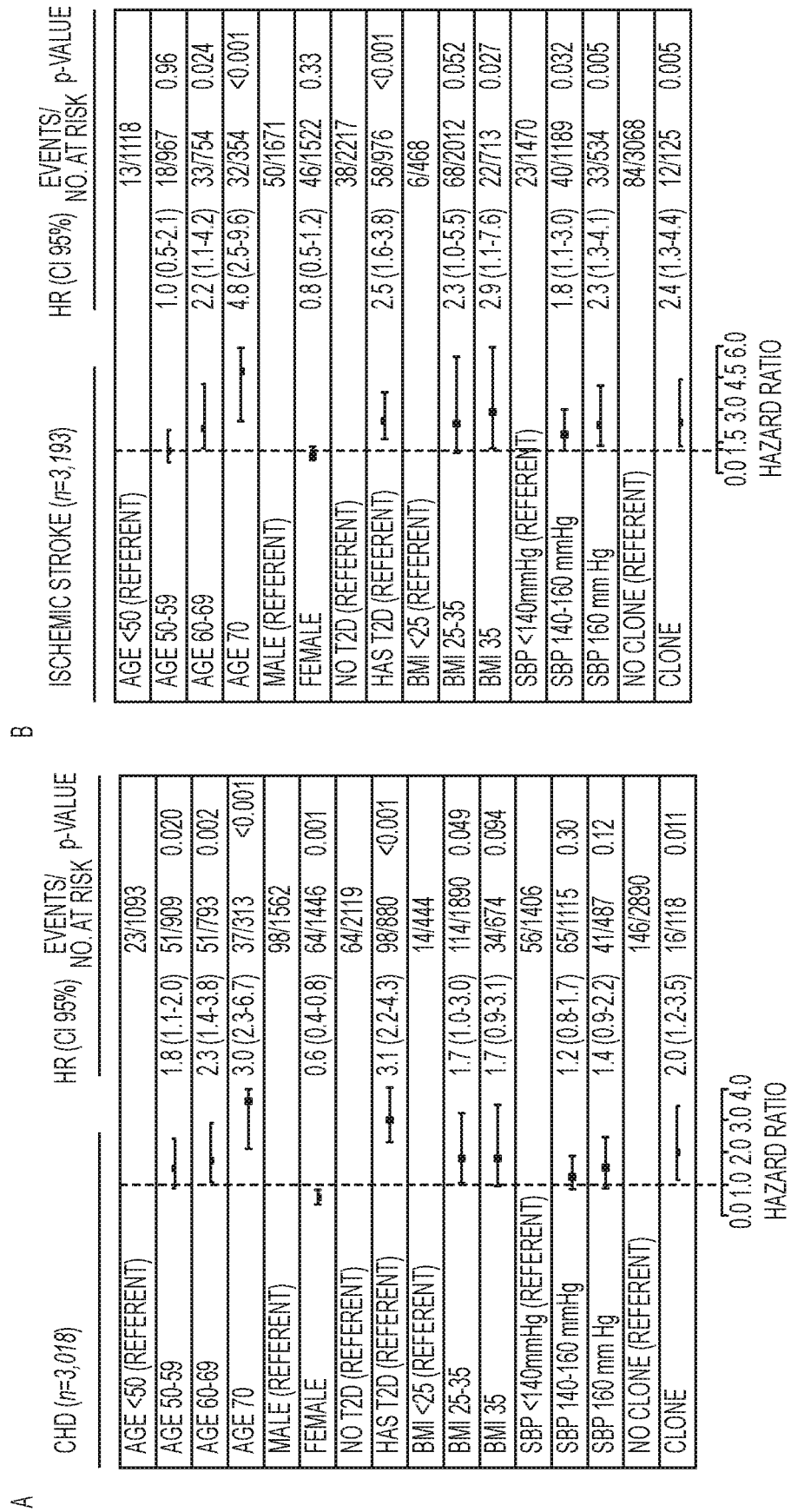
FIG. 13. Risk model for coronary heart disease and ischemic stroke. Regression parameters are same as shown for FIGS. 5C and 5D. Hazard ratios were estimated using competing risks regression with death as the competing risk. P-values are derived from the Fine-Gray test. Individuals with prior coronary heart disease (CHD) were excluded for CHD analysis, and individuals with prior ischemic stroke were excluded for stroke analysis. A) Coronary heart disease, B) ischemic stroke.

Because Applicants found that the presence of a somatic mutation was significantly associated with higher RDW, Applicants also examined whether harboring mutations was synergistic with elevated RDW for risk of death. High RDW has been associated with increased all-cause mortality in the aging and critically ill population (Patel K V et al. Archives of internal medicine 2009; 169:515-23, Perlstein T S et al. Archives of internal medicine 2009; 169:588-94, Bazick H S et al. Critical care medicine 2011; 39: 1913-21), but the mechanism behind this association is uncertain. Information on RDW was available on 2,409 subjects in 2 cohorts. In an analysis adjusted for age, sex, and T2D status, Applicants found that having a mutation in conjunction with an RDW>14.5% (the upper limit of normal) was associated with a marked increase in the risk of death compared to those without mutations and normal RDW (HR 3.7, p<0.001, by fixed-effects meta-analysis with beta-coefficients estimated from Cox models for the two cohorts). In contrast, those with no mutation and high RDW had a more modest increase in mortality (FIG. 4C, FIG. 12).

Association of somatic clones with cardiometabolic disease. A recent paper reported that large, somatic chromosomal alterations in peripheral blood cells were associated with having T2D (Bonnefond A et al. Nature genetics 2013; 45: 1040-3). Applicants also found that somatic mutations in genes known to cause hematologic malignancies were significantly associated with increased risk of T2D, even after adjustment for potential confounding variables (OR 1.3, p<0.001, FIGS. 11, 12). Those with T2D were slightly more likely to have mutations than those without T2D at each age group (FIG. 8).

Cardiovascular disease is the leading cause of death worldwide. Given the association of somatic mutations with all-cause mortality beyond that explicable by hematologic malignancy and T2D, Applicants performed association analyses from two cohorts comprising 3,353 subjects with available data on coronary heart disease (CHD) and ischemic stroke (IS). After excluding those with prevalent events, Applicants found that those carrying a mutation had increased cumulative incidence of both CHD and IS (FIG. 5A and 5B). In multivariable analyses that included age, sex, T2D, systolic blood pressure, and body mass index as covariates, the hazard ratio of incident CHD and IS was 2.0 (95% CI 1.2-3.5, P=0.015) and 2.6 (95% CI 1.3-4.8. P=0.003) in the individuals carrying a somatic mutation as compared to those without (FIG. 5C and 5D, FIG. 8).

For a subset of individuals, the traditional risk factors of smoking, total cholesterol, and high-density lipoprotein were also available; the presence of a somatic mutation remained significantly associated with incident CHD and IS even in the presence of these risk factors, and the risk was even greater in those with VAF>0.10 (Supplementary Table S12). Elevated RDW and high-sensitivity C-reactive protein (hsCRP) have also been associated with adverse cardiac outcomes (Tonelli M et al. Circulation 2008; 117: 163-8, Ridker P M et al. The New England journal of medicine 2002; 347: 1557-65), possibly reflecting an underlying inflammatory cause. In a multivariable analysis of 1,795 subjects from JHS, those with a mutation and RDW>14.5% had a markedly increased risk of incident CHD, and this effect was independent of hsCRP (Supplementary Table S13).

Further validation was performed showing the relationship between clonal hematopoesis and risk for cardiovascular disease by analyzing two additional cohort studies. The BioImage Study is a study of the characteristics of subclinical cardiovascular disease, as measured by imaging modalities, unsupervised circulating biomarker measurements, and risk factors that predict progression to overt clinical cardiovascular disease, in a diverse, population-based sample of 7,300 men (aged 55-80) and women (aged 60-80). The socio-demographics of the study population aims to mirror the US population as a whole with approximately 69% of the cohort will be white, 12% African-American, 13% Hispanic, 4% Asian, predominantly of Chinese descent and 2% other (U.S. Census Bureau: 2000). The Malmo Diet and Cancer study is a 10-year prospective case-control study in 45-64-year-old men and women (n=53,000) living in a city with 230,000 inhabitants.

Participants from the nested case-control studies that passed sample quality control (contamination, prevalent cardiovascular disease, germline Ti/Tv, germline total variants/depth, germline F inbreeding coefficient) are displayed (Table 1). Participants were matched by age, sex, diabetes status, and smoking status. LDL cholesterol and total cholesterol are adjusted accounting for statin medications as previously described. Individuals that carried at least one mutation in a gene conferring risk of clonal expansion with a variant allele fraction >0.10 are defined as carrying a somatic clone.

TABLE 1

Baseline characteristics of study participants

|  | BioImage | | Malmo Diet & Cancer | |
| --- | --- | --- | --- | --- |
|  | Cases<br>N = 150 | Controls<br>N = 344 | Cases<br>N = 536 | Controls<br>N = 531 |
| Age, y | 70.2 (5.8) | 70.3 (5.9) | 59.9 (5.4) | 59.9 (5.4) |
| Female | 60 (42.9%) | 136 (39.5%) | 233 (43.5%) | 233 (43.9%) |
| Total cholesterol, mg/dL | 208.8 (38.1) | 214.0 (37.5) | 271.2 (173.1) | 252.7 (133.8) |
| LDL cholesterol, mg/dL | 127.4 (31.4) | 122.9 (32.8) | 186.9 (117.1) | 172.0 (92.5) |
| HDL cholesterol, mg/dL | 51.0 (14.7) | 53.1 (15.1) | 49.1 (13.0) | 51.8 (13.7) |
| Triglycerides, mg/dL | 181.6 (94.1) | 169.6 (93.6) | 127.4 (57.4) | 123.7 (58.9) |
| Diabetes mellitus type 2 | 36 (24.0%) | 89 (25.9%) | 82 (15.3%) | 80 (15.1%) |
| Hypertension | 130 (86.7%) | 256 (74.4%) | 421 (78.5%) | 354 (66.7%) |
| Smoker | 24 (16.0%) | 55 (16.0%) | 167 (31.2%) | 166 (31.3%) |
| BMI | 27.8 (4.7) | 27.4 (4.7) | 26.5 (4.0) | 26.2 (4.0) |
| Somatic clone carrier | 24 (16.0%) | 34 (9.9%) | 31 (5.8%) | 22 (4.1%) |

Figure 18:
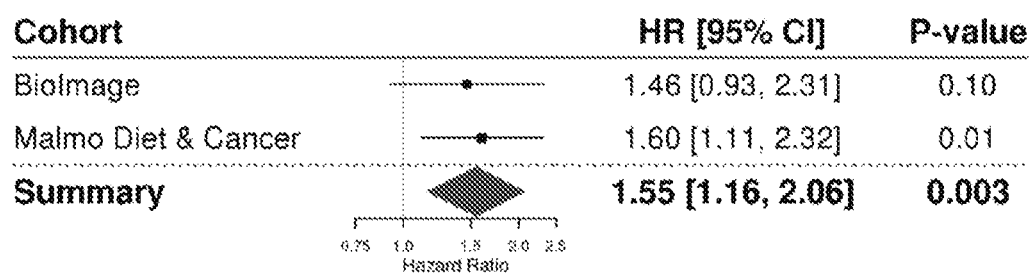
FIG. 18. Risk of cardiovascular events from carrying a somatic clonal mutation. Risk if cardiovascular events (myocardial infarction, coronary revascularization, or stroke) in each cohort and fixed effects meta-analysis are displayed. Effect estimates are derived from a Cox proportional hazards model after accounting for age, sex, ethnicity, diabetes mellitus, smoking, hypertension, LDL cholesterol. There was no evidence of heterogeneity between the effect estimates in the two cohorts (P for heterogeneity=0.79).
Figure 19:
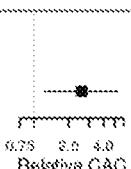
FIG. 19. Coronary arterial calcification quantity by somatic clonal mutation carrier status. Among participants in the BioImage cohort, coronary arterial calcification (CAC) quantity was obtained as the total Agatston score. The relative difference in CAC in somatic clonal mutation carriers compared to non-carriers is estimated from linear regression with log-transformation of CAC quantity.

Applicants show an increased risk of cardiovascular events from carrying a somatic clonal mutation in both studies (FIG. 18). Furthermore, Applicants show that an increase in coronary arterial calcification quantity is associated with somatic clonal mutation carrier status (FIG. 19).

Example 3: Discussion

Applicants find that somatic mutations leading to clonal outgrowth of hematopoietic cells are frequent in the general population. This entity, which Applicants term clonal hematopoiesis with indeterminate potential (CHIP), is present in over 10% of individuals over 70, making it one of the most common known pre-malignant lesions. The exact prevalence of CHIP is dependent on how cancer-causing mutations are defined and on the sensitivity of the technique used to detect mutations, and thus may substantially exceed this estimate. Unlike other pre-malignant lesions, CHIP appears to involve a substantial proportion of the affected tissue in most individuals; based on the proportion of alleles with the somatic mutation, Applicants find that a median of 18% of peripheral blood leukocytes are part of the abnormal clone. CHIP also persists over time; in all tested cases, the mutations were still present after 4 to 8 years.

The genes most commonly mutated in CHIP are DNMT3A, TET2, and ASXL1. This is consistent with previous studies that have found DNMT3A and TET2 mutations to be frequent and early events in AML and MDS (Jan M et al. Science translational medicine 2012; 4: 149ra18, Shlush L I et al. Nature 2014; 506:328-33, Papaemmanuil E et al. The New England journal of medicine 2011; 365: 1384-95, Welch J S et al. Cell 2012; 150:264-78). Murine models of DNMT3A or TET2 loss-of-function demonstrate that mutant HSCs have altered methylation patterns at pluripotency genes and a competitive advantage compared to wild-type HSCs, but mice rarely develop frank malignancy, and then only after long latency (Jeong M et al. Nature genetics 2014; 46:17-23, Koh K P et al. Cell stem cell 2011; 8:200-13, Challen G A et al. Nature genetics 2012; 44:23-31, Moran-Crusio K et al. Cancer cell 2011; 20: 11-24). Similarly, Applicants' data show that humans with CHIP can live for many years without developing hematological malignancies, though they do have increased risk relative to those without mutations.

Certain genes commonly mutated in AML and MDS are absent or very rare in this study. Their rarity likely indicates that they are cooperating rather than initiating mutations. While mutations in genes specific for lymphoid malignancies were rarely detected, it is important to note that TET2 and DNMT3A are frequently mutated in some lymphoid malignancies, and the initiating event for such tumors may occur in a HSC (Neumann M et al. Blood 2013; 121:4749-52, Quivoron C et al. Cancer cell 2011; 20:25-38, Odejide 0 et al. Blood 2014; 123: 1293-6, Asmar F et al Haematologica 2013; 98: 1912-20, Couronne L et al. The New England journal of medicine 2012; 366:95-6). While it is most likely that these mutations occur in a HSC, it also possible that they occur in committed myeloid progenitors or mature lymphoid cells that have acquired long-term self-renewal capacity.

The use of somatic mutations to aid in the diagnosis of patients with clinical MDS is becoming widespread. Applicants' data demonstrate that the majority of individuals with clonal mutations in peripheral blood do not have MDS or another hematological malignancy, nor do the majority develop a clinically diagnosed malignancy in the near term. At this time, it would be premature to genetically screen healthy individuals for the presence of a somatic clone, as the positive predictive value for current or future malignancy is low. Further studies are needed to definitively assess whether the detection of a mutation in conjunction with blood count abnormalities is sufficient to make a presumptive diagnosis of MDS or another hematological malignancy.

Perhaps the most surprising finding in Applicants' study is the lower overall rate of survival in those with clones as compared to those without. This effect is much larger than can be explained by hematological malignancies alone, is synergistic with high RDW (which could be a marker of perturbation of hematopoiesis due to the clone), and may be related to the increased risk of incident CHD and IS in those with clones. The association of somatic mutations with non-hematological disease may be due to confounding by variables that are currently unknown, or may simply represent a shared consequence of the underlying process of aging. Alternatively, it may represent an underlying shared pathophysiology of seemingly unrelated disorders. For example, cells of the monocyte/macrophage lineage are considered important mediators of atherosclerosis and type 2 diabetes (Libby P. 2002; 420:868-74, Olefsky J M, Glass C K. Annual review of physiology 2010; 72:219-46). Applicants propose that one possible explanation for these findings is that somatic mutations that lead to clonal hematopoiesis cause functional abnormalities in differentiated blood cells that modulate the risk of cardiometabolic disease.

In summary, Applicants find that clonal hematopoiesis due to somatic mutation is a common finding in the elderly, and most frequently involves DNMT3A, TET2, and ASXL1. This clinical entity, CHIP, is associated with increased risk of developing hematological malignancy, minimal changes in blood counts, increased overall mortality, and increased risk of cardiometabolic disease.

Example 4: Supplemental Methods

Sample ascertainment and cohort descriptions. Subjects were ascertained as cases and controls for T2D from 22 cohorts in 3 consortia (Supplementary Table 1). Details on sample ascertainment for cases and controls from the most of the GoT2D (8 cohorts, 2,376 subjects) and SIGMA (4 cohorts, 3,435 subjects) consortia have been previously described (Flannick J et al. Nature genetics 2013; 45: 1380-5, Consortium STD et al. Nature 2014; 506:97-101). The other ascertained individuals were part of T2D-GENES (9,990 subjects), a consortium comprised of 10 population-based cohorts. Details on sample ascertainment can be found in Supplementary Table 1. The remaining 1,381 individuals were additional subjects in the Jackson Heart Study (JHS), a large population-based cohort of African-Americans in Jackson, Mississippi, who had given consent for genetic testing but were not in any previously sequenced cohorts (Sempos C T et al. The American journal of the medical sciences 1999; 317: 142-6). Including the 1,027 subjects from JHS enrolled through T2D-GENES (513 with T2D), a total of 2,408 subjects from JHS were in this study. Since 3,400 subjects in JHS were consented for genetic studies, ~70% of consented subjects from JHS are represented in this study, with a modest overall enrichment for T2D.

Subjects for which age was not available (1 16 subjects) or with cell lines as the source DNA (492 subjects) were excluded, including all subjects from the Wellcome Trust Case Control Consortium (WTCCC).

Vital status for Finland-United States Investigation of NIDDM Genetics Study (FUSION), The Botnia Study (Botnia), Helsinki Siblings with Diabetes cohort (Helsinki sib), and Scania Diabetes Register (Diabetes reg) was ascertained from the Finnish or Swedish Hospital Death Registries. Subjects from Botnia, Helsinki sib, and Diabetes reg were pooled for survival analysis. Vital status for subjects from the Multiethnic Cohort (MEC) was ascertained from Center for Medicare Services (CMS) data. Vital status for subjects from the JHS was ascertained from vital records and annual follow-up interviews. For individuals lost to follow-up, if there was no death certificate, the individual was assumed to be alive. Vital status for non-diabetic Ashkenazis in the Longevity Genes Project (LGP) was ascertained from hospital death records and annual follow-up interviews.

Malignancy information for MEC was ascertained through linkage of the MEC with cancer registries of California and Hawaii. Malignancy information for JHS was ascertained from annual interview. Malignancy information for some subjects from FUSION and Botnia was available from the Finnish Hospital Discharge Register and Death Register, but not included because it was deemed to have significant ascertainment bias.

Standard blood cell indices (white blood cell count, hemoglobin, hematocrit, platelet count, and white blood cell differential) were available for most (but not all) subjects from JHS, LGP, Botnia, Malmo-sib, and Helsinki-sib. Information on red blood cell distribution width (RDW) was available on most subjects in JHS and LGP.

Data on cardiovascular outcomes for JHS was obtained from annual patient interview and adjudicated from hospital records. Data on cardiovascular outcomes for FUSION was obtained from Finnish Hospital Discharge and Death Registries. Coronary heart disease (CHD) included fatal and non-fatal myocardial infarctions as well as coronary revascularization procedures. For CHD analysis, those with prior CHD events were excluded. For ischemic stroke analysis, those with prior ischemic stroke were excluded. Lab data (blood pressure, body mass index, serum high density lipoprotein, serum total cholesterol, and high-sensitivity C-reactive protein) was obtained at the same time as blood collection for DNA.

Exome sequencing. DNA was obtained from individual cohorts and further processed at the Broad Institute of MIT and Harvard. DNA libraries were bar coded using the Illumina index read strategy, exon capture was performed using Agilent Sure-Select Human All Exon v2.0, and sequencing was performed by Illumina HiSeq2000. Sequence data were aligned by the Picard pipeline, as hosted on line by SourceForge, using reference genome hg19 with the BWA algorithm (Li H, Durbin R. Bioinformatics 2009; 25:1754-60) and processed with the Genome Analysis Toolkit (GATK) to recalibrate base-quality scores and perform local realignment around known insertions and deletions (indels) (DePristo M A et al. Nature genetics 2011; 43:491-8). BAM files were then analyzed for single nucleotide variants using MuTect (available online and hosted by The Cancer Genome Analysis (CGA) group at the Cancer Program of the Broad Institute; see Cibulskis, K. et al. Nat Biotechnol 2013; 31, 213-219) with Oxo-G filtering (available online and hosted by The Cancer Genome Analysis (CGA) group at the Cancer Program of the Broad Institute; see Costello et al., 2013 Nucleic Acids Research, 41(6), e67) and for indels using Indelocator (a software tool for calling short indels in next generation sequencing data available online and hosted by The Cancer Genome Analysis (CGA) group at the Cancer Program of the Broad Institute), followed by annotation using Oncotator (a tool for annotating human genomic point mutations and indels with data relevant to cancer researchers available online and hosted by The Cancer Genome Analysis (CGA) group at the Cancer Program of the Broad Institute; see Ramos et al., Human Mutation 2015, 36(4), E2423-E2429). All MuTect and Indelocator analyses were performed using the Firehose analysis infrastructure developed and hosted at The Cancer Genome Analysis (CGA) group at the Cancer Program of the Broad Institute.

Variant calling. Cancer genome studies typically compare sequence from tumor and germline DNA, and define somatic mutations as the sequence variants present in tumor but not germline DNA. To circumvent the lack of matched tissue in this study, Applicants defined a list of pathogenic variants reported in the literature and/or the Catalog of Somatic Mutations in Cancer (COSMIC) in human hematologic malignancies from 160 genes (see Lawrence, M S, et al. Nature 2014; 505:495-501, Supplementary Table S2). Applicants specifically excluded genes known to be involved in hematologic malignancy that had a relatively high frequency of heterozygous loss-of-function germline mutations in the population (NF1, SH2B3, BRCA1/2). Identical frameshift variants that were seen 3 or more times from the same ancestry group were also excluded, unless such variants were previously reported as somatic. Frameshift and nonsense mutations were further excluded if they occurred in the first or last 10% of the gene open reading frame (Ng P C et al. PLoS genetics 2008; 4:e1000160), unless mutations in those regions had been previously reported, (e.g. DNMT3A (Walter M J et al. Leukemia 2011; 25:1153-8)). Applicants used minimum variant read counts of 3 for MuTect and 6 for Indelocator. Python scripts were used to parse mutation annotation format (MAF) files produced by MuTect and Indelocator for variants of interest.

To further confirm that Applicants were detecting bona fide somatic mutations, Applicants examined variants in 40 driver genes involved in non-hematologic malignancies (Lawrence M S et al. Nature 2014; 505:495-501). Applicants hypothesized that very few variants would be detected from these genes if Applicants' methodology had high specificity for real mutations. Using the same calling approach as with hematologic genes (Supplementary Table S4), Applicants detected only 10 variants that were the same as those mutated in non-hematologic cancers, and most of these appeared to be rare germline polymorphisms as evidenced by allele fraction (Supplementary Table S5).

Targeted re-sequencing. Validation of variants discovered by whole exome sequencing was done with "Rapid Heme Panel" (RHP), a Laboratory Developed Test designed and validated at a CLIA-certified lab (Center for Advanced Molecular Diagnostics, Brigham and Women's Hospital). RHP uses TruSeq Custom Amplicon Kit (Illumina, Inc. San Diego, CA, USA) and contains 95 genes (50 for AML/MDS, 8 for MPN, 27 for ALL, and 10 others). For oncogenes, known mutation hotspots are targeted; and for tumor suppressor genes the entire coding sequence is analyzed. The average amplicon size is 250-bp and about 50% of the regions are covered on both strands. Library preparation was according to manufacturer's instruction and sequencing was 150 bp paired-end reads with MiSeq v2.2 chemistry. Raw data was analyzed with Illumina on-board Real-Time-Analysis (RTA v.2.4.60.8) software and MiSeq Reporter. The VCF files were filtered with a cutoff for any nucleotide position with 10 or more variant reads or with 5-9 variant reads (if allele frequency >33%) as well as a Q score greater than 30 and germline single nucleotide polymorphisms were removed by comparison to dbSNP database (NCBI Human Build 141). The filtered variant lists were manually reviewed and BAM file examined in Integrated Genome Viewer (IGV, Broad Institute).

For 13 subjects from JHS, DNA obtained from a peripheral blood sample collected 4 to 8 years after the original DNA was available for analysis. RHP was used as described above to assess VAF of the previously detected mutations at the second time point, and to assess for the acquisition of new mutations.

Genes: ABL1, ASXL1, ATM, BCL11B, BCOR, BCORL1, BRAF, BRCC3, CALR, CBL, CBLB, CD79B, CEBPA, CNOT3, CREBBP, CRLF2, CSF1R, CSF3R, CTCF, CTNNB1, CUX1, CXCR4, DMNT3A, DNMT3B, EED, EGFR, EP300, ETV6, EZH2, FANCL, FBXW7, FLT3, GATA1, GATA2, GAT A3, GNAS, GNB1, IDH1, IDH2, IKZF1, IKZF2, IKZF3, IL7R, JAK1, JAK2, JAK3, KIT, KRAS, LUC7L2, MAP2K1, MEF2B, MPL, MYD88, NOTCH1, NOTCH2, NOTCH3, NPM1, NRAS, NT5C2, PAX5, PDGFRA, PDS5B, PHF6, PIGA, PIK3CA, PIM1, PRPF40B, PRPF8, PTEN, PTPN11, RAD21, RET, RIT1, RPL10, RUNX1, SETBP1, SETD2, SF1, SF3A1, SF3B1, SH2B3, SMC1A, SMC3, SRSF2, STAG2, STAT3, TET2, TLR2, TP53, U2AF1, U2AF2, WHSC1, WT1, XPO1, ZRSR2.

Statistics and analysis plan. All statistical analyses were performed using R. Cox proportional hazards and Kaplan-Meier analysis was performed using the survival package of the R software environment provided online by the R Foundation. Competing risks regression (CRR) was used to estimate hazard ratios for developing hematologic malignancy with death as the competing risk (Fine J P and Gray, R J. Journal of the American Statistical Association 1999; 94:496-509). CRR and cumulative incidence analysis was performed using the R cmprsk package-. Fixed-effects meta-analysis using beta-coefficients for risk estimates from individual cohorts was used to provide summary hazard ratios across heterogeneous cohorts. Meta-analysis was performed using the R meta package.

Analyses for factors associated with clonal hematopoiesis were performed using logistic regression with the predetermined variables age, sex, type 2 diabetes status, and ancestry.

Primary outcomes for clinical associations with clonal hematopoiesis were predetermined to be all-cause mortality and hematologic malignancy, using Cox proportional hazards models and CRR, respectively. Association of mutations with blood counts was also a primary analysis. For hematologic malignancy outcomes, only events incident to the time of DNA collection were considered Red cell distribution width was also included as a variable in the survival analysis because of its association with mutations and previous reports of its association with increased mortality.

An analysis of cause specific mortality revealed an increase in cardiovascular deaths. For this reason, Applicants examined incident events of coronary heart disease and ischemic stroke using CRR and the pre-determined variables age, sex, type 2 diabetes status, body mass index, and systolic blood pressure. For some subjects, data was also available on smoking status, total cholesterol, and high-density lipoprotein. This was examined as a subgroup analysis in a separate regression (see Supplementary Tables S12-13).

For some analyses, a cutoff of VAF at 0.10 was used. This value was chosen because it was close to the median VAF in the dataset and is roughly the lower limit of detection using Sanger DNA sequencing, and was thus used to designate large versus small clone size.

Example 5: Supplemental Tables

SUPPLEMENTARY TABLE S1

| | | | | | | |
|---|---|---|---|---|---|---|
| | | | | Clinical | | |
| | | | T2D | information | Cohort descriptions | |
| TOTAL | No T2D | T2D | unknown | available | and sample ascertainment | References |
| Overall (number with clone) | 9303 (367) | 7861 (378) | 18 (1) | | | |
| Female (number with clone) | 4889 (184) | 3845 (173) | 8 (0) | | | |
| Mean age (SD) | 57 (13) | 59 (10) | | | | |

SUPPLEMENTARY TABLE S1-continued

Cohort descriptions and baseline characteristics

| | | | | | | |
|---|---|---|---|---|---|---|
| Mean BMI (SD) | 28 (5.8) | 29 (5.6) | | | | |

Population-based

JHS (Jackson Heart Study)

| | | | | | | |
|---|---|---|---|---|---|---|
| Overall (number with clone) | 1801 (57) | 589 (25) | 18 (1) | Survival, malignancy, blood counts, cardio-vascular events | The Jackson Heart Study is a population-based cohort of 5,301 African-Americans living in the Jackson, Mississippi metropolitan area. Subjects were enrolled as random members of community, volunteers, as part of the Atherosclerosis Risk in Communities (ARIC), or secondary family members. At 12-month intervals after the baseline clinic visit (Exam 1), particapants were contacted by telephone to: update information; confirm vital statistics; document interim medical event, hospitalizations. and functional status; and obtain additional sociocultural information. Questions about medical events, symptoms of cardiovascular disease and functional status were repeated annually. Ongoing cohort surveillance includes abstraction of medical records and death certificates for relevant International Classification of Diseases (ICD) codes and adjudication of nonfatal events and deaths. | Wilson, J.G, et al. (2005). "Study design for genetic analysis in the Jackson Heart Study." Ethnicity and Disease 15: 30-37; Taylor, H.A. (2005). The Jackson Heart Study: An Overview. Ethnicity and Disease 15: 1-3; Fuqua, S.R. et al., (2005). Recruiting Afican-American Research Participation in the Jackson Heart Study: Methods, Response Rates, and Sample Description. Ethnicity and Disease 15: 18-29; Fuqua, S.R. et al., (2005). |
| Female (number with clone) | 1003 (30) | 401 (18) | 8 (0) | | | |
| Mean age (SD) | 51 (13) | 58 (11) | | | | |
| Mean BMI (SD) | 31 (6.8) | 34 (6.4) | | | | |

GoT2D

Botnia (The Botnia Study), Diabetes_reg (Scania Diabetes Registry), Helsinki-sib (Helsinki siblings with diabetes cohort), Malmö-sib (siblings in Malmö, Sweden

| | | | | | |
|---|---|---|---|---|---|
| Overall (number with clone) | 224 (12) | 369 (14) | Survival, blood counts cardio-vascular events | The Botnia Project was started in 1990 to study the risk factors for T2D in western Finland and southern Sweden and includes ~11,000 people from ~1400 families. The Scania Diabetes Registry contains over 7000 diabetes patients recruited at hospitals in Scania, Sweden as from 1996. The majority of the patients come from the city of Malmö, and they account for about 25% of all diabetic patients in the region. Death information was obtained from the Finnish or Swedish Death and Hospital Discharge Registers. Individuals were ranked according to a liability model that measured risk for T2D. Briefly, liability scores were computed as the difference between diabetes status and the predicted risk based on age, BMI and gender; extreme cases were selected to have the highest liability scores (with diabetes but with low predicted risk for diabetes), and extreme controls were selected to have the lowest liability scores (without diabetes but with high predicted risk for diabetes). | Flannick, J., et al. (2013). "Assessing the phenotypic effects in the general population of rare variants in genes for a dominant Mendelian form of diabetes." Nat Genet 45 (11): 1380-1385; Groop, L., et al. (1996). "Metabolic consequences of a family history of NIDDM (the Botnia study): evidence for sex-specific parental effects." Diabetes 45 (11): 1585-1593; Lindholm, E., et al. (2001). "Classifying diabetes according to the new WHO clinical stages." Eur J Epidemiol 17 (11): 983-989. |
| Female (number with clone) | 108 (6) | 211 (5) | | | |
| Mean age (SD) | 65 (10) | 57 (10) | | | |
| Mean BMI (SD) | 30 (3.7) | 25 (2.7) | | | |

SUPPLEMENTARY TABLE S1-continued

Cohort descriptions and baseline characteristics

| | | | | | |
|---|---|---|---|---|---|
| FUSION (Finland-United States Investigation of NIDDM Genetics Study) | | | | | |
| Overall (number with clone) | 474 (27) | 470 (21) | Survival, blood counts cardiovascular events | The Finland-United States Investigation of NIDDM Genetics (FUSION) study is a ong-term effort to identify genetic variants that predispos to type 2 diabetes (T2D) or that impact the variability of T2D-related quantitative traits. Unrelated T2D cases were selected from FUSION affected-sibpair families and from stage 2 replication. NGT controls with higher age and BMI were prioritized and were frequency matched to cases by birth province. | Valle, T., et al. (1998). "Mapping genes for NIDDM. Design of the Finland-United States Investigation of NIDDM Genetics (FUSION) Study." Diabetes Care 21(6): 949-958; Scott, L et al. A genome-wide association study of type 2 diabetes in Finns detects multiple susceptibility variants. Science 316 (5829), 1341-1345 (2007) |
| Female (number with clone) | 213 (11) | 201 (10) | | | |
| Mean age (SD) | 63 (7.2) | 58 (8.0) | | | |
| Mean BMI (SD) | 28 (3.9) | 31 (5.5) | | | |
| KORA | | | | | |
| Overall (number with clone) | 91 (11) | 97 (6) | | KORA is a regional research platform for population-based studies, subsequent follow-up studies and family studies, established in 1996. Cases and controls were all of German ancestry. Cases were identified by self report of T2D in a personal interview which was validated by a questionnaire mailed to the treating physician and/or by medical chart review. Controls were non-diabetic as defined by self-report. | Wichmann, H. E., et al. (2005). "KORA-gen- resource for population genetics, controls and a broad spectrum of disease phenotypes." Gesundheitswesen 67 Suppl 1: S26-30. |
| Female (number with clone) | 58 (9) | 43 (3) | | | |
| Mean age (SD) | 70 (5.6) | 61 (8.1) | | | |
| Mean BMI (SD) | 35 (3.5) | 28 (2.8) | | | |
| MPP (Malmo Preventive Project) | | | | | |
| Overall (number with clone) | 222 (14) | 110 (8) | | The MPP was started in the early 1970's as a screening survey in the middle-aged population of Malmö, the third largest city of Sweden. Subjects born in Malmö and residents of the city were invited for a clinical examination, questionnaire and blood sampling. In all 22,444 men and 10,902 women participated during the period 1974-1992. Cases and controls were selected as for Botnia. | Berglund, G., et al. (2000). "Long-term outcome of the Malmo preventive project: mortality and cardiovascular morbidity." J Intern Med 247(1): 19-29. |
| Female (number with clone) | 87 (7) | 51 (5) | | | |
| Mean age (SD) | 68 (5.2) | 47 (6.1) | | | |
| Mean BMI (SD) | 36 (1.8) | 23 (1.4) | | | |
| STT (UKT2D Consortium, Controls) | | | | | |
| Overall (number with clone) | 319 (14) | * | | Non-diabetic controls selected from the Twins UK Study. A twin pair was considered for selection if there was no recorded family history of diabetes, neither twin was ever recorded as impaired glucose tolerant, there were available quantitative trait and genetic data, and no evidence of admixture. From set of qualifying twin pairs, the best control twin was selected from each pair with the lowest ratio of fasting glucose level to BMI across al: readings. | Moayyeri, A., et al. (2013). "The UK Adult Twin Registry (TwinsUK Resource)." Twin Res Hum Genet 16(1): 144-149. |
| Female (number with clone) | 265 (11) | * | | | |
| Mean age (SD) | 61 (10) | * | | | |
| Mean BMI (SD) | 31 (5.9) | * | | | |

SUPPLEMENTARY TABLE S1-continued

Cohort descriptions and baseline characteristics

SIGMA

MEC (Multiethnic cohort, Hispanics in Los Angeles)

| | | | | | |
|---|---|---|---|---|---|
| Overall (number with clone) | 445 (24) | 496 (27) | Survival, malignancy, cardio- vascular events | The MEC consists of 215,251 men and women in Hawai'i and Los Angeles. Those self-identified as Latinos were used for sequencing in a prior study. Between 1993 and 1996, adults between 45 and 75 years old were enrolled. Potential cohort members were identified through Department of Motor Vehicles drivers' license files, voter registration files and Health Care Financing Administration data files. Between 1995 and 2004, blood specimens were collected from ~67,000 MEC participants. Controls were frequency matched to cases on sex, ethnicity and age at entry into the cohort (5-year age groups) and place of birth (U.S. vs. Mexico, South or Central America). Persons in the cohort who develop cancer are identified through Surveillance, Epidemiology, and End Results (SEER) Program registries that have been established by state statute in Hawai'i and California . . . | Kolonel LN, Henderson BE, Hankin JH, Nomura AM, Wilkens LR, et al. (2000) A multiethnic cohort in Hawai and Los Angeles: baseline characteristics. Am J Epidemiol 151: 346-357. |
| Female (number with clone) | 228 (13) | 263 (14) | | | |
| Mean age (SD) | 68 (7.2) | 68 (7.3) | | | |
| Mean BMI (SD) | 27 (4.3) | 30 (5.7) | | | |

MexB1 (UNAM/ INCMNSZ Diabetes Study)

| | | | | | |
|---|---|---|---|---|---|
| Overall (number with clone) | 543 (7) | 550 (20) | | Cases were recruited at the outpatient diabetes clinic of the Department of Endocrinology and Metabolism of the Instituto Nacional de Ciencias Médicas y Nutrición Salvador Zubirán (INCMNSZ). All Mexican-mestizo individuals were invited to participate in the study. Control subjects were recruited from a cohort of adults aged 45 years or older among government employees, blue collar workers and subjects seeking for attention in medical units for any condition besides those considered as exclusion criteria (diabetes, coronary heart disease, stroke, transient ischemic attack, lower limb amputations, alcoholism (more than 10 servings of alcohol per week) or any disease that in opinion of the researcher may limit life expectancy to less than 2 years). Diagnosis of type 2 diabetes was done following the American Diabetes Association (ADA) criteria | SIGMA T2D Consortium, et al. (2014). "Sequence variants in SLC16A11 are a common risk factor for type 2 diabetes in Mexico." Nature 506 (7486): 97-101. |
| Female (number with clone) | 336 (6) | 326 (13) | | | |
| Mean age (SD) | 55 (9.4) | 55 (13) | | | |
| Mean BMI (SD) | 28 (3.8) | 28 (4.4) | | | |

MexB2 (Diabetes in Mexico Study)

| | | | | | |
|---|---|---|---|---|---|
| Overall (number Study) with clone) | 177 (3) | 393 (11) | | Individuals were recruited from two tertiary level institutions (IMSS and ISSSTE) located in Mexico City. Unrelated healthy subjects older than 45 years and with fasting glucose levels below 100 mg/dL were classified as controls. Unrelated individuals, older than 18 years, with either previcus T2D diagnosis or fasting glucose levels above 125 mg/dL were included as T2D cases. | SIGMA T2D Consortium, et al. (2014). "Sequence varants in SLC16A11 are a common risk factor for type 2 diabetes in Mexico." Nature 506 (7486): 97-101. |
| Female (number with clone) | 134 (3) | 275 (9) | | | |
| Mean age (SD) | 56 (99) | 57 (12) | | | |
| Mean BMI (SD) | 28 (4.6) | 29 (5.5) | | | |

SUPPLEMENTARY TABLE S1-continued

Cohort descriptions and baseline characteristics

MexB3 (Mexico City Diabetes Study)

| | | | | |
|---|---|---|---|---|
| Overall (number with clone) | 550 (23) | 281 (9) | The Mexico City Diabetes Study is a population based prospective investigation. All 35-64 neighborhoods equivalent to 6 census tracks with a total population of 15,000 imabitants) were interviewed and invited to participate in the study. There was a response rate of 67% for the initial exam. Diagnostic criteria for type 2 diabetes were recommended by the ADA. | SIGMA T2D Consortium, et al. (2014). "Sequence variants in SLC16A11 are a common risk factor for type 2 diabetes in Mexico." Nature 506 (7486): 97-101. |
| Female (number with clone) | 334 (14) | 154 (3) | | |
| Mean age (SD) | 62 (7.6) | 64 (7.5) | | |
| Mean BMI (SD) | 29 (4.8) | 30 (5.5) | | |

T2D-GENES

AW (Wake Forest School of Medicine Study)

| | | | | |
|---|---|---|---|---|
| Overall (number with clone) | 531 (18) | 529 (48) | Cases are self-reported diabetics with diabetic nephropathy, recruited from dialysis clinics with age of onset ≥ 25. Controls were recruited from community and internal medicine clinics and had o current diagnosis of diabetes or renal disease. | Palmer, N. D. et al. A genome-wide association search for type 2 diabetes genes in African Americans. PLoS One 7:e29202. (2012) |
| Female (number with clone) | 300 (9) | 317 (28) | | |
| Mean age (SD) | 51 (12) | 64 (9.1) | | |
| Mean BMI (SD) | 30 (7.0) | 29 (6.6) | | |

EK (Korea Association Research Project)

| | | | | |
|---|---|---|---|---|
| Overall (number with clone) | 554 (33) | 521 (10) | Cases selected for age of onset of T2D ≥ 40 years. Participants with early onset T2D and family history were prioritized. Controls were selected for not having current or past diabetes and no diabetic medications. Older subjects with normal glucose were prioritized. | Cho. Y. S. et al. A large-scale genome-wide association study of Asian populations uncovers genetic factors influencing eight quantitative traits. Nat. Genet. 41, 527-534 (2009) |
| Female (number with clone) | 324 (18) | 237 (4) | | |
| Mean age (SD) | 63 (3.6) | 54 (7.5) | | |
| Mean BMI (SD) | 24 (3.1) | 26 (3.3) | | |

Study and Singapore Prospective Study Program

| | | | | |
|---|---|---|---|---|
| Overall (number with clone) | 592 (25) | 476 (24) | Cases were clinicaly ascertained T2D from primary care clinics. Individuals with early age of diagnosis and with at least one first degree relative with T2D were preferentialy selected. Controls were defined as: fasting blood glucose < 6 mmol/l, no personal history of diabetes, and no anti-diabetic medication. Older controls preferentially selected. | Sim, X. et al. Transferability of type 2 diabetes implicated loci in multi-ethnic cohorts from Southeast Asia. PLoS Genet. 7(4), e1001363 (2011) |
| Female (number with clone) | 363 (11) | 250 (11) | | |
| Mean age (SD) | 58 (7.0) | 58 (9.3) | | |
| Mean BMI (SD) | 23 (3.4) | 26 (3.8) | | |

SUPPLEMENTARY TABLE S1-continued

Cohort descriptions and baseline characteristics

HA (Hispanics from San Antonio Family Heart Study, San Antonio Family Diabetes/Gallbladder Study, Veterans Administration Genetic Epidemiology Study, and the Investigation of Nephropathy and Diabetes Study family component)

| | | | | |
|---|---|---|---|---|
| Overall (number with clone) | 142 (3) | 111 (6) | Cases were drawn from four separate family studies and met the following criteria: ADA 2002 criterion, WHO 1999 criteria, or physician reported diangosis with current medical therapy. Controls defined by not having fasting glucose < 126 mg/dL at each visit and no history of prior diabetic medication. | Mitchell, B. D. et al. Genetic and environmental contributions to cardiovascular risk factors in Mexican Americans. The San Antonio Family Heart Study. Circulation 94, 2159-2170 (1996); Hunt, K. J. et al. Genome wide linkage analyses of type 2 diabetes in Mexican Americans: the San Antonio Family Diabetes/Gallbladder Study. Diabetes 54, 2655-2662 (2005); Coletta, D. K. et al. Genome-wide linkage scan for genes influencing plasma triglyceride levels in the Veterans Administration Genetic Epidemiology Study. Diabetes 58, 279-284 (2009); Knowler, W. C. et al. The Family Investigation of Nepropathy and Diabetes (FIND): design and methods. J. Diabetes Complicat. 19, 1-9 (2005) |
| Female (number with clone) | 90 (1) | 62 (4) | | |
| Mean age (SD) | 44 (14) | 51 (12) | | |
| Mean BMI (SD) | 30 (5.5) | 33 (6.3) | | |

HS (Hispanics in Starr County, Texas)

| | | | | |
|---|---|---|---|---|
| Overall (number with clone) | 704 (3) | 751 (32) | Cases defined by fasting glucose ≥ 140 mg/dl on more than 1 occasion or self-reported physician-diagnosed diabetes with current medical therapy. In instances where cases were drawn from families, the individual with youngest age at onset was chosen. Controls ascertained from epidemiologically represented sample of individuals in Starr County, TX with individuals with known diagnosis of diabetes excluded. Controls are significantly younger on average. | Han's, C. L. et al. Diabetes among Mexican Americans in Star: County, Texas. Am. J. Epidemiol. 118, 659-672 (1983); Below JE, et al. Genome-wide association and meta-analysis in populations From Start County, Texas and Mexico City identify type 2 diabetes susceptibility loci and enrichment for eQTLs in top signals. Diabetologia 54, 2047-2055 (2011) |
| Female (number with clone) | 506 (3) | 449 (15) | | |
| Mean age (SD) | 39 (9.9) | 56 (12) | | |
| Mean BMI (SD) | 30 (6.2) | 32 (6.4) | | |

SUPPLEMENTARY TABLE S1-continued

Cohort descriptions and baseline characteristics

SL (London
Life Sciences
Population Study
[UK Indian
Asians])

| | | | | | |
|---|---|---|---|---|---|
| Overall (number with clone) | 538 (24) | 531 (16) | | A population-based cohort study of Indian Asians living in West London, UK with all 4 grandparents born on the Indian subcontinent Prevalent T2D defined as previous physician diagnosis of diabetes on treatment, with onset of diabetes after the age of 18 years and without insulin use in the first year after diagnosis; or fasting plasma glucose > 7.0 mmol/ L. Controls defined as no previous history of diabetes, no anti-diabetic medication, and fasting plasma glucose < 6.0 mmol/L. | Chambers, J.C. et al. Genome-wide association study identifies variants in TMPRSS6 associated with hemoglobin levels. Nat. Genet. 41, 1170-1172 (2009); Chambers, J.C. et al. Common genetic variation near melatonin receptor MTNR1B contributes to raised plasma glucose and increased risk of type 2 diabetes among Indian Asians and European Caucasians. Diabetes 58, 2703-2708 (2009): van der Harst, P. et al. Seventy-five genetic loci influencing the human red blood cell. Nature 492, 369-375(2012) |
| Female (number with clone) | 85 (4) | 75 (2) | | | |
| Mean age (SD) | 63 (9.2) | 53 (5.6) | | | |
| Mean BMI (SD) | 27 (3.5) | 27 (2.9) | | | |

SS (Singapore
Indian Eye Study
[Singapore
Indians])

| | | | | | |
|---|---|---|---|---|---|
| Overall (number with clone) | 585 (15) | 563 (31) | | Cases selected for HbA1c > 6.5% or personal history of diabetes with age at diagnosis available. Preferentially selected cases with at least one first degree relative with T2D. Controls selected for HbA1c < 6%, no personal history of diabetes, and not taking ant diabetes medication. Older controls preferemially selected. | Sim, X et al. Transferability of type 2 diabetes implicated loci in multi-ethnic cohorts from Southeast Asia. PLoS Genet. 7(4), e1001363 (2011) |
| Female (number with clone) | 28 (5) | 250 (14) | | | |
| Mean age (SD) | 56 (10) | 61 (9.7) | | | |
| Mean BMI (SD) | 25 (4.3) | 27 (5.1) | | | |

UA
(Ashkenazis)

| | | | | | |
|---|---|---|---|---|---|
| Overall (number with clone) | 342 (42) | 506 (49) | Survival, blood counts | Subjects in this cohort are of Ashkenazi Jewish having all four grandparents crigin, defined as born in Northern of Eastern Europe; subjects with known or supected Sephardic Jewish or non-Jewish ancestry excluded. T2D cases were selected from two separate DNA collections: 1. Genome-wide, affected- sibling-pair linkage study (Permutt et al. Diabetes 2001) or 2. Study to determine genetic risk for diabetic complications (Blech et al. PLoS One 2011). Controls were selected for fasting blood glucose < 7 mmol/l, no personal history of diabetes, and no anti-diabetic medications. Controls included elderly (>90 years) individuals who were part of the Longevity Genes Project. | Atzmon, G. et al. Lipoprotein genotype and conserved pathway for exceptional longevity in humans. PLoS Biol. 4(4), e113 (2006); Atzmon, G. et al. Evolution in health and medicine Sackler colloquium: Genetic variation in human telomerase is associated with telomere length in Ashkenazi centenarians. Proc Natl Acad Sci USA. 107 (Suppl 1), 1710- 1717 (2010); Permutt, M.A. et al. A genome scan for type 2 diabetes susceptibility loci in a genetically isolated population. Diabetes 50 (3), 681-685 (2001); Blech et al. Predicting diabetic nephropathy using a multifactorial genetic model. PLOS One 6(4), e18743 (2011) |
| Female (number with clone) | 195 (20) | 242 (18) | | | |
| Mean age (SD) | 79 (13) | 66 (8.6) | | | |
| Mean BMI (SD) | 25 (4.3) | 27 (3.2) | | | |

SUPPLEMENTARY TABLE S1-continued

Cohort descriptions and baseline characteristics

UM (Metabolic Syndrome in Men Study)

| | | | | |
|---|---|---|---|---|
| Overall (number with clone) | 500 (9) | 487 (24) | The METSIM Study includes 10,197 men, aged from 45 to 73 years, randomly selected from the population register of the town of Kuopio, Eastern Finland, and examined in 2005-2010. The aim of the study is to investigate genetic and non-genetic factors associated with the risk of type 2 diabetes (T2D), cardiovascular disease (CVD), and insulin resistance-related traits in a cross-sectional and longitudinal setting. Unrelated T2D cases with family history of diabetes were selected. Unrelated NGT controls were selected, prioritizing older individuals with no family history of diabetes. | Stancakova, A. et al. Changes in insulin sensitivity and insulin release in relation to glycemia and glucose tolerance in 6,414 Finnish men. Diabetes 58, 1212-1221 (2009) |
| Female (number with clone) | * | * | | |
| Mean age (SD) | 55 (4.6) | 60 (6.7) | | |
| Mean BMI (SD) | 26 (3.2) | 31 (5.1) | | |

SUPPLEMENTARY TABLE S2

List of hematopoietic genes and variants queried

| Gene name | Reported mutations used for variant calling | Accession | Number of variants found |
|---|---|---|---|
| ARID1A | Frameshift/nonsense, A305V, M872T | NM_006015 | 0 |
| ASXL1 | Frameshift/nonsense in exon 11-12 | NM_015338 | 62 |
| BCL10 | Frameshift/nonsense/splice-site | NM_003921 | 0 |
| BCL11B | Frameshift/nonsense/splice-site, A360T, C432Y, H445Y, R447H, G452K, H479Y, G596S, L617Q, G847R | NM_138576 | 1 |
| BCL6 | R40H, Y111H, P341H, S350L, R585W, Q679K | NM_001130845 | 0 |
| BCOR | Frameshift/nonsense/splice-site | NM_001123385 | 4 |
| BCORL1 | Frameshift/nonsense/splice-site | NM_021946 | 2 |
| BIRC3 | Frameshift/nonsense/splice-site exon 2 | NM_182962 | 1 |
| BRAF | G464E, G464V, G466E, G466V, G469R, G469E, G469A, G469V, V471F, V472S, N581S, I582M, I592M, I592V, D594N, D594G, D594V, D594E, F595L, F595S, G596R, L597V, L597S, L597Q, L597R, A598V, V600M, V600L, V600K, V600R, V600E, V600A, V600G, V600D, K601E, K601N, R603*, W604R, W604G, S605G, S605F, S605N, G606E, G606A, G606V, H608R, H608L, G615R, S616P, S616F, L618S, L618W | NM_00433 | 2 |
| BRCC3 | Frameshift/nonsense/splice-site | NM_024332 | 6 |
| BTG1 | M1I, H2Y, P3R, Y5H, M11I, S23A, F25C, R27H, K29Q, L31F, Q36H, L37M, Q38E, F40C, E46D, E46Q, A49P, P58L, E59D, L94V, I115V, E117D, N165S | NM_001731 | 0 |
| BTG2 | A45T, A45E | NM_006763 | 0 |
| CARD11 | E93D, G123S, G126D, T128M, F130I, R179W, K182N, M183L, K215M, D230N, L232LI, M240MGLNKM, K244T, S250P, S250P, L251P, L251P, V266*, D338G, T353*, D357V, Y361H, M365K, D387V, D401V, R418S, R423W, E432K, E626K | NM_032415 | 1 |
| CBL | RING finger missense p.381-421 | NM_005188 | 12 |
| CBLB | RING finger missense p.372-412 | NM_170662 | 0 |
| CCND3 | Frameshift/nonsense/splice-site, T211A, P212L, V215G | NM_001760 | 0 |
| CD58 | Frameshift/nonsense/splice-site, G210C, G210S | NM_001779 | 1 |
| CD70 | L60R, G66R, F186S | NM_001252 | 0 |
| CD79A | del191-226, del179-226, del191-208 | NM_001783 | 0 |
| CD79B | V9A, D89G, Y92F, D193G, D194G, Y196C, Y197C, Y197D, Y197H, T207fs, Y208*, V212A, del195_197, del196_229, del193_229, del205_229 | NM_000626 | 1 |
| CDKN2A | Frameshift/nonsense/splice-site | NM_000077 | 0 |
| CDKN2B | Frameshift/nonsense/splice-site | NM_004936 | 0 |
| CEBPA | Frameshift/nonsense/splice-site | NM_004364 | 0 |
| CHD2 | H620L, F1146L, L1270F | NM_001271 | 0 |
| CNOT3 | Frameshift/nonsense, E20K, R57W, R57Q, E70K | NM_014516 | 1 |
| CREBBP | Frameshift/nonsense/splice-site, D1435E, R1446L, R1446H, R1446C, Y1450C, P1476R, Y1482H, H1487Y, W1502C, Y1503D, Y1503H, Y1503F, S1680del | NM_004380 | 6 |
| CRLF2 | F232C | NM_022148 | 0 |
| CSF1R | L301F, L301S, Y969C, Y969N, Y969F, Y969H, Y969D | NM_005211 | 0 |
| CSF3R | T615A, T618I, truncating c.741-791 | NM_000760 | 0 |
| CTCF | Frameshift/nonsense, R377C, R377H, P378A, P378L | NM_006565 | 0 |
| CUX1 | Frameshift/nonsense | NM_181552 | 3 |
| DDX3X | R276K, R376S, R376C, D506Y, R528C, R528H, R534S, R534H, P568L | NM_001356 | 2 |

SUPPLEMENTARY TABLE S2-continued

List of hematopoietic genes and variants queried

| Gene name | Reported mutations used for variant calling | Accession | Number of variants found |
|---|---|---|---|
| DIS3 | R780K, R780T, R780H, R780S, D488H, P480Q, D488N, S477R, R467Q, M662R, R689Q, R514K, R382Q | NM_014953 | 0 |
| DNMT3A | Frameshift/nonsense/splice-site, P307S, P307R, R326H, R326L, R326C, R326S, R366P, R366H, R366G, A368T, F414L, F414S, F414C, C497Y, Q527H, Q527P, Y533C, G543A, G543S, G543C, L547H, L547P, L547F, M548I, M548K, G550R, W581R, W581G, W581C, G646V, G646E, L653W, L653F, V657A, V657M, R659H, Y660C, R676W, R676Q, G685R, G685E, G685A, D686Y, D686G, G699R, G699S, G699D, P700S, P700R, P700Q, D702N, D702Y, V704M, V704G, I705F, I705T, I705S, C710S, S714C, N717S, N717I, P718L, R720H, R720G, Y724C, R729Q, R729W, R729G, F731L, F732del, F732S, F732L, F734L, F734C, Y735C, Y735N, Y735S, R736H, R736C, R736P, L737H, L737V, L737F, L737R, A741V, R749C, R749L, F751L, F752del, F752C, F752L, F752I, F752V, L754R, L754H, F755S, F755I, F755L, M761I, M761V, G762C, S770W, S770P, R771Q, F772I, F772V, L773R, E774K, E774D, D781G, R792H, G796V, G796N, N797Y, N797H, P799R, P799H, R803S, P804S, P804L, S828N, K829R, Q842E, P849L, D857N, W860R, F868S G869S, G869V, M880V, S881R, S881I, R882H, R882P, R882C, R882G, Q886P, G890D, L901R, L901H, P904L, F909C, A910P | NM_022552 | 403 |
| EBF1 | Frameshift/nonsense, M1R, S7G, F54S, G143V, G171D, Q196P, N237K, S238T, S238Y, R381S | NM_024007 | 0 |
| EED | Frameshift/nonsense/splice-site, L240Q, I363M | NM_C03797 | 0 |
| EP300 | Frameshift/nonsense/splice_site, VF1148_1149del, D1399N, D1399Y, P1452L, Y1467N, Y1467H, Y1467C, R1627W, A1629V | NM_001429 | 1 |
| ETV6 | Frameshift/nonsense/splice-site | NM_001987 | 1 |
| EZH2 | Frameshift/nonsense/splice-site, Q62R, N102S, F145S, F145C, F145Y, F145L, G159R, E164D, R202Q, K238E, E244K, R283Q, H232R, P488S, R497Q, R561H, T568I, K629E, Y641N, Y641H, Y641S, Y641C, Y641F, D659Y, D659G, V674M, A677G, A677V, R679C, R679H, R685C, R685H, A687V, N688I, N688K, H689Y, S690P, I708V, I708T, I708M, E720K, E740K | NM_001203247 | 2 |
| EZR | I245M | NM_003379 | 0 |
| FAM46C | Frameshift/nonsense/splice-site | NM_017709 | 1 |
| FAS | Frameshift/nonsense/splice-site | NM_000043 | 0 |
| FBX011 | Frameshift/nonsense/splice-site | NM_001190274 | 0 |
| FBXW7 | Frameshift/nonsense/splice-site, E74A, D101V, F280L, R465H, R505C, C597E, R1165Q | NM_033632 | 1 |
| FLT3 | V579A, V592A, V592I, F594L, M737I, FY590-591GD, D835Y, D835H, D835E, del835 | NM_004119 | 1 |
| FOXP1 | Frameshift/nonsense/splice-site | NM_032682 | 1 |
| FYN | L174R, R176C, Y531H | NM_002037 | 0 |
| GATA1 | Frameshift/nonsense/splice-site | NM_002049 | 0 |
| GATA2 | Frameshift/nonsense/splice-site, R293Q, N317H, A318T, A318V, A318G, C320D, L321P, L321F, L321V, Q328P, R330Q, R361L, L359V, A372T, R384G, R384K | NM_001145661 | 0 |
| GATA3 | Frameshift/nonsense/spice-site ZNF domain, R276W, R276Q, N286T, L348V, | NM_001002295 | 0 |
| GNA13 | I34T, G57S, S62F, M68K, Q134R, Y145F, L152F, E167D, Q169H, R264H, E273K, V322G, Y362G, L371F | NM_006572 | 0 |
| GNAS | R201 (844)S, R201(844)C, R201(844)H, R201(844)L, Q227(870)K, Q227(370)R, Q227(870)L, Q227(870)H, R374(1017)C | NM_016592 | 8 |
| GNB1 | K57N, K57M, K57E, K57T, I80T, I80N | NM_002074 | 22 |
| HIST1H1B | S89N, S89R, G101D, G73A, K84N, A123D | NM_005322 | 0 |
| HIST1H1C | P118S, P129A, K156R, K187R, K/G81/83N/A | NM_005319 | 1 |
| HIST1H1D | Frameshift/nonsense | NM_005320 | 0 |
| HIST1H1E | A158T, P196S, K202E, K205R | NM_005321 | 0 |
| HIST1H3B | A48S, S87N, S87T | NM_003537 | 0 |
| HLA-A | Frameshift/nonsense, G124D, A164T | NM_002116 | 0 |
| ID3 | Frameshift/nonsense/splice-site, S39R, V55Q, P56S, L64F, S65R, I74V, L80R, H96R, | NM_002167 | 0 |
| IDH1 | R132C, R132G, R132H, R132L, R132P, R132V, V178I | NM_005896 | 0 |
| IDH2 | R140W, R140Q, R140L, R140G, R172W, R172G, R172K, R172T, R172M, R172N, R172S | NM_002168 | 3 |
| IKBKB | K171E | NM_001556 | 0 |
| IKZF1 | Frameshift/nonsense | NM_006060 | 1 |
| IKZF2 | Frameshift/nonsense | NM_016260 | 0 |
| IKZF3 | Frameshift/nonsense | NM_012481 | 0 |
| IL7R | exon 6 cysteine insertion | NM_002185 | 0 |
| INTS12 | M445I | NM_020395 | 0 |
| IRF4 | N2S, S18T, I32V, L40V, Q60K, Q60H | NM_002460 | 0 |
| IRF8 | Frameshift/ nonsense from c.377-426, S34T, S55A, T80A, K108E, | NM_002163 | 0 |
| JAK1 | T478A, T478S, V623A, A634D, L653F, R724H, R724Q, R782M, L783F | NM_002227 | 0 |
| JAK2 | N533D, N533Y, N533S, H538R, K539E, K539I, I540T, I540V, V617F, R683S, R583G, del/ins537-539L, del/ins538-539L, del/ins540-543MK, del/ins540-544MK, del/ins541-543K, del542-543, del543-544, ins11546-547 | NM_004972 | 31 |

SUPPLEMENTARY TABLE S2-continued

List of hematopoietic genes and variants queried

| Gene name | Reported mutations used for variant calling | Accession | Number of variants found |
|---|---|---|---|
| JAK3 | M511T, M511I, A572V, A572T, A573V, R657Q, V715I, V715A | NM_000215 | 1 |
| JARID2 | Frameshift/nonsense/splice-site | NM_004973 | 1 |
| KDM6A | Frameshift/nonsense/splice-site, del419 | NM_021140 | 2 |
| KIT | ins503, V559A, V559D, V559G, V559I, V560D, V560A, V560G, V560E, del560, E561K, del579, P627L, P627T, R634W, K642E, K642Q, V654A, V654E, H697Y, H697D, E761D, K807R, D816H, D816Y, D816F, D816I, D816V, D816H, del551-559 | NM_000222 | 1 |
| KLHL6 | F49L, L58P, T64S, T64I, L65V, L65P, Q81, L90V, R98T, R98W | NM_130446 | 1 |
| KRAS | G12D, G12A, G12E, G12V, G13D, G13C, G13Y, C13F, G13R, G13A, G13V, G13E, I58I, G60D, G60A, G60V, Q61K, Q61E, Q61P, Q61R, Q61L, Q61H, K117E, K117N, A146T, A146P, A146V | NN_033360 | 3 |
| LEF1 | Frameshift/nonsense | NM_016269 | 0 |
| LRRK2 | E155K, I543S | NM_198578 | 0 |
| LTB | Frameshift/nonsense | NM_002341 | 0 |
| LUC7L2 | Frameshift/nonsense/splice-site | NM_016019 | 3 |
| MALT1 | V381F, Y750S | NM_006785 | 0 |
| MAP2K1 | F53L, Q56P, K57T, K57N, K57E, I103N, C121S, N122D, P124Q | NM_002755 | 0 |
| MAP3K14 | H683Q | NM_003954 | 0 |
| MED12 | E33K, L36P, G44S, A59P, R521H, L1224F | NM_005120 | 0 |
| MEF2B | Frameshift/nonsense/splice-site, I8F, L67R, Y69C, Y69H, E77K, N81K, N81Y, D83V, D83A | NM_001145785 | 0 |
| MLL | Frameshift/nonsense | NM_005933 | 0 |
| MLL2 | Frameshift/nonsense | NM_003482 | 4 |
| MPL | S505G, S505N, S505C, L510P, del513, W515A, W515R, W515K, W515S, W515L, A519T, A519V, Y591D, W515-518KT | NM_005373 | 2 |
| MXRA5 | Frameshift/nonsense/splice-site | NM_015419 | 0 |
| MYD88 | V217F, S219C, M240T, S251N, P266, L273P | NM_001172567 | 2 |
| NOTCH1 | Frameshift/nonsense | NM_017617 | 2 |
| NOTCH2 | Frameshift/nonsense | NM_024408 | 2 |
| NPM1 | Frameshift p.W288fs (insertion at c.859 860, 860 861, 862 863, 863 864) | NM_002520 | 0 |
| NRAS | G12S, G12R, G12C, G12N, G12P, G12Y, G12D, G12A, G12V, G12E, G13S, G13R, G13C, G13N, G13P, G13Y, G13D, G13A, G13V, G13E, G60E, G60R, Q61R, Q61L, Q61K, Q61P, Q61H, Q61Q | NM_002524 | 6 |
| P2RY8 | M52K, Y82C, R86C, A142S, C144Y, M189I, A251T, N254S, F255I, V256M | NM_178129 | 0 |
| PAPDS | Frameshift/nonsense | NM_001040284 | 0 |
| PAX5 | Frameshift/nonsense/splice-site, S66N, P80R, | NM_016734 | 0 |
| PDS5B | Frameshift/nonsense/splice-site, R1292Q | NM_015032 | 0 |
| PDSS2 | Frameshift/nonsense | NM_020381 | 1 |
| PHF6 | Frameshift/nonsense/splice-site, A40D, M125I, S246Y, F263L, R274Q, C297Y, H302Y, H329L | NM_001015877 | 1 |
| PIK3CA | I543V, Q545G, G1007D, L1026P, M1040I, D1045N, H1047R | NM_006218 | 1 |
| POT1 | Frameshift/nonsense/splice-site before OB domain (c.274), M1L, Y36N, K90E, Q94R, Y223C, H266L, G272V, C591W | NM_015450 | 0 |
| POU2AF1 | P27A | NM_006235 | 0 |
| POU2F2 | T223A, T223S, T239S, R282H, T307I, G392R | NM_002698 | 0 |
| PRDM1 | Frameshift/nonsense/splice-site | NM_001198 | 3 |
| PRPF40B | Frameshift/nonsense/splice-site, P15H, M58I, P405L, P562S, | NM_001031698 | 1 |
| PRPF8 | M1307I | NM_006445 | 0 |
| PTEN | Frameshift/nonsense/splice-site, D24G, R47G, F56V, L57W, H61R, K66N, Y68H, C71Y, F81C, Y88C, D92G, D92V, D92E, H93Y, H93D, H93Q, N94I, P95L, I101T, C105F, C105S, D107Y, L112V, H123Y, C124R, C124S, K125E, A126D, K128N, R130G, R130Q, R130L, G132D, I135V, I135K, C136R, C136F, K144Q, A151T, D153Y, D153N, Y155H, Y155C, R159K, R159S, R161K, R161I, G165R, G165E, S170N, S170I, R173C, Y174D, Y177C, H196Y, R234W, G251C, D252Y, F271S, D326G | NM_000314 | 0 |
| PTPN1 | exon 1 frameshift/nonsense, Q9E | NM_002827 | 0 |
| PTPN11 | G60V, G60R, G60A, D61Y, D61V, D61G, Y63C, E69K, E69G, E69D, E69Q, F71L, F71K, A72V, A72T, A72L, T73I, E76K, E76Q, E76M, E76A, E76G, E139G, E139D, N308D, N308T, N339S, P491S, S502P, S502A, S502L, G503V, G503G, G503A, G503E, Q506P, T507A, T507K | NM_002834 | 3 |
| RAD21 | Frameshift/nonsense/splice-site, R65Q, H208R, Q474R | NM_006265 | 6 |
| RBBP4 | E330K | NM_005610 | 0 |
| RHOA | C16R, G17V, G17E, T19I, D120Y | NM_001664 | 0 |
| RIT1 | Frameshift/nonsense, Q79, E81Q, E81G, F82L, F82C, F82I, F82V, M90I, R122L | NM_006912 | 1 |
| RPL10 | R98S, Q123P | NM_006013 | 0 |
| RPL5 | Frameshift/nonsense/splice-site, Q63R | NM_000969 | 0 |
| RPS15 | G132S, A135V, A135G, S139A, K145N | NM_001018 | 1 |
| RPS2 | R200G | NM_002952 | 0 |
| RUNX1 | Frameshift/nonsense/splice-site, S73F, H78Q, H78L, R80C, R80P, R80H, L85P, P86L, P86H, S114L, D133Y, L134P, R135G, R135K, R135S, R139Q, R142S, A165V, R174Q, R177L, R177Q, A224T, D171G, D171V, D171N, R205W, R293Q | NM_001001890 | 0 |

SUPPLEMENTARY TABLE S2-continued

List of hematopoietic genes and variants queried

| Gene name | Reported mutations used for variant calling | Accession | Number of variants found |
|---|---|---|---|
| SETBP1 | D868N, D868T, S869N, G870S, I871T, D880N, D880Q | NM_015559 | 0 |
| SETD2 | Frameshift/nonsense, V1190M | NM_014159 | 4 |
| SETDB1 | Frameshift/nonsense, K715E | NM_001145415 | 1 |
| SF1 | Frameshift/nonsense/splice-site, T454M, T474A, Y476C, A508G | NM_004630 | 2 |
| SF3A1 | Frameshift/nonsense/splice-site, A57S, M117I, K166T, Y271C | NM_005877 | 1 |
| SF3B1 | G347V, R387W, R387Q, E592K, E622D, Y623C, R625L, R625C, H662Q, H662D, K666N, K666T, K666E, K666R, K700E, V701F, A708T, G740R, G740E, A744P, D781G, E783K | NM_012433 | 27 |
| SFRS2 | Y44H, P95H, P95L, P95T, P95R, P95A, P107H, P95fs | NM_003016 | 11 |
| SGK1 | Frameshift/nonsense/splice-site | NM_001143676 | 0 |
| SMC1A | K190T, R586W, M689V, R807H, R1090H, R1090C | NM_006306 | 1 |
| SMC3 | Frameshift/nonsense, R155I, Q367E, D392V, K571R, R661P, G662C | NM_005445 | 1 |
| SOCS1 | Frameshift/nonsense/splice-site, R48W | NM_003745 | 0 |
| SPRY4 | I113N, G117R | NM_001127496 | 0 |
| STAG1 | Frameshift/nonsense/splice-site, H1085Y | NM_005862 | 1 |
| STAG2 | Frameshift/nonsense/splice-site | NM_006603 | 1 |
| STAT3 | M206K, G618R, Y640F, N642H, N647I, D661N, D661H, D661Y, D661V | NM_139276 | 4 |
| STAT5A | N642H | NM_003152 | 0 |
| STAT5B | N642H, Y665F | NM_012448 | 0 |
| STAT6 | N417Y, N417S, D419H, D419G, D419V, N421K, N430T, N430S | NM_001178081 | 0 |
| SUZ12 | Frameshift/nonsense | NM_015355 | 1 |
| SWAP70 | Frameshift/nonsense/splice-site | NM_015055 | 0 |
| TBL1XR1 | Frameshift/nonsense/splice-site | NM_024665 | 1 |
| TCF3 | N551K, V557E, V557G, D561E, D561V, D561N, M572K | NM_003200 | 0 |
| TET1 | Frameshift/nonsense/splice-site, V128F, H1297Y, R1656C, V2120M, | NM_030625 | 1 |
| TET2 | Frameshift/nonsense/splice-site, S282F, N312S, L346P, S460F, D666G, P941S, C1135Y | NM_001127208 | 72 |
| TMEM30A | Frameshift/nonsense | NM_018247 | 0 |
| TNF | L47F, H52Y, P58S | NM_000594 | 0 |
| TNFAIP3 | Frameshift/nonsense, D117V, M476I, P574L | NM_006290 | 3 |
| TNFRSF14 | Frameshift/nonsense/splice-site, Y26N, Y26D, C42P, C42W, A102P | NM_003820 | 2 |
| TP53 | Frameshift/nonsense/splice-site, S46F, G105C, G105R, G105D, G108S, G108C, R110L, R110C, T118A, T118R, T118I, K132Q, K132E, K132W, K132R, K132M, K132N, C135W, C135S, C135F, C135G, Q136K, Q136E, Q136P, Q136R, Q136L, Q136H, A138P, A138V, A138A, A138T, T140I, C141R, C141G, C141A, C141Y, C141S, C141F, C141W, V143M, V143A, V143E, L145Q, L145R, P151T, P151A, P151S, P151H, P152S, P152R, P152L, T155P, R158H, R158L, A159V, A159P, A159S, A159D, A161T, A161D, Y163N, Y163H, Y163D, Y163S, Y163C, K164E, K164M, K164N, K164P, H168Y, H168N, H168R, H168L, H168Q, M169I, M169T, M169V, T170M, E171K, E171Q, E171G, E171A, E171V, E171D, | NM_001126112 | 33 |
| TRAF | Frameshift/nonsense | NM_145725 | 0 |
| TYW1 | R555Q, E601K | NM_018264 | 0 |
| U2AF | D14G, S34F, S34Y, R35L, R156H, R156Q, Q157R, Q157P | NM_006758 | 5 |
| U2AF2 | R18W, Q143L, M144I, L187V, Q190L | NM_007279 | 0 |
| UBR5 | Frameshift/nonsense/splice-site exon 58 | NM_015902 | 0 |
| WT1 | Frameshift/nonsense/splice-site | NM_024426 | 0 |
| XBP1 | L167I, P326R | NM_001079539 | 0 |
| XPO1 | E571A, E571K | NM_003400 | 0 |
| ZNF471 | G483, P486, R423 | NM_020813 | 0 |
| ZRSR2 | Frameshift/nonsense, R126P, E133G, C181F, H191Y, I202N, F239V, F239Y, N261Y, C280R, C302R, C326R, H330R, N382K | NM_005089 | 3 |
| Total | | | 805 |

SUPPLEMENTARY TABLE S3

Called somatic variants in 160 hematopoeitic genes

| Gene name | Chromosome | Start position | Variant Type | Reference Allele | Variant Allele | Varient Classification |
|---|---|---|---|---|---|---|
| ASXL1 | 20 | 31021211 | SNP | C | T | Nonsense_Mutation |
| ASXL1 | 20 | 31021211 | SNP | C | T | Nonsense_Mutation |
| ASXL1 | 20 | 31021211 | SNP | C | T | Nonsense_Mutation |
| ASXL1 | 20 | 31021211 | SNP | C | T | Nonsense_Mutation |
| ASXL1 | 20 | 31021211 | SNP | C | T | Nonsense_Mutation |
| ASXL1 | 20 | 31021250 | SNP | C | T | Nonsense_Mutation |
| ASXL1 | 20 | 31021250 | SNP | C | T | Nonsense_Mutation |
| ASXL1 | 20 | 31021250 | SNP | C | T | Nonsense_Mutation |
| ASXL1 | 20 | 31021250 | SNP | C | T | Nonsense_Mutation |
| ASXL1 | 20 | 31021250 | SNP | C | T | Nonsense_Mutation |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| ASXL1 | 20 | 31021276 | DEL | C | — | Frame_Shift_Del |
| ASXL1 | 20 | 31021283 | SNP | C | T | Nonsense_Mutation |
| ASXL1 | 20 | 31021295 | SNP | C | T | Nonsense_Mutation |
| ASXL1 | 20 | 31021332 | SNP | C | G | Nonsense_Mutation |
| ASXL1 | 20 | 31021332 | SNP | C | G | Nonsense_Mutation |
| ASXL1 | 20 | 31021535 | SNP | C | T | Nonsense_Mutation |
| ASXL1 | 20 | 31021538 | SNP | G | T | Nonsense_Mutation |
| ASXL1 | 20 | 31021543 | DEL | TG | — | Frame_Shift_Del |
| ASXL1 | 20 | 31021543 | DEL | TG | — | Frame_Shift_Del |
| ASXL1 | 20 | 31021550 | SNP | C | T | Nonsense_Mutation |
| ASXL1 | 20 | 31021553 | SNP | G | T | Nonsense_Mutation |
| ASXL1 | 20 | 31021553 | DEL | GA | — | Frame_Shift_Del |
| ASXL1 | 20 | 31021586 | SNP | C | T | Nonsense_Mutation |
| ASXL1 | 20 | 31021627 | INS | — | GAAGATC | Frame_Shift_Ins |
| ASXL1 | 20 | 31021637 | SNP | C | T | Nonsense_Mutation |
| ASXL1 | 20 | 31021647 | INS | — | TAACACT | Frame_Shift_Ins |
| ASXL1 | 20 | 31022238 | SNP | C | T | Nonsense_Mutation |
| ASXL1 | 20 | 31022263 | SNP | G | A | Nonsense_Mutation |
| ASXL1 | 20 | 31022286 | INS | — | A | Frame_Shift_Ins |
| ASXL1 | 20 | 31022288 | SNP | C | A | Nonsense_Mutation |
| ASXL1 | 20 | 31022297 | SNP | C | A | Nonsense_Mutation |
| ASXL1 | 20 | 31022363 | INS | — | T | Frame_Shift_Ins |
| ASXL1 | 20 | 31022403 | DEL | CACCACTGCCATAGAGAGGCGGC | — | Frame_Shift_Del |
| ASXL1 | 20 | 31022416 | DEL | GAGAGGCGGCCACCACTGCCATC | — | Frame_Shift_Del |
| ASXL1 | 20 | 31022441 | INS | — | G | Frame_Shift_Ins |
| ASXL1 | 20 | 31022441 | INS | — | G | Frame_Shift_Ins |
| ASXL1 | 20 | 31022441 | INS | — | G | Frame_Shift_Ins |
| ASXL1 | 20 | 31022441 | INS | — | G | Frame_Shift_Ins |
| ASXL1 | 20 | 31022441 | INS | — | G | Frame_Shift_Ins |
| ASXL1 | 20 | 31022589 | SNP | C | T | Nonsense_Mutation |
| ASXL1 | 20 | 31022592 | SNP | C | T | Nonsense_Mutation |
| ASXL1 | 20 | 31022592 | SNP | C | T | Nonsense_Mutation |
| ASXL1 | 20 | 31022592 | SNP | C | T | Nonsense_Mutation |
| ASXL1 | 20 | 31022599 | DEL | A | — | Frame_Shift_Del |
| ASXL1 | 20 | 31022643 | DEL | G | — | Frame_Shift_Del |
| ASXL1 | 20 | 31022757 | SNP | C | T | Nonsense_Mutation |
| ASXL1 | 20 | 31022784 | SNP | C | T | Nonsense_Mutation |
| ASXL1 | 20 | 31022793 | SNP | C | T | Nonsense_Mutation |
| ASXL1 | 20 | 31022817 | SNP | C | T | Nonsense_Mutation |
| ASXL1 | 20 | 31022817 | SNP | C | T | Nonsense_Mutation |
| ASXL1 | 20 | 31022853 | SNP | C | T | Nonsense_Mutation |
| ASXL1 | 20 | 31022922 | SNP | C | T | Nonsense_Mutation |
| ASXL1 | 20 | 31022922 | SNP | C | T | Nonsense_Mutation |
| ASXL1 | 20 | 31022982 | DEL | T | — | Frame_Shift_Del |
| ASXL1 | 20 | 31022983 | SNP | T | G | Nonsense_Mutation |
| ASXL1 | 20 | 31023271 | INS | — | A | Frame_Shift_Ins |
| ASXL1 | 20 | 31023354 | SNP | G | T | Nonsense_Mutation |
| ASXL1 | 20 | 31023381 | DEL | CTTA | — | Frame_Shift_Del |
| ASXL1 | 20 | 31023528 | DEL | T | — | Frame_Shift_Del |
| ASXL1 | 20 | 31023554 | DEL | C | — | Frame_Shift_Del |
| ASXL1 | 20 | 31023625 | SNP | G | A | Nonsense_Mutation |
| ASXL1 | 20 | 31023702 | SNP | C | T | Nonsense_Mutation |
| BC11B | 14 | 99641387 | SNP | C | T | Missense_Mutation |
| BCOR | X | 39922072 | INS | — | G | Frame_Shift_Ins |
| BCOR | X | 39930272 | DE | CG | — | Frame_Shift_Del |
| BCOR | X | 39933743 | DEL | T | — | Frame_Shift_Del |
| BCOR | X | 39934170 | INS | — | T | Frame_Shift_Ins |
| BCORL1 | X | 129147623 | SNP | C | G | Nonsense_Mutation |
| BCORL1 | X | 129159270 | SNP | C | T | Nonsense_Mutation |
| BIRC3 | 11 | 102195867 | INS | — | G | Frame_Shift_Ins |
| BRAF | 7 | 140453136 | SNP | A | T | Missense_Mutation |
| BRAF | 7 | 140481402 | SNP | C | T | Missense_Mutation |
| BRCC3 | X | 154305490 | SNP | C | T | Nonsense_Mutation |
| BRCC3 | X | 154305490 | SNP | C | T | Nonsense_Mutation |
| BRCC3 | X | 154305514 | SNP | C | T | Nonsense_Mutation |
| BRCC3 | X | 154305514 | SNP | C | T | Nonsense_Mutation |
| BRCC3 | X | 154306935 | SNP | G | A | Nonsense_Mutation |
| BRCC3 | X | 154306978 | SNP | G | T | Splice_Site |
| CARD11 | 7 | 2976745 | SNP | G | A | Missense_Mutation |
| CBL | 11 | 119148921 | SNP | T | C | Missense_Mutation |
| CBL | 11 | 119148922 | SNP | G | A | Missense_Mutation |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| CBL | 11 | 119148922 | SNP | G | C | Missense_Mutation |
| CBL | 11 | 119148924 | SNP | A | G | Missense_Mutation |
| CBL | 11 | 119148929 | SNP | A | G | Missense_Mutation |
| CBL | 11 | 119148991 | SNP | G | A | Missense_Mutation |
| CBL | 11 | 119148991 | SNP | G | A | Missense_Mutation |
| CBL | 11 | 119148991 | SNP | G | A | Missense_Mutation |
| CBL | 11 | 119149235 | SNP | G | A | Missense_Mutation |
| CBL | 11 | 119149235 | SNP | G | A | Missense_Mutation |
| CBL | 11 | 119149244 | SNP | T | A | Missense_Mutation |
| CBL | 11 | 119149251 | SNP | G | A | Missense_Mutation |
| CD58 | 1 | 117078587 | SNP | C | T | Missense_Mutation |
| CD798 | 17 | 62006798 | SNP | T | G | Missense_Mutation |
| CNOT3 | 19 | 54646887 | SNP | G | A | Missense_Mutation |
| CREBBP | 16 | 3786067 | DEL | T | — | Frame_Shift_Del |
| CREBBP | 16 | 3817721 | DEL | T | — | Frame_Shift_Del |
| CREBBP | 16 | 382805615 | INS | — | C | Frame_Shift_Ins |
| CREBBP | 16 | 3828080 | INS | — | G | Frame_Shift_Ins |
| CREBBP | 16 | 3843447 | SNP | G | A | Nonsense_Mutation |
| CREBBP | 16 | 3860722 | INS | — | G | Frame_Shift_Ins |
| CUX1 | 7 | 101559473 | SNP | C | T | Nonsense_Mutation |
| CUX1 | 7 | 101747648 | SNP | C | T | Nonsense_Mutation |
| CUX1 | 7 | 101837121 | SNP | G | A | Splice_Site |
| DDX3X | X | 41196685 | INS | — | C | Frame_Shift_Ins |
| DDX3X | X | 41205659 | DEL | CAGCAGTATGTAT | — | Splice_Site |
| DNMT3A | 2 | 25457160 | DEL | A | — | Frame_Shift_Del |
| DNMT3A | 2 | 25457160 | DEL | A | — | Frame_Shift_Del |
| DNMT3A | 2 | 25457176 | SNP | G | A | Missense_Mutation |
| DNMT3A | 2 | 25457176 | SNP | G | A | Missense_Mutation |
| DNMT3A | 2 | 25457176 | SNP | G | A | Missense_Mutation |
| DNMT3A | 2 | 25457176 | SNP | G | A | Missense_Mutation |
| DNMT3A | 2 | 25457176 | SNP | G | A | Missense_Mutation |
| DNMT3A | 2 | 25457179 | DEL | GC | — | Frame_Shift_Del |
| DNMT3A | 2 | 25457181 | INS | — | A | Frame_Shift_Ins |
| DNMT3A | 2 | 25457185 | SNP | A | T | Missense_Mutation |
| DNMT3A | 2 | 25457207 | INS | — | C | Frame_Shift_Ins |
| DNMT3A | 2 | 25457218 | SNP | C | T | Missense_Mutation |
| DNMT3A | 2 | 25457238 | INS | — | A | Frame_Shift_Ins |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | G | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | G | Missense_Mutation |
| DNMT3A | 2 | 25457242 | SNF | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | G | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | T | Missense_Mutation |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| DNMT3A | 2 | 25457242 | SNP | C | T | Missense_Mutation |
| DNMT3A | 2 | 25457242 | SNP | C | T | Missense_Mutation |
| DNMT3A | 2 | 25457242 | SNP | C | G | Missense_Mutation |
| DNMT3A | 2 | 25457242 | SNP | C | T | Missense_Mutation |
| DNMT3A | 2 | 25457242 | SNP | C | T | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457243 | SNP | G | A | Missense_Mutation |
| DNMT3A | 2 | 25457245 | SNP | C | A | Missense_Mutation |
| DNMT3A | 2 | 25457249 | SNP | T | C | Missense_Mutation |
| DNMT3A | 2 | 25457249 | SNP | T | C | Missense_Mutation |
| DNMT3A | 2 | 25457281 | SNP | C | A | Missense_Mutation |
| DNMT3A | 2 | 25457283 | DEL | A | — | Frame_Shift_Del |
| DNMT3A | 2 | 25458593 | SNP | C | T | Nonsense_Mutation |
| DNMT3A | 2 | 25458595 | INS | — | T | Frame_Shift_Ins |
| DNMT3A | 2 | 25458595 | SNP | A | G | Missense_Mutation |
| DNMT3A | 2 | 25458595 | SNP | A | G | Missense_Mutation |
| DNMT3A | 2 | 25458597 | DEL | AA | — | Frame_Shift_Del |
| DNMT3A | 2 | 25458602 | DEL | G | — | Frame_Shift_Del |
| DNMT3A | 2 | 25458622 | DEL | AG | — | Frame_Shift_Del |
| DNMT3A | 2 | 25458635 | DEL | CTGGT | — | Frame_Shift_Del |
| DNMT3A | 2 | 25458653 | INS | — | A | Frame_Shift_Ins |
| DNMT3A | 2 | 25458692 | DEL | G | — | Frame_Shift_Del |
| DNMT3A | 2 | 25458695 | SNP | C | T | Splice_Site |
| DNMT3A | 2 | 25458696 | SNP | T | C | Splice_Site |
| DNMT3A | 2 | 25458696 | SNP | T | C | Splice_Site |
| DNMT3A | 2 | 25458696 | SNP | T | C | Splice_Site |
| DNMT3A | 2 | 25458696 | SNP | T | C | Splice_Site |
| DNMT3A | 2 | 25459804 | SNP | C | T | Splice_Site |
| DNMT3A | 2 | 25459804 | SNP | C | T | Splice_Site |
| DNMT3A | 2 | 25459872 | SNP | G | A | Missense_Mutation |
| DNMT3A | 2 | 25462011 | SNP | G | T | Missense_Mutation |
| DNMT3A | 2 | 25462015 | DEL | G | — | Frame_Shift_Del |
| DNMT3A | 2 | 25462020 | SNP | C | A | Missense_Mutation |
| DNMT3A | 2 | 25462022 | SNP | C | T | Nonsense_Mutation |
| DNMT3A | 2 | 25462053 | DEL | A | — | Frame_Shift_Del |
| DNMT3A | 2 | 25463171 | SNP | C | G | Missense_Mutation |
| DNMT3A | 2 | 25463171 | SNP | C | T | Splice_Site |
| DNMT3A | 2 | 25463175 | SNP | A | C | Missense_Mutation |
| DNMT3A | 2 | 25463179 | SNP | A | C | Missense_Mutation |
| DNMT3A | 2 | 25463181 | SNP | C | T | Missense_Mutation |
| DNMT3A | 2 | 25463181 | SNP | C | T | Missense_Mutation |
| DNMT3A | 2 | 25463181 | SNP | C | T | Missense_Mutation |
| DNMT3A | 2 | 25463181 | SNP | C | T | Missense_Mutation |
| DNMT3A | 2 | 25463182 | SNP | G | A | Nonsense_Mutation |
| DNMT3A | 2 | 25463182 | SNP | G | A | Nonsense_Mutation |
| DNMT3A | 2 | 25463182 | SNP | G | A | Nonsense_Mutation |
| DNMT3A | 2 | 25463182 | SNP | G | A | Nonsense_Mutation |
| DNMT3A | 2 | 25463182 | SNP | G | A | Nonsense_Mutation |
| DNMT3A | 2 | 25463182 | SNP | G | A | Nonsense_Mutation |
| DNMT3A | 2 | 25463182 | SNP | G | A | Nonsense_Mutation |
| DNMT3A | 2 | 25463182 | SNP | G | A | Nonsense_Mutation |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| DNMT3A | 2 | 25463184 | SNP | G | C | Missense_Mutation |
| DNMT3A | 2 | 25463184 | SNP | G | C | Missense_Mutation |
| DNMT3A | 2 | 25463185 | SNP | A | G | Missense_Mutation |
| DNMT3A | 2 | 25463197 | SNP | T | A | Nonsense_Mutation |
| DNMT3A | 2 | 25463208 | DEL | C | — | Frame_Shift_Del |
| DNMT3A | 2 | 25463211 | DEL | AT | — | Frame_Shift_Del |
| DNMT3A | 2 | 25463212 | SNP | T | C | Missense_Mutation |
| DNMT3A | 2 | 25463213 | DEL | G | — | Frame_Shift_Del |
| DNMT3A | 2 | 25463228 | SNP | A | C | Missense_Mutation |
| DNMT3A | 2 | 25463229 | SNP | A | G | Missense_Mutation |
| DNMT3A | 2 | 25463229 | SNP | A | G | Missense_Mutation |
| DNMT3A | 2 | 25463229 | SNP | A | G | Missense_Mutation |
| DNMT3A | 2 | 25463230 | SNP | A | T | Missense_Mutation |
| DNMT3A | 2 | 25463230 | SNP | A | T | Missense_Mutation |
| DNMT3A | 2 | 25463231 | DEL | G | — | Frame_Shift_Del |
| DNMT3A | 2 | 25463232 | SNP | A | T | Missense_Mutation |
| DNMT3A | 2 | 25463235 | SNP | C | T | Nonsense_Mutation |
| DNMT3A | 2 | 25463236 | DEL | AGA | — | In_Frame_Del |
| DNMT3A | 2 | 25463237 | SNP | G | C | Missense_Mutation |
| DNMT3A | 2 | 25463238 | DEL | A | — | Frame_Shift_Del |
| DNMT3A | 2 | 25463239 | SNP | A | C | Missense_Mutation |
| DNMT3A | 2 | 25463239 | SNP | A | T | Missense_Mutation |
| DNMT3A | 2 | 25463239 | SNP | A | C | Missense_Mutation |
| DNMT3A | 2 | 25463240 | DEL | G | — | Frame_Shift_Del |
| DNMT3A | 2 | 25463240 | DEL | G | — | Frame_Shift_Del |
| DNMT3A | 2 | 25463240 | SNP | G | C | Missense_Mutation |
| DNMT3A | 2 | 25463243 | DEL | G | — | Frame_Shift_Del |
| DNMT3A | 2 | 25463246 | DNP | GC | AA | Missense_Mutation |
| DNMT3A | 2 | 5463247 | SNP | C | T | Missense_Mutation |
| DNMT3A | 2 | 25463267 | INS | — | CG | Frame_Shift_Ins |
| DNMT3A | 2 | 25463283 | SNP | A | T | Missense_Mutation |
| DNMT3A | 2 | 25463283 | SNP | A | G | Missense_Mutation |
| DNMT3A | 2 | 25463283 | SNP | A | C | Missense_Mutation |
| DNMT3A | 2 | 25463286 | SNP | C | T | Missense_Mutation |
| DNMT3A | 2 | 25463286 | SNP | C | T | Missense_Mutation |
| DNMT3A | 2 | 25463286 | SNP | C | T | Missense_Mutation |
| DNMT3A | 2 | 25463286 | SNP | C | G | Missense_Mutation |
| DNMT3A | 2 | 25463286 | SNP | C | T | Missense_Mutation |
| DNMT3A | 2 | 25463287 | SNP | G | A | Missense_Mutation |
| DNMT3A | 2 | 25463287 | DEL | G | — | Frame_Shift_Del |
| DNMT3A | 2 | 25463287 | SNP | G | A | Missense_Mutation |
| DNMT3A | 2 | 25463287 | SNP | G | A | Missense_Mutation |
| DNMT3A | 2 | 25463288 | INS | — | A | Frame_Shift_Ins |
| DNMT3A | 2 | 25463288 | SNP | G | C | Nonsense_Mutation |
| DNMT3A | 2 | 25463289 | SNP | T | C | Missense_Mutation |
| DNMT3A | 2 | 25463289 | SNP | T | C | Missense_Mutation |
| DNMT3A | 2 | 25463289 | SNP | T | C | Missense_Mutation |
| DNMT3A | 2 | 25463289 | SNP | T | C | Missense_Mutation |
| DNMT3A | 2 | 25463289 | SNP | T | C | Missense_Mutation |
| DNMT3A | 2 | 25463289 | SNP | T | C | Missense_Mutation |
| DNMT3A | 2 | 25463289 | SNP | T | G | Missense_Mutation |
| DNMT3A | 2 | 25463289 | SNP | T | C | Missense_Mutation |
| DNMT3A | 2 | 25463291 | SNP | G | C | Missense_Mutation |
| DNMT3A | 2 | 25463292 | SNP | A | C | Missense_Mutation |
| DNMT3A | 2 | 25463296 | INS | — | A | Frame_Shift_Ins |
| DNMT3A | 2 | 25463298 | SNP | A | G | Missense_Mutation |
| DNMT3A | 2 | 25463298 | DEL | AAG | — | In_Frame_Del |
| DNMT3A | 2 | 25463298 | SNP | A | G | Missense_Mutation |
| DNMT3A | 2 | 25463298 | DEL | AAG | — | In_Frame_Del |
| DNMT3A | 2 | 25463298 | DEL | AAG | — | In_Frame_Del |
| DNMT3A | 2 | 25463299 | DEL | AGAAG | — | Frame_Shift_Del |
| DNMT3A | 2 | 25463300 | SNP | G | T | Missense_Mutation |
| DNMT3A | 2 | 25463307 | SNP | C | T | Missense_Mutation |
| DNMT3A | 2 | 25463308 | SNP | G | A | Missense_Mutation |
| DNMT3A | 2 | 25463308 | SNP | G | A | Missense_Mutation |
| DNMT3A | 2 | 25463308 | SNP | G | A | Missense_Mutation |
| DNMT3A | 2 | 25463308 | SNP | G | C | Missense_Mutation |
| DNMT3A | 2 | 25463308 | SNP | G | A | Missense_Mutation |
| DNMT3A | 2 | 25463308 | SNP | G | A | Missense_Mutation |
| DNMT3A | 2 | 25463320 | SNP | C | T | Splice_Site |
| DNMT3A | 2 | 25463320 | SNP | C | T | Splice_Site |
| DNMT3A | 2 | 25463508 | SNP | C | T | Splice_Site |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| DNMT3A | 2 | 25463508 | SNP | C | T | Splice_Site |
| DNMT3A | 2 | 25463508 | SNP | C | T | Splice_Site |
| DNMT3A | 2 | 25463508 | SNP | C | T | Splice_Site |
| DNMT3A | 2 | 25463508 | SNP | C | T | Splice_Site |
| DNMT3A | 2 | 25463509 | SNP | C | T | Splice_Site |
| DNMT3A | 2 | 25463523 | SNP | C | T | Missense_Mutation |
| DNMT3A | 2 | 25463529 | DEL | G | — | Frame_Shift_Del |
| DNMT3A | 2 | 25463532 | SNP | T | A | Missense_Mutation |
| DNMT3A | 2 | 25463541 | SNP | G | C | Missense_Mutation |
| DNMT3A | 2 | 25463541 | SNP | G | C | Missense_Mutation |
| DNMT3A | 2 | 25463541 | SNP | G | C | Missense_Mutation |
| DNMT3A | 2 | 25463554 | SNP | A | T | Missense_Mutation |
| DNMT3A | 2 | 25463554 | SNP | A | T | Missense_Mutation |
| DNMT3A | 2 | 25463568 | SNP | A | G | Missense_Mutation |
| DNMT3A | 2 | 25463568 | SNP | A | G | Missense_Mutation |
| DNMT3A | 2 | 25463571 | SNP | A | C | Missense_Mutation |
| DNMT3A | 2 | 25463578 | SNP | C | A | Missense_Mutation |
| DNMT3A | 2 | 25463578 | SNP | C | T | Missense_Mutation |
| DNMT3A | 2 | 25463583 | DEL | G | — | Frame_Shift_Del |
| DNMT3A | 2 | 25463583 | SNP | G | C | Missense_Mutation |
| DNMT3A | 2 | 25463584 | SNP | G | A | Missense_Mutation |
| DNMT3A | 2 | 25463586 | SNP | C | T | Missense_Mutation |
| DNMT3A | 2 | 25463587 | SNP | C | T | Missense_Mutation |
| DNMT3A | 2 | 25463587 | SNP | C | T | Missense_Mutation |
| DNMT3A | 2 | 25463587 | SNP | C | T | Missense_Mutation |
| DNMT3A | 2 | 25463596 | SNP | G | A | Nonsense_Mutation |
| DNMT3A | 2 | 25463601 | SNP | T | C | Splice_Site |
| DNMT3A | 2 | 25463601 | SNP | T | C | Splice_Site |
| DNMT3A | 2 | 25464428 | INS | — | A | Splice_Site |
| DNMT3A | 2 | 25464429 | SNP | A | C | Splice_Site |
| DNMT3A | 2 | 25464430 | SNP | C | T | Splice_Site |
| DNMT3A | 2 | 25464456 | SNP | T | A | Missense_Mutation |
| DNMT3A | 2 | 25464457 | SNP | C | A | Missense_Mutation |
| DNMT3A | 2 | 25464459 | SNP | C | T | Missense_Mutation |
| DNMT3A | 2 | 25464459 | SNP | C | G | Missense_Mutation |
| DNMT3A | 2 | 25464460 | SNP | C | T | Missense_Mutation |
| DNMT3A | 2 | 25464486 | SNP | C | T | Missense_Mutation |
| DNMT3A | 2 | 25464505 | INS | — | G | Frame_Shift_Ins |
| DNMT3A | 2 | 25464534 | SNP | T | C | Missense_Mutation |
| DNMT3A | 2 | 25464537 | SNP | C | T | Missense_Mutation |
| DNMT3A | 2 | 25464537 | SNP | C | T | Missense_Mutation |
| DNMT3A | 2 | 25464544 | SNP | C | T | Missense_Mutation |
| DNMT3A | 2 | 25464544 | SNP | C | T | Missense_Mutation |
| DNMT3A | 2 | 25464544 | SNP | C | T | Missense_Mutation |
| DNMT3A | 2 | 25464547 | SNP | G | A | Nonsense_Mutation |
| DNMT3A | 2 | 25464554 | SNP | C | A | Missense_Mutation |
| DNMT3A | 2 | 25467022 | SNP | A | G | Splice_Site |
| DNMT3A | 2 | 25467023 | SNP | C | T | Splice_Site |
| DNMT3A | 2 | 25467032 | SNP | G | A | Nonsense_Mutation |
| DNMT3A | 2 | 25467065 | DEL | G | — | Frame_Shift_Del |
| DNMT3A | 2 | 25467073 | SNP | C | T | Nonsense_Mutation |
| DNMT3A | 2 | 25467083 | SNP | G | A | Nonsense_Mutation |
| DNMT3A | 2 | 25467083 | SNP | G | A | Nonsense_Mutation |
| DNMT3A | 2 | 25467083 | SNP | G | A | Nonsense_Mutation |
| DNMT3A | 2 | 25467083 | SNP | G | A | Nonsense_Mutation |
| DNMT3A | 2 | 25467083 | SNP | G | A | Nonsense_Mutation |
| DNMT3A | 2 | 25467083 | SNP | G | A | Nonsense_Mutation |
| DNMT3A | 2 | 25467111 | DEL | G | — | Frame_Shift_Del |
| DNMT3A | 2 | 25467132 | SNP | C | T | Nonsense_Mutation |
| DNMT3A | 2 | 25467134 | SNP | A | C | Missense_Mutation |
| DNMT3A | 2 | 25467407 | SNP | A | C | Splice_Site |
| DNMT3A | 2 | 25467408 | SNP | C | A | Splice_Site |
| DNMT3A | 2 | 25467408 | SNP | C | G | Splice_Site |
| DNMT3A | 2 | 25467428 | SNP | C | T | Missense_Mutation |
| DNMT3A | 2 | 25467428 | SNP | C | T | Missense_Mutation |
| DNMT3A | 2 | 25467436 | SNP | A | T | Missense_Mutation |
| DNMT3A | 2 | 25467436 | SNP | A | C | Missense_Mutation |
| DNMT3A | 2 | 25467436 | SNP | A | T | Missense_Mutation |
| DNMT3A | 2 | 25467437 | SNP | G | A | Missense_Mutation |
| DNMT3A | 2 | 25467437 | SNP | G | A | Missense_Mutation |
| DNMT3A | 2 | 25467447 | INS | — | C | Frame_Shift_Ins |
| DNMT3A | 2 | 25467448 | SNP | C | G | Missense_Mutation |
| DNMT3A | 2 | 25467449 | SNP | C | A | Missense_Mutation |
| DNMT3A | 2 | 25467449 | SNP | C | T | Missense_Mutation |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| DNMT3A | 2 | 25467465 | SNP | G | T | Nonsense_Mutation |
| DNMT3A | 2 | 25467468 | SNP | G | T | Nonsense_Mutation |
| DNMT3A | 2 | 25467471 | DEL | G | — | Frame_Shift_Del |
| DNMT3A | 2 | 25467476 | SNP | G | A | Nonsense_Mutation |
| DNMT3A | 2 | 25467481 | DEL | C | — | Frame_Shift_Del |
| DNMT3A | 2 | 25467492 | SNP | G | C | Nonsense_Mutation |
| DNMT3A | 2 | 25467493 | DEL | TA | — | Frame_Shift_Del |
| DNMT3A | 2 | 25467496 | SNP | T | G | Missense_Mutation |
| DNMT3A | 2 | 25467497 | SNP | G | A | Nonsense_Mutation |
| DNMT3A | 2 | 25467503 | DEL | CA | — | Frame_Shift_Del |
| DNMT3A | 2 | 25467522 | SNP | C | G | Splice_Site |
| DNMT3A | 2 | 25467523 | SNP | T | C | Splice_Site |
| DNMT3A | 2 | 25468121 | SNP | C | T | Splice_Site |
| DNMT3A | 2 | 25468121 | SNP | C | T | Splice_Site |
| DNMT3A | 2 | 25468128 | INS | — | T | Frame_Shift_Ins |
| DNMT3A | 2 | 25468145 |  | C | A | Nonsense_Mutation |
| DNMT3A | 2 | 25468153 | INS | — | G | Frame_Shift_Ins |
| DNMT3A | 2 | 25468165 | DEL | A | — | Frame_Shift_Del |
| DNMT3A | 2 | 25468181 | DEL | T | — | Frame_Shift_Del |
| DNMT3A | 2 | 25468182 | DEL | C | — | Frame_Shift_Del |
| DNMT3A | 2 | 25468186 | SNP | C | T | Missense_Mutation |
| DNMT3A | 2 | 25468202 | SNP | C | G | Splice_Site |
| DNMT3A | 2 | 25468203 | DEL | T | — | Splice_Site |
| DNMT3A | 2 | 25468887 | SNP | A | C | Splice_Site |
| DNMT3A | 2 | 25468899 | DEL | C | — | Frame_Shift_Del |
| DNMT3A | 2 | 25468899 | DEL | C | — | Frame_Shift_Del |
| DNMT3A | 2 | 25468907 | SNP | T | A | Nonsense_Mutation |
| DNMT3A | 2 | 25468919 | SNP | C | A | Nonsense_Mutation |
| DNMT3A | 2 | 25468934 | SNP | C | T | Splice_Site |
| DNMT3A | 2 | 25468935 | SNP | T | G | Splice_Site |
| DNMT3A | 2 | 25469028 | SNP | C | T | Splice_Site |
| DNMT3A | 2 | 25469028 | SNP | C | T | Splice_Site |
| DNMT3A | 2 | 25469028 | SNP | C | T | Splice_Site |
| DNMT3A | 2 | 25469041 | SNP | C | A | Nonsense_Mutation |
| DNMT3A | 2 | 25469048 | DEL | A | — | Frame_Shift_Del |
| DNMT3A | 2 | 25469063 | DEL | G | — | Frame_Shift_Del |
| DNMT3A | 2 | 25469083 | SNP | T | A | Nonsense_Mutation |
| DNMT3A | 2 | 25469096 | DEL | GG | — | Frame_Shift_Del |
| DNMT3A | 2 | 25469154 | DEL | ACTT | — | Frame_Shift_Del |
| DNMT3A | 2 | 25469156 | DEL | T | — | Frame_Shift_Del |
| DNMT3A | 2 | 25469165 | DEL | GGGATTCTTCTCT | — | Frame_Shift_Del |
| DNMT3A | 2 | 25469488 | SNP | C | T | Splice_Site |
| DNMT3A | 2 | 25469527 | SNP | A | C | Missense_Mutation |
| DNMT3A | 2 | 25469527 | SNP | A | C | Missense_Mutation |
| DNMT3A | 2 | 25469541 | SNP | C | T | Nonsense_Mutation |
| DNMT3A | 2 | 25469541 | SNP | C | T | Nonsense_Mutation |
| DNMT3A | 2 | 25469541 | SNP | C | T | Nonsense_Mutation |
| DNMT3A | 2 | 25469542 | DEL | CATT | — | Frame_Shift_Del |
| DNMT3A | 2 | 25469553 | DEL | GG | — | Frame_Shift_Del |
| DNMT3A | 2 | 25469564 | SNP | G | A | Nonsense_Mutation |
| DNMT3A | 2 | 25469564 | SNP | G | A | Nonsense_Mutation |
| DNMT3A | 2 | 25469566 | INS | — | T | Frame_Shift_Ins |
| DNMT3A | 2 | 25469607 | INS | — | CA | Frame_Shift_Ins |
| DNMT3A | 2 | 25469613 | INS | — | G | Frame_Shift_Ins |
| DNMT3A | 2 | 25469614 | DEL | G | — | Frame_Shift_Del |
| DNMT3A | 2 | 25469614 | DEL | G | — | Frame_Shift_Del |
| DNMT3A | 2 | 25469625 | DEL | C | — | Frame_Shift_Del |
| DNMT3A | 2 | 25469625 | DEL | C | — | Frame_Shift_Del |
| DNMT3A | 2 | 25469646 | SNP | C | G | Splice_Site |
| DNMT3A | 2 | 25469647 | SNP | T | C | Splice_Site |
| DNMT3A | 2 | 25469919 | SNP | C | T | Splice_Site |
| DNMT3A | 2 | 25469919 | SNP | C | T | Splice_Site |
| DNMT3A | 2 | 25469922 | SNP | G | A | Nonsense_Mutation |
| DNMT3A | 2 | 25469922 | SNP | G | A | Nonsense_Mutation |
| DNMT3A | 2 | 25469945 | SNP | C | T | Missense_Mutation |
| DNMT3A | 2 | 25469945 | SNP | C | T | Missense_Mutation |
| DNMT3A | 2 | 25469946 | SNP | G | C | Missense_Mutation |
| DNMT3A | 2 | 25469976 | SNP | G | A | Nonsense_Mutation |
| DNMT3A | 2 | 25469976 | SNP | G | A | Nonsense_Mutation |
| DNMT3A | 2 | 25469984 | DEL | G | — | Frame_Shift_Del |
| DNMT3A | 2 | 25470029 | INS | — | G | Splice_Site |
| DNMT3A | 2 | 25470467 | DEL | A | — | Frame_Shift_Del |
| DNMT3A | 2 | 25470480 | SNP | C | A | Nonsense_Mutation |
| DNMT3A | 2 | 25470484 | SNP | C | T | Nonsense_Mutation |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| DNMT3A | 2 | 25470485 | SNP | C | T | Nonsense_Mutation |
| DNMT3A | 2 | 25470493 | SNP | C | T | Nonsense_Mutation |
| DNMT3A | 2 | 25470493 | SNP | C | T | Nonsense_Mutation |
| DNMT3A | 2 | 25470494 | SNP | C | T | Nonsense_Mutation |
| DNMT3A | 2 | 25470497 | SNP | C | T | Missense_Mutation |
| DNMT3A | 2 | 25470497 | SNP | C | T | Missense_Mutation |
| DNMT3A | 2 | 25470497 | SNP | C | A | Missense_Mutation |
| DNMT3A | 2 | 25470497 | SNP | C | T | Missense_Mutation |
| DNMT3A | 2 | 25470497 | SNP | C | T | Missense_Mutation |
| DNMT3A | 2 | 25470498 | SNP | G | A | Missense_Mutation |
| DNMT3A | 2 | 25470498 | SNP | G | A | Missense_Mutation |
| DNMT3A | 2 | 25470498 | SNP | G | T | Missense_Mutation |
| DNMT3A | 2 | 25470498 | SNP | G | A | Missense_Mutation |
| DNMT3A | 2 | 25470498 | SNP | G | A | Missense_Mutation |
| DNMT3A | 2 | 25470498 | SNP | G | A | Missense_Mutation |
| DNMT3A | 2 | 25470498 | SNP | G | A | Missense_Mutation |
| DNMT3A | 2 | 25470498 | SNP | G | A | Missense_Mutation |
| DNMT3A | 2 | 25470516 | SNP | G | A | Nonsense_Mutation |
| DNMT3A | 2 | 25470516 | SNP | G | A | Nonsense_Mutation |
| DNMT3A | 2 | 25470516 | SNP | G | A | Nonsense_Mutation |
| DNMT3A | 2 | 25470516 | SNP | G | A | Nonsense_Mutation |
| DNMT3A | 2 | 25470516 | SNP | G | A | Nonsense_Mutation |
| DNMT3A | 2 | 25470516 | SNP | G | A | Nonsense_Mutation |
| DNMT3A | 2 | 25470516 | SNP | G | A | Nonsense_Mutation |
| DNMT3A | 2 | 25470516 | SNP | G | A | Nonsense_Mutation |
| DNMT3A | 2 | 25470532 | SNP | C | T | Nonsense_Mutation |
| DNMT3A | 2 | 25470555 | SNP | G | A | Missense_Mutation |
| DNMT3A | 2 | 25470556 | SNP | C | T | Nonsense_Mutation |
| DNMT3A | 2 | 25470559 | SNP | C | T | Nonsense_Mutation |
| DNMT3A | 2 | 25470559 | SNP | C | T | Nonsense_Mutation |
| DNMT3A | 2 | 25470560 | SNP | C | T | Nonsense_Mutation |
| DNMT3A | 2 | 25470583 | SNP | C | T | Nonsense_Mutation |
| DNMT3A | 2 | 25470594 | DEL | C | — | Frame_Shift_Del |
| DNMT3A | 2 | 25470594 | SNP | C | A | Nonsense_Mutation |
| DNMT3A | 2 | 25470904 | SNP | A | C | Splice_Site |
| DNMT3A | 2 | 25470905 | SNP | C | T | Splice_Site |
| DNMT3A | 2 | 25470905 | SNP | C | T | Splice_Site |
| DNMT3A | 2 | 25470905 | SNP | C | A | Splice_Site |
| DNMT3A | 2 | 25470955 | INS | — | C | Frame_Shift_Ins |
| DNMT3A | 2 | 25470982 | DEL | GT | — | Frame_Shift_Del |
| DNMT3A | 2 | 25471011 | DEL | G | — | Frame_Shift_Del |
| DNMT3A | 2 | 25471016 | SNP | G | A | Nonsense_Mutation |
| DNMT3A | 2 | 25471016 | SNP | G | A | Nonsense_Mutation |
| DNMT3A | 2 | 25471030 | DEL | G | — | Frame_Shift_Del |
| DNMT3A | 2 | 25471030 | DEL | G | — | Frame_Shift_Del |
| DNMT3A | 2 | 25471039 | DEL | T | — | Frame_Shift_Del |
| DNMT3A | 2 | 25471040 | SNP | C | A | Nonsense_Mutation |
| DNMT3A | 2 | 25471048 | INS | — | TC | Frame_Shift_Ins |
| DNMT3A | 2 | 25471052 | INS | — | A | Frame_Shift_Ins |
| DNMT3A | 2 | 25471069 | DEL | T | — | Frame_Shift_Del |
| DNMT3A | 2 | 25471082 | DEL | C | — | Frame_Shift_Del |
| DNMT3A | 2 | 25523009 | SNP | G | A | Splice_Site |
| EP300 | 22 | 41523642 | INS | — | C | Frame_Shift_Ins |
| ETV6 | 12 | 12022502 | DEL | C | — | Frame_Shift_Del |
| EZH2 | 7 | 148506461 | SNP | C | T | Missense_Mutation |
| EZH2 | 7 | 148515097 | INS | — | T | Frame_Shift_Ins |
| FAM46C | 1 | 118165768 | INS | — | C | Frame_Shift_Ins |
| FBXW | 4 | 153268225 | INS | — | A | Splice_Site |
| FLT3 | 13 | 28608281 | SNP | A | G | Missense_Mutation |
| FOXP1 | 3 | 71026170 | INS | — | T | Frame_Shift_Ins |
| GNAS | 20 | 57484420 | SNP | C | G | Missense_Mutation |
| GNAS | 20 | 57484420 | SNP | C | T | Missense_Mutation |
| GNAS | 20 | 57484420 | SNP | C | A | Missense_Mutation |
| GNAS | 20 | 57484421 | SNP | G | A | Missense_Mutation |
| GNAS | 20 | 57484421 | SNP | G | A | Missense_Mutation |
| GNAS | 20 | 57484421 | SNP | G | A | Missense_Mutation |
| GNAS | 20 | 57484421 | SNP | G | A | Missense_Mutation |
| GNB1 | 1 | 1747227 | SNP | C | A | Missense_Mutation |
| GNB1 | 1 | 1747227 | SNP | C | A | Missense_Mutation |
| GNB1 | 1 | 1747228 | SNP | T | A | Missense_Mutation |
| GNB1 | 1 | 1747228 | SNP | T | A | Missense_Mutation |
| GNB1 | 1 | 1747228 | SNP | T | A | Missense_Mutation |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| GNB1 | 1 | 1747229 | SNP | T | C | Missense_Mutation |
| GNB1 | 1 | 1747229 | SNP | T | C | Missense_Mutation |
| GNB1 | 1 | 1747229 | SNP | T | C | Missense_Mutation |
| GNB1 | 1 | 1747229 | SNP | T | C | Missense_Mutation |
| GNB1 | 1 | 1747229 | SNP | T | C | Missense_Mutation |
| GNB1 | 1 | 1747229 | SNP | T | C | Missense_Mutation |
| GNB1 | 1 | 1747229 | SNP | T | C | Missense_Mutation |
| GNB1 | 1 | 1747229 | SNP | T | C | Missense_Mutation |
| GNB1 | 1 | 1747229 | SNP | T | C | Missense_Mutation |
| GNB1 | 1 | 1747229 | SNP | T | C | Missense_Mutation |
| GNB1 | 1 | 1747229 | SNP | T | C | Missense_Mutation |
| GNB1 | 1 | 1747229 | SNP | T | C | Missense_Mutation |
| GNB1 | 1 | 1747229 | SNP | T | C | Missense_Mutation |
| GNB1 | 1 | 1747229 | SNP | T | C | Missense_Mutation |
| GNB1 | 1 | 1747229 | SNP | T | C | Missense_Mutation |
| GNB1 | 1 | 1747229 | SNP | T | C | Missense_Mutation |
| HIST1H1C | 6 | 26056332 | SNP | T | A | Nonsense_Mutation |
| IDH2 | 15 | 90631934 | SNP | C | T | Missense_Mutation |
| IDH2 | 15 | 90631934 | SNP | C | T | Missense_Mutation |
| IDH2 | 15 | 90631934 | SNP | C | T | Missense_Mutation |
| IKZF1 | 7 | 50468196 | SNP | C | A | Nonsense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK2 | 9 | 5073770 | SNP | G | T | Missense_Mutation |
| JAK3 | 19 | 17949108 | SNP | C | T | Missense_Mutation |
| JARID2 | 6 | 15501273 | INS | — | G | Frame_Shift_Ins |
| KDM6A | X | 44879925 | SNP | C | T | Nonsense_Mutation |
| KDM6A | X | 44942739 | DEL | C | — | Frame_Shift_Del |
| KIT | 4 | 55594197 | SNP | C | T | Missense_Mutation |
| KLHL6 | 3 | 3273150 | SNP | T | A | Missense_Mutation |
| KRAS | 12 | 25378561 | SNP | G | A | Missense_Mutation |
| KRAS | 12 | 25378647 | SNP | T | G | Missense_Mutation |
| KRAS | 12 | 25398285 | SNP | C | A | Missense_Mutation |
| LUC7L2 | 7 | 139083380 | DEL | C | — | Frame_Shift_Del |
| LUC7L2 | 7 | 139086898 | SNP | C | T | Nonsense_Mutation |
| LUC7L2 | 7 | 139097301 | SNP | C | T | Nonsense_Mutation |
| MLL2 | 19 | 36213944 | INS | — | C | Frame_Shift_Ins |
| MLL2 | 12 | 49427936 | INS | — | T | Frame_Shift_Ins |
| MLL2 | 12 | 49434301 | SNP | G | A | Nonsense_Mutation |
| MLL2 | 12 | 49444933 | DEL | G | — | Frame_Shift_Del |
| MPL | 1 | 43814993 | DEL | CTG | — | In_Frame_Del |
| MPL | 1 | 43815009 | SNP | G | T | Missense_Mutation |
| MYD88 | 3 | 38182641 | SNP | T | C | Missense_Mutation |
| MYD88 | 3 | 38182641 | SNP | T | C | Missense_Mutation |
| NOTCH1 | 9 | 139400000 | SNP | C | A | Nonsense_Mutation |
| NOTCH1 | 9 | 139413957 | DEL | T | — | Frame_Shift_Del |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| NOTCH2 | 1 | 120467977 | SNP | C | A | Nonsense_Mutation |
| NOTCH2 | 1 | 120611991 | SNP | C | T | Nonsense_Mutation |
| INRAS | 1 | 115256528 | SNP | T | G | Missense_Mutation |
| NRAS | 1 | 115256529 | SNP | T | C | Missense_Mutation |
| NRAS | 1 | 115256530 | SNP | G | T | Missense_Mutation |
| NRAS | 1 | 115256532 | SNP | C | T | Missense_Mutation |
| NRAS | 1 | 115258744 | SNP | C | T | Missense_Mutation |
| NRAS | 1 | 115258745 | SNP | C | G | Missense_Mutation |
| PDSS2 | 6 | 107655446 | DEL | G | — | Frame_Shift_Del |
| PHF6 | X | 133551280 | SNP | G | T | Nonsense_Mutation |
| PIK3CA | 3 | 178916726 | SNP | G | A | Missense_Mutation |
| PRDM1 | 6 | 106553280 | INS | — | C | Frame_Shift_Ins |
| PRDM1 | 6 | 106553536 | INS | — | C | Frame_Shift_Ins |
| PRDM1 | 6 | 106553596 | INS | — | C | Frame_Shift_Ins |
| PRPF40B | 12 | 50027850 | SNP | C | T | Nonsense_Mutation |
| PTPN11 | 12 | 112888172 | SNP | A | G | Missense_Mutation |
| PTPN11 | 12 | 112888172 | SNP | A | G | Missense_Mutation |
| PTPN11 | 12 | 112888189 | SNP | G | C | Missense_Mutation |
| RAD21 | 8 | 117862942 | INS | — | T | Frame_Shift_Ins |
| RAD21 | 8 | 117863003 | SNP | G | A | Nonsense_Mutation |
| RAD21 | 8 | 117864908 | DEL | GGTCTTCTGG | — | Frame_Shift_Del |
| RAD21 | 8 | 117869618 | DEL | TAGGAGGTTAG | — | Frame_Shift_Del |
| RAD21 | 8 | 117875449 | SNP | C | T | Missense_Mutation |
| RAD21 | 8 | 117875476 | SNP | G | C | Nonsense_Mutation |
| RIT1 | 1 | 155874194 | INS | — | A | Frame_Shift_Ins |
| RPS15 | 19 | 1440427 | SNP | C | G | Missense_Mutation |
| SETD2 | 3 | 47084145 | INS | — | G | Frame_Shift_Ins |
| SETD2 | 3 | 47103730 | DEL | TTTAT | — | Frame_Shift_Del |
| SETD2 | 3 | 47125328 | INS | — | G | Frame_Shift_Ins |
| SETD2 | 3 | 47158225 | SNP | G | A | Nonsense_Mutation |
| SETDB1 | 1 | 150933381 | INS | — | C | Frame_Shift_Ins |
| SF1 | 11 | 64533489 | INS | — | G | Frame_Shift_Ins |
| SF1 | 11 | 64536811 | SNP | C | G | Splice_Site |
| SF3A1 | 22 | 30737857 | INS | — | G | Frame_Shift_Ins |
| SF3B1 | 2 | 198266489 | SNP | C | T | Missense_Mutation |
| SF3B1 | 2 | 198266611 | SNP | C | T | Missense_Mutation |
| SF3B1 | 2 | 198266834 | SNP | T | C | Missense_Mutation |
| SF3B1 | 2 | 198266834 | SNP | T | C | Missense_Mutation |
| SF3B1 | 2 | 198266834 | SNP | T | C | Missense_Mutation |
| SF3B1 | 2 | 198266834 | SNP | T | C | Missense_Mutation |
| SF381 | 2 | 198266834 | SNP | T | C | Missense_Mutation |
| SF3B1 | 2 | 198266834 | SNP | T | C | Missense_Mutation |
| SF3B1 | 2 | 198266834 | SNP | T | C | Missense_Mutation |
| SF3B1 | 2 | 198266834 | SNP | T | C | Missense_Mutation |
| SF3B1 | 2 | 198266834 | SNP | T | C | Missense_Mutation |
| SF3B1 | 2 | 198266834 | SNP | T | C | Missense_Mutation |
| SF3B1 | 2 | 198267359 | SNP | C | A | Missense_Mutation |
| SF3B1 | 2 | 198267359 | SNP | C | A | Missense_Mutation |
| SF3B1 | 2 | 198267359 | SNP | C | G | Missense_Mutation |
| SF3B1 | 2 | 198267359 | SNP | C | G | Missense_Mutation |
| SF3B1 | 2 | 198267359 | SNP | C | G | Missense_Mutation |
| SF3B1 | 2 | 198267359 | SNP | C | A | Missense_Mutation |
| SF3B1 | 2 | 198267359 | SNP | C | A | Missense_Mutation |
| SF3B1 | 2 | 198267359 | SNP | C | A | Missense_Mutation |
| SF3B1 | 2 | 198267360 | SNP | T | C | Missense_Mutation |
| SF3B1 | 2 | 198267361 | SNP | T | C | Missense_Mutation |
| SF3B1 | 2 | 198267361 | SNP | T | G | Missense_Mutation |
| SF3B1 | 2 | 198267371 | SNP | G | T | Missense_Mutation |
| SF3B1 | 2 | 198272802 | SNP | G | A | Missense_Mutation |
| SFRS2 | 17 | 74732959 | SNP | G | A | Missense_Mutation |
| SFRS2 | 17 | 74732959 | SNP | G | C | Missense_Mutation |
| SFRS2 | 17 | 74732959 | SNP | G | T | Missense_Mutation |
| SFRS2 | 17 | 74732959 | SNP | G | C | Missense_Mutation |
| SFRS2 | 17 | 74732959 | SNP | G | T | Missense_Mutation |
| SFRS2 | 17 | 74732959 | SNP | G | A | Missense_Mutation |
| SFRS2 | 17 | 74732959 | SNP | G | C | Missense_Mutation |
| SFRS2 | 17 | 74732959 | SNP | G | T | Missense_Mutation |
| SFRS2 | 17 | 74732959 | SNP | G | T | Missense_Mutation |
| SFRS2 | 17 | 74732960 | SNP | G | T | Missense_Mutation |
| SFRS2 | 17 | 74733113 | SNP | A | G | Missense_Mutation |
| SMC1A | X | 53409443 | SNP | C | T | Missense_Mutation |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| SMC3 | 10 | 112343707 | SNP | C | T | Nonsense_Mutation |
| STAG1 | 3 | 136078015 | SNP | G | A | Nonsense_Mutation |
| STAG2 | X | 123200061 | SNP | T | A | Nonsense_Mutation |
| STAT3 | 17 | 40474420 | SNP | C | A | Missense_Mutation |
| STAT3 | 17 | 40474420 | SNP | C | A | Missense_Mutation |
| STAT3 | 17 | 40474420 | SNP | C | A | Missense_Mutation |
| STAT3 | 17 | 40475058 | SNP | C | G | Missense_Mutation |
| SUZ12 | 17 | 30315461 | DEL | AG | — | Frame_Shift_Del |
| TBL1XR1 | 3 | 176750884 | SNP | G | A | Nonsense_Mutation |
| TET1 | 10 | 70442645 | SNP | G | A | Missense_Mutation |
| TET2 | 4 | 106155316 | INS | — | A | Frame_Shift_Ins |
| TET2 | 4 | 106155353 | DEL | A | — | Frame_Shift_Del |
| TET2 | 4 | 106155403 | DEL | TC | — | Frame_Shift_Del |
| TET2 | 4 | 106155544 | DEL | G | — | Frame_Shift_Del |
| TET2 | 4 | 106155585 | DEL | T | — | Frame_Shift_Del |
| TET2 | 4 | 106155640 | DEL | AT | — | Frame_Shift_Del |
| TET2 | 4 | 106155761 | INS | — | A | Frame_Shift_Ins |
| TET2 | 4 | 106155879 | DEL | G | — | Frame_Shift_Del |
| TFT2 | 4 | 106155921 | DEL | C | — | Frame_Shift_Del |
| TET2 | 4 | 106156030 | INS | — | T | Frame_Shift_Ins |
| TET2 | 4 | 106156120 | SNP | C | T | Nonsense_Mutation |
| TET2 | 4 | 106156246 | SNP | C | T | Nonsense_Mutation |
| TET2 | 4 | 106156304 | SNP | C | G | Nonsense_Mutation |
| TET2 | 4 | 106156315 | INS | — | T | Frame_Shift_Ins |
| TET2 | 4 | 106156358 | DEL | C | — | Frame_Shift_Del |
| TET2 | 4 | 106156371 | DEL | C | — | Frame_Shift_Del |
| TET2 | 4 | 106156421 | INS | — | T | Frame_Shift_Ins |
| TET2 | 4 | 106156452 | DEL | A | — | Frame_Shift_Del |
| TET2 | 4 | 106156540 | SNP | C | T | Nonsense_Mutation |
| TET2 | 4 | 106156590 | INS | — | GTTC | Frame_Shift_Ins |
| TET2 | 4 | 106156625 | SNP | C | G | Nonsense_Mutation |
| TET2 | 4 | 106156665 | DEL | T | — | Frame_Shift_Del |
| TET2 | 4 | 106156687 | SNP | C | T | Nonsense_Mutation |
| TET2 | 4 | 106156693 | DEL | T | — | Frame_Shift_Del |
| TET2 | 4 | 106156694 | SNP | T | A | Nonsense_Mutation |
| TET2 | 4 | 106156729 | SNP | C | T | Nonsense_Mutation |
| TET2 | 4 | 106156790 | SNP | G | A | Nonsense_Mutation |
| TET2 | 4 | 106156820 | DEL | A | — | Frame_Shift_Del |
| TET2 | 4 | 106156835 | INS | — | A | Frame_Shift_Ins |
| TET2 | 4 | 106156862 | SNP | C | G | Nonsense_Mutation |
| TET2 | 4 | 106156862 | SNP | C | G | Nonsense_Mutation |
| TET2 | 4 | 106156936 | DEL | G | — | Frame_Shift_Del |
| TET2 | 4 | 106157003 | DEL | A | — | Frame_Shift_Del |
| TET2 | 4 | 106157106 | DEL | A | — | Frame_Shift_Del |
| TET2 | 4 | 106157155 | DEL | AG | — | Frame_Shift_Del |
| TET2 | 4 | 106157173 | INS | — | A | Frame_Shift_Ins |
| TET2 | 4 | 106157212 | SNP | C | T | Nonsense_Mutation |
| TET2 | 4 | 106157236 | DEL | T | — | Frame_Shift_Del |
| TET2 | 4 | 106157299 | SNP | C | T | Nonsense_Mutation |
| TET2 | 4 | 106157306 | SNP | C | A | Nonsense_Mutation |
| TET2 | 4 | 106157313 | DEL | C | — | Frame_Shift_Del |
| TET2 | 4 | 106157326 | DEL | C | — | Frame_Shift_Del |
| TET2 | 4 | 106157349 | DEL | AAAG | — | Frame_Shift_Del |
| TET2 | 4 | 106157371 | SNP | C | T | Nonsense_Mutation |
| TET2 | 4 | 106157384 | INS | — | C | Frame_Shift_Ins |
| TET2 | 4 | 106157407 | SNP | C | T | Nonsense_Mutation |
| TET2 | 4 | 106157493 | INS | — | A | Frame_Shift_Ins |
| TET2 | 4 | 106157615 | DEL | A | — | Frame_Shift_Del |
| TET2 | 4 | 106157616 | DEL | C | — | Frame_Shift_Del |
| TET2 | 4 | 106157671 | DEL | A | — | Frame_Shift_Del |
| TET2 | 4 | 106157695 | SNP | C | T | Nonsense_Mutation |
| TET2 | 4 | 106157731 | DEL | C | — | Frame_Shift_Del |
| TET2 | 4 | 106157816 | INS | — | GTCTG | Frame_Shift_Ins |
| TET2 | 4 | 106157824 | SNP | C | T | Nonsense_Mutation |
| TET2 | 4 | 106157827 | SNP | C | T | Nonsense_Mutation |
| TET2 | 4 | 106157833 | DEL | GC | — | Frame_Shift_Del |
| TET2 | 4 | 106157845 | SNP | C | T | Nonsense_Mutation |
| TET2 | 4 | 106157845 | SNP | C | T | Nonsense_Mutation |
| TET2 | 4 | 106158065 | INS | — | A | Frame_Shift_Ins |
| TET2 | 4 | 106158140 | INS | — | A | Frame_Shift_Ins |
| TET2 | 4 | 106158160 | SNP | C | T | Nonsense_Mutation |
| TET2 | 4 | 106158187 | SNP | C | T | Nonsense_Mutation |
| TET2 | 4 | 106158226 | INS | — | AT | Frame_Shift_Ins |
| TET2 | 4 | 106158332 | DEL | C | — | Frame_Shift_Del |
| TET2 | 4 | 106158356 | DEL | CT | — | Frame_Shift_Del |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| TET2 | 4 | 106158408 | DEL | TT | — | Frame_Shift_Del |
| TET2 | 4 | 106158408 | DEL | T | — | Frame_Shift_Del |
| TET2 | 4 | 106158439 | DEL | AC | — | Frame_Shift_Del |
| TET2 | 4 | 106158479 | INS | — | T | Frame_Shift_Ins |
| TET2 | 4 | 106158503 | SNP | G | A | Missense_Mutation |
| TET2 | 4 | 106158509 | SNP | G | A | Splice_Site |
| TET2 | 4 | 106158509 | SNP | G | A | Splice_Site |
| TNFAIP3 | 6 | 138196014 | SNP | C | T | Nonsense_Mutation |
| TNFAIP3 | 6 | 138196885 | SNP | C | T | Nonsense_Mutation |
| TNFAIP3 | 6 | 138198296 | SNP | G | T | Nonsense_Mutation |
| TNFRSF14 | 1 | 2489781 | SNP | G | C | Splice_Site |
| TNFRSF14 | 1 | 2491327 | DEL | G | — | Frame_Shift_Del |
| TP53 | 17 | 7574003 | SNP | G | A | Nonsense_Mutation |
| TP53 | 17 | 7577090 | SNP | C | T | Missense_Mutation |
| TP53 | 17 | 7577090 | SNP | C | T | Missense_Mutation |
| TP53 | 17 | 7577094 | SNP | G | A | Missense_Mutation |
| TP53 | 17 | 7577097 | SNP | C | T | Missense_Mutation |
| TP53 | 17 | 7577100 | SNP | T | C | Missense_Mutation |
| TP53 | 17 | 7577538 | SNP | C | T | Missense_Mutation |
| TP53 | 17 | 7577538 | SNP | C | T | Missense_Mutation |
| TP53 | 17 | 757548 | SNP | C | A | Missense_Mutation |
| TP53 | 17 | 7577559 | SNP | G | C | Missense_Mutation |
| TP53 | 17 | 7577578 | SNP | T | C | Missense_Mutation |
| TP53 | 17 | 7578190 | SNP | T | C | Missense_Mutation |
| TP53 | 17 | 7578191 | SNP | A | G | Missense_Mutation |
| TP53 | 17 | 7578271 | SNP | T | C | Missense_Mutation |
| TP53 | 17 | 7578389 | SNP | G | A | Missense_Mutation |
| TP53 | 17 | 7578400 | SNP | G | C | Missense_Mutation |
| TP53 | 17 | 7578406 | SNP | C | T | Missense_Mutation |
| TP53 | 17 | 7578406 | SNP | C | T | Missense_Mutation |
| TP53 | 17 | 7578406 | SNP | C | T | Missense_Mutation |
| TP53 | 17 | 7578412 | SNP | A | T | Missense_Mutation |
| TP53 | 17 | 7578457 | SNP | C | T | Missense_Mutation |
| TP53 | 17 | 7578463 | SNP | C | T | Missense_Mutation |
| TP53 | 17 | 7578475 | SNP | G | A | Missense_Mutation |
| TP53 | 17 | 7578492 | SNP | C | T | Nonsense_Mutation |
| TP53 | 17 | 7578493 | SNP | C | T | Nonsense_Mutation |
| TP53 | 17 | 7578536 | SNP | T | C | Missense_Mutation |
| TP53 | 17 | 7578536 | SNP | T | C | Missense_Mutation |
| TP53 | 17 | 7579315 | INS | — | C | Frame_Shift_Ins |
| TP53 | 17 | 7579358 | SNP | C | A | Missense_Mutation |
| TP53 | 17 | 7579359 | SNP | G | A | Missense_Mutation |
| TP53 | 17 | 7579359 | SNP | G | A | Missense_Mutation |
| TP53 | 17 | 7579470 | INS | — | G | Frame_Shift_Ins |
| TP53 | 17 | 7579471 | DEL | G | — | Frame_Shift_Del |
| U2AF1 | 21 | 44514780 | SNP | C | T | Missense_Mutation |
| U2AF1 | 21 | 44514780 | SNP | C | T | Missense_Mutation |
| U2AF1 | 21 | 44524456 | SNP | G | A | Missense_Mutation |
| U2AF1 | 21 | 44524456 | SNP | G | A | Missense_Mutation |
| U2AF1 | 21 | 44527564 | SNP | T | C | Missense_Mutation |
| ZRSR2 | X | 15822298 | SNP | G | C | Missense_Mutation |
| ZRSR2 | X | 15838385 | SNP | C | T | Nonsense_Mutation |
| ZRSR2 | X | 15841188 | DEL | A | — | Frame_Shift_Del |

| Protein Change | cDNA change | Accession | Variant allele fraction | Variant allele count | Reference allele count | ID |
|---|---|---|---|---|---|---|
| p.R404* | c.1210C > T | NM_015338 | 0.302326 | 26 | 60 | id16093 |
| p.R404* | c.1210C > T | NM_015338 | 0.106796 | 11 | 92 | id5983 |
| p.R404* | c.1210C > T | NM_015338 | 0.063291 | 5 | 74 | id3697 |
| p.R404* | c.1210C > T | NM_015338 | 0.194444 | 14 | 58 | id6530 |
| p.R404* | c.1210C > T | NM_015338 | 0.052083 | 5 | 91 | id12539 |
| p.R417* | c.1250G > A | NM_015338 | 0.04878 | 6 | 117 | id6912 |
| p.R417* | c.1250G > A | NM_015338 | 0.052632 | 5 | 90 | id17093 |
| p.R417* | c.1250G > A | NM_015338 | 0.241379 | 28 | 88 | id7330 |
| p.R417* | c.1250G > A | NM_015338 | 0.177305 | 25 | 116 | id4593 |
| p.R417* | c.1250G > A | NM_015338 | 0.069767 | 6 | 80 | id10535 |
| p.Y425fs | c.1275delC | NM_015338 | 0.2 | 16 | 65 | id17167 |
| p.Q428* | c.1282C > T | NM_015338 | 0.051948 | 4 | 73 | id15889 |
| p.Q432* | c.1294C > T | NM_015338 | 0.232877 | 17 | 56 | id12542 |
| p.S444* | c.1331C > T | NM_015338 | 0.041237 | 4 | 93 | id9683 |
| p.S444* | c.1331C > T | NM_015338 | 0.047619 | 7 | 140 | id3121 |
| p.Q512* | c.1534C > T | NM_015338 | 0.122449 | 24 | 172 | id3907 |
| p.E513* | c.1537G > T | NM_015338 | 0.052632 | 7 | 126 | id12605 |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| p.T514fs | c.1542_1543delTG | NM_015338 | 0.24 | 58 | 179 | id9964 |
| p.T514fs | c.1542_1543delTG | NM_015338 | 0.09 | 20 | 201 | id14785 |
| p.Q517* | c.1549C > T | NM_015338 | 0.067873 | 15 | 206 | id15925 |
| p.E518* | c.1552_1553delGA | NM_015338 | 0.095238 | 12 | 114 | id15929 |
| p.E518fs | c.1552_1553delGA | NM_015338 | 0.16 | 41 | 220 | id16839 |
| p.Q529* | c.1585C > T | NM_015338 | 0.179775 | 32 | 146 | id15189 |
| p.L542fs | c.1626_1627insGAAGATC | NM_015338 | 0.13 | 14 | 91 | id16126 |
| p.Q546* | c.1636C > T | NM_015338 | 0.194444 | 21 | 87 | id15951 |
| p.R549fs | c.1646_1647insTAACACT | NM_015338 | 0.05 | 10 | 206 | id2117 |
| p.Q575* | c.1723C > T | NM_015338 | 0.166667 | 10 | 50 | id2349 |
| p.W583* | c.1748G > A | NM_015338 | 0.08 | 6 | 69 | id11045 |
| p.Y591fs | c.1771_1772insA | NM_015338 | 0.32 | 29 | 61 | id5794 |
| p.Y591* | c.1771_1772insA | NM_015338 | 0.101695 | 18 | 159 | id13763 |
| p.C594* | c.1782C > A | NM_015338 | 0.16129 | 10 | 52 | id884 |
| p.D616fs | c.1848_1849insT | NM_015338 | 0.23 | 10 | 33 | id1924 |
| p.H630fs | c.1888_1910delCACCACTGCCATAGAGAGGCGGC | NM_015338 | 0.18 | 8 | 37 | id6015 |
| p.R634fs | c.1901_1923delGAGAGGCGGCCACCACTGCCATC | NM_015338 | 0.22 | 13 | 45 | id4773 |
| p.G642fs | c.1926_1927insG | NM_015340 | 0.33 | 6 | 12 | id13857 |
| p.G642fs | c.1926_1927insG | NM_015338 | 0.24 | 6 | 19 | id15227 |
| p.G642fs | c.1926_1927insG | NM_015339 | 0.38 | 6 | 10 | id3122 |
| p.G642fs | c.1926_1927insG | NM_015341 | 0.38 | 8 | 13 | id10828 |
| p.G642fs | c.1926_1927insG | NM_015342 | 0.31 | 11 | 24 | id13059 |
| p.Q692* | c.2074C > T | NM_015338 | 0.067416 | 6 | 83 | id12078 |
| p.R693* | c.2077C > T | NM_015338 | 0.108108 | 4 | 33 | id12402 |
| p.R693* | c.2077C > T | NM_015338 | 0.166667 | 5 | 25 | id5859 |
| p.R693* | c.2077C > T | NM_015338 | 0.156863 | 8 | 43 | id4532 |
| p.Q695fs | c.2064delA | NM_015338 | 0.19 | 9 | 38 | id2275 |
| p.G710fs | c.2128delG | NM_015338 | 0.34 | 11 | 21 | id14955 |
| p.Q748* | c.2242C > T | NM_015338 | 0.3 | 9 | 21 | id15381 |
| p.Q757* | c.2269C > T | NM_015338 | 0.279412 | 19 | 49 | id9809 |
| p.Q760* | c.2278C > T | NM_015338 | 0.125 | 4 | 28 | id12782 |
| p.Q768* | c.2302C > T | NM_015338 | 0.1 | 5 | 45 | id2116 |
| p.Q768* | c.2302C > T | NM_015338 | 0.06 | 3 | 47 | id11131 |
| p.Q780* | c.2338C > T | NM_015338 | 0.292308 | 19 | 46 | id9635 |
| p.Q803* | c.2407C > T | NM_015338 | 0.112903 | 7 | 55 | id10826 |
| p.Q803* | c.2407C > T | NM_015338 | 0.296296 | 16 | 38 | id11861 |
| p.L823fs | c.2467delT | NM_015338 | 0.08 | 10 | 111 | id2961 |
| p.L823* | c.2467delT | NM_015338 | 0.060403 | 9 | 140 | id1808 |
| p.I919fs | c.2756_2757insA | NM_015338 | 0.22 | 18 | 64 | id9984 |
| p.E947* | c.2840A > G | NM_015338 | 0.08 | 6 | 69 | id1754 |
| p.L956fs | c.2866_2869delCTTA | NM_015338 | 0.31 | 25 | 56 | id14964 |
| p.F1005fs | c.3013delT | NM_015338 | 0.1 | 11 | 98 | id4445 |
| p.S1013fs | c.3039delC | NM_015338 | 0.12 | 11 | 81 | id13638 |
| p.W1037* | c.3110G > A | NM_015338 | 0.072581 | 9 | 115 | id16502 |
| p.Q1063* | c.3187C > T | NM_015338 | 0.052632 | 6 | 108 | id3226 |
| p.G596S | c.1786G > A | NM_138576 | 0.404255 | 19 | 28 | id3170 |
| p.H1367fs | c.4099_4100insC | NM_001123385 | 0.05 | 6 | 120 | id1443 |
| p.S1064fs | c.3191_3192delCG | NM_001123385 | 0.1 | 12 | 109 | id5900 |
| p.S286fs | c.856delA | NM_001123385 | 0.43 | 12 | 16 | id3439 |
| p.N143fs | c.428_429insA | NM_001123385 | 0.03 | 6 | 185 | id6419 |
| p.S292* | c.875C > G | NM_021946 | 0.162791 | 7 | 36 | id16590 |
| p.R1332* | c.3994C > T | NM_021946 | 0.09375 | 6 | 58 | id3227 |
| p.G209fs | c.627_628insG | NM_182962 | 0.04 | 7 | 163 | id11974 |
| p.V600E | c.1799T > A | NM_004333 | 0.196429 | 11 | 45 | id9117 |
| p.G469E | c.1406G > A | NM_004333 | 0.12973 | 24 | 161 | id15992 |
| p.R81* | c.241C > T | NM_024332 | 0.143791 | 22 | 131 | id6955 |
| p.R81* | c.241C > T | NM_024332 | 0.084337 | 7 | 76 | id10444 |
| p.R89* | c.265C > T | NM_024332 | 0.067416 | 6 | 83 | id10536 |
| p.R89* | c.265C > T | NM_024332 | 0.116667 | 7 | 53 | id14164 |
| p.W120* | c.360G > A | NM_024332 | 0.04 | 7 | 168 | id8978 |
| c.e5+1 | c.403_splice | NM_024332 | 0.104348 | 12 | 103 | id8963 |
| p.R423W | c.1267C > T | NM_032415 | 0.073171 | 3 | 38 | id5921 |
| p.C381R | c.1141T > C | NM_005188 | 0.122807 | 7 | 50 | id4445 |
| p.C381Y | c.1142G > A | NM_005188 | 0.34375 | 11 | 21 | id15991 |
| p.C381S | c.1142G > C | NM_005188 | 0.071429 | 3 | 39 | id5319 |
| p.K382E | c.1144A > G | NM_005188 | 0.064103 | 5 | 73 | id3465 |
| p.I383M | c.1149A > G | NM_005188 | 0.06383 | 6 | 88 | id12878 |
| p.C404Y | c.1211G > A | NM_005188 | 0.113333 | 17 | 133 | id8673 |
| p.C404Y | c.1211G > A | NM_005188 | 0.072917 | 7 | 89 | id15632 |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| p.C404Y | c.1211G > A | NM_005188 | 0.101562 | 13 | 115 | id10499 |
| p.G415S | c.1243G > A | NM_005188 | 0.046875 | 6 | 122 | id16015 |
| p.G415S | c.1243G > A | NM_005188 | 0.056 | 7 | 118 | id15505 |
| p.F418I | c.1252T > A | NM_005188 | 0.082278 | 13 | 145 | id3807 |
| p.R420Q | c.1259G > A | NM_005188 | 0.052632 | 6 | 108 | id10937 |
| p.G210S | c.628G > A | NM_001779 | 0.368 | 46 | 79 | id15637 |
| p.Y196S | c.587A > C | NM_000626 | 0.086957 | 8 | 84 | id6059 |
| p.E20K | c.58G > A | NM_014516 | 0.055556 | 12 | 204 | id1662 |
| p.E1566fs | c.4698delA | NM_004380 | 0.03 | 7 | 236 | id1443 |
| p.I1084fs | c.3250delA | NM_004380 | 0.05 | 8 | 149 | id8258 |
| p.A690fs | c.2068_2069insG | NM_004380 | 0.03 | 6 | 182 | id10673 |
| p.Q682fs | c.2044_2045insC | NM_004380 | 0.07 | 12 | 166 | id3674 |
| p.R386* | c.1156C > T | NM_004380 | 0.054054 | 6 | 105 | id14548 |
| p.Q286fs | c.856_857insC | NM_004380 | 0.08 | 10 | 122 | id6570 |
| p.Q37* | c.1124A > T | NM_181552 | 0.125 | 17 | 119 | id3807 |
| p.R147* | c.4430G > A | NM_181552 | 0.113636 | 15 | 117 | id12656 |
| c.e13 −1 | c.1077_splice | NM_181552 | 0.121212 | 4 | 29 | id2276 |
| p.S24fs | c.70_71insC | NM_001356 | 0.09 | 18 | 190 | id17182 |
| c.e13+1 | c.1497_splice | NM_001356 | 0.17 | 20 | 97 | id6943 |
| p.F909fs | c.2727delT | NM_022552 | 0.04 | 7 | 183 | id8553 |
| p.F909fs | c.2727delT | NM_022552 | 0.05 | 7 | 142 | id15476 |
| p.P904L | c.2711C > T | NM_022552 | 0.164706 | 14 | 71 | id3391 |
| p.P904L | c.2711C > T | NM_022552 | 0.057143 | 4 | 66 | id12744 |
| p.P904L | c.2711C > T | NM_022552 | 0.054054 | 4 | 70 | id8866 |
| p.P904L | c.2711C > T | NM_022552 | 0.093333 | 7 | 68 | id14640 |
| p.P904L | c.2711C > T | NM_022552 | 0.068493 | 5 | 68 | id15401 |
| p.P904L | c.2711C > T | NM_022552 | 0.197368 | 15 | 61 | id13118 |
| p.A903fs | c.2707_2708delGC | NM_022552 | 0.06 | 6 | 88 | id1518 |
| p.F902fis | c.2705_2706insT | NM_022552 | 0.06 | 7 | 118 | id6054 |
| p.L901H | c.2702T > A | NM_022552 | 0.083333 | 6 | 66 | id14602 |
| p.W893fs | c.2679_2680insG | NM_022552 | 0.08 | 6 | 67 | id12337 |
| p.G890D | c.2669G > A | NM_022552 | 0.0625 | 3 | 45 | id1006 |
| p.L883fs | c.2648_2649insT | NM_022552 | 0.09 | 7 | 68 | id3225 |
| p.R882H | c.2645G > A | NM_022552 | 0.078947 | 3 | 35 | id16125 |
| p.R882H | c.2645G > A | NM_022552 | 0.320755 | 17 | 36 | id3816 |
| p.R882H | c.2645G > A | NM_022552 | 0.290323 | 27 | 66 | id3392 |
| p.R882H | c.2645G > A | NM_022552 | 0.231707 | 19 | 63 | id14954 |
| p.R882H | c.2645G > A | NM_022552 | 0.381818 | 21 | 34 | id6065 |
| p.R882H | c.2645G > A | NM_022552 | 0.302632 | 23 | 53 | id8970 |
| p.R882H | c.2645G > A | NM_022552 | 0.068966 | 4 | 54 | id12364 |
| p.R882H | c.2645G > A | NM_022552 | 0.210526 | 8 | 30 | id14900 |
| p.R882H | c.2645G > A | NM_022552 | 0.06383 | 3 | 44 | id1586 |
| p.R882P | c.2645G > C | NM_022552 | 0.136986 | 10 | 63 | id3327 |
| p.R882H | c.2645G > A | NM_022552 | 0.081081 | 6 | 68 | id6943 |
| p.R882P | c.2645G > C | NM_022552 | 0.087719 | 5 | 52 | id9681 |
| p.R882H | c.2645G > A | NM_022552 | 0.069767 | 3 | 40 | id10973 |
| p.R882H | c.2645G > A | NM_022552 | 0.153846 | 8 | 44 | id13747 |
| p.R882H | c.2645G > A | NM_022552 | 0.089888 | 8 | 81 | id6895 |
| p.R882P | c.2645G > C | NM_022552 | 0.183099 | 13 | 58 | id3247 |
| p.R882H | c.2645G > A | NM_022552 | 0.142857 | 12 | 72 | id4970 |
| p.R882H | c.2645G > A | NM_022552 | 0.202899 | 14 | 55 | id15710 |
| p.R882H | c.2645G > A | NM_022552 | 0.492958 | 35 | 36 | id6805 |
| p.R882H | c.2645G > A | NM_022552 | 0.084507 | 6 | 65 | id8646 |
| p.R882P | c.2645G > C | NM_022552 | 0.190476 | 12 | 51 | id12236 |
| p.R882H | c.2645G > A | NM_022552 | 0.136364 | 12 | 76 | id6767 |
| p.R882H | c.2645G > A | NM_022552 | 0.072727 | 4 | 51 | id10899 |
| p.R882H | c.2645G > A | NM_022552 | 0.136364 | 9 | 57 | id14751 |
| p.R882H | c.2645G > A | NM_022552 | 0.258621 | 15 | 43 | id15615 |
| p.R882H | c.2645G > A | NM_022552 | 0.169492 | 10 | 49 | id15630 |
| p.R882H | c.2645G > A | NM_022552 | 0.061728 | 5 | 76 | id1921 |
| p.R882H | c.2645G > A | NM_022552 | 0.065217 | 3 | 43 | id15600 |
| p.R882H | c.2645G > A | NM_022552 | 0.377358 | 20 | 33 | id17014 |
| p.R882H | c.2645G > A | NM_022552 | 0.078431 | 4 | 47 | id9232 |
| p.R882H | c.2645G > A | NM_022552 | 0.072727 | 4 | 51 | id13491 |
| p.R882H | c.2645G > A | NM_022552 | 0.090909 | 7 | 70 | id4533 |
| p.R882H | c.2645G > A | NM_022552 | 0.089744 | 7 | 71 | id5608 |
| p.R882H | c.2645G > A | NM_022552 | 0.285714 | 12 | 30 | id1519 |
| p.R882H | c.2645G > A | NM_022552 | 0.155556 | 7 | 38 | id15436 |
| p.R882H | c.2645G > A | NM_022552 | 0.211538 | 11 | 41 | id5422 |
| p.R882H | c.2645G > A | NM_022552 | 0.057143 | 4 | 66 | id2809 |
| p.R882H | c.2645G > A | NM_022552 | 0.242105 | 23 | 72 | id2743 |
| p.R882P | c.2645G > C | NM_022552 | 0.107143 | 6 | 50 | id5188 |
| p.R882H | c.2645G > A | NM_022552 | 0.057143 | 4 | 66 | id2698 |
| p.R882H | c.2645G > A | NM_022552 | 0.113924 | 9 | 70 | id12547 |
| p.R882H | c.2645G > A | NM_022552 | 0.1 | 7 | 63 | id2672 |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| p.R882C | c.2644C > T | NM_022552 | 0.122449 | 6 | 43 | id16177 |
| p.R882C | c.2644C > T | NM_022552 | 0.076923 | 3 | 36 | id16090 |
| p.R882C | c.2644C > T | NM_022552 | 0.065574 | 4 | 57 | id9965 |
| p.R882C | c.2644C > T | NM_022552 | 0.075 | 3 | 37 | id2320 |
| p.R882C | c.2644C > T | NM_022552 | 0.102941 | 7 | 61 | id15309 |
| p.R882C | c.2644C > T | NM_022552 | 0.076923 | 3 | 36 | id15857 |
| p.R882C | c.2644C > T | NM_022552 | 0.135593 | 8 | 51 | id13686 |
| p.R882C | c.2644C > T | NM_022552 | 0.104167 | 5 | 43 | id2059 |
| p.R882C | c.2644C > T | NM_022552 | 0.226667 | 17 | 58 | id3197 |
| p.R882C | c.2644C > T | NM_022552 | 0.302326 | 13 | 30 | id3170 |
| p.R882C | c.2644C > T | NM_022552 | 0.065217 | 6 | 86 | id4835 |
| p.R882C | c.2644C > T | NM_022552 | 0.097561 | 8 | 74 | id3681 |
| p.R882C | c.2644C > T | NM_022552 | 0.205882 | 14 | 54 | id14695 |
| p.R882C | c.2644C > T | NM_022552 | 0.076923 | 5 | 60 | id6592 |
| p.R882C | c.2644C > T | NM_022552 | 0.117647 | 4 | 30 | id1759 |
| p.R882C | c.2644C > T | NM_022552 | 0.114286 | 4 | 31 | id14601 |
| p.R882C | c.2644C > T | NM_022552 | 0.064516 | 4 | 58 | id3613 |
| p.R882C | c.2644C > T | NM_022552 | 0.375 | 30 | 50 | id4532 |
| p.R882C | c.2644C > T | NM_022552 | 0.085714 | 3 | 32 | id6567 |
| p.R882C | c.2644C > T | NM_022552 | 0.066667 | 4 | 56 | id13423 |
| p.R882C | c.2644C > T | NM_022552 | 0.1 | 7 | 63 | id5194 |
| p.R882C | c.2644C > T | NM_022552 | 0.372881 | 22 | 37 | id14241 |
| p.R882C | c.2644C > T | NM_022552 | 0.175439 | 10 | 47 | id10367 |
| p.R882C | c.2644C > T | NM_022552 | 0.052632 | 4 | 72 | id714 |
| p.R882C | c.2644C > T | NM_022552 | 0.196078 | 10 | 41 | id362 |
| p.S881I | c.2642G > T | NM_022552 | 0.09434 | 5 | 48 | id5767 |
| p.M880V | c.2638A > G | NM_022552 | 0.266667 | 16 | 44 | id2054 |
| p.M880V | c.2638A > G | NM_022552 | 0.061538 | 4 | 61 | id8376 |
| p.G869V | c.2606G > T | NM_022552 | 0.083333 | 4 | 44 | id3283 |
| p.F868fs | c.2604delT | NM_022552 | 0.24 | 13 | 41 | id9594 |
| p.W860* | c.2578T > C | NM_022552 | 0.169811 | 9 | 44 | id15965 |
| p.L859fs | c.2575_2576delTT | NM_022552 | 0.07 | 00 | 111 | id3141 |
| p.W860R | c.2578T > C | NM_022552 | 0.288889 | 13 | 32 | id16986 |
| p.W860R | c.2578T > C | NM_022552 | 0.036232 | 5 | 133 | id6619 |
| p.L859fs | c.2575_2576delTT | NM_022552 | 0.07 | 6 | 85 | id2249 |
| p.D85fs | c.2571delC | NM_022552 | 0.1 | 7 | 62 | id9931 |
| p.V850fs | c.2550_2551delCT | NM_022552 | 0.14 | 11 | 66 | id5711 |
| p.D845fs | c.2534_2538delAC | NM_022552 | 0.21 | 15 | 57 | id17135 |
| p.I840fs | c.2519_2520insT | NM_022552 | 0.14 | 12 | 71 | id13494 |
| p.F827fs | c.2481delC | NM_022552 | 0.16 | 18 | 93 | id15890 |
| c.e22 −1 | c.2479_splice | NM_022552 | 0.071429 | 4 | 52 | id15335 |
| c.e22 −1 | c.2479_splice | NM_022552 | 0.146667 | 11 | 64 | id8979 |
| c.e22 −1 | c.2479_splice | NM_022552 | 0.051948 | 4 | 73 | id15858 |
| c.e22 −1 | c.2479_splice | NM_022552 | 0.0625 | 4 | 60 | id10900 |
| c.e22 −1 | c.2479_splice | NM_022552 | 0.103448 | 9 | 78 | id11120 |
| c.e21+1 | c.2478_splice | NM_022552 | 0.114286 | 4 | 31 | id6005 |
| c.e21+1 | c.2478_splice | NM_022552 | 0.166667 | 3 | 15 | id17046 |
| p.P804L | c.2411C > T | NM_022552 | 0.18 | 9 | 41 | id2965 |
| p.P799H | c.2396C > A | NM_022552 | 0.166667 | 4 | 20 | id1345 |
| p.L798fs | c.2392delC | NM_022552 | 0.19 | 10 | 44 | id15563 |
| p.G796V | c.2387G > T | NM_022552 | 0.090909 | 4 | 40 | id8952 |
| p.W795* | c.2385G > A | NM_022552 | 0.12069 | 7 | 51 | id3421 |
| p.V785fs | c.2354delT | NM_022552 | 0.21 | 13 | 50 | id3033 |
| p.E774D | c.2322G > C | NM_022552 | 0.061069 | 8 | 123 | id3224 |
| c.e19+1 | c.2322_splice | NM_022552 | 0.487179 | 38 | 40 | id12147 |
| p.L773R | c.2318T > G | NM_022552 | 0.03937 | 5 | 122 | id12726 |
| p.F772V | c.2314T > G | NM_022552 | 0.038462 | 6 | 150 | id17117 |
| p.R771Q | c.2312G > A | NM_022552 | 0.076923 | 7 | 84 | id3722 |
| p.R771Q | c.2312G > A | NM_022552 | 0.05042 | 6 | 13 | id1923 |
| p.R771Q | c.2312G > A | NM_022552 | 0.055556 | 8 | 136 | id3034 |
| p.R771Q | c.2312G > A | NM_022552 | 0.044444 | 4 | 86 | id1070 |
| p.R771* | c.2312G > A | NM_022552 | 0.051095 | 7 | 130 | id16177 |
| p.R771* | c.2312G > A | NM_022552 | 0.223022 | 31 | 108 | id9845 |
| p.R771* | c.2312G > A | NM_022552 | 0.191589 | 41 | 173 | id6978 |
| p.R771* | c.2312G > A | NM_022552 | 0.088235 | 12 | 24 | id10935 |
| p.R771* | c.2312G > A | NM_022552 | 0.065728 | 14 | 199 | id4836 |
| p.R771* | c.2312G > A | NM_022552 | 0.04375 | 7 | 153 | id2776 |
| p.R771* | c.2312G > A | NM_022552 | 0.112069 | 13 | 103 | id14242 |
| p.R771* | c.2312G > A | NM_022552 | 0.224599 | 42 | 145 | id8817 |
| p.S770W | c.2309C > G | NM_022552 | 0.09434 | 10 | 96 | id15610 |
| p.S770W | c.2309C > G | NM_022552 | 0.046053 | 7 | 145 | id15584 |
| p.S770P | c.2308T > C | NM_022552 | 0.03876 | 5 | 124 | id14786 |
| p.K766* | c.2296A > T | NM_022552 | 0.049505 | 5 | 96 | id8982 |
| p.G762fs | c.2285delG | NM_022552 | 0.04 | 9 | 217 | id2523 |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| p.M761fs | c.2281_2282delAT | NM_022552 | 0.28 | 38 | 96 | id1600 |
| p.M761V | c.2281A > G | NM_022552 | 0.047847 | 10 | 199 | id2963 |
| p.A760fs | c.2280delC | NM_022552 | 0.07 | 14 | 198 | id9680 |
| p.F755L | c.2265T > G | NM_022552 | 0.048276 | 7 | 138 | id9897 |
| p.F755S | c.2264T > C | NM_022552 | 0.247619 | 26 | 79 | id16185 |
| p.F755S | c.2264T > C | NM_022552 | 0.064286 | 9 | 131 | id14878 |
| p.F755S | c.2264T > C | NM_022552 | 0.043103 | 5 | 111 | id8657 |
| p.F755I | c.2263T > A | NM_022552 | 0.121622 | 9 | 65 | id16013 |
| p.F755I | c.2263T > A | NM_022552 | 0.043478 | 6 | 132 | id5386 |
| p.L754fs | c.2262delC | NM_022552 | 0.34 | 41 | 78 | id12579 |
| p.L754H | c.2261T > A | NM_022552 | 0.070796 | 8 | 105 | id9280 |
| p.W753* | c.2258G > A | NM_022552 | 0.282258 | 35 | 89 | id15952 |
| p.F752del | c.2255_2257delTCT | NM_022552 | 0.04 | 6 | 142 | id2365 |
| p.F752L | c.2256C > G | NM_022552 | 0.0625 | 6 | 90 | id8525 |
| p.F752fs | c.2255delT | NM_022552 | 0.09 | 12 | 128 | id3758 |
| p.F752V | c.2254T > G | NM_022552 | 0.093168 | 15 | 146 | id12121 |
| p.F752I | c.2254T > A | NM_022552 | 0.165414 | 22 | 111 | id13396 |
| p.F752V | c.2254T > G | NM_022552 | 0.047945 | 7 | 139 | id8192 |
| p.F751fs | c.2253delC | NM_022552 | 0.07 | 9 | 117 | id3805 |
| p.F751fs | c.2253delC | NM_022552 | 0.04 | 7 | 184 | id6954 |
| p.F751L | c.2253C > G | NM_022552 | 0.3125 | 35 | 77 | id6937 |
| p.P750fs | c.2250delC | NM_022552 | 0.04 | 9 | 208 | id4361 |
| p.R749L | c.2246_2247GC > TT | NM_022552 | 0.302326 | 26 | 60 | id8792 |
| p.R749H | c.2246G > A | NM_022552 | 0.042857 | 6 | 134 | id1756 |
| p.R742fs | c.2225_2226insCG | NM_022552 | 0.23 | 21 | 72 | id16702 |
| p.L737H | c.2210T > A | NM_022552 | 0.11236 | 10 | 79 | id9422 |
| p.L737P | c.2210T > C | NM_022552 | 0.070175 | 12 | 159 | id6671 |
| p.L737R | c.2210T > G | NM_022552 | 0.064103 | 5 | 73 | id6440 |
| p.R736H | c.2207G > A | NM_022552 | 0.035971 | 5 | 134 | id2222 |
| p.R736H | c.2207G > A | NM_022552 | 0.206897 | 12 | 46 | id15683 |
| p.R736H | c.2207G > A | NM_022552 | 0.130841 | 14 | 93 | id9230 |
| p.R736P | c.2207G > C | NM_022552 | 0.051282 | 6 | 111 | id2964 |
| p.R736H | c.2207G > A | NM_022552 | 0.202703 | 15 | 59 | id1522 |
| p.R736C | c.2206C > T | NM_022552 | 0.069767 | 6 | 80 | id10935 |
| p.R736fs | c.2206delC | NM_022552 | 0.04 | 7 | 151 | id4834 |
| p.R736C | c.2206C > T | NM_022552 | 0.045455 | 5 | 105 | id1400 |
| p.R736C | c.2206C > T | NM_022552 | 0.107143 | 9 | 75 | id11823 |
| p.R736C | c.2206C > T | NM_022552 | 0.066667 | 4 | 56 | id8297 |
| p.Y735fs | c.2204_2205insT | NM_022552 | 0.07 | 6 | 85 | id3425 |
| p.Y735* | c.2204_2205insT | NM_022552 | 0.122807 | 7 | 50 | id3119 |
| p.Y735C | c.2204A > G | NM_022552 | 0.060606 | 6 | 93 | id9953 |
| p.Y735C | c.2204A > G | NM_022552 | 0.0625 | 6 | 90 | id14999 |
| p.Y735C | c.2204A > G | NM_022552 | 0.125 | 11 | 77 | id12769 |
| p.Y735C | c.2204A > G | NM_022552 | 0.15493 | 11 | 60 | id8729 |
| p.Y735C | c.2204A > G | NM_022552 | 0.104478 | 7 | 60 | id6944 |
| p.Y735C | c.2204A > G | NM_022552 | 0.064935 | 5 | 72 | id2196 |
| p.Y735C | c.2204A > G | NM_022552 | 0.068966 | 6 | 81 | id13765 |
| p.Y735S | c.2204A > C | NM_022552 | 0.044444 | 4 | 86 | id3558 |
| p.Y735C | c.2204A > G | NM_022552 | 0.14 | 7 | 43 | id15574 |
| p.F734L | c.2202C > G | NM_022552 | 0.045455 | 5 | 105 | id2350 |
| p.F734C | c.2201T > G | NM_022552 | 0.1 | 8 | 72 | id11518 |
| p.F732fs | c.2196_2197insT | NM_022552 | 0.09 | 9 | 88 | id15312 |
| p.F732S | c.2195T > C | NM_022552 | 0.084746 | 5 | 54 | id18808 |
| p.731_732FF > F | c.2193_2195delCTT | NM_022552 | 0.05 | 7 | 124 | id3448 |
| p.F732S | c.2185C > T | NM_022552 | 0.092105 | 7 | 69 | id9932 |
| p.731_732FF > F | c.2193_2195delCTT | NM_022552 | 0.04 | 5 | 155 | id6823 |
| p.731_732FF > F | c.2193_2195delCTT | NM_022552 | 0.21 | 19 | 73 | id5924 |
| p.L730fs | c.2190_2194delCTTCT | NM_022552 | 0.08 | 8 | 88 | id8675 |
| p.F731L | c.2193C > A | NM_022552 | 0.067797 | 4 | 55 | id9875 |
| p.R729Q | c.2186G > A | NM_022552 | 0.053763 | 5 | 88 | id5320 |
| p.R729W | c.2185C > T | NM_022552 | 0.098592 | 7 | 64 | id2396 |
| p.R729W | c.2185C > T | NM_022552 | 0.088889 | 4 | 41 | id16068 |
| p.R729W | c.2185C > T | NM_022552 | 0.098361 | 6 | 55 | id15009 |
| p.R729W | c.2185C > T | NM_022552 | 0.05 | 4 | 76 | id8983 |
| p.R729G | c.2185C > G | NM_022552 | 0.088608 | 7 | 72 | id6003 |
| p.R729W | c.2185C > T | NM_022552 | 0.051948 | 4 | 73 | id2025 |
| p.R729W | c.2185C > T | NM_022552 | 0.074074 | 6 | 75 | id15128 |
| c.e19 −1 | c.2174_splice | NM_022552 | 0.040404 | 4 | 95 | id2319 |
| c.e19 −1 | c.2174_splice | NM_022552 | 0.052632 | 4 | 72 | id14459 |
| c.e19 −1 | c.2174_splice | NM_022552 | 0.072464 | 5 | 64 | id1939 |
| c.e19 −1 | c.2174_splice | NM_022552 | 0.04902 | 5 | 97 | id5800 |
| c.e19 −1 | c.2174_splice | NM_022552 | 0.057143 | 6 | 99 | id7308 |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| c.e19 −1 | c.2174_splice | NM_022552 | 0.054054 | 6 | 105 | id1242 |
| c.e19 −1 | c.2174_splice | NM_022552 | 0.037594 | 10 | 256 | id6108 |
| c.e19 −1 | c.2174_splice | NM_022552 | 0.054795 | 4 | 69 | id1343 |
| p.R720H | c.2159G > A | NM_022552 | 0.068323 | 11 | 150 | id8630 |
| p.P718fs | c.2153delC | NM_022552 | 0.06 | 8 | 136 | id12206 |
| p.N717I | c.2150A > T | NM_022552 | 0.079812 | 17 | 196 | id6708 |
| p.S714C | c.2141C > G | NM_022552 | 0.036765 | 5 | 131 | id16144 |
| p.S714C | c.2141C > G | NM_022552 | 0.042553 | 4 | 90 | id15164 |
| p.S714C | c.2141C > G | NM_022552 | 0.055556 | 5 | 85 | id14273 |
| p.C710S | c.2128T > A | NM_022552 | 0.125926 | 17 | 118 | id3426 |
| p.C710S | c.2128T > A | NM_022552 | 0.045161 | 7 | 148 | id4883 |
| p.I705T | c.2114T > C | NM_022552 | 0.044444 | 4 | 86 | id13787 |
| p.I705T | c.2114T > C | NM_022552 | 0.103774 | 11 | 95 | id8691 |
| p.V704G | c.2111T > G | NM_022552 | 0.042373 | 5 | 113 | id12386 |
| p.D702Y | c.2104G > T | NM_022552 | 0.062069 | 9 | 136 | id16127 |
| p.D702N | c.2104G > A | NM_022552 | 0.139241 | 11 | 68 | id8614 |
| p.P700fs | c.2099delC | NM_022552 | 0.07 | 6 | 80 | id16162 |
| p.P700R | c.2099C > G | NM_022552 | 0.059524 | 5 | 79 | id8775 |
| p.P700S | c.2098C > T | NM_022552 | 0.338028 | 24 | 47 | id15026 |
| p.G699D | c.2096G > A | NM_022552 | 0.17284 | 14 | 67 | id1719 |
| p.G699S | c.2095G > A | NM_022552 | 0.116667 | 7 | 53 | id3790 |
| p.G699S | c.2095G > A | NM_022552 | 0.207207 | 23 | 88 | id3196 |
| p.G699S | c.2095G > A | NM_022552 | 0.226667 | 17 | 58 | id12570 |
| p.Q696* | c.2086C > T | NM_022552 | 0.275 | 44 | 116 | id9013 |
| c.e18 −1 | c.2083_splice | NM_022552 | 0.197183 | 14 | 57 | id2365 |
| c.e18 −1 | c.2083_splice | NM_022552 | 0.129032 | 8 | 54 | id5795 |
| c.e17+1 | c.2082_splice | NM_022552 | 0.28 | 11 | 29 | id2306 |
| c.e17+1 | c.2082_splice | NM_022552 | 0.063492 | 4 | 59 | id15906 |
| c.e17+1 | c.2082_splice | NM_022552 | 0.104167 | 5 | 43 | id16591 |
| p.D686V | c.2057A > T | NM_022552 | 0.122807 | 7 | 50 | id9977 |
| p.D686Y | c.2056G > T | NM_022552 | 0.083333 | 4 | 44 | id12975 |
| p.G685E | c.2054G > A | NM_022552 | 0.114286 | 4 | 31 | id3840 |
| p.G685A | c.2054G > C | NM_022552 | 0.083333 | 4 | 44 | id11374 |
| p.G685R | c.2053G > A | NM_022552 | 0.080645 | 5 | 57 | id14857 |
| p.R676Q | c.2027G > A | NM_022552 | 0.102041 | 5 | 44 | id16161 |
| p.S669fs | c.2007_2008insC | NM_022552 | 0.27 | 13 | 36 | id16841 |
| p.Y660C | c.1979A > G | NM_022552 | 0.075 | 3 | 37 | id4444 |
| p.R659H | c.1976G > A | NM_022552 | 0.238095 | 5 | 16 | id16060 |
| p.R659H | c.1976G > A | NM_022552 | 0.066667 | 3 | 42 | id17165 |
| p.V657M | c.1969G > A | NM_022552 | 0.136364 | 3 | 19 | id14784 |
| p.V657M | c.1969G > A | NM_022552 | 0.111111 | 3 | 24 | id3950 |
| p.V657M | c.1969G > A | NM_022552 | 0.117647 | 6 | 45 | id8852 |
| p.Q656* | c.1966C > T | NM_022552 | 0.125 | 4 | 28 | id11568 |
| p.L653F | c.1959G > T | NM_022552 | 0.195122 | 8 | 33 | id2375 |
| c.e15+1 | c.1851_splice | NM_022552 | 0.195078 | 10 | 41 | id13422 |
| c.e15+1 | c.1851_splice | NM_022552 | 0.0625 | 4 | 60 | id6567 |
| p.Q615* | c.1843C > T | NM_022552 | 0.074627 | 5 | 62 | id14957 |
| p.R604fs | c.1870delC | NM_022552 | 0.12 | 6 | 43 | id17044 |
| p.W601* | c.1802G > A | NM_022552 | 0.117647 | 8 | 60 | id8648 |
| p.R598* | c.1792C > T | NM_022552 | 0.225806 | 14 | 48 | id16194 |
| p.R599* | c.1792C > T | NM_022552 | 0.083333 | 3 | 33 | id14858 |
| p.R598* | c.1792C > T | NM_022552 | 0.086207 | 5 | 53 | id2009 |
| p.R598* | c.1792C > T | NM_022552 | 0.246154 | 16 | 49 | id14719 |
| p.R598* | c.1792C > T | NM_022552 | 0.06383 | 3 | 44 | id13566 |
| p.R598* | c.1792C > T | NM_022552 | 0.105263 | 8 | 68 | id2962 |
| p.R598* | c.1792C > T | NM_022552 | 0.069767 | 3 | 40 | id11375 |
| p.H588fs | c.1764delC | NM_022552 | 0.24 | 15 | 47 | id15339 |
| p.W581* | c.1741T > G | NM_022552 | 0.282051 | 11 | 28 | id6869 |
| p.W581G | c.1741T > G | NM_022552 | 0.115385 | 3 | 23 | id16011 |
| c.e14+1 | c.1667_splice | NM_022552 | 0.090909 | 4 | 40 | id3119 |
| c.e14+1 | c.1667_splice | NM_022552 | 0.0625 | 4 | 60 | id8406 |
| c.e14+1 | c.1667_splice | NM_022552 | 0.215686 | 11 | 40 | id2828 |
| p.G550R | c.1648G > A | NM_022552 | 0.127273 | 7 | 48 | id2304 |
| p.G550R | c.1648G > A | NM_022552 | 0.065217 | 3 | 43 | id15052 |
| p.L547H | c.1640T > A | NM_022552 | 0.129412 | 11 | 74 | id14955 |
| p.L547R | c.1640T > G | NM_022552 | 0.083333 | 3 | 33 | id8962 |
| p.L547H | c.1640T > A | NM_022552 | 0.107692 | 7 | 58 | id12146 |
| p.L547F | c.1639C > T | NM_022552 | 0.25 | 19 | 57 | id9916 |
| p.L547F | c.1639C > T | NM_022552 | 0.173077 | 9 | 43 | id8674 |
| p.G543fs | c.1628_1629insG | NM_022552 | 0.05 | 6 | 105 | id2607 |
| p.G543A | c.1628C > C | NM_022552 | 0.052632 | 4 | 72 | id12180 |
| p.G543C | c.1627G > T | NM_022552 | 0.140845 | 10 | 61 | id5941 |
| p.G543S | c.1627G > A | NM_022552 | 0.08 | 6 | 69 | id10674 |
| p.C537* | c.1611C > A | NM_022552 | 0.111111 | 11 | 88 | id1774 |
| p.Y536* | c.1608C > A | NM_022552 | 0.126582 | 10 | 69 | id14901 |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| p.S535fs | c.1605delC | NM_022552 | 0.22 | 21 | 74 | id3357 |
| p.Q534* | c.1600C > T | NM_022552 | 0.047059 | 4 | 81 | id1471 |
| p.G532fs | c.1595delG | NM_022552 | 0.06 | 7 | 112 | id13672 |
| p.Y528* | c.1582_1583delTA | NM_022552 | 0.078947 | 3 | 35 | id16331 |
| p.Y528fs | c.1582_1583delTA | NM_022552 | 0.11 | 8 | 68 | id7028 |
| p.Q527P | c.1580A > C | NM_022552 | 0.123288 | 9 | 64 | id2858 |
| p.Q527* | c.1580A > C | NM_022552 | 0.160714 | 9 | 47 | id15539 |
| p.C524fs | c.1572_1573delTG | NM_022552 | 0.12 | 6 | 43 | id2055 |
| c.e14 −1 | c.1555_splice | NM_022552 | 0.194805 | 15 | 62 | id3359 |
| c.e14 −1 | c.1555_splice | NM_022552 | 0.050505 | 5 | 94 | id4534 |
| c.e13+1 | c.1554_splice | NM_022552 | 0.093023 | 8 | 78 | id14835 |
| c.e13+1 | c.1554_splice | NM_022552 | 0.095238 | 4 | 38 | id1870 |
| p.N516fs | c.1547_1548insA | NM_022552 | 0.11 | 10 | 79 | id12758 |
| p.G511* | c.1531G > T | NM_022552 | 0.047619 | 6 | 120 | id5891 |
| p.L508fs | c.1522_1523insC | NM_022552 | 0.1 | 12 | 106 | id14752 |
| p.L504fs | c.1511delT | NM_022552 | 0.1 | 8 | 73 | id2118 |
| p.S499fs | c.1495delA | NM_022552 | 0.07 | 11 | 137 | id5858 |
| p.G498fs | c.1494delG | NM_022552 | 0.08 | 10 | 121 | id3360 |
| p.C497Y | c.1490G > A | NM_022552 | 0.104348 | 12 | 103 | id9043 |
| c.e13 −1 | c.1475_splice | NM_022552 | 0.04 | 4 | 96 | id3227 |
| c.e13 −1 | c.1475_splice | NM_022552 | 0.06 | 6 | 99 | id4969 |
| c.e13 −1 | c.1475_splice | NM_022552 | 0.060606 | 6 | 93 | id2258 |
| p.R488fs | c.1464delG | NM_022552 | 0.07 | 7 | 92 | id7288 |
| p.R488fs | c.1464delG | NM_022552 | 0.06 | 6 | 102 | id1412 |
| p.K486* | c.1456A > T | NM_022552 | 0.06 | 6 | 94 | id15373 |
| p.E482* | c.1444G > T | NM_022552 | 0.184211 | 14 | 62 | id12235 |
| c.e12 −1 | c.1430_splice | NM_022552 | 0.102041 | 5 | 44 | id15827 |
| c.e12 −1 | c.1430_splice | NM_022552 | 0.055556 | 5 | 85 | id16096 |
| c.e12 −1 | c.1430_splice | NM_022552 | 0.055556 | 6 | 102 | id3449 |
| c.e12 −1 | c.1430_splice | NM_022552 | 0.046154 | 6 | 124 | id9784 |
| c.e12 −1 | c.1430_splice | NM_022552 | 0.038095 | 8 | 202 | id4837 |
| p.E473* | c.1417G > T | NM_022552 | 0.089655 | 13 | 132 | id6770 |
| p.I470fs | c.1410delT | NM_022552 | 0.11 | 15 | 118 | id16080 |
| p.P465fs | c.1395delC | NM_022552 | 0.05 | 7 | 138 | id9719 |
| p.K459* | c.1375A > | NM_022552 | 0.041096 | 9 | 210 | id1925 |
| p.A454fs | c.1361_1362delCC | NM_022552 | 0.24 | 56 | 175 | id3344 |
| p.E434fs | c.1301_1304delAAGT | NM_022552 | 0.06 | 24 | 360 | id6788 |
| p.E434fs | c.1301_1304delAAGT | NM_022552 | 0.03 | 6 | 190 | id8483 |
| p.E427fs | c.1281_1293delAGAGAAGAATCCC | NM_022552 | 0.09 | 19 | 198 | id16176 |
| c.e10+1 | c.1279_splice | NM_022552 | 0.060976 | 5 | 77 | id4443 |
| p.F414C | c.1241T > G | NM_022552 | 0.07563 | 9 | 110 | id9420 |
| p.F414C | c.1241T > G | NM_022552 | 0.090909 | 11 | 110 | id10738 |
| p.W409* | c.1227G > A | NM_022552 | 0.117647 | 12 | 90 | id6084 |
| p.W409* | c.1227G > A | NM_022552 | 0.043103 | 5 | 111 | id12467 |
| p.W409* | c.1227G > A | NM_022552 | 0.079365 | 10 | 116 | id1860 |
| p.E408fs | c.1223_1226delAA | NM_022552 | 0.11 | 10 | 81 | id14929 |
| p.P405fs | c.1214_1215delCC | NM_022552 | 0.08 | 9 | 108 | id15015 |
| p.Q402* | c.1204C > T | NM_022552 | 0.045752 | 7 | 146 | id8920 |
| p.Q402* | c.1204C > T | NM_022552 | 0.131868 | 12 | 79 | id3510 |
| p.V401fs | c.1201_1202insA | NM_022552 | 0.08 | 14 | 171 | id2808 |
| p.C387fs | c.1160_1161insTG | NM_022552 | 0.04 | 10 | 266 | id8934 |
| p.P385fs | c.1154delC | NM_022552 | 0.06 | 20 | 322 | id16036 |
| p.P385fs | c.1154delC | NM_022552 | 0.08 | 21 | 239 | id8994 |
| p.P385fs | c.1154delC | NM_022552 | 0.05 | 11 | 218 | id6559 |
| p.G381fs | c.1143delG | NM_022552 | 0.04 | 11 | 253 | id15874 |
| p.G381fs | c.1143delG | NM_022552 | 0.12 | 36 | 274 | id15866 |
| c.e10 −1 | c.1123_splice | NM_022552 | 0.060241 | 5 | 78 | id12659 |
| c.e10 −1 | c.1123_splice | NM_022552 | 0.072464 | 10 | 128 | id13854 |
| c.e9+1 | c.1122_splice | NM_022552 | 0.115385 | 3 | 23 | id6691 |
| c.e9+1 | c.1122_splice | NM_022552 | 0.290323 | 9 | 22 | id16501 |
| p.Q374* | c.1121A > C | NM_022552 | 0.133333 | 6 | 39 | id17176 |
| p.Q374* | c.1121A > C | NM_022552 | 0.190476 | 4 | 17 | id11908 |
| p.R366H | c.1097G > A | NM_022552 | 0.083333 | 3 | 33 | id10859 |
| p.R366H | c.1097G > A | NM_022552 | 0.078947 | 3 | 35 | id10082 |
| p.R366G | c.1096C > G | NM_022552 | 0.073171 | 3 | 38 | id4535 |
| p.Q356* | c.1066C > T | NM_022552 | 0.092593 | 5 | 49 | id9595 |
| p.Q356* | c.1066C > T | NM_022552 | 0.087912 | 8 | 83 | id890 |
| p.A353fs | c.1058delC | NM_022552 | 0.21 | 14 | 52 | id15877 |
| c.e9 −1 | c.1015_splice | NM_022552 | 0.41 | 9 | 13 | id12897 |
| p.F336fs | c.1007delT | NM_022552 | 0.03 | 8 | 246 | id12009 |
| p.G332* | c.994G > T | NM_022552 | 0.078652 | 7 | 82 | id6025 |
| p.W330* | c.989_991delGGT | NM_022552 | 0.066038 | 7 | 99 | id5896 |
| p.W330* | c.989_991delGGT | NM_022552 | 0.064516 | 6 | 87 | id12786 |
| p.W327* | c.981G > A | NM_022552 | 0.077519 | 10 | 119 | id5022 |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| p.W327* | c.981G > A | NM_022552 | 0.049587 | 6 | 115 | id928 |
| p.W327* | c.981G > A | NM_022552 | 0.103448 | 12 | 104 | id15000 |
| p.R326H | c.977G > A | NM_022552 | 0.082569 | 9 | 100 | id9718 |
| p.R326H | c.977G > A | NM_022552 | 0.044944 | 4 | 85 | id12336 |
| p.R326L | c.977G > T | NM_022552 | 0.25 | 21 | 63 | id4839 |
| p.R326H | c.977G > A | NM_022552 | 0.059524 | 5 | 79 | id12997 |
| p.R326H | c.977G > A | NM_022552 | 0.162602 | 20 | 103 | id7161 |
| p.R326C | c.976C > T | NM_022552 | 0.042105 | 4 | 91 | id11044 |
| p.R326C | c.976C > T | NM_022552 | 0.045455 | 4 | 84 | id2197 |
| p.R326S | c.976C > A | NM_022552 | 0.229885 | 20 | 67 | id17118 |
| p.R326C | c.976C > T | NM_022552 | 0.044944 | 4 | 85 | id4694 |
| p.R326C | c.976C > T | NM_022552 | 0.04902 | 5 | 97 | id1859 |
| p.R326C | c.976C > T | NM_022552 | 0.193548 | 18 | 75 | id2999 |
| p.R326C | c.976C > T | NM_022552 | 0.045455 | 4 | 84 | id13251 |
| p.R326C | c.976C > T | NM_022552 | 0.04878 | 4 | 78 | id1279 |
| p.R326C | c.976C > T | NM_022552 | 0.236842 | 27 | 87 | id4044 |
| p.R320* | c.958C > T | NM_022552 | 0.156863 | 8 | 43 | id2402 |
| p.R320* | c.958C > T | NM_022552 | 0.333333 | 21 | 42 | id14930 |
| p.R320* | c.958C > T | NM_022552 | 0.051282 | 6 | 111 | id15764 |
| p.R320* | c.958C > T | NM_022552 | 0.067416 | 6 | 83 | id11418 |
| p.R320* | c.958C > T | NM_022552 | 0.054054 | 6 | 105 | id13315 |
| p.R320* | c.958C > T | NM_022552 | 0.102804 | 11 | 96 | id1472 |
| p.R320* | c.958C > T | NM_022552 | 0.058824 | 5 | 80 | id15130 |
| p.R320* | c.958C > T | NM_022552 | 0.061404 | 7 | 107 | id7185 |
| p.R320* | c.958C > T | NM_022552 | 0.112676 | 8 | 63 | id12510 |
| p.W314* | c.942G > A | NM_022552 | 0.05 | 4 | 76 | id14163 |
| p.P307S | c.919C > T | NM_022552 | 0.07462 | 5 | 62 | id5900 |
| p.W306* | c.916T > C | NM_022552 | 0.060241 | 5 | 78 | id10739 |
| p.W305* | c.915G > A | NM_022552 | 0.057971 | 4 | 65 | id5942 |
| p.W305* | c.915G > A | NM_022552 | 0.045977 | 4 | 83 | id1145 |
| p.W305* | c.915G > A | NM_022552 | 0.326087 | 15 | 31 | id3438 |
| p.W297* | c.889T > G | NM_022552 | 0.056075 | 6 | 101 | id12120 |
| p.E294fs | c.880delG | NM_022552 | 0.2 | 23 | 90 | id8730 |
| p.E294* | c.880delG | NM_022552 | 0.186047 | 16 | 70 | id1768 |
| c.e7+1 | c.855_splice | NM_022552 | 0.097561 | 4 | 37 | id4692 |
| c.e7+1 | c.855_splice | NM_022552 | 0.222222 | 10 | 35 | id11641 |
| c.e7+1 | c.855_splice | NM_022552 | 0.081967 | 5 | 56 | id16034 |
| c.e7+1 | c.855_splice | NM_022552 | 0.121212 | 4 | 29 | id6449 |
| p.A269fs | c.805_806insG | NM_022552 | 0.13 | 8 | 52 | id1868 |
| p.T260fs | c.778_779delAC | NM_022552 | 0.06 | 13 | 192 | id3379 |
| p.P250fs | c.750delC | NM_022552 | 0.25 | 27 | 80 | id15727 |
| p.Q249* | c.745C > T | NM_022552 | 0.147059 | 15 | 87 | id12637 |
| p.Q249* | c.745C > T | NM_022552 | 0.047619 | 6 | 120 | id5252 |
| p.P244fs | c.731delC | NM_022552 | 0.14 | 15 | 92 | id5902 |
| p.P244fs | c.731delC | NM_022552 | 0.06 | 9 | 147 | id14666 |
| p.E241fs | c.722delA | NM_022552 | 0.06 | 7 | 106 | id3226 |
| p.E241* | c.722delA | NM_022552 | 0.082474 | 8 | 89 | id6851 |
| p.K238fs | c.712_713insGA | NM_022552 | 0.06 | 8 | 126 | id9185 |
| p.S236fs | c.708_709insT | NM_022552 | 0.05 | 6 | 121 | id2345 |
| p.Q231fs | c.692delA | NM_022552 | 0.07 | 8 | 112 | id17166 |
| p.V227fs | c.679delG | NM_022552 | 0.26 | 18 | 51 | id11008 |
| c.e3+1 | c.177_splice | NM_022552 | 0.407407 | 11 | 16 | id8961 |
| p.R353fs | c.1058_1059insC | NM_001429 | 0.08 | 21 | 231 | id4590 |
| p.S203fs | c.608delC | NM_001987 | 0.03 | 6 | 194 | id3843 |
| p.R679H | c.2036G > A | NM_001203247 | 0.047297 | 7 | 141 | id15352 |
| p.S366fs | c.1096_1097insA | NM_001203247 | 0.04 | 8 | 177 | id6929 |
| p.L93fs | c.273_279insC | NM_017709 | 0.14 | 20 | 122 | id16047 |
| c.e4 −1 | c.585_splice | NM_033632 | 0.12 | 6 | 44 | id6058 |
| p.V592A | c.1775T > C | NM_004119 | 0.066667 | 7 | 98 | id6574 |
| p.K484fs | c.1451_1452insA | NM_032682 | 0.05 | 7 | 134 | id15631 |
| p.R844G | c.2530C > G | NM_016592 | 0.260504 | 31 | 88 | id12468 |
| p.R844C | c.2530C > T | NM_016592 | 0.128205 | 10 | 68 | id9846 |
| o.R844S | c.2530C > A | NM_016592 | 0.080645 | 5 | 57 | id16703 |
| p.R844H | c.2531G > A | NM_016592 | 0.066667 | 5 | 70 | id6830 |
| p.R844H | c.2531G > A | NM_016592 | 0.121951 | 5 | 36 | id12269 |
| p.R844H | c.2531G > A | NM_016592 | 0.054348 | 5 | 87 | id4939 |
| p.R844H | c.2531G > A | NM_016592 | 0.05 | 4 | 76 | id5860 |
| p.R844H | c.2531G > A | NM_016592 | 0.155556 | 7 | 38 | id15544 |
| p.K57N | c.171G > T | NM_002074 | 0.098039 | 5 | 46 | id3168 |
| p.K57N | c.171G > T | NM_002074 | 0.131579 | 5 | 33 | id13397 |
| p.K57M | c.170A > T | NM_002074 | 0.096154 | 5 | 47 | id12470 |
| p.K57M | c.170A > T | NM_002074 | 0.083333 | 5 | 55 | id4360 |
| p.K57M | c.170A > T | NM_002074 | 0.211538 | 11 | 41 | id8456 |
| p.K57E | c.169A > G | NM_002074 | 0.214286 | 9 | 33 | id11645 |
| p.K57E | c.169A > G | NM_002074 | 0.121212 | 4 | 29 | id8807 |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| p.K57E | c.169A > G | NM_002074 | 0.285714 | 10 | 25 | id11639 |
| p.K57E | c.169A > G | NM_002074 | 0.090909 | 3 | 30 | id3437 |
| p.K57E | c.169A > G | NM_002074 | 0.16 | 4 | 21 | id3822 |
| p.K57E | c.169A > G | NM_002074 | 0.088235 | 3 | 31 | id8979 |
| p.K57E | c.169A > G | NM_002074 | 0.321429 | 9 | 19 | id5020 |
| p.K57E | c.169A > G | NM_002074 | 0.065217 | 3 | 43 | id4971 |
| p.K57E | c.169A > G | NM_002074 | 0.384615 | 15 | 24 | id10936 |
| p.K57E | c.169A > G | NM_002074 | 0.4375 | 14 | 18 | id8647 |
| p.K57E | c.169A > G | NM_002074 | 0.081633 | 4 | 45 | id4772 |
| p.K57E | c.169A > G | NM_002074 | 0.068966 | 4 | 54 | id15602 |
| p.K57E | c.169A > G | NM_002074 | 0.075 | 3 | 37 | id9339 |
| p.K57E | c.169A > G | NM_002074 | 0.278689 | 17 | 44 | id6556 |
| p.K57E | c.169A > G | NM_002074 | 0.208333 | 10 | 38 | id12008 |
| p.K57E | c.169A > G | NM_002074 | 0.130435 | 6 | 40 | id1659 |
| p.K57E | c.169A > G | NM_002074 | 0.104167 | 5 | 43 | id4207 |
| p.K109* | c.326A > G | NM_005319 | 0.055215 | 9 | 154 | id4838 |
| p.R140Q | c.419G > A | NM_002168 | 0.094118 | 8 | 77 | id12629 |
| p.R140Q | c.419G > A | NM_002168 | 0.043011 | 4 | 89 | id11438 |
| p.R140Q | c.419G > A | NM_002168 | 0.126437 | 11 | 76 | id562 |
| p.Y477* | c.1431C > A | NM_006060 | 0.071429 | 3 | 39 | id2011 |
| p.V617F | c.1849G > T | NM_004972 | 0.05814 | 5 | 81 | id16145 |
| p.V617F | c.1849G > T | NM_004972 | 0.217742 | 27 | 97 | id11641 |
| p.V617F | c.1849G > T | NM_004972 | 0.27193 | 31 | 83 | id9951 |
| p.V617F | c.1849G > T | NM_004972 | 0.082569 | 9 | 100 | id9952 |
| p.V617F | c.1849G > T | NM_004972 | 0.058824 | 8 | 128 | id3449 |
| p.V617F | c.1849G > T | NM_004972 | 0.225806 | 21 | 72 | id2348 |
| p.V617F | c.1849G > T | NM_004972 | 0.287356 | 25 | 62 | id1597 |
| p.V617F | c.1849G > T | NM_004972 | 0.109434 | 29 | 236 | id6999 |
| p.V617F | c.1849G > T | NM_004972 | 0.909091 | 140 | 14 | id2189 |
| p.V617F | c.1849G > T | NM_004972 | 0.146789 | 16 | 93 | id5972 |
| p.V617F | c.1849G > T | NM_004972 | 0.091954 | 8 | 79 | id9592 |
| p.V617F | c.1849G > T | NM_004972 | 0.041237 | 4 | 93 | id12296 |
| p.V617F | c.1849G > T | NM_004972 | 0.420561 | 45 | 62 | id13636 |
| p.V617F | c.1849G > T | NM_004972 | 0.040816 | 4 | 94 | id9457 |
| p.V617F | c.1849G > T | NM_004972 | 0.072289 | 12 | 154 | id4774 |
| p.V617F | c.1849G > T | NM_004972 | 0.888 | 111 | 14 | id5825 |
| p.V617F | c.1849G > T | NM_004972 | 0.089888 | 8 | 81 | id16987 |
| p.V617F | c.1849G > T | NM_004972 | 0.062992 | 8 | 119 | id15181 |
| p.V617F | c.1849G > T | NM_004972 | 0.252252 | 28 | 83 | id11973 |
| p.V617F | c.1849G > T | NM_004972 | 0.043956 | 4 | 87 | id15486 |
| p.V617F | c.1849G > T | NM_004972 | 0.071429 | 8 | 104 | id16838 |
| p.V617F | c.1849G > T | NM_004972 | 0.097015 | 13 | 121 | id13371 |
| p.V617F | c.1849G > T | NM_004972 | 0.048544 | 10 | 196 | id1470 |
| p.V617F | c.1849G > T | NM_004972 | 0.241935 | 30 | 94 | id12573 |
| p.V617F | c.1849G > T | NM_004972 | 0.073171 | 9 | 114 | id6354 |
| p.V617F | c.1849G > T | NM_004972 | 0.05618 | 5 | 84 | id15417 |
| p.V617F | c.1849G > T | NM_004972 | 0.048193 | 8 | 158 | id1341 |
| p.V617P | c.1849G > T | NM_004972 | 0.438462 | 57 | 73 | id5286 |
| p.V617F | c.1849G > T | NM_004972 | 0.090909 | 9 | 90 | id3877 |
| p.V617F | c.1849G > T | NM_004972 | 0.111111 | 9 | 72 | id12878 |
| p.V617F | c.1849G > T | NM_004972 | 0.051095 | 7 | 130 | id428 |
| p.M511I | c.1533G > A | NM_000215 | 0.225108 | 52 | 179 | id1146 |
| p.L694fs | c.2081_2082insG | NM_004973 | 0.06 | 6 | 90 | id1308 |
| p.R172* | c.514C > T | NM_021140 | 0.647059 | 55 | 30 | id12922 |
| p.P1107fs | c.3319delC | NM_021140 | 0.27 | 8 | 22 | id3440 |
| p.R634W | c.1900C > T | NM_000222 | 0.113636 | 10 | 78 | id3248 |
| p.R98W | c.292A > T | NM_130446 | 0.061728 | 5 | 76 | id14548 |
| p.A146V | c.437C > T | NM_033360 | 0.083333 | 4 | 44 | id15632 |
| p.K117N | c.351A > C | NM_033360 | 0.2625 | 21 | 59 | id13666 |
| p.G12C | c.34G > T | NM_033360 | 0.125 | 3 | 21 | id4833 |
| p.D64fs | c.192delC | NM_016019 | 0.1 | 18 | 160 | id7124 |
| p.Q91* | c.271C > T | NM_016019 | 0.119048 | 5 | 37 | id5952 |
| p.R262* | c.785G > A | NM_016019 | 0.128788 | 17 | 115 | id4691 |
| p.R924fs | c.2770_2771insC | NM_003482 | 0.05 | 6 | 126 | id12338 |
| p.K3551fs | c.10653_10654insA | NM_003482 | 0.13 | 16 | 111 | id7288 |
| p.Q2418* | c.7252C > T | NM_003482 | 0.069767 | 3 | 40 | id17045 |
| p.R845fs | c.2533delC | NM_003482 | 0.03 | 7 | 215 | id8776 |
| p.L513del | c.1528_1530delCTG | NM_005373 | 0.03 | 6 | 190 | id15871 |
| p.W515L | c.1544G > T | NM_005373 | 0.632653 | 62 | 36 | id3439 |
| p.L273P | c.318T > C | NM_001172567 | 0.10989 | 10 | 81 | id4362 |
| p.L273P | c.818T > C | NM_001172567 | 0.128205 | 10 | 68 | id12559 |
| p.E1450* | c.4348G > A | NM_017617 | 0.06383 | 3 | 44 | id12729 |
| p.N268fs | c.803delA | NM_017617 | 0.02 | 6 | 272 | id966 |
| p.E1488* | c.4462G > T | NM_024408 | 0.044944 | 12 | 255 | id11553 |
| p.W10* | c.30G > A | NM_024408 | 0.090909 | 3 | 30 | id12422 |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| p.Q61H | c.183A > C | NM_002524 | 0.107914 | 15 | 124 | id15579 |
| p.Q61R | c.182A > G | NM_002524 | 0.045198 | 8 | 169 | id2857 |
| p.Q61K | c.181C > A | NM_002524 | 0.055276 | 11 | 188 | id15859 |
| p.G60E | c.179G > A | NM_002524 | 0.049296 | 7 | 135 | id7257 |
| p.G13D | c.38G > A | NM_002524 | 0.065421 | 14 | 200 | id16047 |
| p.G13R | c.37G > C | NM_002524 | 0.057971 | 12 | 195 | id5915 |
| p.N129fs | c.387delC | NM_020381 | 0.52 | 47 | 43 | id4938 |
| p.G306* | c.916C > T | NM_001015877 | 0.161765 | 11 | 57 | id9810 |
| p.R38H | c.113G > A | NM_006218 | 0.39759 | 33 | 50 | id9419 |
| p.L415fs | c.1245_1246insC | NM_001198 | 0.5 | 39 | 39 | id2010 |
| p.A501fs | c.1501_1502insC | NM_001198 | 0.09 | 6 | 58 | id6622 |
| p.T521fs | c.1561_1562insC | NM_001198 | 0.15 | 6 | 35 | id6724 |
| p.Q241* | c.721C > T | NM_001031698 | 0.22 | 11 | 39 | id11569 |
| p.Y63C | c.188A > G | NM_002834 | 0.040404 | 4 | 95 | id15878 |
| p.Y63C | c.188A > G | NM_002834 | 0.382609 | 44 | 71 | id4772 |
| p.E69Q | c.205G > C | NM_002834 | 0.20354 | 23 | 90 | id9785 |
| p.I512fs | c.1534_1535insA | NM_006265 | 0.08 | 7 | 76 | id16143 |
| p.Q492* | c.1474C > T | NM_006265 | 0.04878 | 4 | 78 | id1013 |
| p.P398fs | c.1192_1201delCCAGAAGACC | NM_006265 | 0.07 | 6 | 79 | id8977 |
| p.S189fs | c.566_576delCTAACCTCCTA | NM_006265 | 0.17 | 13 | 64 | id16332 |
| p.R65Q | c.194G > A | NM_006265 | 0.234483 | 34 | 111 | id3404 |
| p.S56* | c.167C > G | NM_006265 | 0.254777 | 40 | 117 | id12270 |
| p.R112fs | c.336_337insT | NM_006912 | 0.07 | 7 | 96 | id8573 |
| p.A135G | c.404C > G | NM_001018 | 0.277778 | 25 | 65 | id3771 |
| p.P2381fs | c.7143_7144insC | NM_014159 | 0.04 | 7 | 177 | id7288 |
| p.N2138fs | c.6413_6417delATAAA | NM_014159 | 0.05 | 18 | 356 | id12181 |
| p.Q2048fs | c.6142_6143insC | NM_014159 | 0.02 | 6 | 259 | id1369 |
| p.R1492* | c.4474C > T | NM_014159 | 0.142857 | 13 | 78 | id7102 |
| p.H948fs | c.2843_2844insC | NM_001145415 | 0.03 | 6 | 193 | id7288 |
| p.Q574fs | c.1720_1721insC | NM_004630 | 0.11 | 6 | 47 | id6458 |
| c.e7 −1 | c.664_splice | NM_004630 | 0.104167 | 5 | 43 | id15592 |
| p.P298fs | c.894_895insC | NM_005877 | 0.05 | 7 | 143 | id7140 |
| p.E783K | c.2347G > A | NM_012433 | 0.075269 | 7 | 86 | id4885 |
| p.G742D | c.2225G > A | NM_012433 | 0.070175 | 4 | 53 | id8807 |
| p.K700E | c.2098A > G | NM_012433 | 0.213333 | 16 | 59 | id16099 |
| p.K700E | c.2098A > G | NM_012433 | 0.1 | 7 | 63 | id16100 |
| p.K700E | c.2098A > G | NM_012433 | 0.230769 | 12 | 40 | id12421 |
| p.K700E | c.2098A > G | NM_012433 | 0.058824 | 4 | 64 | id3358 |
| p.K700E | c.2098A > G | NM_012433 | 0.140187 | 15 | 92 | id3345 |
| p.K700E | c.2098A > G | NM_012433 | 0.070175 | 4 | 53 | id14902 |
| p.K700E | c.2098A > G | NM_012433 | 0.133333 | 10 | 65 | id3195 |
| p.K700E | c.2098A > G | NM_012433 | 0.075 | 6 | 74 | id9423 |
| p.K700E | c.2098A > G | NM_012433 | 0.113208 | 6 | 47 | id15231 |
| p.K700E | c.2098A > G | NM_012433 | 0.105263 | 6 | 51 | id5722 |
| p.K700E | c.2098A > G | NM_012433 | 0.071429 | 5 | 65 | id1002 |
| p.K666N | c.1998G > C | NM_012433 | 0.170543 | 22 | 107 | id3460 |
| p.K666N | c.1998G > C | NM_012433 | 0.056818 | 5 | 83 | id16012 |
| p.K666N | c.1998G > C | NM_012433 | 0.078947 | 3 | 35 | id15991 |
| p.K666N | c.1998G > C | NM_012433 | 0.051282 | 4 | 74 | id13848 |
| p.K666N | c.1998G > C | NM_012433 | 0.174603 | 11 | 52 | id2084 |
| p.K666N | c.1998G > C | NM_012433 | 0.348485 | 23 | 43 | id13636 |
| p.K666N | c.1998G > C | NM_012433 | 0.084507 | 6 | 65 | id9421 |
| p.K666N | c.1998G > C | NM_012433 | 0.061728 | 5 | 76 | id5804 |
| p.K666N | c.1998G > C | NM_012433 | 0.067669 | 9 | 124 | id3092 |
| p.K666R | c.1997A > G | NM_012433 | 0.477612 | 32 | 35 | id12296 |
| p.K666E | c.1996G > A | NM_012433 | 0.097826 | 9 | 83 | id8760 |
| p.K666Q | c.1996A > C | NM_012433 | 0.321429 | 27 | 57 | id13638 |
| p.H662Q | c.1986C > A | NM_012433 | 0.055556 | 5 | 85 | id13868 |
| p.R387W | c.1159C > T | NM_012433 | 0.173469 | 17 | 81 | id2250 |
| p.P95L | c.284C > T | NM_003016 | 0.27907 | 12 | 31 | id16191 |
| p.P95R | c.284C > G | NM_003016 | 0.084746 | 5 | 54 | id16184 |
| p.P95H | c.284C > A | NM_003016 | 0.084746 | 5 | 54 | id3410 |
| p.P95R | c.284C > G | NM_003016 | 0.22857 | 8 | 27 | id3332 |
| p.P95H | c.284C > A | NM_003016 | 0.083333 | 6 | 66 | id3299 |
| p.P95L | c.284C > T | NM_003016 | 0.12766 | 6 | 41 | id13556 |
| p.P95R | c.284C > G | NM_003016 | 0.196078 | 10 | 41 | id3026 |
| p.P95H | c.284C > A | NM_003016 | 0.289474 | 11 | 27 | id15181 |
| p.P95H | c.284C > A | NM_003016 | 0.122807 | 7 | 50 | id3927 |
| p.P95T | c.283C > A | NM_003016 | 0.087719 | 5 | 52 | id16192 |
| p.Y44H | c.130T > C | NM_003016 | 0.166667 | 4 | 20 | id15776 |
| p.R1090H | c.3269G>A | NM_003016 | 0.1 | 3 | 27 | id8615 |
| p.R360* | c.1078C > T | NM_005445 | 0.111111 | 5 | 40 | id6729 |
| p.R971* | c.2911C > T | NM_005862 | 0.476744 | 41 | 45 | id16988 |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| p.C711* | c.2133T > A | NM_006603 | 0.082353 | 7 | 78 | id3061 |
| p.D661Y | c.1981G > T | NM_139276 | 0.075 | 15 | 185 | id5064 |
| p.D661Y | c.1981G > T | NM_139276 | 0.035897 | 7 | 188 | id13856 |
| p.D661Y | c.1981G > T | NM_139276 | 0.0301 | 9 | 290 | id11824 |
| p.G618R | c.1852G > C | NM_139276 | 0.116279 | 10 | 76 | id15379 |
| p.S382fs | c.1146_1147delAG | NM_015355 | 0.09 | 7 | 67 | id5830 |
| p.R431* | c.12910 > T | NM_024665 | 0.054945 | 5 | 86 | id9755 |
| p.R1656H | c.4967G > A | NM_030625 | 0.040404 | 4 | 95 | id15581 |
| p.R73fs | c.217_218insA | NM_001127208 | 0.22 | 23 | 80 | id16185 |
| p.Y85f | c.254delA | NM_001127208 | 0.21 | 13 | 50 | id16184 |
| p.S123fs | c.357_368delTC | NM_001127208 | 0.05 | 9 | 161 | id6767 |
| p.E170fs | c.508delG | NM_001127208 | 0.13 | 12 | 83 | id6962 |
| p.D162fs | c.486delT | NM_001127208 | 0.17 | 10 | 49 | id14838 |
| p.I181fs | c.541_542delAT | NM_001127208 | 0.18 | 12 | 53 | id14877 |
| p.T221fs | c.662_663insA | NM_001127208 | 0.41 | 29 | 41 | id6024 |
| p.L260fs | c.780delG | NM_001127208 | 0.39 | 17 | 27 | id15531 |
| p.I274fs | c.822delC | NM_001127208 | 0.15 | 6 | 35 | id16146 |
| p.L311fs | c.931_932insT | NM_001127208 | 0.29 | 9 | 22 | id12755 |
| p.Q341* | c.1021C > T | NM_001127208 | 0.297297 | 1 | 26 | id3816 |
| p.Q383* | c.1147C > T | NM_001127208 | 0.06383 | 6 | 88 | id13812 |
| p.S423* | c.1268C > G | NM_001127208 | 0.242718 | 25 | 78 | id12421 |
| p.L427fs | c.1279_1280insT | NM_001127208 | 0.05 | 10 | 210 | id6395 |
| p.S420fs | c.1259delC | NM_001127208 | 0.06 | 8 | 117 | id4591 |
| p.S424fs | c.1272delC | NM_001127208 | 0.42 | 23 | 32 | id16100 |
| p.S462fs | c.1385_1386insT | NM_001127208 | 0.12 | 11 | 79 | id6669 |
| p.I472fs | c.1416delA | NM_001127208 | 0.41 | 24 | 35 | id9978 |
| p.Q481* | c.1441C > T | NM_001127208 | 0.105263 | 6 | 51 | id8613 |
| p.T518fs | c.1554_1555insGTTC | NM_001127208 | 0.07 | 11 | 139 | id6946 |
| p.S530* | c.1589C > G | NM_001127208 | 0.234043 | 22 | 72 | id9844 |
| p.S543fs | c.1629delT | NM_001127208 | 0.2 | 21 | 83 | id8992 |
| p.S543fs | c.1588C > T | NM_001127208 | 0.090909 | 3 | 30 | id13286 |
| p.Q530* | c.1594delT | NM_001127208 | 0.07 | 7 | 91 | id5667 |
| p.L532* | c.1594delT | NM_001127208 | 0.137931 | 4 | 25 | id13788 |
| p.R544* | c.1630C > T | NM_001127208 | 0.089744 | 7 | 71 | id9033 |
| p.W585* | c.1754G > A | NM_001127208 | 0.066667 | 7 | 98 | id10707 |
| p.Q595fs | c.1784delA | NM_001127208 | 0.11 | 12 | 94 | id9756 |
| p.L579fs | c.1736_1737insA | NM_001127208 | 0.04 | 6 | 134 | id5827 |
| p.S588* | c.1763C > G | NM_001127208 | 0.085714 | 9 | 96 | id17116 |
| p.S588* | c.1763C > G | NM_001127208 | 0.070423 | 5 | 66 | id13618 |
| p.G634fs | c.1900delG | NM_001127208 | 0.28 | 29 | 73 | id6827 |
| p.Q656fs | c.1967delA | NM_001127208 | 0.2 | 7 | 28 | id9231 |
| p.P690fs | c.2070delA | NM_001127208 | 0.1 | 7 | 62 | id7339 |
| p.R686fs | c.2056_2057delAG | NM_001127208 | 0.04 | 7 | 160 | id5554 |
| p.E692fs | c.2074_2075insA | NM_001127208 | 0.15 | 18 | 103 | id14876 |
| p.Q705* | c.2113C > T | NM_001127208 | 0.181818 | 14 | 63 | id3142 |
| p.F713fs | c.2137del | NM_001127208 | 0.06 | 6 | 88 | id8785 |
| p.Q734* | c.2201A > G | NM_001127208 | 0.181818 | 14 | 63 | id12570 |
| p.S757* | c.2270C > A | NM_001127208 | 0.148936 | 14 | 80 | id10777 |
| p.L759fs | c.2277delC | NM_001127208 | 0.39 | 36 | 57 | id12296 |
| p.Q764fs | c.2290delC | NM_001127208 | 0.24 | 26 | 81 | id9503 |
| p.I771fs | c.2313_2316delAA | NM_001127208 | 0.05 | 9 | 162 | id6622 |
| p.Q779* | c.2335C > G | NM_001127208 | 0.068493 | 5 | 68 | id11567 |
| p.H783fs | c.2348_2349insC | NM_001127208 | 0.08 | 8 | 95 | id9593 |
| p.Q770* | c.2308C > T | NM_001127208 | 0.087912 | 8 | 83 | id16702 |
| p.E819fs | c.2457_2458insA | NM_001127208 | 0.16 | 11 | 59 | id6628 |
| p.H839fs | c.2516delA | NM_001127208 | 0.16 | 8 | 43 | id5794 |
| p.H839fs | c.2516delA | NM_001127208 | 0.11 | 11 | 90 | id6042 |
| p.K858fs | c.2572delA | NM_001127208 | 0.18 | 11 | 50 | id15401 |
| p.Q866* | c.2596C > T | NM_001127208 | 0.207547 | 11 | 42 | id16170 |
| p.L878fs | c.2632delC | NM_001127208 | 0.29 | 14 | 34 | id7611 |
| p.M906fs | c.2717_2718insGTCTG | NM_001127208 | 0.08 | 6 | 68 | id3168 |
| p.Q909* | c.2725C > T | NM_001127208 | 0.113208 | 6 | 47 | id15069 |
| p.Q910* | c.2728C > T | NM_001127208 | 0.142857 | 7 | 42 | id3120 |
| p.A912fs | c.2734_2735delGC | NM_001127208 | 0.16 | 9 | 49 | id14836 |
| p.Q937* | c.2809C > T | NM_001127208 | 0.068182 | 3 | 41 | id9874 |
| p.Q916* | c.2746C > T | NM_001127208 | 0.104478 | 7 | 60 | id14980 |
| p.P989fs | c.2966_2967insA | NM_001127208 | 0.16 | 10 | 53 | id8791 |
| p.A1014fs | c.3041_3042insA | NM_001127208 | 0.28 | 17 | 44 | id2276 |
| p.Q1042* | c.3124C > T | NM_001127208 | 0.04895 | 7 | 136 | id6161 |
| p.Q1030* | c.3088C > T | NM_001127208 | 0.396825 | 25 | 38 | id2189 |
| p.H1064fs | c.3190_3191insAT | NM_001127208 | 0.06 | 6 | 88 | id10415 |
| p.T1078fs | c.3233delC | NM_001127208 | 0.05 | 6 | 124 | id8806 |
| p.T1107fs | c.3320_3321delCT | NM_001127208 | 0.08 | 8 | 95 | id2308 |
| p.N1103fs | c.3309_3310delTT | NM_001127208 | 0.05 | 6 | 105 | id14667 |
| p.N1103fs | c.3309_3310delTT | NM_001127208 | 0.22 | 23 | 82 | id12573 |

SUPPLEMENTARY TABLE S3-continued

Called somatic variants in 160 hematopoeitic genes

| Gene name | Chromosome | Start position | Variant Type | Reference Allele | Variant Allele | Varient Classification |
|---|---|---|---|---|---|---|
| p.T1114fs | c.3340_3341delAC | NM_001127208 | 0.08 | 6 | 69 | id15950 |
| p.Q1127fs | c.3380_3381insT | NM_001127208 | 0.33 | 27 | 55 | id6026 |
| p.C1135Y | #N/A | NM_001127208 | 0.278689 | 17 | 44 | id9984 |
| c.e3+1 | c.3472_splice | NM_001127208 | 0.3 | 27 | 63 | id11641 |
| c.e3+1 | c.3472_splice | NM_001127208 | 0.153153 | 17 | 94 | id10803 |
| p.Q110* | c.328C > T | NM_006290 | 0.0625 | 4 | 60 | id5021 |
| p.R183* | c.548G > A | NM_006290 | 0.09379 | 9 | 87 | id16445 |
| p.E297* | c.889G > T | NM_006290 | 0.177419 | 11 | 51 | id15210 |
| c.e3 −1 | c.179_splice | NM_003820 | 0.102941 | 7 | 61 | id14548 |
| p.G124fs | c.370delG | NM_003820 | 0.39 | 7 | 11 | id12761 |
| p.R342* | c.1024C > T | NM_001126112 | 0.067797 | 4 | 55 | id3959 |
| p.R283H | c.848G > A | NM_001126112 | 0.421053 | 24 | 33 | id9876 |
| p.R283H | c.848G > A | NM_001126112 | 0.076923 | 4 | 48 | id9684 |
| p.R282W | c.844C > T | NM_001126112 | 0.071429 | 3 | 39 | id16017 |
| p.D281N | c.841G > A | NM_001126112 | 0.327586 | 19 | 39 | id2305 |
| p.R280G | c.838A > G | NM_001126112 | 0.087719 | 5 | 52 | id16933 |
| p.R248Q | c.743G > A | NM_001126112 | 0.537736 | 57 | 49 | id4884 |
| p.R248Q | c.743G > A | NM_001126112 | 0.164706 | 14 | 71 | id4005 |
| p.G245C | c.733G > T | NM_001126112 | 0.056338 | 8 | 134 | id6889 |
| p.S241C | c.722C > G | NM_001126112 | 0.1875 | 9 | 39 | id17155 |
| p.N235D | c.703A > G | NM_001126112 | 0.081633 | 4 | 45 | id14981 |
| p.Y220C | c.659A > G | NM_001126112 | 0.085106 | 4 | 43 | id5608 |
| p.Y220H | c.658T > C | NM_001126112 | 0.139535 | 6 | 37 | id3142 |
| p.H193R | c.578A > G | NM_001126112 | 0.0625 | 3 | 45 | id6883 |
| p.R181C | c.541C > T | NM_001126112 | 0.080645 | 5 | 57 | id14694 |
| p.P177R | c.530C > G | NM_001126112 | 0.193548 | 12 | 50 | id5804 |
| p.R175H | c.524G > A | NM_001126112 | 0.047619 | 4 | 80 | id9682 |
| p.R175H | c.524G > A | NM_001126112 | 0.186047 | 8 | 35 | id15836 |
| p.R175H | c.524G > A | NM_001126112 | 0.048544 | 5 | 98 | id9552 |
| p.V173E | c.518T > A | NM_001126112 | 0.089888 | 8 | 81 | id10986 |
| p.R158H | c.473G > A | NM_001126112 | 0.082474 | 8 | 89 | id4972 |
| p.R156H | c.467G > A | NM_001126112 | 0.041237 | 4 | 93 | id13772 |
| p.P152L | c.455C > T | NM_001126112 | 0.127273 | 7 | 48 | id17168 |
| p.W146* | c.438G > A | NM_001126112 | 0.092308 | 6 | 59 | id13823 |
| p.W146* | c.438G > A | NM_001126112 | 0.146341 | 6 | 35 | id16840 |
| p.K132E | c.394A > G | NM_001126112 | 0.065217 | 3 | 43 | id15972 |
| p.K132E | c.394A > G | NM_001126112 | 0.219512 | 9 | 32 | id15950 |
| p.C124fs | c.371_372insG | NM_001126112 | 0.09 | 13 | 133 | id14877 |
| p.R110L | c.329G > T | NM_001126112 | 0.104762 | 11 | 94 | id14122 |
| p.R110C | c.328C > T | NM_001126112 | 0.207547 | 11 | 42 | id16019 |
| p.R110C | c.328C > T | NM_001126112 | 0.439394 | 29 | 37 | id16285 |
| p.P72fs | c.216delC | NM_001126112 | 0.03 | 14 | 418 | id7283 |
| p.P72fs | c.216delC | NM_001126112 | 0.17 | 31 | 149 | id15592 |
| p.R156H | c.467G > A | NM_006758 | 0.329897 | 32 | 65 | id2344 |
| p.R156H | c.467G > A | NM_006758 | 0.475 | 38 | 42 | id6999 |
| p.S34F | c.101C > T | NM_006758 | 0.12963 | 7 | 47 | id11641 |
| p.S34F | c.101C > T | NM_006758 | 0.190476 | 4 | 17 | id4102 |
| p.D14G | c.41A > G | NM_006758 | 0.068966 | 6 | 81 | id15962 |
| p.R126P | c.377G > C | NM_005089 | 0.75 | 15 | 5 | id8081 |
| p.R295* | c.883C > T | NM_005089 | 0.443038 | 35 | 44 | id13539 |
| p.G424fs | c.1272delA | NM_005089 | 0.58 | 11 | 8 | id7280 |

Supplementary Table S4
List of non-hematopoietic genes and variants queried

| Gene name | Reported mutations used for variant calling | Accession | Number of variants found |
|---|---|---|---|
| ACVR1B | Frameshift/nonsense, G368spl, R420spl, G219E, G219W, D268N, M345I, I346F, A357T, H358Y, H374R, D376N, A446V, D490N, D490V | NM_004302 | 0 |
| AKT1 | E17K, L52R, Q79K, W80R | NM_005163 | 0 |
| APC | Frameshift/nonsense c150-1500, R141spl, R216spl, R2204* | NM_001127511 | 1 |
| APOL2 | S127L, S127C, G128D | NM_030882 | 0 |
| ARHGAP35 | Frameshift/ns | NM_004491 | 0 |
| ARID2 | Frameshift/ns, D174Y, D174G, R247H, R247S, R285W, R285Q | NM_152641 | 0 |
| ATP5B | S386L, K459T | NM_001686 | 0 |
| B2M | Frameshift/ns | NM_004048 | 0 |
| BAP1 | Frameshift/nonsense, G23spl, D311spl, N78S, R227H, R227C | NM_004656 | 0 |
| CASP8 | Frameshift/ns | NM_033355 | 4 |
| CDH1 | Frameshift/ns, E243K, E243Q, R732Q, P825L | NM_004360 | 0 |

Supplementary Table S4
List of non-hematopoietic genes and variants queried

| Gene name | Reported mutations used for variant calling | Accession | Number of variants found |
|---|---|---|---|
| CDKN1B | Frameshift/ns | NM_004064 | 0 |
| CDKN2A | Q50*, V51spl, R58*, G65spl, D74V, D74Y, R80*, H83R, H83Y, D84N, D84V, E88*, D108V, D108N, D108Y, W110*, P114L, P114T, E120*, Y129*, D153spl | NM_000077 | 0 |
| CHD1 | M1I, I1080spl, R1189Q | NM_001270 | 0 |
| CHD4 | E34spl, P251L, P251S, R975H, R1105W, R1105Q, R1162W, R1162Q, R1338I, R877Q, R877W | NM_001273 | 0 |
| CTNNB1 | D32Y, D32A, D32G, D32N, S33C, S33P, S33Y, G34R, G34E, G34V, I35S, H36Y, S37F, S37C, S37A, T41A, T41I, S45F, S45C, S45Y | NM_001904 | 0 |
| EGFR | L62R, G63R, R108K, R108G, S220P, R222C, R222L, R252C, R252P, A289V, A289T, H304Y, P596L, P596S, G598V, E709K, G719A, G719D, S768I, S768T, L838M, L858R, L861Q, L861R | NM_005228 | 0 |
| ERBB2 | S310F, S310Y, R678Q, L755S, L755R, D769H, D769N, D769Y, V777L, V842I, R896H, M916I, E1244D, E1244Q | NM_004448 | 0 |
| ERBB3 | M91I, V104L, V104M, D297N, D297Y, D297V, K329E, K329T, T355A, T355I, E928G, S1216F | NM_001982 | 0 |
| EZH1 | Frameshift/ns | NM_001991 | 0 |
| FGFR3 | R248C, S249C, G380R, K650T, K650E, P716H | NM_000142 | 0 |
| GPS2 | Frameshift/ns | NM_004489 | 1 |
| HRAS | G12A, G12D, G12S, G13R, G13V, G13C, Q61R, Q61L, Q61K | NM_176795 | 0 |
| KDM5C | Frameshift/ns, E23K, E23Q, E386Q, R585C, R585H, C730F, C730R, E1247K | NM_004187 | 0 |
| KEAP1 | S144F, I145F, V155A, V155F, R169C, R260Q, R260L, R272C, R272H, R320P, R320Q, R320M, R415H, R415C, G417E, G417V, G417R, D422N, G423V, R470S, R470H, R470C, G480W, E493V, E493D, M503I, M503K, W544R, W544C, G603W | NM_012289 | 0 |
| MAP2K4 | Frameshift/nonsense, I73spl, R134W, S184L, S251I, P272spl, L297spl, R287H, P306R, P306H, L362spl, K363spl, L385P, L385V | NM_003010 | 0 |
| MAP3K1 | Frameshift/ns, S1330L, S1330W, C1437S, C1437F | NM_005921 | 1 |
| MTOR | L1460P, C1483R, C1483Y, C1483F, E1799K, F1888V, F1888L, F1888L, I1973F, T1977K, T1977I, T1977S, V2006L, V2006I, S2215Y | NM_004958 | 0 |
| NFE2L2 | W24C, W24R, Q26R, Q26K, D27G, D27H, D29N, D29H, D29Y, L30F, L30H, G31A, G31V, G31R, R34P, R34G, R34Q, E79K, E79Q, T80P, T80R, T80K, G81V, G81S, G81C, G81D, E82D, A124G, A124V | NM_006164 | 1 |
| PBRM1 | Frameshift/ns | NM_181042 | 0 |
| PIK3CA | R38C, R38L, R38H, R38S, E39K, E81K, R88Q, C90Y, C90G, R93W, R93Q, G106V, G106R, R108L, R108H, E110del, K111R, K111E, K111N, K111del, L113del, R115L, G118spl, V344G, V344A, V344M, N345K, D350G, D350N, G364R, E365V, E365K, C420R, C420G, G451V, G451R, E453K, E453Q, E453D, P471A, P471L, E542K, E542Q, E545K, E545A, E545Q, E545D, E545G, Q546R, Q546P, Q546K, E726K, C901F, D939G, M10041, G1007R, Y1021C, Y1021H, T1025A, T1025S, M1043V, M1043I, N1044K, N1044Y, H1047R, H1047L, G1049R | NM_006218 | 0 |
| PIK3R1 | Frameshift/nonsense, P129L, P129S, R340spl, G376R, Y452C, Y452N, Y452I, D464N, D464Y, R503Q, R514C, R514L, D560H, D560D, D560N, L573P, Y580C, Y580D, M582spl | NM_181523 | 1 |
| RASA1 | Frameshift/nonsense, S122L, S418spl, R789L, R789Q, M802I, P868spl | NM_002890 | 0 |
| RB1 | Frameshift/nonsense, N405spl | NM_000321 | 0 |
| SEPT12 | G56spl, R210spl, I211spl, R242spl, D243spl, R244* | NM_144605 | 0 |
| SMAD4 | Frameshift/ns, R97H, D351N, P356R, P356L, R361H, R361C, G386D, G510E, G510D, D537G, D537V, D537T, P544S, P544L | NM_005359 | 0 |
| SMARCA4 | P12L, P12S, R381Q, A406T, T786N, T786I, T910MV, P913L, P913V, R966W, R1125G, R1125S, R1125M, R1192H, R1192C, Q1195K, Q1195L, A1231D, A1231T, G1232C, G1232S | NM_003072 | 0 |
| SPOP | E50K, M117V, S119N, S119R, R121Q, W131G, W131R, F133C, F133L, F133S, D140N, D140H | NM_001007228 | 0 |
| STK11 | Frameshift/nonsensesplice-site | NM_000455 | 0 |
| VHL | Frameshift/nonsensesplice-site, N78S, N78D, N78Y, W88R, W88L, L89P, L89H, S111R, S111H, H115N, V130L, V130D, I151N, I151T, I151F, L158P, L158V, C162R, C162F, C162Y, L169P, L184P, L188P, L188R | NM_000551 | 1 |
| Total | | | 10 |

Supplementary Table S5
Called variants in non-hematopoeitic genes

| Gene name | Chromosome | Start position | Variant Type | Reference Allele | Variant Allele | Variant Classification | Protein Change |
|---|---|---|---|---|---|---|---|
| APC | 5 | 112175212 | DEL | AAAAG | — | Frame_Shift_Del | p.I1307fs |
| CASP8 | 2 | 202149654 | DEL | C | — | Frame_Shift_Del | p.N306fs |
| CASP8 | 2 | 202149654 | DEL | C | — | Frame_Shift_Del | p.N306fs |
| CASP8 | 2 | 202149901 | SNP | C | T | Nonsense_Mutation | p.Q389* |
| CASP8 | 2 | 202149901 | SNP | C | T | Nonsense_Mutation | p.Q389* |
| GPS2 | 17 | 7217689 | SNP | G | G | Nonsense_Mutation | p.Q80* |
| MAP3K1 | 5 | 56152535 | SNP | G | G | Nonsense_Mutation | p.W197* |

-continued

Supplementary Table S5
Called variants in non-hematopoeitic genes

| | | | | | | | |
|---|---|---|---|---|---|---|---|
| NFE2L2 | 2 | 17898009 | SNP | G | A | Missense_Mutaton | p.A124V |
| PIK3R1 | 5 | 67589168 | SNP | C | C | Nonsense_Mutation | p.R386* |
| VHL | 3 | 10191614 | SNP | C | T | Nonsense_Mutation | p.Q203* |

| Gene name | cDNA Change | Accession | Variant allele fraction | Variant allele count | Reference allele count | ID |
|---|---|---|---|---|---|---|
| APC | c3921_3925 | NM_001127611 | 0.28 | 29 | 74 | id3447 |
| CASPS | c.018delC | 10d_033355 | 0.51 | 94 | 89 | id8185 |
| CASPS | c.918delC | NM_033355 | 0.47 | 95 | 109 | id7570 |
| CASPS | c.1165C>T | NM_033355 | 0.387756 | 19 | 30 | id16144 |
| CASPS | c.1165C>T | NM_033355 | 0.385714 | 27 | 43 | id4204 |
| GPS2 | c.238C>T | NM_004489 | 0.098361 | 12 | 110 | id11021 |
| NAP3K1 | c.591G>A | NM_005921 | 0.422414 | 49 | 67 | id6408 |
| NFE2L2 | c.371C>T | NM_006164 | 0.069767 | 3 | 40 | id14589 |
| PIK3R1 | c.1156C>T | NM_181523 | 0.107143 | 3 | 25 | id11720 |
| VHL | c.607C>T | NM_000551 | 0.333333 | 15 | 26 | id13940 |

Supplementary Table S6
Logistic regression for factors associated with clonality
Logistic regression was performed using the variables age (as a continuous variable), ancestry, sex, T2D, and age/sex interaction. Other interaction terms were modeled, but none were significant. Proportion of variance explained is derived by analysis of variance (ANOVA) for the generalized linear model, and is equal to deviance for the variable divided by residual deviance for the null model.

| | Beta coefficient | OR(95 CI) | p-value | Variance explained |
|---|---|---|---|---|
| Age | 0.07 | 1.08(1.07-1.09) | <0.001 | 0.06 |
| European (referent) | | | | 0.003 |
| African-American | 0.11 | 1.12(0.9-1.39) | 0.3 | |
| East-Asian | 0.02 | 1.02(0.79-1.31) | 0.86 | |
| Hispanic | -0.39 | 0.68(0.55-0.83) | <0.001 | |
| South Asian | -0.2 | 0.82(0.63-1.05) | 0.125 | |
| No T2D (referent) | | | | 0.002 |
| Has T2D | 0.26 | 1.3(1.12-1.51) | <0.001 | |
| Male (referent) | | | | 0.001 |
| Female | 0.83 | | 0.066 | |
| Age:Female | 0.02 | 0.98(0.97-1) | 0.023 | 0.001 |

Supplementary Table S7
Logistic regression for factors associated with clonality by ancestry group
Logistic regression was performed using the variables age (as a continuous variable), sex, T2D, and age/sex interaction for each ancestry group. Proportion of variance explained is derived by analysis of variance (ANOVA) for the generalized linear model, and is equal to deviance for the variable divided by residual deviance for the null model.

| | Beta coefficient | OR(95 CI) | p-value | Variance explained |
|---|---|---|---|---|
| African-American | | | | |
| Age | 0.07 | 1.08(1.05-1.1) | <0.001 | 0.08 |
| Female | 0.37 | 1.45(0.21-10.2) | 0.7 | 0.002 |
| Has T2D | 0.24 | 1.27(0.9-1.79) | 0.18 | 0.002 |
| Age:Sex | -0.01 | 0.99(0.96-1.02) | 0.52 | 0.0003 |
| East Asian | | | | |
| Age | 0.1 | 1.11(1.06-1.16) | <0.001 | 0.03 |
| Female | 1.3 | 3.65(0.08-172) | 0.51 | 0.003 |
| Has T2D | -0.12 | 0.89(0.57-1.38) | 0.61 | 0.0003 |
| Age:Sex | -0.03 | 0.97(0.92-1.03) | 0.385 | 0.0006 |

-continued

Supplementary Table S7
Logistic regression for factors associated with clonality by ancestry group
Logistic regression was performed using the variables age (as a continuous variable), sex, T2D, and age/sex interaction for each ancestry group. Proportion of variance explained is derived by analysis of variance (ANOVA) for the generalized linear model, and is equal to deviance for the variable divided by residual deviance for the null model.

| | Beta coefficient | OR(95 CI) | p-value | Variance explained |
|---|---|---|---|---|
| European | | | | |
| Age | 0.07 | 1.07(1.06-1.09) | <0.001 | 0.05 |
| Female | 1.73 | 5.62(1.26-25) | 0.023 | 0.001 |
| Has T2D | 0.31 | 1.36(1.04-1.79) | 0.026 | 0.003 |
| Age:Sex | -0.03 | 0.97(0.95-0.99) | 0.013 | 0.0033 |
| Hispanic | | | | |
| Age | 0.08 | 1.08(1.06-1.11) | <0.001 | 0.08 |
| Female | 0.69 | 2(0.27-15.6) | 0.5 | 0.00001 |
| Has T2D | 0.22 | 1.24(0.9-1.72) | 0.18 | 0.001 |
| Age:Sex | -0.01 | 0.99(0.96-1.02) | 0.485 | 0.0003 |
| South Asian | | | | |
| Age | 0.08 | 1.08(1.05-1.11) | <0.001 | 0.07 |
| Female | -0.82 | 0.44(0.01-12.3) | 0.64 | 0.0001 |
| Has T2D | 0.49 | 1.53(1.04-2.56) | 0.033 | 0.007 |
| Age:Sex | 0.01 | 1.01(0.96-1.07) | 0.677 | 0.0002 |

Supplementary Table S8
Logistic regression for factors associated with RDW >14.5%
Individuals were from Jackson Heart Study or UA control cohort.

| Covariate | OR (95% CI) | p-value |
|---|---|---|
| Age 60-69 | 1.3(0.9-1.8) | 0.17 |
| Age 70-79 | 1.8(1.2-2.7) | 0.002 |
| Age 80-89 | 2.7(1.3-5.2) | 0.005 |
| Age >90 | 1.7(0.9-3.1) | 0.09 |
| Female | 1.1(0.8-1.5) | 0.76 |
| Has T2D | 0.9(0.7-1.2) | 0.45 |
| DNMT3a mutation | 1.9(1-3.6) | 0.048 |

Supplementary Table S8
Logistic regression for factors associated with RDW >14.5% Individuals were from Jackson Heart Study or UA control cohort.

| Covariate | OR (95% CI) | p-value |
|---|---|---|
| WBC | 1.1(1.0-1.1) | 0.092 |
| Hemoglobin | 0.7(0.7-0.8) | <0.001 |
| Platelet count | 1.0(1.0-1.0) | 0.65 |

Supplementary Table S9
Association of cytopenias with clonality
Individuals were classified as having cytopenia as defined in Methods. Statistical comparisons were performed using Fisher's exact test. WBC—white blood cell count, Hgb hemoglobin, Plt—platelet count. Individuals were from Jackson Heart Study, Longevity Genes Project, Botnia, Helsinki-sib, and Malmo-sib. Of the 5 individuals with multiple cytopenias and clonal mutations, 2 had 2 detectable mutations suggesting that these might be undiagnosed cases of MDS.

| | Clone | No Clone | |
|---|---|---|---|
| Low WBC | 6 | 59 | 65 |
| Normal WBC | 119 | 2628 | 2747 |
| | 125 | 2687 | |
| | OR 2.2(0.8-5.2), p = 0.066 | | |
| Low High | 30 | 616 | 65 |
| Normal High | 109 | 2350 | 2459 |
| | 339 | 2966 | |
| | OR 1.0(0.7-1.6), p = 0.83 | | |
| Low Plt | 4 | 107 | 111 |
| Normal Plt | 132 | 2789 | 2921 |
| | 336 | 2896 | |
| | OR 0.8(0.2-2.1), p = 0.82 | | |
| Low cytopenia | 4 | 107 | 111 |
| Normal Plt | 132 | 2789 | 2921 |
| | 336 | 2896 | |
| | OR 1.0(0.6-1.5), p = 1 | | |

Lower limit of normal for blood counts were defined as follows: White blood cell count: African-Americans $3.0 \times 10^9$/L, white $4.0 \times 10^9$/L
Hemoglobin: African-American women 11.2 g/dL, African-American men 12.5 g/dL, white women 11.9 g/dL, white men 13.4 g/dL
Platelet count: $150 \times 10^9$/L

Supplementary Table S10
Association of clonality with known versus unknown causes of anemia During clinical evaluation, most patients with anemia can be found to have an attributable cause. Using subjects from the Jackson Heart Study, Applicants assessed whether the anemia was attributable to iron defiency, anemia of chronic inflammation, or renal insufficiency. Individuals with clonality were less likely to have anemia attributable to one of these causes

Iron deficiency anemia/microcytic anemia mean corpuscular volume <80 fL
ferritin <20 ng/mL
ferritin 20-100 ng/L WITH EITHER total iron binding capacity >370 mcg/dL OR serum iron <50 mcg/dL OR iron saturation <20%

Anemia of chronic disease serum iron <65 mcg/dL WITH total iron binding capacity <250 mcg/dL
ferritin >350 ng/mL for males
ferritin >300 ng/mL for females

Renal insufficiency estimated glomerular filtration rate <30 mL/min/1.73 m²

| | Clone | No Clone | |
|---|---|---|---|
| Known cause | 2 | 360 | 362 |
| Unknown cause | 7 | 151 | 158 |
| | 9 | 511 | |
| | OR 0.1(0-0.6), p = 0.004 | | |

Supplementary Table S11
Details on subjects that developed hematologic malignancies

| | | | | | Incident Cases | | | | | | |
|---|---|---|---|---|---|---|---|---|---|---|---|
| Age at Sampling | Diagnosis | Cohort | Adjudicated | Latency (years) | Mutation on WES (VAF) | Mutations on RHP (VAF) | WBC | HGB | PLT | Death | Cause of Death |
| 77 | CANCER OF SPLEEN a | AJ | No | 6 | JAK2 p.V617F (0.23) | NA | 7.8 | 11 | 247 | Yes | CARCINOMA UNSPECIFIED SITE |
| 64 | LEUKEMIA (prior NHL) b | AJ | No | 7 | ASXL1 p.0616fs (0.23) | ASXL1 p.D616fs (0.18) | 3.5 | 12.9 | 189 | No | |
| 57 | LYMPHOMA c | AJ | No | 2 | DNMT3A p R882H (0.29) | NA | 14.3 (51.3% lymphocytes)d | 11 | 248 | No | |

Supplementary Table S11
Details on subjects that developed hematologic malignancies

| | | | | | | | | | | | |
|---|---|---|---|---|---|---|---|---|---|---|---|
| 85 | DLBCL, large intestine e | MEC | Yes | 5 | TET2 p.C1135Y (0.28)/ASXL1 p.1919fs (0.22) | TET2 p.C1135Y (0.35)/TET2 p.G1192V (0.30)/ASXL1 p.1919fs (0.26) | | | | No | |
| 82 | MDS-RAEB | MEC | Yes | 7 | ASXL1 p. T514fs (0.24) | ASXL1 p. T514fs (0.30)/TET2 p.1616fs (0.15) | | | | Yes | Myeloid leukemia |
| 50 | LYMPHOMA | AJ | No | 4 | None | NA | 6.3 | 14.4 | 220 | Yes | COMPLI-CATIONS DUE TO LYMPHOMA |
| 48 | LYMPHOMA | AJ | No | 1 | None | NA | 4.6 | 14.3 | 225 | Yes | RENAL FAILURE |
| 57 | LYMPHOMA | AJ | No | 7 | None | None | 7.4 | 13.7 | 280 | Yes | HYPOXIC RESPI-RATORY FAILURE |
| 62 | LEUKEMIA | AJ | No | 9 | None | NA | 2.6 | 13.9 | 168 | No | |
| 51 | BLOOD | AJ | No | 8 | None | NA | 5.7 | 13.7 | 318 | No | |
| 67 | LEUKEMIA | AJ | No | 9 | None | None | | | | No | |
| 64 | MULTIPLE MYELOMA | AJ | No | 9 | None | NA | 4.4 | 11.4 | 298 | No | |
| 59 | LYMPHOMA | AJ | No | 8 | None | NA | | 13.2 | 195 | No | |
| 61 | ACUTE MYELOID LEUKEMIA | AJ | No | 10 | None | None | | 11.7 | 158 | Yes | ACUTE MYELOID LEUKEMIA |
| 51 | LEUKEMIA | AJ | No | 10 | None | NA | 4.8 | 11 | 334 | No | |
| 66 | Multiple myeloma | MEC | Yes | 8 | None | NA | | | | No | |

Prevalent Cases

| Age at Sampling | Diagnosis | Cohort | Adjudicated | Time (years prior) | Mutation on WES (VAF) | Mutations on RHP (VAF) | WBC | HGB | PLT | Death | Cause of Death |
|---|---|---|---|---|---|---|---|---|---|---|---|
| 64 | LEUKEMIA | AJ | No | 7 | None | NA | 3.5 | 12.9 | 189 | No | |
| 48 | LYMPHOMA | AJ | No | 1 | None | NA | 4.6 | 14.3 | 225 | Yes | RENAL FAILURE |
| 76 | LEUKEMIA | AJ | No | 12 | None | NA | | 11.4 | 252 | No | |
| 63 | NHL oropharynx | MEC | Yes | 24 | None | NA | | | | | |
| 64 | NHL (subsequent LEUKEMIA see above) | AJ | No | 7 | ASXL1 p.D616fs (0.23) | ASXL1 p.D616fs (0.18) | 3.5 | 12.9 | 189 | No | |

NHL-Non-Hodgkin's lymphoma, DLBCL-diffuse large B-cell lymphoma, MDS-RAED = myelodysplastic syndrome, refactory anemia with excess blasts AJ = Jackson Heart Study, MEC = Multi-ethnic cohort, Hispanics in Los Angeles WES = whole exome sequencing, RHP = Rapid Heme Panel targeted re-sequencing, VAF = variant allele fraction WBC = white blood cell count (x 10^9 cells/L), HGB = hemoglobin (g/dL), PLT = platelet count (x 10^9 cells/L)

NA = Not available a This is likely splenomegaly secondary to a JAK2-mutated myeloproliferative neoplasm b This likely represents a therapy related AML/MDS, as ASXL1 mutations have never been described in lymphoid malignancies c DNMT3A mutations have been found in peripheral T-cell lymphomas and early T-progenitor ALL d This is the second highest absolute lymphocyte count in the cohort of 2,426 subjects who had a WBC differential. The subject with the highest absolute lymphocyte count also had a DNMT3A mutation.

e TET2 has been reported to be mutated in 6-12% of DLBCL, and the mutations are reported to be found in hematopoietic stem cells Supplementary Table S12

Risks assoccitated with developing incident coronary heart disease and ischemic stroke using traditional risk factors and clonality. Hazard ratios were estimated using competing risks regression with death as the competing risk. P-values are dervied from the Fine-Gray test. Individuals with prior coronary heart disease (CHD) were excluded for CHD analysis, and individuals with prior ischemic stroke were excluded for stroke analysis. Models shown in A or B are from the same population and differ by having covariates either removed or added. A) Coronary heart disease. B) ischemic stroke. Individuals were from Jackson Heart Study and FUSION.

A

| Covariate | Model 1 HR (95% CI) | p-value | Model 2 HR (95% CI) | p-value | Model 3 HR (95% CI) | p-value |
|---|---|---|---|---|---|---|
| | | | n = 2,286 | | | |
| log(Age) | 5.3(2.1-12.8) | <0.001 | 4.7(1.9-11) | <0.001 | 4.6(1.9-11) | <0.001 |
| Has T2D | 3.3(2.1-5.3) | <0.001 | 3.4(2.1-5.4) | <0.001 | 3.5(2.2-5.5) | <0.001 |
| Female | 0.7(0.5-1.1) | 0.11 | 0.7(0.5-1.1) | 0.13 | 0.7(0.5-1.1) | 0.13 |
| HDL <35 mg/dL | 1.1(0.6-2.1) | 0.77 | 1.1(0.6-2.1) | 0.81 | 1.1(0.6-2.1) | 0.78 |
| HDL >60 mg/dL | 0.7(0.4-1.2) | 0.18 | 0.7(0.4-1.3) | 0.25 | 0.7(0.4-1.3) | 0.26 |
| TC >240 mg/dL | 2.1(1.3-3.2) | <0.001 | 2(1.3-3.1) | <0.001 | 2(1.3-3.1) | <0.001 |
| Former or current smoker | 1.6(1.1-2.5) | 0.024 | 1.6(1-2.4) | 0.035 | 1.6(1.1-2.5) | 0.02 |
| Hypertension stage II-IV | 1.6(1-2.5) | 0.06 | 1.4(0.9-2.3) | 0.15 | 1.4(0.9-2.3) | 0.15 |
| BMI >25 | 1.2(0.6-2.5) | 0.55 | 1.4(0.6-2.8) | 0.43 | 1.3(0.6-2.8) | 0.42 |
| Clone present | | | 2.3(1.1-4.8) | 0.026 | | |
| VAF <0.10 | | | | | 1.4(0.5-4) | 0.55 |
| VAF >0.10 | | | | | 4.4(1.9-10.5) | <0.001 |
| Pseudo Log-likelihood | −861 | | −638 | | −656 | |
| Pseudo likelihood ratio test | 10.3 on 9 df | | 109 on 10 df | | 113 on 11 df | |
| | | | n = 2,420 | | | |
| log(Age) | 14.6(4.8-44.7) | <0.001 | 13.3(4.3-40) | <0.001 | 13.1(4.3-40) | <0.001 |
| Has T2D | 2.9(1.7-5) | <0.001 | 2.9(1.7-5) | <0.001 | 3(1.7-5.2) | <0.001 |
| Female | 0.8(0.5-1.3) | 0.44 | 0.9(0.5-1.4) | 0.53 | 0.9(0.5-1.4) | 0.55 |
| HDL <35 mg/dL | 1.2(0.6-2.4) | 0.52 | 1.3(0.7-2.5) | 0.45 | 1.3(0.7-2.5) | 0.45 |
| HDL >60 mg/dL | 1(0.6-1.9) | 0.95 | 0.1(0.6-2) | 0.84 | 1.1(0.6-2) | 0.86 |
| TC >240 mg/dL | 1.3(0.8-2.1) | 0.29 | 1.3(0.8-2.1) | 0.31 | 1.3(0.8-2.1) | 0.29 |
| Former or current smoker | 1.8(1.1-2.9) | 0.014 | 1.8(1.1-2.9) | 0.016 | 1.8(1.1-2.9) | 0.014 |
| Hypertension stage II-IV | 1.8(1-3.1) | 0.37 | 1.7(0.9-2.9) | 0.077 | 1.7(1-2.9) | 0.074 |
| BMI >25 | 1.5(0.6-3.6) | 0.35 | 1.6(0.7-4) | 0.3 | 1.6(0.7-3.9) | 0.3 |
| Clone present | | | 2.2(1.1-4.6) | 0.029 | | |
| VAF <0.10 | | | | | 1.8(0.7-4.6) | 0.2 |
| VAF >0.10 | | | | | 3.1(1.2-8.4) | 0.025 |
| Pseudo Log-likelihood | −464 | | −462 | | −462 | |
| Pseudo likelihood ratio test | 79 on 6 df | | 83 on 10 df | | 83.5 on 11 df | |

SUPPLEMENTARY TABLE S13

Risks associated with developing incident coronary heart disease using traditional risk factors as well as hsCRP, RDW, and clonality.

n = 1,795

| Covariate | Model 1 HR (95% CI) | p-value | Model 2 HR (95% CI) | p-value | Model 3 HR (95% CI) | p-value |
|---|---|---|---|---|---|---|
| log(Age) | 3.3(0.6-17) | 0.17 | 2.7(0.5-13) | 0.23 | 2.8(0.6-14) | 0.21 |
| Has T2D | 2.9(1.4-5.9) | 0.004 | 3(1.5-6) | 0.002 | 3(16-5.8) | <0.001 |
| Female | 0.7(0.3-1.3) | 0.21 | 0.7(0.3-1.3) | | | |
| HDL <35 mg/dL | 1.6(0.6-4.6) | 0.38 | 1.8(0.6-5.1) | 0.29 | | |
| HDL ≥60 mg/dL | 1(0.5-2.1) | 0.99 | 1(0.5-2) | 0.9 | | |
| TC >200 mg/dL | 2.2(1.1-4.1) | 0.021 | 2.3(1.2-4.6) | 0.015 | 2.3(1.2-4.5) | 0.013 |
| Former or current smoker | 2(1.1-3.7) | 0.027 | 2.1(1.1-3.9) | 0.021 | 2(1.1-3.8) | 0.024 |
| SBP ≥160 mm Hg | 2.4(1.2-4.7) | 0.011 | 2.2(1.1-4.4) | 0.023 | 2.2(1.1-4.3) | 0.03 |
| hsCRP >1.0 mg/L | 1.1(0.5-2.5) | 0.76 | 1(0.4-2.3) | 0.99 | | |

SUPPLEMENTARY TABLE S13-continued

Risks associated with developing incident coronary heart disease using traditional risk factors as well as hsCRP, RDW, and clonality.

| | n = 1,795 | | | | | |
| --- | --- | --- | --- | --- | --- | --- |
| | Model 1 | | Model 2 | | Model 3 | |
| Covariate | HR (95% CI) | p-value | HR (95% CI) | p-value | HR (95% CI) | p-value |
| No clone, RDW ≥14.5% | | | 2.3(1.2-4.6) | 0.017 | 2.2(1.1-4.4) | 0.02 |
| Clone, RDW <14.5% | | | 0.9(0.1-7.4) | 0.95 | 1.7(0.4-7.7) | 0.46 |
| Clone, RDW ≥14.5% | | | 9.8(2-48.3) | 0.005 | 9.3(2-43) | 0.005 |
| Pseudo Log-likelihood | −273 | | −268 | | −276 | |
| Pseudo likelihood ratio test | 39.1 on 9 df | | 49.0 on 12 df | | 48.0 on 9 df | |

Hazard ratios were estimated using competing risks regression with death as the competing risk. P-values are derived from the Fine-Gray test. Individuals with prior coronary heart disease (CHD) were excluded for CHD analysis. Models shown in A or B are from the same population and differ by having covariates either removed or added. All individuals were from Jackson Heart Study.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of treating or preventing coronary heart disease (CHD) in a human subject, comprising the steps of:
   (a) sequencing at least part of a genome of one or more cells from a blood sample of the subject, wherein the at least part of said genome comprises a TET2 gene,
   (b) detecting a loss-of-function mutation in the TET2 gene selected from a frameshift mutation and a nonsense mutation; and
   (c) administering a lipid modifying medicine to the subject.

2. The method according to claim 1, wherein the one more cells in the blood sample are hematopoietic stem cells (HSCs), committed myeloid progenitor cells having long term self-renewal capacity or mature lymphoid cells having long term self-renewal capacity.

3. The method according to claim 1, wherein the sequencing is whole exome sequencing (WES).

4. The method according to claim 1, wherein the subject also exhibits one or more risk factors of being a smoker, having a high level of total cholesterol or having high level of high-density lipoprotein (HDL).

5. The method of claim 1, wherein the lipid-modifying medicine is a statin.

6. The method of claim 1, wherein the lipid-modifying medicine is a PCSK9 inhibitor.

7. The method of claim 6, wherein the PCSK9 inhibitor is a monoclonal antibody.

8. A method of treating or preventing CHD in a human subject, wherein the genome of a blood cell in said subject comprises a loss of function mutation in a TET2 gene selected from a frame shift mutation or a nonsense mutation, the method comprising administering a lipid-modifying medicine to the subject.

9. The method according to claim 8, wherein the subject also exhibits one or more risk factors of being a smoker, having a high level of total cholesterol or having high level of high-density lipoprotein (HDL).

10. The method of claim 8, wherein the lipid-modifying medicine is a statin.

11. The method of claim 8, wherein the lipid-modifying medicine is a PCSK9 inhibitor.

12. The method of claim 11, wherein the PCSK9 inhibitor is a monoclonal antibody.

* * * * *